(12) United States Patent
Tanabe et al.

(10) Patent No.: US 9,573,963 B2
(45) Date of Patent: Feb. 21, 2017

(54) FUSED HETEROCYCLIC COMPOUND AND PEST CONTROL APPLICATIONS THEREOF

(71) Applicant: Sumitomo Chemical Company, Limited, Tokyo (JP)

(72) Inventors: Takamasa Tanabe, Takarazuka (JP); Mai Ito, Takarazuka (JP); Chie Shimizu, Tokyo (JP); Yoshihiko Nokura, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/770,552

(22) PCT Filed: Feb. 19, 2014

(86) PCT No.: PCT/JP2014/054594
§ 371 (c)(1),
(2) Date: Aug. 26, 2015

(87) PCT Pub. No.: WO2014/132971
PCT Pub. Date: Sep. 4, 2014

(65) Prior Publication Data
US 2016/0002260 A1 Jan. 7, 2016

(30) Foreign Application Priority Data

Feb. 28, 2013 (JP) .................................. 2013-038433

(51) Int. Cl.
| | | |
|---|---|---|
| C07D 209/04 | (2006.01) |
| C07D 235/04 | (2006.01) |
| C07D 263/54 | (2006.01) |
| C07D 277/62 | (2006.01) |
| C07D 498/04 | (2006.01) |
| A01N 43/76 | (2006.01) |
| A01N 43/90 | (2006.01) |
| C07D 401/04 | (2006.01) |
| C07D 491/048 | (2006.01) |
| C07D 491/056 | (2006.01) |
| C07D 513/04 | (2006.01) |
| A01N 43/52 | (2006.01) |
| A01N 43/78 | (2006.01) |
| C07D 235/18 | (2006.01) |
| C07D 413/04 | (2006.01) |
| C07D 487/04 | (2006.01) |
| C07D 263/57 | (2006.01) |
| C07D 491/052 | (2006.01) |
| C07D 495/04 | (2006.01) |

(52) U.S. Cl.
CPC ............ *C07D 498/04* (2013.01); *A01N 43/52* (2013.01); *A01N 43/76* (2013.01); *A01N 43/78* (2013.01); *A01N 43/90* (2013.01); *C07D 235/18* (2013.01); *C07D 263/57* (2013.01); *C07D 401/04* (2013.01); *C07D 413/04* (2013.01); *C07D 487/04* (2013.01); *C07D 491/048* (2013.01); *C07D 491/052* (2013.01); *C07D 491/056* (2013.01); *C07D 495/04* (2013.01); *C07D 513/04* (2013.01)

(58) Field of Classification Search
CPC ... C07D 209/04; C07D 235/04; C07D 263/54; C07D 277/62
USPC .............................. 548/469, 304.4, 217, 152
See application file for complete search history.

(56) References Cited

U.S. PATENT DOCUMENTS 4,900,751 A * 2/1990 Cox ...................... C07D 235/28
514/338
4,981,864 A 1/1991 von der Saal et al.
(Continued)

FOREIGN PATENT DOCUMENTS

| | | | |
|---|---|---|---|
| AT | 392788 | * | 6/1991 |
| EP | 209707 | * | 1/1987 |

(Continued)

OTHER PUBLICATIONS

Sluka et al., Collection of Czechoslovak Chemical Communications (1976), 41(12), 3628-34.*

(Continued)

*Primary Examiner* — Niloofar Rahmani
(74) *Attorney, Agent, or Firm* — Panitch Schwarze Belisario & Nadel LLP

(57) ABSTRACT

A fused heterocyclic compound represented by formula (1) or an N-oxide thereof has an excellent control effect on pests:

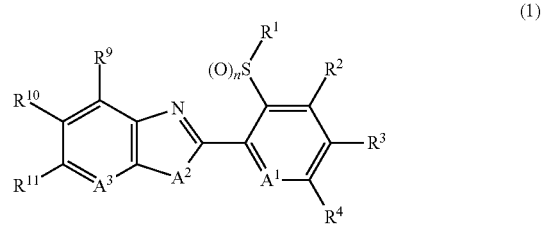

wherein $A^1$ represents N or the like, $A^2$ represents $NR^6$ or the like, $A^3$ represents $CR^{12}$ or the like, $R^1$ represents a C1 to C6 chain hydrocarbon group or the like, $R^2$, $R^4$ and $R^5$ are the same or different and represent a C1 to C3 alkyl group optionally having one or more halogen atoms or the like, $R^3$ represents a C1 to C6 chain hydrocarbon group or the like, $R^6$ represents a C1 to C6 chain hydrocarbon group or the like, any one set of $R^9$ and $R^{10}$, $R^{10}$ and $R^{11}$, and $R^{11}$ and $R^{12}$ in $R^9$, $R^{10}$, $R^{11}$ and $R^{12}$, together with the carbon atoms to which they are bound, forms a ring, and n represents 0, 1 or 2.

10 Claims, No Drawings

(56) References Cited

U.S. PATENT DOCUMENTS

| | | | |
|---|---|---|---|
| 7,329,682 B2* | 2/2008 | Park Choo | A61K 31/423 514/377 |
| 9,278,983 B2* | 3/2016 | Takyo | A01N 43/52 |
| 2004/0209776 A1 | 10/2004 | Farooq et al. | |
| 2012/0108586 A1 | 5/2012 | Iwakoshi et al. | |
| 2014/0018373 A1 | 1/2014 | Takyo et al. | |
| 2014/0194290 A1 | 7/2014 | Takahashi et al. | |
| 2015/0246911 A1 | 9/2015 | Takahashi et al. | |

FOREIGN PATENT DOCUMENTS

| | | |
|---|---|---|
| JP | 2014024840 A | 2/2014 |
| WO | 2013191189 A1 | 12/2013 |

OTHER PUBLICATIONS

Ried et al., Chemische Berichte (1978), 111(4), 1521-6.*

Choi et al., Bioorganic & Medicinal Chemistry (2006), 14(4), 1229-1235.*

Coppola et al., Synthetic Communications (2008), 38(20), 3500-3507.*

International Search Report issued Apr. 22, 2014 in International Application No. PCT/JP2014/054594.

* cited by examiner

FUSED HETEROCYCLIC COMPOUND AND PEST CONTROL APPLICATIONS THEREOF

CROSS-REFERENCE TO RELATED APPLICATION

This application is a Section 371 of International Application No. PCT/JP2014/054594, filed Feb. 19, 2014, which was published in the Japanese language on Sep. 4, 2014, under International Publication No. WO 2014/132971 A1, and the disclosure of which is incorporated herein by reference.

TECHNICAL FIELD

The present invention relates to a fused heterocyclic compound and a use thereof for pest control.

BACKGROUND ART

It is known in WO2009/131237 that a certain type of fused heterocyclic compound is effective in pest control.

SUMMARY OF THE INVENTION

The present invention provides a compound having an excellent control effect on pests.

The present invention is as described below.

[1] A fused heterocyclic compound represented by formula (1):

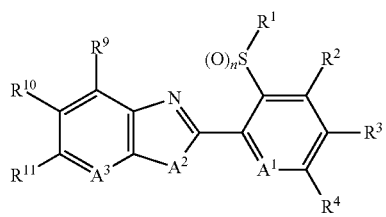

(1)

wherein
$A^1$ represents N or $CR^5$;
$A^2$ represents $NR^6$, S or O;
$A^3$ represents N or $CR^{12}$;
$R^1$ represents a C1 to C6 chain hydrocarbon group optionally having one or more atoms or groups selected from group α or a C3 to C6 alicyclic hydrocarbon group optionally having one or more atoms or groups selected from group β;
$R^2$, $R^4$ and $R^5$ are the same or different and represent a C1 to C3 alkyl group optionally having one or more halogen atoms, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
$R^3$ represents a C1 to C6 chain hydrocarbon group optionally having one or more atoms or groups selected from group α, a phenyl group optionally having one or more atoms or groups selected from group δ, a 5- or 6-membered heterocyclic group optionally having one or more atoms or groups selected from group δ, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
$R^6$ represents a C1 to C6 chain hydrocarbon group optionally having one or more atoms or groups selected from group γ, $C(O)R^7$, $CO_2R^7$ or a hydrogen atom;

$R^7$ and $R^8$ are the same or different and represent a C1 to C6 chain hydrocarbon group optionally having one or more halogen atoms or a hydrogen atom;
in $R^9$, $R^{10}$, $R^{11}$ and $R^{12}$, any one set of $R^9$ and $R^{10}$, $R^{10}$ and $R^{11}$, and $R^{11}$ and $R^{12}$, together with the carbon atoms to which they are bound, forms ring J;
those which do not form the ring J in $R^9$, $R^{10}$, $R^{11}$ and $R^{12}$ are the same or different and represent a C1 to C6 chain hydrocarbon group optionally having one or more atoms or groups selected from group α, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
the ring J represents a benzene ring, a 5- or 6-membered aromatic heterocyclic ring or a 5-, 6-, 7- or 8-membered non-aromatic ring (wherein the benzene ring and the 5- or 6-membered aromatic heterocyclic ring optionally have one or more atoms or groups selected from group δ, and the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =$NOR^{13}$, each divalent group binds to the same carbon among carbons constituting the ring of the 5-, 6-, 7- or 8-membered non-aromatic ring;
n represents 0, 1 or 2; and
m represents 0, 1 or 2,
wherein, in $S(O)_mR^7$, when m is 1 or 2, $R^7$ represents a C1 to C6 chain hydrocarbon group optionally having one or more halogen atoms;

Group α: a group consisting of C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms, Group β: a group consisting of C1 to C6 alkyl groups optionally having one or more halogen atoms, C1 to C6 alkoxy groups optionally having one or more halogen atoms, and halogen atoms, Group γ: a group consisting of C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, phenyl groups optionally having one or more atoms or groups selected from group δ, 5- or 6-membered heterocyclic groups optionally having one or more atoms or groups selected from group δ, cyano groups, hydroxy groups, and halogen atoms, Group δ: a group consisting of C1 to C3 alkyl groups optionally having one or more halogen atoms, C1 to C3 alkoxy groups optionally having one or more halogen atoms, C1 to C3 alkylamino groups optionally having one or more halogen atoms, C2 to C6 dialkylamino groups optionally having one or more halogen atoms, C1 to C3 alkylsulfanyl groups optionally having one or more halogen atoms, C1 to C3 alkylsulfinyl groups optionally having one or more halogen atoms, C1 to C3 alkylsulfonyl groups optionally having one or more halogen atoms, C2 to C4 alkylcarbonyl groups optionally having one or more halogen atoms, C2 to C4 alkoxycarbonyl groups optionally having one or more halogen atoms, nitro groups, amino groups, cyano groups, and halogen atoms, Group ε: a group consisting of C1 to C3 alkyl groups optionally having one or more halogen atoms, C1 to C3 alkoxy groups optionally having one or more halogen atoms, C1 to C3 alkylamino groups optionally having one or more halogen atoms, C2 to C6 dialkylamino groups optionally having one or more halogen atoms, C1 to C3 alkylsulfanyl groups optionally having one or more halogen atoms, C1 to C3 alkylsulfinyl groups optionally having one or more halogen atoms, C1 to C3 alkylsulfonyl groups optionally having one or more halogen atoms, C2 to C4 alkylcarbonyl groups optionally having one or more halogen atoms, C2 to C4 alkoxycarbonyl groups optionally having one or more halogen atoms, nitro groups, amino groups, cyano groups, halogen atoms, divalent groups represented by =S, divalent groups represented by =O, and divalent groups represented by =NOR$^{13}$ (wherein R$^{13}$ represents a C1 to C6 alkyl group optionally having one or more halogen atoms or a hydrogen atom), or an N-oxide thereof (hereinafter, the fused heterocyclic compound represented by the formula (1) and the N-oxide thereof are referred to as the compound of the present invention) (in the case of the N-oxide, n represents 2, and m represents 2).

[2] The compound according to [1], wherein

R$^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms or a C3 to C6 cycloalkyl group optionally having one or more halogen atoms or one or more C1 to C3 alkyl groups;

R$^2$, R$^4$ and R$^5$ are the same or different and are a C1 to C3 alkyl group optionally having one or more halogen atoms, a halogen atom or a hydrogen atom;

R$^3$ is a C1 to C6 alkyl group optionally having one or more halogen atoms, a 5- or 6-membered heterocyclic group optionally having one or more atoms or groups selected from group δ, OR$^7$, S(O)$_m$R$^7$, C(O)R$^7$, CO$_2$R$^7$, C(O)NR$^7$R$^8$, a cyano group, a halogen atom or a hydrogen atom;

R$^6$ is C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom; and R$^7$ and R$^8$ are the same or different and are a C1 to C6 alkyl group optionally having one or more halogen atoms or a hydrogen atom.

[3] The compound according to [1] or [2], wherein the ring J is a benzene ring (wherein the benzene ring optionally has one or more atoms or groups selected from group δ).

[4] The compound according to [1] or [2], wherein the ring J is a 5- or 6-membered aromatic heterocyclic ring (wherein the 5- or 6-membered aromatic heterocyclic ring optionally has one or more atoms or groups selected from group δ).

[5] The compound according to [1] or [2], wherein the ring J is a 5-, 6-, 7- or 8-membered non-aromatic ring (wherein the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring).

[6] The compound according to [1] or [2], wherein R$^9$ and R$^{10}$, together with the carbon atoms to which they are bound, form ring J.

[7] The compound according to [1] or [2], wherein R$^{10}$ and R$^{11}$, together with the carbon atoms to which they are bound, form ring J.

[8] The compound according to [1] or [2], wherein A$^3$ is CR$^{12}$, and R$^{11}$ and R$^{12}$, together with the carbon atoms to which they are bound, form ring J.

[9] The compound according to any of [1] to [8], wherein A$^1$ is N.

[10] The compound as defined in any of [1] to [8], wherein A$^1$ is CR$^5$.

[11] The compound as defined in any of [1] to [10], wherein A$^2$ is NR$^6$.

[12] The compound as defined in any of [1] to [10], wherein A$^2$ is S.

[13] The compound as defined in any of [1] to [10], wherein A$^2$ is O.

[14] A pest control agent which comprises the compound as defined in any of [1] to [13], and an inert carrier.

[15] A method for controlling pests comprising applying an effective amount of the compound as defined in any of [1] to [13] to a pest or a pest-infested area.

MODE FOR CARRYING OUT THE INVENTION

The groups used in the description of the present specification will be described below with examples.

The halogen atom in this invention refers to a fluorine atom, a chlorine atom, a bromine atom, and an iodine atom.

Examples of the C1 to C6 alkyl group in this invention include a methyl group, an ethyl group, a propyl group, an isopropyl group, a butyl group, an isobutyl group, a sec-butyl group, a tert-butyl group, a pentyl group, a neopentyl group, and a hexyl group.

Examples of the C1 to C3 alkyl group in this invention include a methyl group, an ethyl group, a propyl group, and an isopropyl group.

Examples of the C2 to C6 alkenyl group in this invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

Examples of the C2 to C6 alkynyl group in this invention include an ethynyl group, a propargyl group, a 2-butynyl group, a 3-butynyl group, a 1-pentynyl group, and a 1-hexynyl group.

The C1 to C6 chain hydrocarbon group optionally having one or more atoms or groups selected from group α in this invention refers to a straight-chain or branched-chain hydrocarbon group having a carbon atom number of 1 to 6, in which hydrogen atoms bound to the carbon atom are optionally substituted by one or more atoms or groups selected from group α, and herein, when the C1 to C6 chain hydrocarbon group has two or more atoms or groups selected from group α, the atoms or groups selected from group α may be the same or different from each other.

Examples of the C1 to C6 chain hydrocarbon group optionally having one or more atoms or groups selected from group α include C1 to C6 alkyl groups optionally having one or more atoms or groups selected from group α such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2,-trifluoroethyl group, a pentafluoroethyl group, a 2-(methylsulfanyl)ethyl group, a 2-(ethylsulfanyl)ethyl group, a 2-(methylsulfinyl)ethyl group, a 2-(methylsulfonyl)ethyl group, a 2-hydroxyethyl group, a cyclopropylmethyl group, a 1-methylcyclopropylmethyl group and a 2,2-difluorocyclopropylmethyl group; C2 to C6 alkenyl groups optionally having one or more atoms or groups selected from group α such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group α such as an ethynyl group, a propargyl group, a 2-butynyl group, a 3-butynyl group, a 1-pentynyl group, a 1-hexynyl group and a 4,4,4-trifluoro-2-butynyl group.

The C1 to C6 chain hydrocarbon group optionally having one or more atoms or groups selected from group γ in this invention refers to a straight-chain or branched-chain hydrocarbon group having a carbon atom number of 1 to 6, in which hydrogen atoms bound to the carbon atom are optionally substituted by one or more atoms or groups selected from group γ, and herein, when the C1 to C6 chain hydrocarbon group has two or more atoms or groups selected from group γ, the atoms or groups selected from group γ may be the same or different from each other.

Examples of the C1 to C6 chain hydrocarbon group optionally having one or more atoms or groups selected from group γ include C1 to C6 alkyl groups optionally having one or more atoms or groups selected from group γ such as a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2,-trifluoroethyl group, a pentafluoroethyl group, a 2-(methylsulfanyl)ethyl group, a 2-(ethylsulfanyl)ethyl group, a 2-(methylsulfinyl)ethyl group, a 2-(methylsulfonyl)ethyl group, a 2-hydroxyethyl group, a cyclopropylmethyl group, a 1-methylcyclopropylmethyl group, a 2,2-difluorocyclopropylmethyl group, a phenylmethyl group, a 4-chlorophenylmethyl group, a 4-trifluoromethylphenylmethyl group, a tetrahydrofuran-2-ylmethyl group, a tetrahydropyran-2-ylmethyl group, a tetrahydropyran-3-ylmethyl group, a thiazol-5-ylmethyl group, a 2-chlorothiazol-5-ylmethyl group, a pyridin-3-ylmethyl group, a 6-chloropyridin-3-ylmethyl group and a 6-trifluoromethylpyridin-3-ylmethyl group; C2 to C6 alkenyl groups optionally having one or more atoms or groups selected from group γ such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more atoms or groups selected from group γ such as an ethynyl group, a propargyl group, a 2-butynyl group, a 3-butynyl group, a 1-pentynyl group, a 1-hexynyl group and a 4,4,4-trifluoro-2-butynyl group.

Examples of the C1 to C6 chain hydrocarbon group optionally having one or more halogen atoms in this invention include C1 to C6 alkyl groups optionally having one or more halogen atoms such as a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group and a heptafluoroisopropyl group; C2 to C6 alkenyl groups optionally having one or more halogen atoms such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group and a pentafluoroallyl group; and C2 to C6 alkynyl groups optionally having one or more halogen atoms such as an ethynyl group, a propargyl group, a 2-butynyl group, a 3-butynyl group, a 1-pentynyl group, a 1-hexynyl group and a 4,4,4-trifluoro-2-butynyl group.

Examples of the C1 to C6 alkyl group optionally having one or more halogen atoms or one or more cyclopropyl groups (wherein the cyclopropyl group optionally has one or more halogen atoms or one or more C1 to C3 alkyl groups) in this invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, a heptafluoroisopropyl group, a cyclopropylmethyl group, a 2-cyclopropylethyl group, and a 1-cyclopropylethyl group.

Examples of the C1 to C6 alkyl group optionally having one or more halogen atoms in this invention include a methyl group, an ethyl group, a propyl group, an isopropyl group, a butyl group, an isobutyl group, a sec-butyl group, a tert-butyl group, a pentyl group, a neopentyl group, a hexyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the C1 to C3 alkyl group optionally having one or more halogen atoms in this invention include a methyl group, an ethyl group, a propyl group, an isopropyl group, a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the C1 to C3 alkyl group having a thiazolyl group optionally having one or more atoms or groups selected from group δ in this invention include a (thiazol-5-yl)methyl group, a (2-chlorothiazol-5-yl)methyl group, and a 1-(2-chlorothiazol-5-yl)ethyl group.

Examples of the C1 to C3 alkyl group having a pyridyl group optionally having one or more atoms or groups selected from the group δ in this invention include a (pyridin-5-yl)methyl group, a (2-chloropyridin-5-yl)methyl group, a 1-(2-chloropyridin-5-yl)ethyl group, and a (2-trifluoromethylpyridin-5-yl)methyl group.

Examples of the C2 to C6 alkenyl group optionally having one or more halogen atoms in this invention include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, and a pentafluoroallyl group.

Examples of the C2 to C6 alkynyl group optionally having one or more halogen atoms in this invention include an ethynyl group, a propargyl group, a 2-butynyl group, a 3-butynyl group, a 1-pentynyl group, a 1-hexynyl group, and a 4,4,4-trifluoro-2-butynyl group.

The C3 to C6 alicyclic hydrocarbon group optionally having one or more atoms or groups selected from group β in the compound of the present invention refers to a cyclic alicyclic hydrocarbon group having a carbon atom number of 3 to 6, in which hydrogen atoms bound to the carbon atom are optionally substituted by one or more atoms or groups selected from group β, and herein, when the C3 to C6 alicyclic hydrocarbon group has two or more atoms or groups selected from group β, the atoms or groups selected from group β may be the same or different from each other.

Examples of the C3 to C6 alicyclic hydrocarbon group optionally having one or more atoms or groups selected from group β include a cyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxycyclohexyl group, a 3-methoxycyclohexyl group, a 4-methoxycyclohexyl group, a 1-fluorocyclohexyl group, a 2-fluorocyclohexyl group, a 3-fluorocyclohexyl group, and a 4-fluorocyclohexyl group.

Examples of the C3 to C6 cycloalkyl group in this invention include a cyclopropyl group, a cyclobutyl group, a cyclopentyl group, and a cyclohexyl group.

Examples of the C3 to C6 cycloalkyl groups optionally having one or more halogen atoms or one or more C1 to C3 alkyl groups in this invention include a cyclopropyl group, a 1-methylcyclopropyl group, a 2-methylcyclopropyl group, a 1-fluorocyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

The phenyl group optionally having one or more atoms or groups selected from group δ in this invention refers to a phenyl group in which hydrogen atoms of the phenyl group are optionally substituted by one or more atoms or groups selected from group δ, and herein, when the phenyl group has two or more atoms or groups selected from group δ, the atoms or groups selected from group δ may be the same or different from each other.

Examples of the phenyl group optionally having one or more atoms or groups selected from group δ include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 2-trifluoromethoxyphenyl group, a 3-trifluoromethoxyphenyl group, a 4-trifluoromethoxyphenyl group, a 2-trifluoromethylsulfanylphenyl group, a 3-trifluoromethylsulfanylphenyl group, a 4-trifluoromethylsulfanylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-acetylphenyl group, and a 4-methoxycarbonylphenyl group.

The heterocyclic group in this invention refers to a heterocyclic residue containing one or more nitrogen atoms, oxygen atoms or sulfur atoms, other than carbon atoms, as ring-constituting atoms, in the ring structure. Examples of the heterocyclic ring of the heterocyclic group include 5-membered non-aromatic heterocyclic rings such as a pyrrolidine ring, a tetrahydrofuran ring and a tetrahydrothiophene ring, 5-membered aromatic heterocyclic rings such as a pyrrole ring, a pyrazole ring, an imidazole ring, a furan ring, a thiophene ring, an oxazole ring and a thiazole ring, 6-membered non-aromatic heterocyclic rings such as a piperidine ring, a tetrahydropyran ring, a tetrahydrothiopyran ring, a piperazine ring and a morpholine ring, and 6-membered aromatic heterocyclic rings such as a pyridine ring, a pyrimidine ring, a pyridazine ring and a pyrazine ring.

In addition, in this invention, the 5-membered heterocyclic group refers to a 5-membered non-aromatic heterocyclic group and a 5-membered aromatic heterocyclic group, and the 6-membered heterocyclic group refers to a 6-membered non-aromatic heterocyclic group and a 6-membered aromatic heterocyclic group.

Examples of the 5- or 6-membered heterocyclic group optionally having one or more atoms or groups selected from group δ in this invention include 5- or 6-membered non-aromatic heterocyclic groups optionally having one or more atoms or groups selected from group δ such as a pyrrolidin-1-yl group, a 3,3,4,4-tetrafluoropyrrolidin-1-yl group, a tetrahydrofuran-2-yl group, a piperidin-1-yl group, a morpholin-4-yl group and a thiomorpholin-4-yl group; and 5- or 6-membered aromatic heterocyclic groups optionally having one or more atoms or groups selected from group δ such as a 2-pyrrolyl group, a 2-furyl group, a 3-furyl group, a 5-pyrazolyl group, a 4-pyrazolyl group, a 1-pyrrolyl group, a 1-methyl-2-pyrrolyl group, a 2-methylsulfanyl-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a pyrazinyl group, a 4-pyrimidinyl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group and a 5-trifluoromethoxypyridin-2-yl group.

Examples of the 5- or 6-membered aromatic heterocyclic groups in this invention include a 2-pyrrolyl group, a 2-furyl group, a 3-furyl group, a 5-pyrazolyl group, a 4-pyrazolyl group, a 1-pyrrolyl group, a pyrazol-1-yl group, an imidazol-1-yl group, a 1,2,4-triazol-1-yl group, a 1,2,3,4-tetrazol-1-yl group, a 1,2,3,5-tetrazol-1-yl group, a 2-thienyl group, a 3-thienyl group, a pyrazinyl group, a 4-pyrimidinyl group, a 5-pyrimidinyl group, a 2-pyridyl group, a 3-pyridyl group, a 4-pyridyl group, and a 2-pyrimidinyl group.

Examples of the C1 to C6 alkoxy groups optionally having one or more halogen atoms in this invention include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

Examples of the C1 to C3 alkoxy groups optionally having one or more halogen atoms in this invention include a methoxy group, a trifluoromethoxy group, an ethoxy group, a 2,2,2-trifluoroethoxy group, a propoxy group, and an isopropoxy group.

Examples of the C1 to C6 alkylsulfanyl groups optionally having one or more halogen atoms in this invention include a methylsulfanyl group, an ethylsulfanyl group, a propylsulfanyl group, an isopropylsulfanyl group, a butylsulfanyl group, a pentylsulfanyl group, a hexylsulfanyl group, a trifluoromethylsulfanyl group, a 2,2,2-trifluoroethylsulfanyl group, and a pentafluoroethylsulfanyl group.

Examples of the C1 to C3 alkylsulfanyl groups optionally having one or more halogen atoms in this invention include a methylsulfanyl group, a trifluoromethylsulfanyl group, an ethylsulfanyl group, a propylsulfanyl group, and an isopropylsulfanyl group.

Examples of the C1 to C6 alkylsulfinyl groups optionally having one or more halogen atoms in this invention include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

Examples of the C1 to C3 alkylsulfinyl groups optionally having one or more halogen atoms in this invention include a methylsulfinyl group, a trifluoromethylsulfinyl group, an ethylsulfinyl group, a propylsulfinyl group, and an isopropylsulfinyl group.

Examples of the C1 to C6 alkylsulfonyl groups optionally having one or more halogen atoms in this invention include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

Examples of the C1 to C3 alkylsulfonyl groups optionally having one or more halogen atoms in this invention include a methylsulfonyl group, a trifluoromethylsulfonyl group, an ethylsulfonyl group, a propylsulfonyl group, and an isopropylsulfonyl group.

Examples of the C2 to C6 alkylcarbonyl groups optionally having one or more halogen atoms in this invention include an acetyl group, a propionyl group, a butyryl group, a pentanoyl group, a hexanoyl group, and a trifluoroacetyl group.

Examples of the C2 to C4 alkylcarbonyl groups optionally having one or more halogen atoms in this invention include an acetyl group, a propionyl group, a butyryl group, and a trifluoroacetyl group.

Examples of the C2 to C6 alkoxycarbonyl groups optionally having one or more halogen atoms in this invention include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethoxycarbonyl group.

Examples of the C2 to C4 alkoxycarbonyl groups optionally having one or more halogen atoms in this invention include a methoxycarbonyl group, an ethoxycarbonyl group, a propoxycarbonyl group, and a 2,2,2-trifluoroethoxycarbonyl group.

Examples of the C1 to C3 alkylamino groups optionally having one or more halogen atoms in this invention include a methylamino group, an ethylamino group, a 2,2,2-trifluoroethylamino group, a propylamino group, and an isopropylamino group.

Examples of the C2 to C6 dialkylamino groups optionally having one or more halogen atoms in this invention include a dimethylamino group, a diethylamino group, a bis(2,2,2-trifluoroethyl)amino group, and a dipropylamino group.

The 5-, 6-, 7- or 8-membered non-aromatic ring in this invention refers to a 5-, 6-, 7- or 8-membered non-aromatic heterocyclic ring containing one or more nitrogen atoms, oxygen atoms or sulfur atoms (wherein, S has a form of S(O)m, and m represents 0, 1 or 2), other than carbon atoms, as a ring constituting a 5-, 6-, 7- or 8-membered alicyclic hydrocarbon in which the ring-constituting atoms are all carbon atoms and ring-constituting atoms, in the ring structure. Examples of the 5-, 6-, 7- or 8-membered alicyclic hydrocarbon include cyclopentane, cyclohexane, cyclohexene, cycloheptane and cyclooctane, and examples of the 5-, 6-, 7- or 8-membered non-aromatic heterocyclic ring include a pyrrolidine ring, a tetrahydrofuran ring, a piperidyl ring, a morpholyl ring and a thiomorpholyl ring.

In this invention, specific examples of a compound in which, in $R^9$, $R^{10}$, $R^{11}$ and $R^{12}$, any one set of $R^9$ and $R^{10}$, $R^{10}$ and $R^{11}$, and $R^{11}$ and $R^{12}$, together with the carbon atoms to which they are bound, forms ring J, and those which do not form the ring J in $R^9$, $R^{10}$, $R^{11}$ and $R^{12}$ are the same or different and represent a C1 to C6 chain hydrocarbon group optionally having one or more atoms or groups selected from group α, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom include formula (1-K1) wherein $R^9$ and $R^{10}$, together with the carbon atoms to which they are bound, form ring J, formula (1-K2) wherein $R^{10}$ and $R^{11}$, together with the carbon atoms to which they are bound, form ring J, and formula (1-K3) wherein $A^3$ is $CR^{12}$, and $R^{11}$ and $R^{12}$, together with the carbon atoms to which they are bound, form ring J, in the formula (1).

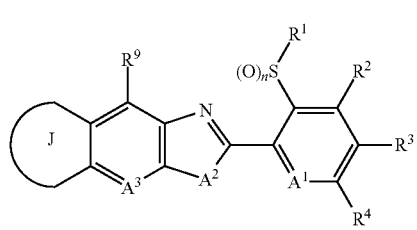
(1-K1)

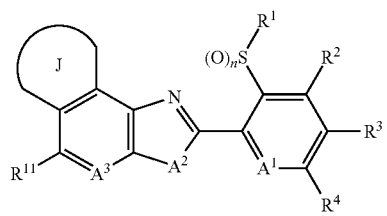
(1-K2)

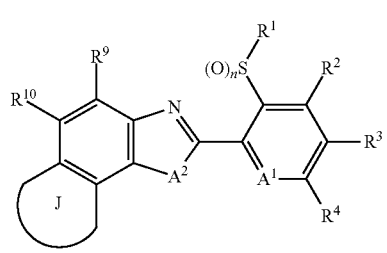
(1-K3)

In the formulae, symbols represent the same meaning as in the formula (1).

Examples of the formula (1-K1) include following compounds.

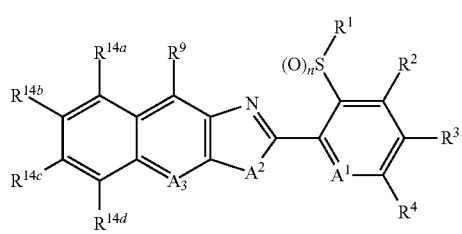
(1-K1-1)

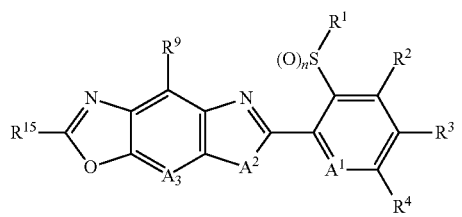
(1-K1-2)

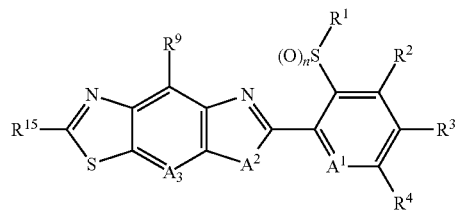
(1-K1-3)

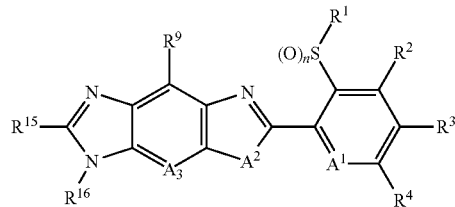
(1-K1-4)

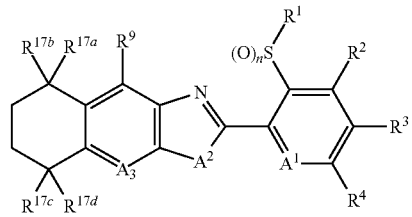
(1-K1-5)

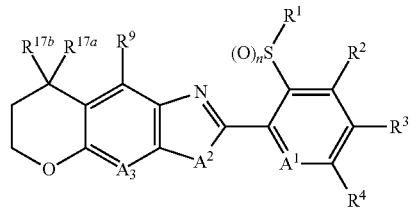
(1-K1-6)

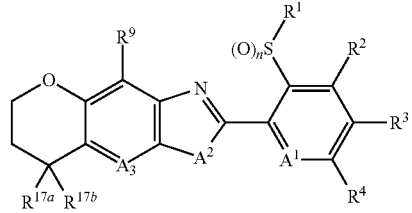
(1-K1-7)

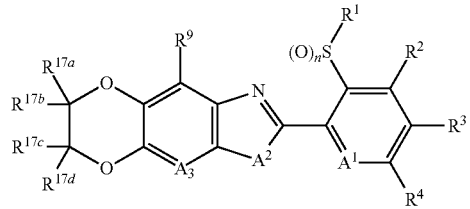
(1-K1-8)

(1-K1-9)

-continued

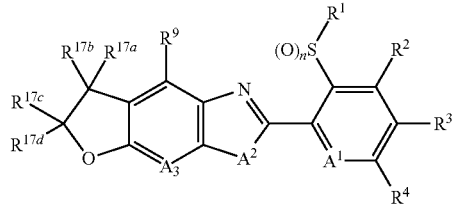
(1-K1-10)

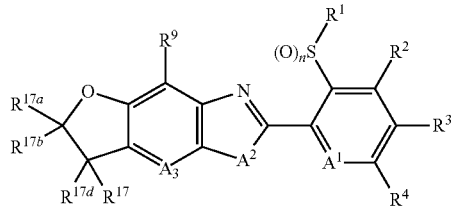
(1-K1-11)

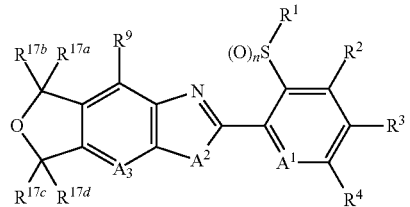
(1-K1-12)

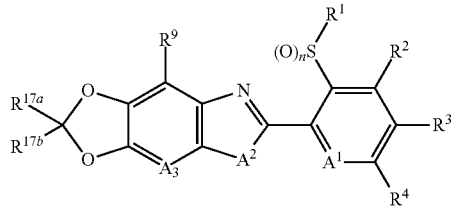
(1-K1-13)

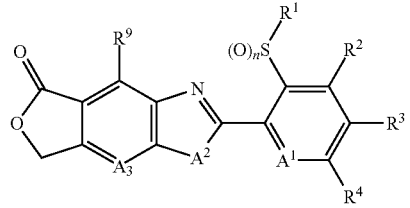
(1-K1-14)

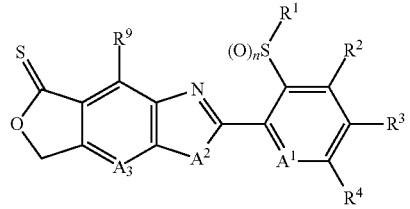
(1-K1-15)

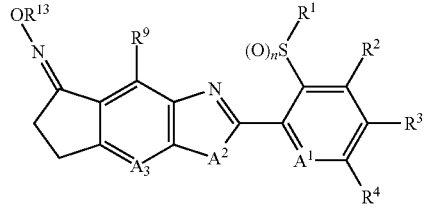
(1-K1-16)

In the formulae, $R^{14a}$, $R^{14b}$, $R^{14c}$ and $R^{14d}$ are the same or different and are a C1 to C3 alkyl group optionally having one or more halogen atoms, a C1 to C3 alkoxy group optionally having one or more halogen atoms, a C1 to C3 alkylamino group optionally having one or more halogen atoms, a C2 to C6 dialkylamino group optionally having one or more halogen atoms, a nitro group, an amino group, a cyano group or a halogen atom;

q is 0, 1 or 2;

$R^{15}$s are the same or different, and is a C1 to C3 alkyl group optionally having one or more halogen atoms, a C1 to C3 alkoxy groups optionally having one or more halogen atoms, a halogen atom or a hydrogen atom;

$R^{16}$s are the same or different, and is a C1 to C3 alkyl group optionally having one or more halogen atoms or a hydrogen atom;

$R^{17a}$, $R^{17b}$, $R^{17c}$ and $R^{17d}$ are the same or different, and is a C1 to C3 alkyl group optionally having one or more halogen atoms, a halogen atom or a hydrogen atom; and other symbols represent the same meaning as in the formula (1).

Examples of the formula (1-K2) include following compounds.

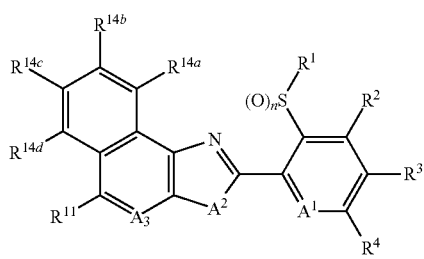
(1-K2-1)

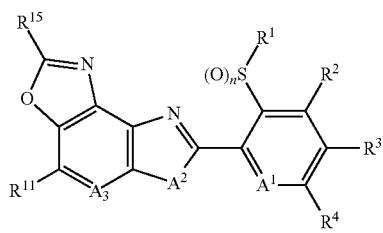
(1-K2-2)

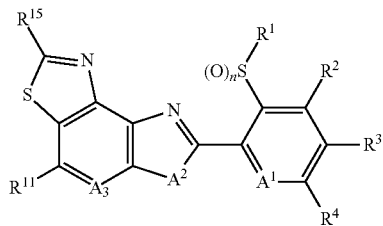
(1-K2-3)

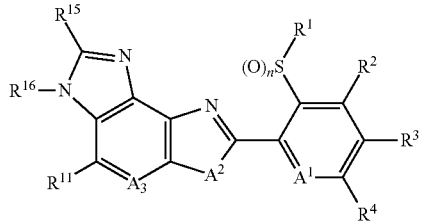
(1-K2-4)

In the formulae, symbols represent the same meaning as described above.

Examples of the formula (1-K3) include following compounds.

-continued
(1-K3-2)
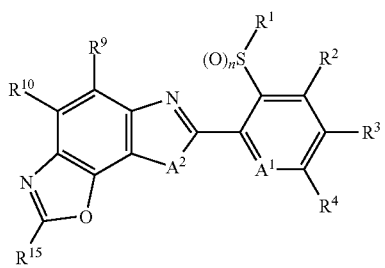
(1-K3-3)
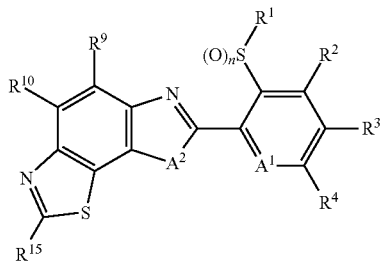
(1-K3-4)
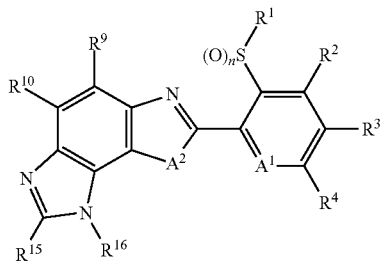
(1-K3-5)
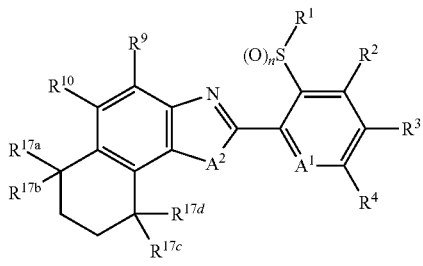
(1-K3-6)
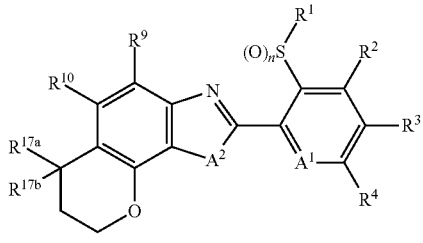
(1-K3-7)
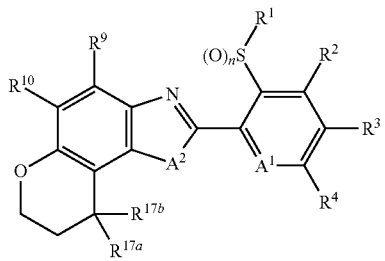
-continued
(1-K3-8)
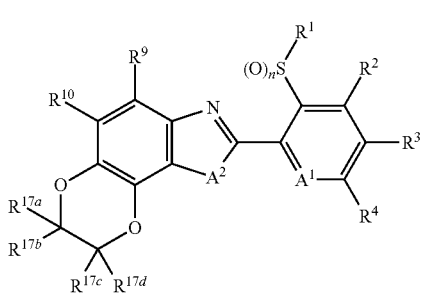
(1-K3-9)
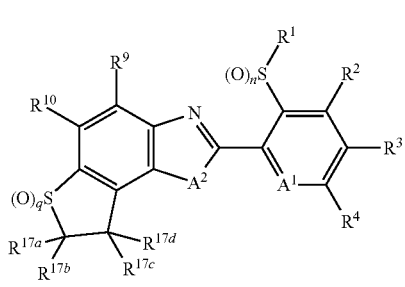
(1-K3-10)
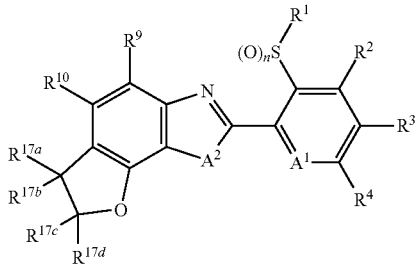
(1-K3-11)
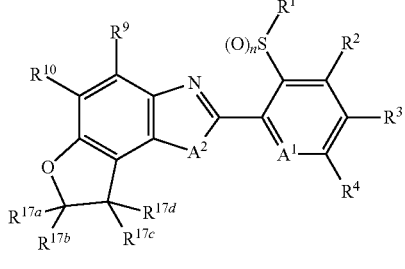
(1-K3-12)
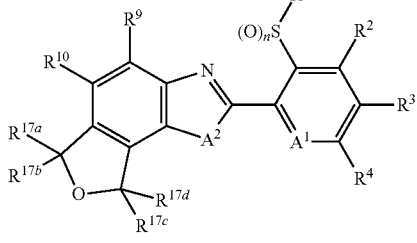
(1-K3-13)
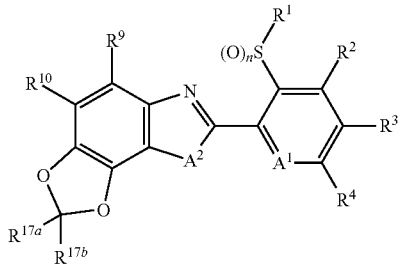

-continued

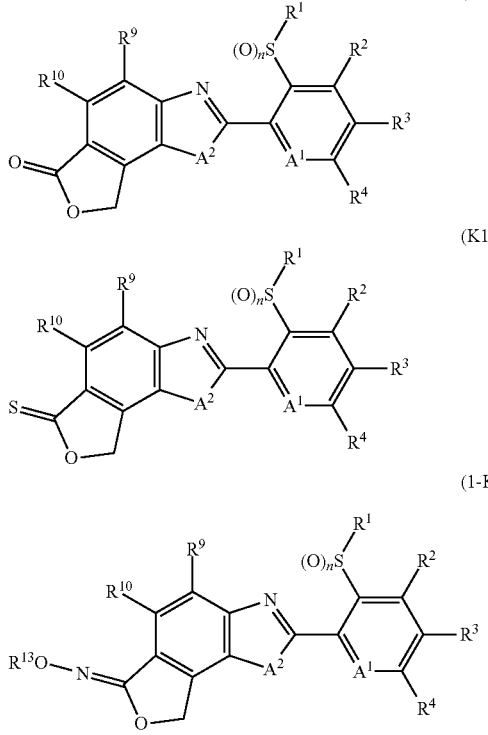

(1-K3-14)

(K1-3-15)

(1-K3-16)

In the formulae, symbols represent the same meaning as described above.

The N-oxide in this invention is a compound in which the nitrogen atom constituting the ring on the heterocyclic group is oxidized. Examples of the heterocyclic group that may form an N-oxide include a pyridyl group.

In the compound of the present invention, examples of the N-oxide include the compounds represented by the formula (1A) to the formula (1E) set forth below.

Examples of the compound of the present invention include the following compounds.
In the formula (1), compounds wherein $A^1$ is N;
In the formula (1), compounds wherein $A^1$ is $CR^5$;
In the formula (1), compounds wherein $A^2$ is $NR^6$;
In the formula (1), compounds wherein $A^2$ is O;
In the formula (1), compounds wherein $A^2$ is S;
In the formula (1), compounds wherein $A^3$ is N;
In the formula (1), compounds wherein $A^3$ is $CR^{12}$;
In the formula (1), compounds wherein $A^1$ is N, and $A^2$ is $NR^6$;
In the formula (1), compounds wherein $A^1$ is N, and $A^2$ is O;
In the formula (1), compounds wherein $A^1$ is N, and $A^2$ is S;
In the formula (1), compounds wherein $A^1$ is $CR^5$, and $A^2$ is $NR^6$;
In the formula (1), compounds wherein $A^1$ is $CR^5$, and $A^2$ is O;
In the formula (1), compounds wherein $A^1$ is $CR^5$, and $A^2$ is S;
In the formula (1), compounds wherein $A^1$ is N, and $A^3$ is N;
In the formula (1), compounds wherein $A^1$ is N, and $A^3$ is $CR^{12}$;
In the formula (1), compounds wherein $A^1$ is $CR^5$, and $A^3$ is N;
In the formula (1), compounds wherein $A^1$ is $CR^5$, and $A^3$ is $CR^{12}$;
In the formula (1), compounds wherein $A^2$ is $NR^6$, and $A^3$ is N;
In the formula (1), compounds wherein $A^2$ is $NR^6$, and $A^3$ is $R^{22}$;
In the formula (1), compounds wherein $A^2$ is O, and $A^3$ is N;
In the formula (1), compounds wherein $A^2$ is O, and $A^3$ is $CR^{12}$;
In the formula (1), compounds wherein $A^2$ is S, and $A^3$ is N;
In the formula (1), compounds wherein $A^2$ is S, and $A^3$ is $CR^{12}$;
In the formula (1), compounds wherein $A^1$ is N, $A^2$ is $NR^6$, and $A^3$ is N;
In the formula (1), compounds wherein $A^1$ is N, $A^2$ is $NR^6$, and $A^3$ is $CR^{12}$;
In the formula (1), compounds wherein $A^1$ is N, $A^2$ is O, and $A^3$ is N;
In the formula (1), compounds wherein $A^1$ is N, $A^2$ is O, and $A^3$ is $CR^{12}$;
In the formula (1), compounds wherein $A^1$ is N, $A^2$ is S, and $A^3$ is N;
In the formula (1), compounds wherein $A^1$ is N, $A^2$ is S, and $A^3$ is $CR^{12}$;
In the formula (1), compounds wherein $A^1$ is $CR^5$, $A^2$ is $NR^6$, and $A^3$ is N;
In the formula (1), compounds wherein $A^1$ is $CR^5$, $A^2$ is $NR^6$, and $A^3$ is $CR^{12}$;
In the formula (1), compounds wherein $A^1$ is $CR^5$, $A^2$ is O, and $A^3$ is N;
In the formula (1), compounds wherein $A^1$ is $CR^5$, $A^2$ is O, and $A^3$ is $CR^{12}$;
In the formula (1), compounds wherein $A^1$ is $CR^5$, $A^2$ is S, and $A^3$ is N;
In the formula (1), compounds wherein $A^1$ is $CR^5$, $A^2$ is S, and $A^3$ is $CR^{12}$;
In the formula (1), compounds wherein $R^1$ is a C1 to C6 chain hydrocarbon group optionally having one or more atoms or groups selected from group α;
In the formula (1), compounds wherein $R^1$ is a C1 to C6 chain hydrocarbon group optionally having one or more halogen atoms or one or more cyclopropyl groups;
In the formula (1), compounds wherein $R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, or a C2 to C6 alkynyl group optionally having one or more halogen atoms;
In the formula (1), compounds wherein $R^1$ is a C1 to C6 alkyl group optionally having one or more halogen atoms or one or more cyclopropyl groups (wherein the cyclopropyl group optionally has one or more halogen atoms or one or more C1 to C3 alkyl groups);
In the formula (1), compounds wherein $R^1$ is a C1 to C6 alkyl group optionally having one or more halogen atoms;
In the formula (1), compounds wherein $R^1$ is a C2 to C6 alkenyl group optionally having one or more halogen atoms;
In the formula (1), compounds wherein $R^1$ is a C2 to C6 alkynyl group optionally having one or more halogen atoms;
In the formula (1), compounds wherein $R^1$ is a C2 to C6 alkyl group optionally having one or more halogen atoms;
In the formula (1), compounds wherein $R^1$ is a C2 to C3 alkyl group optionally having one or more halogen atoms;
In the formula (1), compounds wherein $R^1$ is a C1 to C6 alkyl group, a C2 to C6 alkenyl group or a C2 to C6 alkynyl group;
In the formula (1), compounds wherein $R^1$ is a C1 to C6 alkyl group;

In the formula (1), compounds wherein $R^1$ is a C2 to C6 alkyl group;
In the formula (1), compounds wherein $R^1$ is a C2 to C3 alkyl group;
In the formula (1), compounds wherein $R^1$ is a methyl group, an ethyl group, a propyl group, an isopropyl group, a trifluoromethyl group, a 2,2,2-trifluoroethyl group or a cyclopropylmethyl group;
In the formula (1), compounds wherein $R^1$ is a methyl group, an ethyl group, a propyl group or an isopropyl group;
In the formula (1), compounds wherein $R^1$ is an ethyl group, a cyclopropyl group or a cyclopropylmethyl group;
In the formula (1), compounds wherein $R^1$ is a methyl group;
In the formula (1), compounds wherein $R^1$ is an ethyl group;
In the formula (1), compounds wherein $R^1$ is a cyclopropyl group;
In the formula (1), compounds wherein $R^1$ is a cyclopropylmethyl group;
In the formula (1), compounds wherein $R^1$ is a C3 to C6 alicyclic hydrocarbon group optionally having one or more atoms or groups selected from group β;
In the formula (1), compounds wherein $R^1$ is a C3 to C6 cycloalkyl group optionally having one or more halogen atoms or one or more C1 to C3 alkyl groups;
In the formula (1), compounds wherein $R^1$ is a C3 to C6 alicyclic hydrocarbon group optionally having one or more halogen atoms;
In the formula (1), compounds wherein $R^1$ is a C3 to C6 cycloalkyl group optionally having one or more halogen atoms;
In the formula (1), compounds wherein $R^1$ is a C3 to C6 cycloalkyl group;
In the formula (1), compounds wherein $R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups;
In the formula (1), compounds wherein $R^2$, $R^4$ and $R^5$ are the same or different and are a C1 to C3 alkyl group optionally having one or more halogen atoms, $OR^7$, $S(O)_mR^7$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
In the formula (1), compounds wherein $R^2$, $R^4$ and $R^5$ are the same or different and are a C1 to C3 alkyl group optionally having one or more halogen atoms, a halogen atom or a hydrogen atom;
In the formula (1), compounds wherein $R^2$, $R^4$ and $R^5$ are the same or different and are a C1 to C3 alkyl group optionally having one or more halogen atoms or a hydrogen atom;
In the formula (1), compounds wherein $R^2$, $R^4$ and $R^5$ are the same or different and are $OR^7$ or a hydrogen atom;
In the formula (1), compounds wherein $R^2$, $R^4$ and $R^5$ are the same or different and are $S(O)_mR^7$ or a hydrogen atom;
In the formula (1), compounds wherein $R^2$, $R^4$ and $R^5$ are the same or different and are $C(O)R^7$ or a hydrogen atom;
In the formula (1), compounds wherein $R^2$, $R^4$ and $R^5$ are the same or different and are $CO_2R^7$ or a hydrogen atom;
In the formula (1), compounds wherein $R^2$, $R^4$ and $R^5$ are the same or different and are $C(O)NR^7R^8$ or a hydrogen atom;
In the formula (1), compounds wherein $R^2$, $R^4$ and $R^5$ are the same or different and are $NR^7R^8$ or a hydrogen atom;
In the formula (1), compounds wherein $R^2$, $R^4$ and $R^5$ are the same or different and are $NR^7C(O)R^8$ or a hydrogen atom;
In the formula (1), compounds wherein $R^2$, $R^4$ and $R^5$ are the same or different and are $NR^7CO_2R^8$ or a hydrogen atom;
In the formula (1), compounds wherein $R^2$, $R^4$ and $R^5$ are the same or different and are a cyano group or a hydrogen atom;
In the formula (1), compounds wherein $R^2$, $R^4$ and $R^5$ are the same or different and are a nitro group or a hydrogen atom;
In the formula (1), compounds wherein $R^2$, $R^4$ and $R^5$ are the same or different and are a halogen atom or a hydrogen atom;
In the formula (1), compounds wherein $R^2$, $R^4$ and $R^5$ are the same or different and are a fluorine atom or a hydrogen atom;
In the formula (1), compounds wherein $R^2$, $R^4$ and $R^5$ are the same or different and are a chlorine atom or a hydrogen atom;
In the formula (1), compounds wherein $R^2$, $R^4$ and $R^5$ are the same or different and are a bromine atom or a hydrogen atom;
In the formula (1), compounds wherein $R^2$, $R^4$ and $R^5$ are the same or different and are an iodine atom or a hydrogen atom;
In the formula (1), compounds wherein $R^2$ and $R^4$ are a hydrogen atom, and $R^5$ is a halogen atom or a hydrogen atom;
In the formula (1), compounds wherein $R^2$ and $R^4$ are a hydrogen atom, and $R^5$ is a methyl group;
In the formula (1), compounds wherein $R^2$ and $R^4$ are a hydrogen atom, and $R^5$ is a fluorine atom;
In the formula (1), compounds wherein $R^2$ and $R^4$ are a hydrogen atom, and $R^5$ is a chlorine atom;
In the formula (1), compounds wherein $R^2$ and $R^4$ are a hydrogen atom, and $R^5$ is a bromine atom;
In the formula (1), compounds wherein $R^2$ and $R^4$ are a hydrogen atom, and $R^5$ is an iodine atom;
In the formula (1), compounds wherein $R^3$ is a C1 to C6 chain hydrocarbon group optionally having one or more atoms or groups selected from group α, a 5- or 6-membered heterocyclic group optionally having one or more atoms or groups selected from group δ, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
In the formula (1), compounds wherein $R^3$ is a C1 to C6 chain hydrocarbon group optionally having one or more atoms or groups selected from group α, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
In the formula (1), compounds wherein $R^3$ is a C1 to C6 chain hydrocarbon group optionally having one or more atoms or groups selected from group α or a hydrogen atom;
In the formula (1), compounds wherein $R^3$ is a phenyl group optionally having one or more atoms or groups selected from group δ or a hydrogen atom;
In the formula (1), compounds wherein $R^3$ is a 5- or 6-membered heterocyclic group optionally having one or more atoms or groups selected from group δ or a hydrogen atom;
In the formula (1), compounds wherein $R^3$ is $OR^7$ or a hydrogen atom;
In the formula (1), compounds wherein $R^3$ is $S(O)_mR^7$ or a hydrogen atom;
In the formula (1), compounds wherein $R^3$ is $SO_2NR^7R^8$ or a hydrogen atom;
In the formula (1), compounds wherein $R^3$ is $C(O)R^7$ or a hydrogen atom;

In the formula (1), compounds wherein $R^3$ is $CO_2R^7$ or a hydrogen atom;
In the formula (1), compounds wherein $R^3$ is $C(O)NR^7R^8$ or a hydrogen atom;
In the formula (1), compounds wherein $R^3$ is $NR^7R^8$ or a hydrogen atom;
In the formula (1), compounds wherein $R^3$ is $NR^7C(O)R^8$ or a hydrogen atom;
In the formula (1), compounds wherein $R^3$ is $NR^7CO_2R^8$ or a hydrogen atom;
In the formula (1), compounds wherein $R^3$ is a cyano group or a hydrogen atom;
In the formula (1), compounds wherein $R^3$ is a nitro group or a hydrogen atom;
In the formula (1), compounds wherein $R^3$ is a halogen atom or a hydrogen atom;
In the formula (1), compounds wherein $R^3$ is a C1 to C6 chain hydrocarbon group optionally having one or more atoms or groups selected from group α;
In the formula (1), compounds wherein $R^3$ is a phenyl group optionally having one or more atoms or groups selected from group δ;
In the formula (1), compounds wherein $R^3$ is a 5- or 6-membered heterocyclic group optionally having one or more atoms or groups selected from group δ;
In the formula (1), compounds wherein $R^3$ is $OR^7$;
In the formula (1), compounds wherein $R^3$ is $S(O)_mR^7$;
In the formula (1), compounds wherein $R^3$ is $SO_2NR^7R^8$;
In the formula (1), compounds wherein $R^3$ is $C(O)R^7$;
In the formula (1), compounds wherein $R^3$ is $CO_2R^7$;
In the formula (1), compounds wherein $R^3$ is $C(O)NR^7R^8$;
In the formula (1), compounds wherein $R^3$ is $NR^7R^8$;
In the formula (1), compounds wherein $R^3$ is $NR^7(O)R^8$;
In the formula (1), compounds wherein $R^3$ is $NR^7CO_2R^8$;
In the formula (1), compounds wherein $R^3$ is a cyano group;
In the formula (1), compounds wherein $R^3$ is a nitro group;
In the formula (1), compounds wherein $R^3$ is a halogen atom;
In the formula (1), compounds wherein $R^3$ is a C1 to C6 chain hydrocarbon group optionally having one or more halogen atoms or a hydrogen atom;
In the formula (1), compounds wherein $R^3$ is a phenyl group optionally having one or more halogen atoms or a hydrogen atom;
In the formula (1), compounds wherein $R^3$ is a 5- or 6-membered heterocyclic group optionally having one or more halogen atoms or a hydrogen atom;
In the formula (1), compounds wherein $R^3$ is a C1 to C6 alkyl group optionally having one or more halogen atoms or a hydrogen atom;
In the formula (1), compounds wherein $R^3$ is a methyl group, a trifluoromethyl group, a methoxy group, a trifluoromethoxy group, a methylsulfanyl group, a methylsulfinyl group, a methylsulfonyl group, a trifluoromethylsulfanyl group, a trifluoromethylsulfinyl group, a trifluoromethylsulfonyl group, a methylcarbonyl group, a methoxycarbonyl group, an ethoxycarbonyl group, a methylaminocarbonyl group, a dimethylaminocarbonyl group, a cyano group, a fluorine atom, a chlorine atom, a bromine atom, an iodine atom or a hydrogen atom;
In the formula (1), compounds wherein $R^3$ is a methyl group;
In the formula (1), compounds wherein $R^3$ is a trifluoromethyl group;
In the formula (1), compounds wherein $R^3$ is a trifluoromethylsulfanyl group;
In the formula (1), compounds wherein $R^3$ is a trifluoromethylsulfonyl group;
In the formula (1), compounds wherein $R^3$ is a methylcarbonyl group;
In the formula (1), compounds wherein $R^3$ is a methoxycarbonyl group;
In the formula (1), compounds wherein $R^3$ is an ethoxycarbonyl group;
In the formula (1), compounds wherein $R^3$ is a methylaminocarbonyl group;
In the formula (1), compounds wherein $R^3$ is a dimethylaminocarbonyl group;
In the formula (1), compounds wherein $R^3$ is a fluorine atom;
In the formula (1), compounds wherein $R^3$ is a chlorine atom;
In the formula (1), compounds wherein $R^3$ is a bromine atom;
In the formula (1), compounds wherein $R^3$ is an iodine atom;
In the formula (1), compounds wherein $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom;
In the formula (1), compounds wherein $R^2$, $R^4$ and $R^5$ are the same or different and are a C1 to C3 alkyl group optionally having one or more halogen atoms, a halogen atom or a hydrogen atom, and $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom;
In the formula (1), compounds wherein $R^2$, $R^4$ and $R^5$ are the same or different and are a halogen atom or a hydrogen atom, and $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom;
In the formula (1), compounds wherein $R^2$, $R^4$ and $R^5$ are the same or different and are a halogen atom or a hydrogen atom, and $R^3$ is a C1 to C6 alkyl group optionally having one or more halogen atoms, $OR^7$, $S(O)_mR^7$, $C(O)R^7$, $CO_2R^7$, $C(O)NR^7R^8$, a cyano group, a halogen atom or a hydrogen atom;
In the formula (1), compounds wherein $R^2$, $R^4$ and $R^5$ are the same or different and are a halogen atom or a hydrogen atom, and $R^3$ is a C1 to C6 alkyl group optionally having one or more halogen atoms, a halogen atom or a hydrogen atom;
In the formula (1), compounds wherein, when $R^2$, $R^4$ and $R^5$ are a hydrogen atom, and $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom;
In the formula (1), compounds wherein $R^2$, $R^4$ and $R^5$ are a hydrogen atom, and $R^3$ is a C1 to C6 alkyl group optionally having one or more halogen atoms, a halogen atom or a hydrogen atom;
In the formula (1), compounds wherein $R^2$, $R^4$ and $R^5$ are a hydrogen atom, and $R^3$ is a C1 to C6 alkyl group optionally having one or more halogen atoms or a hydrogen atom;
In the formula (1), compounds wherein $R^2$, $R^4$ and $R^5$ are a hydrogen atom, and $R^3$ is a halogen atom or a hydrogen atom;

In the formula (1), compounds wherein $R^2$, $R^4$ and $R^5$ are a hydrogen atom, and $R^3$ is a C1 to C6 alkyl group optionally having one or more halogen atoms;
In the formula (1), compounds wherein $R^2$, $R^4$ and $R^5$ are a hydrogen atom, and $R^3$ is a halogen atom;
In the formula (1), compounds wherein $R^2$, $R^4$ and $R^5$ are a hydrogen atom, and $R^3$ is a methyl group;
In the formula (1), compounds wherein $R^2$, $R^4$ and $R^5$ are a hydrogen atom, and $R^3$ is a trifluoromethyl group;
In the formula (1), compounds wherein $R^2$, $R^4$ and $R^5$ are a hydrogen atom, and $R^3$ is a trifluoromethylsulfanyl group;
In the formula (1), compounds wherein $R^2$, $R^4$ and $R^5$ are a hydrogen atom, and $R^3$ is a trifluoromethylsulfonyl group;
In the formula (1), compounds wherein $R^2$, $R^4$ and $R^5$ are a hydrogen atom, and $R^3$ is a methylcarbonyl group;
In the formula (1), compounds wherein $R^2$, $R^4$ and $R^5$ are a hydrogen atom, and $R^3$ is a methoxycarbonyl group;
In the formula (1), compounds wherein $R^2$, $R^4$ and $R^5$ are a hydrogen atom, and $R^3$ is an ethoxycarbonyl group;
In the formula (1), compounds wherein $R^2$, $R^4$ and $R^5$ are a hydrogen atom, and $R^3$ is a methylaminocarbonyl group;
In the formula (1), compounds wherein $R^2$, $R^4$ and $R^5$ are a hydrogen atom, and $R^3$ is a dimethylaminocarbonyl group;
In the formula (1), compounds wherein $R^2$, $R^4$ and $R^5$ are a hydrogen atom, and $R^3$ is a fluorine atom;
In the formula (1), compounds wherein $R^2$, $R^4$ and $R^5$ are a hydrogen atom, and $R^3$ is a chlorine atom;
In the formula (1), compounds wherein $R^2$, $R^4$ and $R^5$ are a hydrogen atom, and $R^3$ is a bromine atom;
In the formula (1), compounds wherein $R^2$, $R^4$ and $R^5$ are a hydrogen atom, and $R^3$ is an iodine atom;
In the formula (1), compounds wherein $R^2$ is a hydrogen atom;
In the formula (1), compounds wherein $R^3$ is a hydrogen atom;
In the formula (1), compounds wherein $R^4$ is a hydrogen atom;
In the formula (1), compounds wherein $R^5$ is a hydrogen atom;
In the formula (1), compounds wherein $R^2$ and $R^3$ are a hydrogen atom;
In the formula (1), compounds wherein $R^2$ and $R^4$ are a hydrogen atom;
In the formula (1), compounds wherein $R^2$ and $R^5$ are a hydrogen atom;
In the formula (1), compounds wherein $R^3$ and $R^4$ are a hydrogen atom;
In the formula (1), compounds wherein $R^3$ and $R^5$ are a hydrogen atom;
In the formula (1), compounds wherein $R^4$ and $R^5$ are a hydrogen atom;
In the formula (1), compounds wherein $R^2$, $R^3$ and $R^4$ are a hydrogen atom;
In the formula (1), compounds wherein $R^2$, $R^3$ and $R^5$ are a hydrogen atom;
In the formula (1), compounds wherein $R^2$, $R^4$ and $R^5$ are a hydrogen atom;
In the formula (1), compounds wherein $R^3$, $R^4$ and $R^5$ are a hydrogen atom;
In the formula (1), compounds wherein $R^2$, $R^3$, $R^4$ and $R^5$ are a hydrogen atom;
In the formula (1), compounds wherein $R^6$ is a C1 to C6 chain hydrocarbon group optionally having one or more atoms or groups selected from group γ or a hydrogen atom;
In the formula (1), compounds wherein $R^6$ is a C1 to C6 chain hydrocarbon group optionally having one or more atoms or groups selected from group γ;
In the formula (1), compounds wherein $R^6$ is $C(O)R^7$ or a hydrogen atom;
In the formula (1), compounds wherein $R^6$ is $CO_2R^7$ or a hydrogen atom;
In the formula (1), compounds wherein $R^6$ is a hydrogen atom;
In the formula (1), compounds wherein $R^6$ is a C1 to C6 chain hydrocarbon group optionally having one or more halogen atoms, $C(O)R^7$, $CO_2R^7$ or a hydrogen atom;
In the formula (1), compounds wherein $R^6$ is a C1 to C6 alkyl group optionally having one or more halogen atoms, $C(O)R^7$, $CO_2R^7$ or a hydrogen atom;
In the formula (1), compounds wherein $R^6$ is a C1 to C6 alkyl group optionally having one or more halogen atoms or a hydrogen atom;
In the formula (1), compounds wherein $R^6$ is a C1 to C6 alkyl group optionally having one or more halogen atoms;
In the formula (1), compounds wherein $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom;
In the formula (1), compounds wherein $R^6$ is a C1 to C3 alkyl group having a thiazolyl group optionally having one or more atoms or groups selected from group δ;
In the formula (1), compounds wherein $R^6$ is a C1 to C3 alkyl group having a pyridyl group optionally having one or more atoms or groups selected from group δ;
In the formula (1), compounds wherein $R^6$ is a methyl group, an ethyl group, a propyl group, a cyclopropylmethyl group, a 2,2,2-trifluoroethyl group, a methoxymethyl group, an ethoxymethyl group, a 2-methoxyethyl group, a methylcarbonyl group, a methoxycarbonyl group, a 6-chloropyridyl-3-ylmethyl group, a 2-chlorothiazoyl-5-ylmethyl group or a hydrogen atom;
In the formula (1), compounds wherein $R^6$ is a methyl group;
In the formula (1), compounds wherein $R^6$ is an ethyl group;
In the formula (1), compounds wherein $R^6$ is a propyl group;
In the formula (1), compounds wherein $R^6$ is a cyclopropylmethyl group;
In the formula (1), compounds wherein $R^6$ is a methoxymethyl group;
In the formula (1), compounds wherein $R^6$ is a methylcarbonyl group;
In the formula (1), compounds wherein $R^6$ is a methoxycarbonyl group;
In the formula (1), compounds wherein $R^6$ is a 6-chloropyridyl-3-ylmethyl group;
In the formula (1), compounds wherein $R^6$ is a 2-chlorothiazoyl-5-ylmethyl group;
In the formula (1), compounds wherein $R^6$ is a hydrogen atom;
In the formula (1), compounds wherein the ring J is a benzene ring (wherein the benzene ring optionally has one or more atoms or groups selected from group δ);
In the formula (1), compounds wherein the ring J is a 5- or 6-membered aromatic heterocyclic ring (wherein the 5- or 6-membered aromatic heterocyclic ring optionally has one or more atoms or groups selected from group δ);
In the formula (1), compounds wherein the ring J is a 5-, 6-, 7- or 8-membered non-aromatic ring (wherein the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring);
In the formula (1), compounds wherein R$^9$ and R$^{10}$, together with the carbon atoms to which they are bound, form ring J;
In the formula (1), compounds wherein R$^9$ and R$^{10}$, together with the carbon atoms to which they are bound, form ring J, and the ring J is a benzene ring (wherein the benzene ring optionally has one or more atoms or groups selected from group δ);
In the formula (1), compounds wherein R$^9$ and R$^{10}$, together with the carbon atoms to which they are bound, form ring J, and the ring J is a 5- or 6-membered aromatic heterocyclic ring (wherein the 5- or 6-membered aromatic heterocyclic ring optionally has one or more atoms or groups selected from group δ);
In the formula (1), compounds wherein R$^9$ and R$^{10}$, together with the carbon atoms to which they are bound, form ring J, and the ring J is a 5-, 6-, 7- or 8-membered non-aromatic ring (wherein the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring);
In the formula (1), compounds wherein R$^{10}$ and R$^{11}$, together with the carbon atoms to which they are bound, form ring J;
In the formula (1), compounds wherein R$^{10}$ and R$^{11}$, together with the carbon atoms to which they are bound, form ring J, and the ring J is a benzene ring (wherein the benzene ring optionally has one or more atoms or groups selected from group δ);
In the formula (1), compounds wherein R$^{10}$ and R$^{11}$, together with the carbon atoms to which they are bound, form ring J, and the ring J is a 5- or 6-membered aromatic heterocyclic ring (wherein the 5- or 6-membered aromatic heterocyclic ring optionally has one or more atoms or groups selected from group δ);
In the formula (1), compounds wherein R$^{10}$ and R$^{11}$, together with the carbon atoms to which they are bound, form ring J, and the ring J is a 5-, 6-, 7- or 8-membered non-aromatic ring (wherein the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring);
In the formula (1), compounds wherein R$^{10}$ and R$^{11}$, together with the carbon atoms to which they are bound, form ring J, and the ring J is a 5- or 6-membered non-aromatic ring (the 5- or 6-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5- or 6-membered non-aromatic ring);

In the formula (1), compounds wherein R$^{11}$ and R$^{12}$, together with the carbon atoms to which they are bound, form ring J;
In the formula (1), compounds wherein R$^{11}$ and R$^{12}$, together with the carbon atoms to which they are bound, form ring J, and the ring J is a benzene ring (wherein the benzene ring optionally has one or more atoms or groups selected from group δ);
In the formula (1), compounds wherein R$^{11}$ and R$^{12}$, together with the carbon atoms to which they are bound, form ring J, and the ring J is a 5- or 6-membered aromatic heterocyclic ring (wherein the 5- or 6-membered aromatic heterocyclic ring optionally has one or more atoms or groups selected from group δ);
In the formula (1), compounds wherein A$^3$ is CR$^{12}$, and R$^{11}$ and R$^{12}$, together with the carbon atoms to which they are bound, form ring J, and the ring J is a 5-, 6-, 7- or 8-membered non-aromatic ring (wherein the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring);
Compounds represented by formula (1-K1),

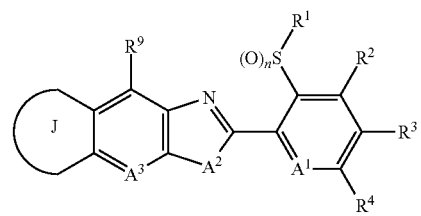

(1-K1)

wherein symbols represent the same meaning as described above, or N-oxides thereof;
In the formula (1-K1), compounds wherein A$^1$ is N;
In the formula (1-K1), compounds wherein A$^1$ is CR$^5$;
In the formula (1-K1), compounds wherein A$^2$ is NR$^6$;
In the formula (1-K1), compounds wherein A$^2$ is O;
In the formula (1-K1), compounds wherein A$^2$ is S;
In the formula (1-K1), compounds wherein A$^3$ is N;
In the formula (1-K1), compounds wherein A$^3$ is CR$^{12}$;
In the formula (1-K1), compounds wherein A$^1$ is N, and A$^2$ is NR$^6$;
In the formula (1-K1), compounds wherein A$^1$ is N, and A$^2$ is O;
In the formula (1-K1), compounds wherein A$^1$ is N, and A$^2$ is S;
In the formula (1-K1), compounds wherein A$^1$ is CR$^5$, and A$^2$ is NR$^6$;
In the formula (1-K1), compounds wherein A$^1$ is CR$^5$, and A$^2$ is O;
In the formula (1-K1), compounds wherein A$^1$ is CR$^5$, and A$^2$ is S;
In the formula (1-K1), compounds wherein A$^1$ is N, A$^2$ is NR$^6$, and A$^3$ is N;
In the formula (1-K1), compounds wherein A$^1$ is N, A$^2$ is NR$^6$, and A$^3$ is CR$^{12}$;
In the formula (1-K1), compounds wherein A$^1$ is N, A$^2$ is O, and A$^3$ is N;
In the formula (1-K1), compounds wherein A$^1$ is N, A$^2$ is O, and A$^3$ is CR$^{12}$;

In the formula (1-K1), compounds wherein $A^1$ is N, $A^2$ is S, and $A^3$ is N;
In the formula (1-K1), compounds wherein $A^1$ is N, $A^2$ is S, and $A^3$ is $CR^{12}$;
In the formula (1-K1), compounds wherein $A^1$ is $CR^5$, $A^2$ is $NR^6$, and $A^3$ is N;
In the formula (1-K1), compounds wherein $A^1$ is $CR^5$, $A^2$ is $NR^6$, and $A^3$ is $CR^{12}$;
In the formula (1-K1), compounds wherein $A^1$ is $CR^5$, $A^2$ is O, and $A^3$ is N;
In the formula (1-K1), compounds wherein $A^1$ is $CR^5$, $A^2$ is O, and $A^3$ is $CR^{12}$;
In the formula (1-K1), compounds wherein $A^1$ is $CR^5$, $A^2$ is S, and $A^3$ is N;
In the formula (1-K1), compounds wherein $A^1$ is $CR^5$, $A^2$ is S, and $A^3$ is $CR^{12}$;
Compounds represented by formula (1-K1-1),

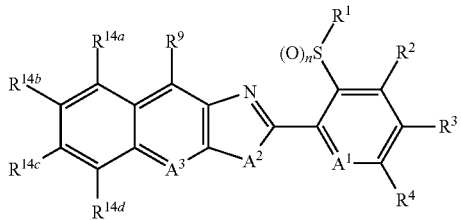

(1-K1-1)

wherein symbols represent the same meaning as described above, or N-oxides thereof;
In the formula (1-K1-1), compounds wherein $A^1$ is N;
In the formula (1-K1-1), compounds wherein $A^1$ is $CR^5$;
In the formula (1-K1-1), compounds wherein $A^2$ is $NR^6$;
In the formula (1-K1-1), compounds wherein $A^2$ is O;
In the formula (1-K1-1), compounds wherein $A^2$ is S;
In the formula (1-K1-1), compounds wherein $A^3$ is N;
In the formula (1-K1-1), compounds wherein $A^3$ is $CR^{12}$;
In the formula (1-K1-1), compounds wherein $A^1$ is N, and $A^2$ is $NR^6$;
In the formula (1-K1-1), compounds wherein $A^1$ is N, and $A^2$ is O;
In the formula (1-K1-1), compounds wherein $A^1$ is N, and $A^2$ is S;
In the formula (1-K1-1), compounds wherein $A^1$ is $CR^5$, and $A^2$ is $NR^6$;
In the formula (1-K1-1), compounds wherein $A^1$ is $CR^5$, and $A^2$ is O;
In the formula (1-K1-1), compounds wherein $A^1$ is $CR^5$, and $A^2$ is S;
In the formula (1-K1-1), compounds wherein $A^1$ is N, $A^2$ is $NR^6$, and $A^3$ is N;
In the formula (1-K1-1), compounds wherein $A^1$ is N, $A^2$ is $NR^6$, and $A^3$ is $CR^{12}$;
In the formula (1-K1-1), compounds wherein $A^1$ is N, $A^2$ is O, and $A^3$ is N;
In the formula (1-K1-1), compounds wherein $A^1$ is N, $A^2$ is O, and $A^3$ is $CR^{12}$;
In the formula (1-K1-1), compounds wherein $A^1$ is N, $A^2$ is S, and $A^3$ is N;
In the formula (1-K1-1), compounds wherein $A^1$ is N, $A^2$ is S, and $A^3$ is $CR^{12}$;
In the formula (1-K1-1), compounds wherein $A^1$ is $CR^5$, $A^2$ is $NR^6$, and $A^3$ is N;
In the formula (1-K1-1), compounds wherein $A^1$ is $CR^5$, $A^2$ is $NR^6$, and $A^3$ is $CR^{12}$;
In the formula (1-K1-1), compounds wherein $A^1$ is $CR^5$, $A^2$ is O, and $A^3$ is N;
In the formula (1-K1-1), compounds wherein $A^1$ is $CR^5$, $A^2$ is O, and $A^3$ is $CR^{12}$;
In the formula (1-K1-1), compounds wherein $A^1$ is $CR^5$, $A^2$ is S, and $A^3$ is N;
In the formula (1-K1-1), compounds wherein $A^1$ is $CR^5$, $A^2$ is S, and $A^3$ is $CR^{12}$;
Compounds represented by formula (1-K1-2),

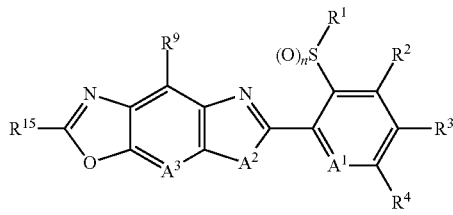

(1-K1-2)

wherein symbols represent the same meaning as described above, or N-oxides thereof;
In the formula (1-K1-2), compounds wherein $A^1$ is N;
In the formula (1-K1-2), compounds wherein $A^1$ is $CR^5$;
In the formula (1-K1-2), compounds wherein $A^2$ is $NR^6$;
In the formula (1-K1-2), compounds wherein $A^2$ is O;
In the formula (1-K1-2), compounds wherein $A^2$ is S;
In the formula (1-K1-2), compounds wherein $A^3$ is N;
In the formula (1-K1-2), compounds wherein $A^3$ is $CR^{12}$;
In the formula (1-K1-2), compounds wherein $A^1$ is N, and $A^2$ is $NR^6$;
In the formula (1-K1-2), compounds wherein $A^1$ is N, and $A^2$ is O;
In the formula (1-K1-2), compounds wherein $A^1$ is N, and $A^2$ is S;
In the formula (1-K1-2), compounds wherein $A^1$ is $CR^5$, and $A^2$ is $NR^6$;
In the formula (1-K1-2), compounds wherein $A^1$ is $CR^5$, and $A^2$ is O;
In the formula (1-K1-2), compounds wherein $A^1$ is $CR^5$, and $A^2$ is S;
In the formula (1-K1-2), compounds wherein $A^1$ is N, $A^2$ is $NR^6$, and $A^3$ is N;
In the formula (1-K1-2), compounds wherein $A^1$ is N, $A^2$ is $NR^6$, and $A^3$ is $CR^{12}$;
In the formula (1-K1-2), compounds wherein $A^1$ is N, $A^2$ is O, and $A^3$ is N;
In the formula (1-K1-2), compounds wherein $A^1$ is N, $A^2$ is O, and $A^3$ is $CR^{12}$;
In the formula (1-K1-2), compounds wherein $A^1$ is N, $A^2$ is S, and $A^3$ is N;
In the formula (1-K1-2), compounds wherein $A^1$ is N, $A^2$ is S, and $A^3$ is $CR^{12}$;
In the formula (1-K1-2), compounds wherein $A^1$ is $CR^5$, $A^2$ is $NR^6$, and $A^3$ is N;
In the formula (1-K1-2), compounds wherein $A^1$ is $CR^5$, $A^2$ is $NR^6$, and $A^3$ is $CR^{12}$;
In the formula (1-K1-2), compounds wherein $A^1$ is $CR^5$, $A^2$ is O, and $A^3$ is N;
In the formula (1-K1-2), compounds wherein $A^1$ is $CR^5$, $A^2$ is O, and $A^3$ is $CR^{12}$;
In the formula (1-K1-2), compounds wherein $A^1$ is $CR^5$, $A^2$ is S, and $A^3$ is N;

In the formula (1-K1-2), compounds wherein $A^1$ is $CR^5$, $A^2$ is S, and $A^3$ is $CR^{12}$;

Compounds represented by formula (1-K1-3),

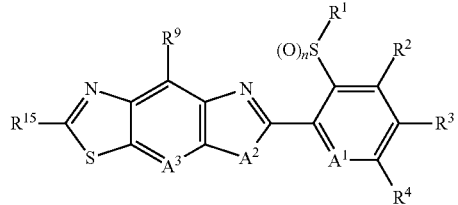

(1-K1-3)

wherein symbols represent the same meaning as described above, or N-oxides thereof;

In the formula (1-K1-3), compounds wherein $A^1$ is N;
In the formula (1-K1-3), compounds wherein $A^1$ is $CR^5$;
In the formula (1-K1-3), compounds wherein $A^2$ is $NR^6$;
In the formula (1-K1-3), compounds wherein $A^2$ is O;
In the formula (1-K1-3), compounds wherein $A^2$ is S;
In the formula (1-K1-3), compounds wherein $A^3$ is N;
In the formula (1-K1-3), compounds wherein $A^3$ is $CR^{12}$;
In the formula (1-K1-3), compounds wherein $A^1$ is N, and $A^2$ is $NR^6$;
In the formula (1-K1-3), compounds wherein $A^1$ is N, and $A^2$ is O;
In the formula (1-K1-3), compounds wherein $A^1$ is N, and $A^2$ is S;
In the formula (1-K1-3), compounds wherein $A^1$ is $CR^5$, and $A^2$ is $NR^6$;
In the formula (1-K1-3), compounds wherein $A^1$ is $CR^5$, and $A^2$ is O;
In the formula (1-K1-3), compounds wherein $A^1$ is $CR^5$, and $A^2$ is S;
In the formula (1-K1-3), compounds wherein $A^1$ is N, $A^2$ is $NR^6$, and $A^3$ is N;
In the formula (1-K1-3), compounds wherein $A^1$ is N, $A^2$ is $NR^6$, and $A^3$ is $CR^{12}$;
In the formula (1-K1-3), compounds wherein $A^1$ is N, $A^2$ is O, and $A^3$ is N;
In the formula (1-K1-3), compounds wherein $A^1$ is N, $A^2$ is O, and $A^3$ is $CR^{12}$;
In the formula (1-K1-3), compounds wherein $A^1$ is N, $A^2$ is S, and $A^3$ is N;
In the formula (1-K1-3), compounds wherein $A^1$ is N, $A^2$ is S, and $A^3$ is $CR^{12}$;
In the formula (1-K1-3), compounds wherein $A^1$ is $CR^5$, $A^2$ is $NR^6$, and $A^3$ is N;
In the formula (1-K1-3), compounds wherein $A^1$ is $CR^5$, $A^2$ is $NR^6$, and $A^3$ is $CR^{12}$;
In the formula (1-K1-3), compounds wherein $A^1$ is $CR^5$, $A^2$ is O, and $A^3$ is N;
In the formula (1-K1-3), compounds wherein $A^1$ is $CR^5$, $A^2$ is O, and $A^3$ is $CR^{12}$;
In the formula (1-K1-3), compounds wherein $A^1$ is $CR^5$, $A^2$ is S, and $A^3$ is N;
In the formula (1-K1-3), compounds wherein $A^1$ is $CR^5$, $A^2$ is S, and $A^3$ is $CR^{12}$;

Compounds represented by formula (1-K1-4),

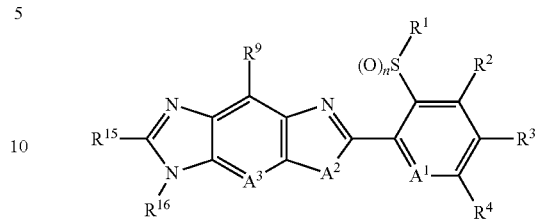

(1-K1-4)

wherein symbols represent the same meaning as described above, or N-oxides thereof;

In the formula (1-K1-4), compounds wherein $A^1$ is N;
In the formula (1-K1-4), compounds wherein $A^1$ is $CR^5$;
In the formula (1-K1-4), compounds wherein $A^2$ is $NR^6$;
In the formula (1-K1-4), compounds wherein $A^2$ is O;
In the formula (1-K1-4), compounds wherein $A^2$ is S;
In the formula (1-K1-4), compounds wherein $A^3$ is N;
In the formula (1-K1-4), compounds wherein $A^3$ is $CR^{12}$;
In the formula (1-K1-4), compounds wherein $A^1$ is N, and $A^2$ is $NR^6$;
In the formula (1-K1-4), compounds wherein $A^1$ is N, and $A^2$ is O;
In the formula (1-K1-4), compounds wherein $A^1$ is N, and $A^2$ is S;
In the formula (1-K1-4), compounds wherein $A^1$ is $CR^5$, and $A^2$ is $NR^6$;
In the formula (1-K1-4), compounds wherein $A^1$ is $CR^5$, and $A^2$ is O;
In the formula (1-K1-4), compounds wherein $A^1$ is $CR^5$, and $A^2$ is S;
In the formula (1-K1-4), compounds wherein $A^1$ is N, $A^2$ is $NR^6$, and $A^3$ is N;
In the formula (1-K1-4), compounds wherein $A^1$ is N, $A^2$ is $NR^6$, and $A^3$ is $CR^{12}$;
In the formula (1-K1-4), compounds wherein $A^1$ is N, $A^2$ is O, and $A^3$ is N;
In the formula (1-K1-4), compounds wherein $A^1$ is N, $A^2$ is O, and $A^3$ is $CR^{12}$;
In the formula (1-K1-4), compounds wherein $A^1$ is N, $A^2$ is S, and $A^3$ is N;
In the formula (1-K1-4), compounds wherein $A^1$ is N, $A^2$ is S, and $A^3$ is $CR^{12}$;
In the formula (1-K1-4), compounds wherein $A^1$ is $CR^5$, $A^2$ is $NR^6$, and $A^3$ is N;
In the formula (1-K1-4), compounds wherein $A^1$ is $CR^5$, $A^2$ is $NR^6$, and $A^3$ is $CR^{12}$;
In the formula (1-K1-4), compounds wherein $A^1$ is $CR^5$, $A^2$ is O, and $A^3$ is N;
In the formula (1-K1-4), compounds wherein $A^1$ is $CR^5$, $A^2$ is O, and $A^3$ is $CR^{12}$;
In the formula (1-K1-4), compounds wherein $A^1$ is $CR^5$, $A^2$ is S, and $A^3$ is N;
In the formula (1-K1-4), compounds wherein $A^1$ is $CR^5$, $A^2$ is S, and $A^3$ is $CR^{12}$;

Compounds represented by formula (1-K1-5),

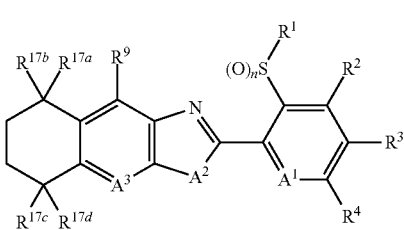

(1-K1-5)

wherein symbols represent the same meaning as described above, or N-oxides thereof;
In the formula (1-K1-5), compounds wherein $A^1$ is N;
In the formula (1-K1-5), compounds wherein $A^1$ is $CR^5$;
In the formula (1-K1-5), compounds wherein $A^2$ is $NR^6$;
In the formula (1-K1-5), compounds wherein $A^2$ is O;
In the formula (1-K1-5), compounds wherein $A^2$ is S;
In the formula (1-K1-5), compounds wherein $A^3$ is N;
In the formula (1-K1-5), compounds wherein $A^3$ is $CR^{12}$;
In the formula (1-K1-5), compounds wherein $A^1$ is N, and $A^2$ is $NR^6$;
In the formula (1-K1-5), compounds wherein $A^1$ is N, and $A^2$ is O;
In the formula (1-K1-5), compounds wherein $A^1$ is N, and $A^2$ is S;
In the formula (1-K1-5), compounds wherein $A^1$ is $CR^5$, and $A^2$ is $NR^6$;
In the formula (1-K1-5), compounds wherein $A^1$ is $CR^5$, and $A^2$ is O;
In the formula (1-K1-5), compounds wherein $A^1$ is $CR^5$, and $A^2$ is S;
In the formula (1-K1-5), compounds wherein $A^1$ is N, $A^2$ is $NR^6$, and $A^3$ is N;
In the formula (1-K1-5), compounds wherein $A^1$ is N, $A^2$ is $NR^6$, and $A^3$ is $CR^{12}$;
In the formula (1-K1-5), compounds wherein $A^1$ is N, $A^2$ is O, and $A^3$ is N;
In the formula (1-K1-5), compounds wherein $A^1$ is N, $A^2$ is O, and $A^3$ is $CR^{12}$;
In the formula (1-K1-5), compounds wherein $A^1$ is N, $A^2$ is S, and $A^3$ is N;
In the formula (1-K1-5), compounds wherein $A^1$ is N, $A^2$ is S, and $A^3$ is $CR^{12}$;
In the formula (1-K1-5), compounds wherein $A^1$ is $CR^5$, $A^2$ is $NR^6$, and $A^3$ is N;
In the formula (1-K1-5), compounds wherein $A^1$ is $CR^5$, $A^2$ is $NR^6$, and $A^3$ is $CR^{12}$;
In the formula (1-K1-5), compounds wherein $A^1$ is $CR^5$, $A^2$ is O, and $A^3$ is N;
In the formula (1-K1-5), compounds wherein $A^1$ is $CR^5$, $A^2$ is O, and $A^3$ is $CR^{12}$;
In the formula (1-K1-5), compounds wherein $A^1$ is $CR^5$, $A^2$ is S, and $A^3$ is N;
In the formula (1-K1-5), compounds wherein $A^1$ is $CR^5$, $A^2$ is S, and $A^3$ is $CR^{12}$;

Compounds represented by formula (1-K1-6),

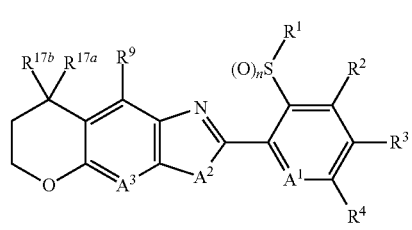

(1-K1-6)

wherein symbols represent the same meaning as described above, or N-oxides thereof;
In the formula (1-K1-6), compounds wherein $A^1$ is N;
In the formula (1-K1-6), compounds wherein $A^1$ is $CR^5$;
In the formula (1-K1-6), compounds wherein $A^2$ is $NR^6$;
In the formula (1-K1-6), compounds wherein $A^2$ is O;
In the formula (1-K1-6), compounds wherein $A^2$ is S;
In the formula (1-K1-6), compounds wherein $A^3$ is N;
In the formula (1-K1-6), compounds wherein $A^3$ is $CR^{12}$;
In the formula (1-K1-6), compounds wherein $A^1$ is N, and $A^2$ is $NR^6$;
In the formula (1-K1-6), compounds wherein $A^1$ is N, and $A^2$ is O;
In the formula (1-K1-6), compounds wherein $A^1$ is N, and $A^2$ is S;
In the formula (1-K1-6), compounds wherein $A^1$ is $CR^5$, and $A^2$ is $NR^6$;
In the formula (1-K1-6), compounds wherein $A^1$ is $CR^5$, and $A^2$ is O;
In the formula (1-K1-6), compounds wherein $A^1$ is $CR^5$, and $A^2$ is S;
In the formula (1-K1-6), compounds wherein $A^1$ is N, $A^2$ is $NR^6$, and $A^3$ is N;
In the formula (1-K1-6), compounds wherein $A^1$ is N, $A^2$ is $NR^6$, and $A^3$ is $CR^{12}$;
In the formula (1-K1-6), compounds wherein $A^1$ is N, $A^2$ is O, and $A^3$ is N;
In the formula (1-K1-6), compounds wherein $A^1$ is N, $A^2$ is O, and $A^3$ is $CR^{12}$;
In the formula (1-K1-6), compounds wherein $A^1$ is N, $A^2$ is S, and $A^3$ is N;
In the formula (1-K1-6), compounds wherein $A^1$ is N, $A^2$ is S, and $A^3$ is $CR^{12}$;
In the formula (1-K1-6), compounds wherein $A^1$ is $CR^5$, $A^2$ is $NR^6$, and $A^3$ is N;
In the formula (1-K1-6), compounds wherein $A^1$ is $CR^5$, $A^2$ is $NR^6$, and $A^3$ is $CR^{12}$;
In the formula (1-K1-6), compounds wherein $A^1$ is $CR^5$, $A^2$ is O, and $A^3$ is N;
In the formula (1-K1-6), compounds wherein $A^1$ is $CR^5$, $A^2$ is O, and $A^3$ is $CR^{12}$;
In the formula (1-K1-6), compounds wherein $A^1$ is $CR^5$, $A^2$ is S, and $A^3$ is N;
In the formula (1-K1-6), compounds wherein $A^1$ is $CR^5$, $A^2$ is S, and $A^3$ is $CR^{12}$;

Compounds represented by formula (1-K1-7),

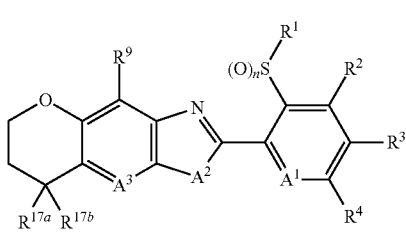

(1-K1-7)

wherein symbols represent the same meaning as described above, or N-oxides thereof;
In the formula (1-K1-7), compounds wherein $A^1$ is N;
In the formula (1-K1-7), compounds wherein $A^1$ is $CR^5$;
In the formula (1-K1-7), compounds wherein $A^2$ is $NR^6$;
In the formula (1-K1-7), compounds wherein $A^2$ is O;
In the formula (1-K1-7), compounds wherein $A^2$ is S;
In the formula (1-K1-7), compounds wherein $A^3$ is N;
In the formula (1-K1-7), compounds wherein $A^3$ is $CR^{12}$;
In the formula (1-K1-7), compounds wherein $A^1$ is N, and $A^2$ is $NR^6$;
In the formula (1-K1-7), compounds wherein $A^1$ is N, and $A^2$ is O;
In the formula (1-K1-7), compounds wherein $A^1$ is N, and $A^2$ is S;
In the formula (1-K1-7), compounds wherein $A^1$ is $CR^5$, and $A^2$ is $NR^6$;
In the formula (1-K1-7), compounds wherein $A^1$ is $CR^5$, and $A^2$ is O;
In the formula (1-K1-7), compounds wherein $A^1$ is $CR^5$, and $A^2$ is S;
In the formula (1-K1-7), compounds wherein $A^1$ is N, $A^2$ is $NR^6$, and $A^3$ is N;
In the formula (1-K1-7), compounds wherein $A^1$ is N, $A^2$ is $NR^6$, and $A^3$ is $CR^{12}$;
In the formula (1-K1-7), compounds wherein $A^1$ is N, $A^2$ is O, and $A^3$ is N;
In the formula (1-K1-7), compounds wherein $A^1$ is N, $A^2$ is O, and $A^3$ is $CR^{12}$;
In the formula (1-K1-7), compounds wherein $A^1$ is N, $A^2$ is S, and $A^3$ is N;
In the formula (1-K1-7), compounds wherein $A^1$ is N, $A^2$ is S, and $A^3$ is $CR^{12}$;
In the formula (1-K1-7), compounds wherein $A^1$ is $CR^5$, $A^2$ is $NR^6$, and $A^3$ is N;
In the formula (1-K1-7), compounds wherein $A^1$ is $CR^5$, $A^2$ is $NR^6$, and $A^3$ is $CR^{12}$;
In the formula (1-K1-7), compounds wherein $A^1$ is $CR^5$, $A^2$ is O, and $A^3$ is N;
In the formula (1-K1-7), compounds wherein $A^1$ is $CR^5$, $A^2$ is O, and $A^3$ is $CR^{12}$;
In the formula (1-K1-7), compounds wherein $A^1$ is $CR^5$, $A^2$ is S, and $A^3$ is N;
In the formula (1-K1-7), compounds wherein $A^1$ is $CR^5$, $A^2$ is S, and $A^3$ is $CR^{12}$;

Compounds represented by formula (1-K1-8),

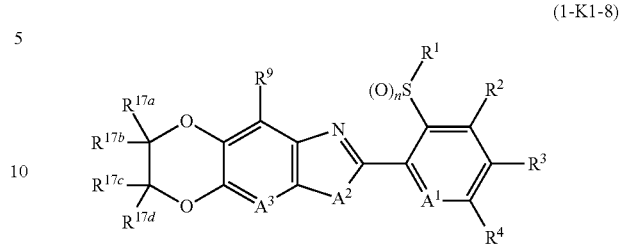

(1-K1-8)

wherein symbols represent the same meaning as described above, or N-oxides thereof;
In the formula (1-K1-8), compounds wherein $A^1$ is N;
In the formula (1-K1-8), compounds wherein $A^1$ is $CR^5$;
In the formula (1-K1-8), compounds wherein $A^2$ is $NR^6$;
In the formula (1-K1-8), compounds wherein $A^2$ is O;
In the formula (1-K1-8), compounds wherein $A^2$ is S;
In the formula (1-K1-8), compounds wherein $A^3$ is N;
In the formula (1-K1-8), compounds wherein $A^3$ is $CR^{12}$;
In the formula (1-K1-8), compounds wherein $A^1$ is N, and $A^2$ is $NR^6$;
In the formula (1-K1-8), compounds wherein $A^1$ is N, and $A^2$ is O;
In the formula (1-K1-8), compounds wherein $A^1$ is N, and $A^2$ is S;
In the formula (1-K1-8), compounds wherein $A^1$ is $CR^5$, and $A^2$ is $NR^6$;
In the formula (1-K1-8), compounds wherein $A^1$ is $CR^5$, and $A^2$ is O;
In the formula (1-K1-8), compounds wherein $A^1$ is $CR^5$, and $A^2$ is S;
In the formula (1-K1-8), compounds wherein $A^1$ is N, $A^2$ is $NR^6$, and $A^3$ is N;
In the formula (1-K1-8), compounds wherein $A^1$ is N, $A^2$ is $NR^6$, and $A^3$ is $CR^{12}$;
In the formula (1-K1-8), compounds wherein $A^1$ is N, $A^2$ is O, and $A^3$ is N;
In the formula (1-K1-8), compounds wherein $A^1$ is N, $A^2$ is O, and $A^3$ is $CR^{12}$;
In the formula (1-K1-8), compounds wherein $A^1$ is N, $A^2$ is S, and $A^3$ is N;
In the formula (1-K1-8), compounds wherein $A^1$ is N, $A^2$ is S, and $A^3$ is $CR^{12}$;
In the formula (1-K1-8), compounds wherein $A^1$ is $CR^5$, $A^2$ is $NR^6$, and $A^3$ is N;
In the formula (1-K1-8), compounds wherein $A^1$ is $CR^5$, $A^2$ is $NR^6$, and $A^3$ is $CR^{12}$;
In the formula (1-K1-8), compounds wherein $A^1$ is $CR^5$, $A^2$ is O, and $A^3$ is N;
In the formula (1-K1-8), compounds wherein $A^1$ is $CR^5$, $A^2$ is O, and $A^3$ is $CR^{12}$;
In the formula (1-K1-8), compounds wherein $A^1$ is $CR^5$, $A^2$ is S, and $A^3$ is N;
In the formula (1-K1-8), compounds wherein $A^1$ is $CR^5$, $A^2$ is S, and $A^3$ is $CR^{12}$;
In the formula (1-K1-8), compounds wherein
$A^3$ is CH,
$R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups, $R^2$, $R^4$ and $R^5$ are the same or different and are a C1 to C3 alkyl group optionally having one or more halogen atoms, a halogen atom or a hydrogen atom, $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom, $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom, $R^7$ and $R^8$ are the same or different and are a C1 to C6 alkyl group optionally having one or more halogen atoms or a hydrogen atom, $R^9$ is a hydrogen atom, and $R^{17a}$, $R^{17b}$, $R^{17c}$ and $R^{17d}$ are the same or different and are a fluorine atom, a chlorine atom or a hydrogen atom; In the formula (1-K1-8), compounds wherein $A^3$ is CH, $R^1$ is a C1 to C6 alkyl group optionally having one or more halogen atoms, $R^2$, $R^4$ and $R^5$ are the same or different and are a halogen atom or a hydrogen atom, $R^3$ is a C1 to C6 alkyl group optionally having one or more halogen atoms, $OR^7$, $S(O)_mR^7$, $C(O)R^7$, $CO_2R^7$, $C(O)NR^7R^8$, a halogen atom or a hydrogen atom, $R^6$ is a C1 to C6 alkyl group optionally having one or more halogen atoms or a hydrogen atom, $R^7$ and $R^8$ are the same or different and are a C1 to C6 alkyl group optionally having one or more halogen atoms or a hydrogen atom, $R^9$ is a hydrogen atom, and $R^{17a}$, $R^{17b}$, $R^{17c}$ and $R^{17d}$ are a fluorine atom;

Compounds represented by formula (1-K1-9), (1-K1-9)

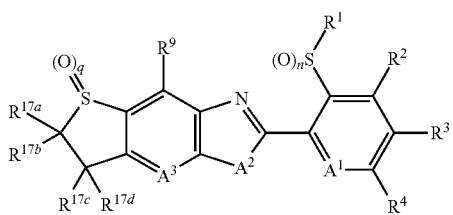

wherein symbols represent the same meaning as described above, or N-oxides thereof;

In the formula (1-K1-9), compounds wherein $A^1$ is N;
In the formula (1-K1-9), compounds wherein $A^1$ is $CR^5$;
In the formula (1-K1-9), compounds wherein $A^2$ is $NR^6$;
In the formula (1-K1-9), compounds wherein $A^2$ is O;
In the formula (1-K1-9), compounds wherein $A^2$ is S;
In the formula (1-K1-9), compounds wherein $A^3$ is N;
In the formula (1-K1-9), compounds wherein $A^3$ is $CR^{12}$;
In the formula (1-K1-9), compounds wherein $A^1$ is N, and $A^2$ is $NR^6$;
In the formula (1-K1-9), compounds wherein $A^1$ is N, and $A^2$ is O;
In the formula (1-K1-9), compounds wherein $A^1$ is N, and $A^2$ is S;
In the formula (1-K1-9), compounds wherein $A^1$ is $CR^5$, and $A^2$ is $NR^6$;
In the formula (1-K1-9), compounds wherein $A^1$ is $CR^5$, and $A^2$ is O;
In the formula (1-K1-9), compounds wherein $A^1$ is $CR^5$, and $A^2$ is S;
In the formula (1-K1-9), compounds wherein $A^1$ is N, $A^2$ is $NR^6$, and $A^3$ is N;
In the formula (1-K1-9), compounds wherein $A^1$ is N, $A^2$ is $NR^6$, and $A^3$ is $CR^{12}$;
In the formula (1-K1-9), compounds wherein $A^1$ is N, $A^2$ is O, and $A^3$ is N;
In the formula (1-K1-9), compounds wherein $A^1$ is N, $A^2$ is O, and $A^3$ is $CR^{12}$;
In the formula (1-K1-9), compounds wherein $A^1$ is N, $A^2$ is S, and $A^3$ is N;
In the formula (1-K1-9), compounds wherein $A^1$ is N, $A^2$ is S, and $A^3$ is $CR^{12}$;
In the formula (1-K1-9), compounds wherein $A^1$ is $CR^5$, $A^2$ is $NR^6$, and $A^3$ is N;
In the formula (1-K1-9), compounds wherein $A^1$ is $CR^5$, $A^2$ is $NR^6$, and $A^3$ is $CR^{12}$;
In the formula (1-K1-9), compounds wherein $A^1$ is $CR^5$, $A^2$ is O, and $A^3$ is N;
In the formula (1-K1-9), compounds wherein $A^1$ is $CR^5$, $A^2$ is O, and $A^3$ is $CR^{12}$;
In the formula (1-K1-9), compounds wherein $A^1$ is $CR^5$, $A^2$ is S, and $A^3$ is N;
In the formula (1-K1-9), compounds wherein $A^1$ is $CR^5$, $A^2$ is S, and $A^3$ is $CR^{12}$;
In the formula (1-K1-9), compounds wherein $A^3$ is CH, $R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups, $R^2$, $R^4$ and $R^5$ are the same or different and are a C1 to C3 alkyl group optionally having one or more halogen atoms, a halogen atom or a hydrogen atom, $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom, $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom, $R^7$ and $R^8$ are the same or different and are a C1 to C6 alkyl group optionally having one or more halogen atoms or a hydrogen atom, $R^9$ is a hydrogen atom, and $R^{17a}$, $R^{17b}$, $R^{17c}$ and $R^{17d}$ are the same or different and are a fluorine atom, a chlorine atom or a hydrogen atom;

In the formula (1-K1-9), compounds wherein $A^3$ is CH, $R^1$ is a C1 to C6 alkyl group optionally having one or more halogen atoms, $R^2$, $R^4$ and $R^5$ are the same or different and are a halogen atom or a hydrogen atom, $R^3$ is a C1 to C6 alkyl group optionally having one or more halogen atoms, $OR^7$, $S(O)_mR^7$, $C(O)R^7$, $CO_2R^7$, $C(O)NR^7R^8$, a halogen atom or a hydrogen atom, $R^6$ is a C1 to C6 alkyl group optionally having one or more halogen atoms or a hydrogen atom, $R^7$ and $R^8$ are the same or different and are a C1 to C6 alkyl group optionally having one or more halogen atoms or a hydrogen atom, $R^9$ is a hydrogen atom, and $R^{17a}$, $R^{17b}$, $R^{17c}$ and $R^{17d}$ are a fluorine atom;

Compounds represented by formula (1-K1-10),

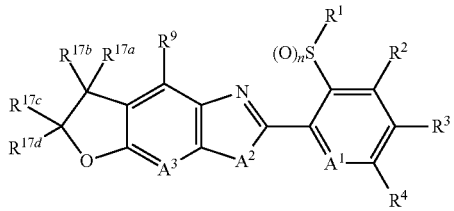

(1-K1-10)

wherein symbols represent the same meaning as described above, or N-oxides thereof;

In the formula (1-K1-10), compounds wherein $A^1$ is N;
In the formula (1-K1-10), compounds wherein $A^1$ is $CR^5$;
In the formula (1-K1-10), compounds wherein $A^2$ is $NR^6$;
In the formula (1-K1-10), compounds wherein $A^2$ is O;
In the formula (1-K1-10), compounds wherein $A^2$ is S;
In the formula (1-K1-10), compounds wherein $A^3$ is N;
In the formula (1-K1-10), compounds wherein $A^3$ is $CR^{12}$;
In the formula (1-K1-10), compounds wherein $A^1$ is N, and $A^2$ is $NR^6$;
In the formula (1-K1-10), compounds wherein $A^1$ is N, and $A^2$ is O;
In the formula (1-K1-10), compounds wherein $A^1$ is N, and $A^2$ is S;
In the formula (1-K1-10), compounds wherein $A^1$ is $CR^5$, and $A^2$ is $NR^6$;
In the formula (1-K1-10), compounds wherein $A^1$ is $CR^5$, and $A^2$ is O;
In the formula (1-K1-10), compounds wherein $A^1$ is $CR^5$, and $A^2$ is S;
In the formula (1-K1-10), compounds wherein $A^1$ is N, $A^2$ is $NR^6$, and $A^3$ is N;
In the formula (1-K1-10), compounds wherein $A^1$ is N, $A^2$ is $NR^6$, and $A^3$ is $CR^{12}$;
In the formula (1-K1-10), compounds wherein $A^1$ is N, $A^2$ is O, and $A^3$ is N;
In the formula (1-K1-10), compounds wherein $A^1$ is N, $A^2$ is O, and $A^3$ is $CR^{12}$;
In the formula (1-K1-10), compounds wherein $A^1$ is N, $A^2$ is S, and $A^3$ is N;
In the formula (1-K1-10), compounds wherein $A^1$ is N, $A^2$ is S, and $A^3$ is $CR^{12}$;
In the formula (1-K1-10), compounds wherein $A^1$ is $CR^5$, $A^2$ is $NR^6$, and $A^3$ is N;

In the formula (1-K1-10), compounds wherein $A^1$ is $CR^5$, $A^2$ is $NR^6$, and $A^3$ is $CR^{12}$;
In the formula (1-K1-10), compounds wherein $A^1$ is $CR^5$, $A^2$ is O, and $A^3$ is N;
In the formula (1-K1-10), compounds wherein $A^1$ is $CR^5$, $A^2$ is O, and $A^3$ is $CR^{12}$;
In the formula (1-K1-10), compounds wherein $A^1$ is $CR^5$, $A^2$ is S, and $A^3$ is N;
In the formula (1-K1-10), compounds wherein $A^1$ is $CR^5$, $A^2$ is S, and $A^3$ is $CR^{12}$;

In the formula (1-K1-10), compounds wherein $A^3$ is CH, $R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups, $R^2$, $R^4$ and $R^5$ are the same or different and are a C1 to C3 alkyl group optionally having one or more halogen atoms, a halogen atom or a hydrogen atom, $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom, $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom, $R^7$ and $R^8$ are the same or different and are a C1 to C6 alkyl group optionally having one or more halogen atoms or a hydrogen atom, $R^9$ is a hydrogen atom, and $R^{17a}$, $R^{17b}$, $R^{17c}$ and $R^{17d}$ are the same or different and are a fluorine atom, a chlorine atom or a hydrogen atom;

In the formula (1-K1-10), compounds wherein $A^3$ is CH, $R^1$ is a C1 to C6 alkyl group optionally having one or more halogen atoms, $R^2$, $R^4$ and $R^5$ are the same or different and are a halogen atom or a hydrogen atom, $R^3$ is a C1 to C6 alkyl group optionally having one or more halogen atoms, $OR^7$, $S(O)_mR^7$, $C(O)R^7$, $CO_2R^7$, $C(O)NR^7R^8$, a halogen atom or a hydrogen atom, $R^6$ is a C1 to C6 alkyl group optionally having one or more halogen atoms or a hydrogen atom, $R^7$ and $R^8$ are the same or different and are a C1 to C6 alkyl group optionally having one or more halogen atoms or a hydrogen atom, $R^9$ is a hydrogen atom, and $R^{17a}$, $R^{17b}$, $R^{17c}$ and $R^{17d}$ are a fluorine atom;

Compounds represented by formula (1-K1-11), (1-K1-11)

wherein symbols represent the same meaning as described above, or N-oxides thereof;
In the formula (1-K1-11), compounds wherein $A^1$ is N;
In the formula (1-K1-11), compounds wherein $A^1$ is $CR^5$;
In the formula (1-K1-11), compounds wherein $A^2$ is $NR^6$;
In the formula (1-K1-11), compounds wherein $A^2$ is O;
In the formula (1-K1-11), compounds wherein $A^2$ is S;
In the formula (1-K1-11), compounds wherein $A^3$ is N;
In the formula (1-K1-11), compounds wherein $A^3$ is $CR^{12}$;
In the formula (1-K1-11), compounds wherein $A^1$ is N, and $A^2$ is $NR^6$;
In the formula (1-K1-11), compounds wherein $A^1$ is N, and $A^2$ is O;
In the formula (1-K1-11), compounds wherein $A^1$ is N, and $A^2$ is S;
In the formula (1-K1-11), compounds wherein $A^1$ is $CR^5$, and $A^2$ is $NR^6$;
In the formula (1-K1-11), compounds wherein $A^1$ is $CR^5$, and $A^2$ is O;
In the formula (1-K1-11), compounds wherein $A^1$ is $CR^5$, and $A^2$ is S;
In the formula (1-K1-11), compounds wherein $A^1$ is N, $A^2$ is $NR^6$, and $A^3$ is N;
In the formula (1-K1-11), compounds wherein $A^1$ is N, $A^2$ is $NR^6$, and $A^3$ is $CR^{12}$;
In the formula (1-K1-11), compounds wherein $A^1$ is N, $A^2$ is O, and $A^3$ is N;
In the formula (1-K1-11), compounds wherein $A^1$ is N, $A^2$ is O, and $A^3$ is $CR^{12}$;
In the formula (1-K1-11), compounds wherein $A^1$ is N, $A^2$ is S, and $A^3$ is N;
In the formula (1-K1-11), compounds wherein $A^1$ is N, $A^2$ is S, and $A^3$ is $CR^{12}$;
In the formula (1-K1-11), compounds wherein $A^1$ is $CR^5$, $A^2$ is $NR^6$, and $A^3$ is N;
In the formula (1-K1-11), compounds wherein $A^1$ is $CR^5$, $A^2$ is $NR^6$, and $A^3$ is $CR^{12}$;
In the formula (1-K1-11), compounds wherein $A^1$ is $CR^5$, $A^2$ is O, and $A^3$ is N;
In the formula (1-K1-11), compounds wherein $A^1$ is $CR^5$, $A^2$ is O, and $A^3$ is $CR^{12}$;
In the formula (1-K1-11), compounds wherein $A^1$ is $CR^5$, $A^2$ is S, and $A^3$ is N;
In the formula (1-K1-11), compounds wherein $A^1$ is $CR^5$, $A^2$ is S, and $A^3$ is $CR^{12}$;
In the formula (1-K1-11), compounds wherein
 $A^3$ is CH,
 $R^2$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups,
 $R^2$, $R^4$ and $R^5$ are the same or different and are a C1 to C3 alkyl group optionally having one or more halogen atoms, a halogen atom or a hydrogen atom,
 $R^1$ is a C1 to C6 alkyl group optionally having one or more halogen atoms, a 5- or 6-membered heterocyclic group optionally having one or more atoms or groups selected from group δ, $OR^7$, $S(O)_m R^7$, $C(O)R^7$, $CO_2 R^7$, $C(O)NR^7 R^8$, a cyano group, a halogen atom or a hydrogen atom,
 $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom,
 $R^7$ and $R^8$ are the same or different and are a C1 to C6 alkyl group optionally having one or more halogen atoms or a hydrogen atom,
 $R^9$ is a hydrogen atom, and
 $R^{17a}$, $R^{17b}$, $R^{17c}$ and $R^{17d}$ are the same or different and are a fluorine atom, a chlorine atom or a hydrogen atom;
In the formula (1-K1-11), compounds wherein
 $A^3$ is CH,
 $R^1$ is a C1 to C6 alkyl group optionally having one or more halogen atoms,
 $R^2$, $R^4$ and $R^5$ are the same or different and are a halogen atom or a hydrogen atom,
 $R^3$ is a C1 to C6 alkyl group optionally having one or more halogen atoms, $OR^7$, $S(O)_m R^7$, $C(O)R^7$, $CO_2 R^7$, $C(O)NR^7 R^7$, a halogen atom or a hydrogen atom,
 $R^6$ is a C1 to C6 alkyl group optionally having one or more halogen atoms or a hydrogen atom,
 $R^7$ and $R^8$ are the same or different and are a C1 to C6 alkyl group optionally having one or more halogen atoms or a hydrogen atom,
 $R^9$ is a hydrogen atom, and
 $R^{17a}$, $R^{17b}$, $R^{17c}$ and $R^{17d}$ are a fluorine atom;
Compounds represented by formula (1-K1-12), (1-K1-12)

wherein symbols represent the same meaning as described above, or N-oxides thereof;
In the formula (1-K1-12), compounds wherein $A^1$ is N;
In the formula (1-K1-12), compounds wherein $A^1$ is $CR^5$;
In the formula (1-K1-12), compounds wherein $A^2$ is $NR^6$;
In the formula (1-K1-12), compounds wherein $A^2$ is O;
In the formula (1-K1-12), compounds wherein $A^2$ is S;
In the formula (1-K1-12), compounds wherein $A^3$ is N;
In the formula (1-K1-12), compounds wherein $A^3$ is $CR^{12}$;
In the formula (1-K1-12), compounds wherein $A^1$ is N, and $A^2$ is $NR^6$;

In the formula (1-K1-12), compounds wherein $A^1$ is N, and $A^2$ is O;
In the formula (1-K1-12), compounds wherein $A^1$ is N, and $A^2$ is S;
In the formula (1-K1-12), compounds wherein $A^1$ is $CR^5$, and $A^2$ is $NR^6$;
In the formula (1-K1-12), compounds wherein $A^1$ is $CR^5$, and $A^2$ is O;
In the formula (1-K1-12), compounds wherein $A^1$ is $CR^5$, and $A^2$ is S;
In the formula (1-K1-12), compounds wherein $A^1$ is N, $A^2$ is $NR^6$, and $A^3$ is N;
In the formula (1-K1-12), compounds wherein $A^1$ is N, $A^2$ is $NR^6$, and $A^3$ is $CR^{12}$;
In the formula (1-K1-12), compounds wherein $A^1$ is N, $A^2$ is O, and $A^3$ is N;
In the formula (1-K1-12), compounds wherein $A^1$ is N, $A^2$ is O, and $A^3$ is $CR^{12}$;
In the formula (1-K1-12), compounds wherein $A^1$ is N, $A^2$ is S, and $A^3$ is N;
In the formula (1-K1-12), compounds wherein $A^1$ is N, $A^2$ is S, and $A^3$ is $CR^{12}$;
In the formula (1-K1-12), compounds wherein $A^1$ is $CR^5$, $A^2$ is $NR^6$, and $A^3$ is N;
In the formula (1-K1-12), compounds wherein $A^1$ is $CR^5$, $A^2$ is $NR^6$, and $A^3$ is $CR^{12}$;
In the formula (1-K1-12), compounds wherein $A^1$ is $CR^5$, $A^2$ is O, and $A^3$ is N;
In the formula (1-K1-12), compounds wherein $A^1$ is $CR^5$, $A^2$ is O, and $A^3$ is $CR^{12}$;
In the formula (1-K1-12), compounds wherein $A^1$ is $CR^5$, $A^2$ is S, and $A^3$ is N;
In the formula (1-K1-12), compounds wherein $A^1$ is $CR^5$, $A^2$ is S, and $A^3$ is $CR^{12}$;
In the formula (1-K1-12), compounds wherein
$A^3$ is CH,
$R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups,
$R^2$, $R^4$ and $R^5$ are the same or different and are a C1 to C3 alkyl group optionally having one or more halogen atoms, a halogen atom or a hydrogen atom,
$R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom,
$R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom,
$R^7$ and $R^8$ are the same or different and are a C1 to C6 alkyl group optionally having one or more halogen atoms or a hydrogen atom,
$R^9$ is a hydrogen atom, and
$R^{17a}$, $R^{17b}$, $R^{17c}$ and $R^{17d}$ are the same or different and are a fluorine atom, a chlorine atom or a hydrogen atom;
In the formula (1-K1-12), compounds wherein
$A^3$ is CH,
$R^1$ is a C1 to C6 alkyl group optionally having one or more halogen atoms,
$R^2$, $R^4$ and $R^5$ are the same or different and are a halogen atom or a hydrogen atom,
$R^3$ is a C1 to C6 alkyl group optionally having one or more halogen atoms, $OR^7$, $S(O)_mR^7$, $C(O)R^7$, $CO_2R^7$, $C(O)NR^7R^8$, a halogen atom or a hydrogen atom,
$R^6$ is a C1 to C6 alkyl group optionally having one or more halogen atoms or a hydrogen atom,
$R^7$ and $R^8$ are the same or different and are a C1 to C6 alkyl group optionally having one or more halogen atoms or a hydrogen atom,
$R^9$ is a hydrogen atom, and
$R^{17a}$, $R^{17b}$, $R^{17c}$ and $R^{17d}$ are a fluorine atom;
In the formula (1-K1-12), compounds wherein
$A^1$ is N or CH,
$A^2$ is $N(CH_3)$ or O,
$A^3$ is CH,
$R^1$ is a C1 to C6 alkyl group optionally having one or more halogen atoms,
$R^2$, $R^3$, $R^4$, $R^5$ and $R^9$ are a hydrogen atom, and
$R^{17a}$, $R^{17b}$, $R^{17c}$ and $R^{17d}$ are a fluorine atom;
In the formula (1-K1-12), compounds wherein
$A^1$ is N or CH,
$A^2$ is $N(CH_3)$ or O,
$A^3$ is CH,
$R^1$ is an ethyl group,
$R^2$, $R^3$, $R^4$, $R^5$ and $R^9$ are a hydrogen atom, and
$R^{17a}$, $R^{17b}$, $R^{17c}$ and $R^{17d}$ are a fluorine atom;
In the formula (1-K1-12), compounds wherein
$A^1$ is N,
$A^2$ is $N(CH_3)$,
$A^3$ is CH,
$R^1$ is an ethyl group,
$R^2$, $R^3$, $R^4$, $R^5$ and $R^9$ are a hydrogen atom, and
$R^{17a}$, $R^{17b}$, $R^{17c}$ and $R^{17d}$ are a fluorine atom;
In the formula (1-K1-12), compounds wherein
$A^1$ is CH,
$A^2$ is $N(CH_3)$,
$A^3$ is CH,
$R^1$ is an ethyl group,
$R^2$, $R^3$, $R^4$, $R^5$ and $R^9$ are a hydrogen atom, and
$R^{17a}$, $R^{17b}$, $R^{17c}$ and $R^{17d}$ are a fluorine atom;
In the formula (1-K1-12), compounds wherein
$A^1$ is N,
$A^2$ is O,
$A^3$ is CH,
$R^1$ is an ethyl group,
$R^2$, $R^3$, $R^4$, $R^5$ and $R^9$ are a hydrogen atom, and
$R^{17a}$, $R^{17b}$, $R^{17c}$ and $R^{17d}$ are a fluorine atom;
In the formula (1-K1-12), compounds wherein
$A^1$ is CH,
$A^2$ is O,
$A^3$ is CH,
$R^4$ is an ethyl group,
$R^2$, $R^3$, $R^4$, $R^5$ and $R^9$ are a hydrogen atom, and
$R^{17a}$, $R^{17b}$, $R^{17c}$ and $R^{17d}$ are a fluorine atom;

Compounds represented by formula (1-K1-13),

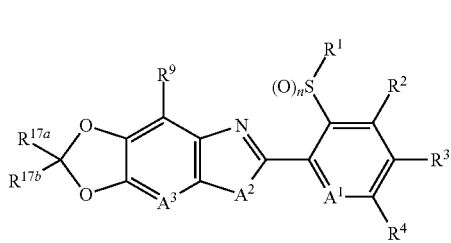
(1-K1-13)

wherein symbols represent the same meaning as described above, or N-oxides thereof;
In the formula (1-K1-13), compounds wherein $A^1$ is N;
In the formula (1-K1-13), compounds wherein $A^1$ is $CR^5$;
In the formula (1-K1-13), compounds wherein $A^2$ is $NR^6$;
In the formula (1-K1-13), compounds wherein $A^2$ is O;
In the formula (1-K1-13), compounds wherein $A^2$ is S;
In the formula (1-K1-13), compounds wherein $A^3$ is N;
In the formula (1-K1-13), compounds wherein $A^3$ is $CR^{12}$;
In the formula (1-K1-13), compounds wherein $A^1$ is N, and $A^2$ is $NR^6$;
In the formula (1-K1-13), compounds wherein $A^1$ is N, and $A^2$ is O;
In the formula (1-K1-13), compounds wherein $A^1$ is N, and $A^2$ is S;
In the formula (1-K1-13), compounds wherein $A^1$ is $CR^5$, and $A^2$ is $NR^6$;
In the formula (1-K1-13), compounds wherein $A^1$ is $CR^5$, and $A^2$ is O;
In the formula (1-K1-13), compounds wherein $A^1$ is $CR^5$, and $A^2$ is S;
In the formula (1-K1-13), compounds wherein $A^1$ is N, $A^2$ is $NR^6$, and $A^3$ is N;
In the formula (1-K1-13), compounds wherein $A^1$ is N, $A^2$ is $NR^6$, and $A^3$ is $CR^{12}$;
In the formula (1-K1-13), compounds wherein $A^1$ is N, $A^2$ is O, and $A^3$ is N;
In the formula (1-K1-13), compounds wherein $A^1$ is N, $A^2$ is O, and $A^3$ is $CR^{12}$;
In the formula (1-K1-13), compounds wherein $A^1$ is N, $A^2$ is S, and $A^3$ is N;
In the formula (1-K1-13), compounds wherein $A^1$ is N, $A^2$ is S, and $A^3$ is $CR^{12}$;
In the formula (1-K1-13), compounds wherein $A^1$ is $CR^5$, $A^2$ is $NR^6$, and $A^3$ is N;
In the formula (1-K1-13), compounds wherein $A^1$ is $CR^5$, $A^2$ is $NR^6$, and $A^3$ is $CR^{12}$;
In the formula (1-K1-13), compounds wherein $A^1$ is $CR^5$, $A^2$ is O, and $A^3$ is N;
In the formula (1-K1-13), compounds wherein $A^1$ is $CR^5$, $A^2$ is O, and $A^3$ is $CR^{12}$;
In the formula (1-K1-13), compounds wherein $A^1$ is $CR^5$, $A^2$ is S, and $A^3$ is N;
In the formula (1-K1-13), compounds wherein $A^1$ is $CR^5$, $A^2$ is S, and $A^3$ is $CR^{12}$;
In the formula (1-K1-13), compounds wherein
  $A^3$ is CH,
  $R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups,
  $R^2$, $R^4$ and $R^5$ are the same or different and are a C1 to C3 alkyl group optionally having one or more halogen atoms, a halogen atom or a hydrogen atom,
  $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom,
  $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom,
  $R^7$ and $R^8$ are the same or different and are a C1 to C6 alkyl group optionally having one or more halogen atoms or a hydrogen atom,
  $R^9$ is a hydrogen atom, and
  $R^{17a}$ and $R^{17b}$ are the same or different and are a fluorine atom, a chlorine atom or a hydrogen atom;
In the formula (1-K1-13), compounds wherein
  $A^3$ is CH,
  $R^1$ is a C1 to C6 alkyl group optionally having one or more halogen atoms,
  $R^2$, $R^4$ and $R^5$ are the same or different and are a halogen atom or a hydrogen atom,
  $R^3$ is a C1 to C6 alkyl group optionally having one or more halogen atoms, $OR^7$, $S(O)_mR^7$, $C(O)R^7$, $CO_2R^7$, $C(O)NR^7R^8$, a halogen atom or a hydrogen atom,
  $R^6$ is a C1 to C6 alkyl group optionally having one or more halogen atoms or a hydrogen atom,
  $R^7$ and $R^8$ are the same or different and are a C1 to C6 alkyl group optionally having one or more halogen atoms or a hydrogen atom,
  $R^9$ is a hydrogen atom, and
  $R^{17a}$ and $R^{17b}$ are a fluorine atom;
In the formula (1-K1-13), compounds wherein
  $A^1$ is N or CH,
  $A^2$ is $N(CH_3)$ or O,
  $A^3$ is CH,
  $R^1$ is a C1 to C6 alkyl group optionally having one or more halogen atoms,
  $R^2$, $R^3$, $R^4$, $R^5$ and $R^9$ are a hydrogen atom, and
  $R^{17a}$ and $R^{17b}$ are a fluorine atom;
In the formula (1-K1-13), compounds wherein
  $A^1$ is N or CH,
  $A^2$ is $N(CH_3)$ or O,
  $A^3$ is CH,
  $R^2$ is an ethyl group,
  $R^2$, $R^3$, $R^4$, $R^5$ and $R^9$ are a hydrogen atom, and
  $R^{17a}$ and $R^{17b}$ are a fluorine atom;
In the formula (1-K1-13), compounds wherein
  $A^1$ is N,
  $A^2$ is $N(CH_3)$,
  $A^3$ is CH,
  $R^1$ is an ethyl group,
  $R^2$, $R^3$, $R^4$, $R^5$ and $R^9$ are a hydrogen atom, and
  $R^{17a}$ and $R^{17b}$ are a fluorine atom;
In the formula (1-K1-13), compounds wherein
  $A^1$ is CH,
  $A^2$ is $N(CH_3)$, $A^3$ is CH,
$R^1$ is an ethyl group,
$R^2$, $R^3$, $R^4$, $R^5$ and $R^9$ are a hydrogen atom, and
$R^{17a}$ and $R^{17b}$ are a fluorine atom;
In the formula (1-K1-13), compounds wherein
$A^1$ is N,
$A^2$ is O,
$A^3$ is CH,
$R^1$ is an ethyl group,
$R^2$, $R^3$, $R^4$, $R^5$ and $R^9$ are a hydrogen atom, and
$R^{17a}$ and $R^{17b}$ are a fluorine atom;
In the formula (1-K1-13), compounds wherein
$A^1$ is CH,
$A^2$ is O,
$A^3$ is CH,
$R^1$ is an ethyl group,
$R^2$, $R^3$, $R^4$, $R^5$ and $R^9$ are a hydrogen atom, and
$R^{17a}$ and $R^{17b}$ are a fluorine atom;
Compounds represented by formula (1-K1-14), (1-K1-14)

wherein symbols represent the same meaning as described above, or N-oxides thereof;
In the formula (1-K1-14), compounds wherein $A^1$ is N;
In the formula (1-K1-14), compounds wherein $A^1$ is $CR^5$;
In the formula (1-K1-14), compounds wherein $A^2$ is $NR^6$;
In the formula (1-K1-14), compounds wherein $A^2$ is O;
In the formula (1-K1-14), compounds wherein $A^2$ is S;
In the formula (1-K1-14), compounds wherein $A^3$ is N;
In the formula (1-K1-14), compounds wherein $A^3$ is $CR^{12}$;
In the formula (1-K1-14), compounds wherein $A^1$ is N, and $A^2$ is $NR^6$;
In the formula (1-K1-14), compounds wherein $A^1$ is N, and $A^2$ is O;
In the formula (1-K1-14), compounds wherein $A^1$ is N, and $A^2$ is S;
In the formula (1-K1-14), compounds wherein $A^1$ is $CR^5$, and $A^2$ is $NR^6$;
In the formula (1-K1-14), compounds wherein $A^1$ is $CR^5$, and $A^2$ is O;
In the formula (1-K1-14), compounds wherein $A^1$ is $CR^5$, and $A^2$ is S;
In the formula (1-K1-14), compounds wherein $A^1$ is N, $A^2$ is $NR^6$, and $A^3$ is N;
In the formula (1-K1-14), compounds wherein $A^1$ is N, $A^2$ is $NR^6$, and $A^3$ is $CR^{12}$;
In the formula (1-K1-14), compounds wherein $A^1$ is N, $A^2$ is O, and $A^3$ is N;
In the formula (1-K1-14), compounds wherein $A^1$ is N, $A^2$ is O, and $A^3$ is $CR^{12}$;
In the formula (1-K1-14), compounds wherein $A^1$ is N, $A^2$ is S, and $A^3$ is N;
In the formula (1-K1-14), compounds wherein $A^1$ is N, $A^2$ is S, and $A^3$ is $CR^{12}$;
In the formula (1-K1-14), compounds wherein $A^1$ is $CR^5$, $A^2$ is $NR^6$, and $A^3$ is N;
In the formula (1-K1-14), compounds wherein $A^1$ is $CR^5$, $A^2$ is $NR^6$, and $A^3$ is $CR^{12}$;
In the formula (1-K1-14), compounds wherein $A^1$ is $CR^5$, $A^2$ is O, and $A^3$ is N;
In the formula (1-K1-14), compounds wherein $A^1$ is $CR^5$, $A^2$ is O, and $A^3$ is $CR^{12}$;
In the formula (1-K1-14), compounds wherein $A^1$ is $CR^5$, $A^2$ is S, and $A^3$ is N;
In the formula (1-K1-14), compounds wherein $A^1$ is $CR^5$, $A^2$ is S, and $A^3$ is $CR^{12}$;
Compounds represented by formula (1-K1-15), (1-K1-15)

wherein symbols represent the same meaning as described above, or N-oxides thereof;
In the formula (1-K1-15), compounds wherein $A^1$ is N;
In the formula (1-K1-15), compounds wherein $A^1$ is $CR^5$;
In the formula (1-K1-15), compounds wherein $A^2$ is $NR^6$;
In the formula (1-K1-15), compounds wherein $A^2$ is O;
In the formula (1-K1-15), compounds wherein $A^2$ is S;
In the formula (1-K1-15), compounds wherein $A^3$ is N;
In the formula (1-K1-15), compounds wherein $A^3$ is $CR^{12}$;
In the formula (1-K1-15), compounds wherein $A^1$ is N, and $A^2$ is $NR^6$;
In the formula (1-K1-15), compounds wherein $A^1$ is N, and $A^2$ is O;
In the formula (1-K1-15), compounds wherein $A^1$ is N, and $A^2$ is S;
In the formula (1-K1-15), compounds wherein $A^1$ is $CR^5$, and $A^2$ is $NR^6$;
In the formula (1-K1-15), compounds wherein $A^1$ is $CR^5$, and $A^2$ is O;
In the formula (1-K1-15), compounds wherein $A^1$ is $CR^5$, and $A^2$ is S;
In the formula (1-K1-15), compounds wherein $A^1$ is N, $A^2$ is $NR^6$, and $A^3$ is N;
In the formula (1-K1-15), compounds wherein $A^1$ is N, $A^2$ is $NR^6$, and $A^3$ is $CR^{12}$;
In the formula (1-K1-15), compounds wherein $A^1$ is N, $A^2$ is O, and $A^3$ is N;
In the formula (1-K1-15), compounds wherein $A^1$ is N, $A^2$ is O, and $A^3$ is $CR^{12}$;
In the formula (1-K1-15), compounds wherein $A^1$ is N, $A^2$ is S, and $A^3$ is N;
In the formula (1-K1-15), compounds wherein $A^1$ is N, $A^2$ is S, and $A^3$ is $CR^{12}$;
In the formula (1-K1-15), compounds wherein $A^1$ is $CR^5$, $A^2$ is $NR^6$, and $A^3$ is N;
In the formula (1-K1-15), compounds wherein $A^1$ is $CR^5$, $A^2$ is $NR^6$, and $A^3$ is $CR^{12}$;
In the formula (1-K1-15), compounds wherein $A^1$ is $CR^5$, $A^2$ is O, and $A^3$ is N;
In the formula (1-K1-15), compounds wherein $A^1$ is $CR^5$, $A^2$ is O, and $A^3$ is $CR^{12}$;
In the formula (1-K1-15), compounds wherein $A^1$ is $CR^5$, $A^2$ is S, and $A^3$ is N;

In the formula (1-K1-15), compounds wherein $A^1$ is $CR^5$, $A^2$ is S, and $A^3$ is $CR^{12}$;

Compounds represented by formula (1-K1-16),

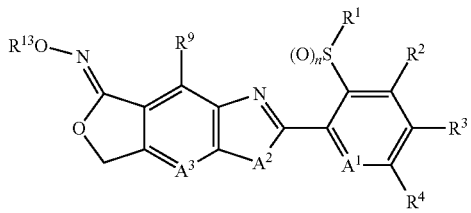

(1-K1-16)

wherein symbols represent the same meaning as described above, or N-oxides thereof;
In the formula (1-K1-16), compounds wherein $A^1$ is N;
In the formula (1-K1-16), compounds wherein $A^1$ is $CR^5$;
In the formula (1-K1-16), compounds wherein $A^2$ is $NR^6$;
In the formula (1-K1-16), compounds wherein $A^2$ is O;
In the formula (1-K1-16), compounds wherein $A^2$ is S;
In the formula (1-K1-16), compounds wherein $A^3$ is N;
In the formula (1-K1-16), compounds wherein $A^3$ is $CR^{12}$;
In the formula (1-K1-16), compounds wherein $A^1$ is N, and $A^2$ is $NR^6$;
In the formula (1-K1-16), compounds wherein $A^1$ is N, and $A^2$ is O;
In the formula (1-K1-16), compounds wherein $A^1$ is N, and $A^2$ is S;
In the formula (1-K1-16), compounds wherein $A^1$ is $CR^5$, and $A^2$ is $NR^6$;
In the formula (1-K1-16), compounds wherein $A^1$ is $CR^5$, and $A^2$ is O;
In the formula (1-K1-16), compounds wherein $A^1$ is $CR^5$, and $A^2$ is S;
In the formula (1-K1-16), compounds wherein $A^1$ is N, $A^2$ is $NR^6$, and $A^3$ is N;
In the formula (1-K1-16), compounds wherein $A^1$ is N, $A^2$ is $NR^6$, and $A^3$ is $CR^{12}$;
In the formula (1-K1-16), compounds wherein $A^1$ is N, $A^2$ is O, and $A^3$ is N;
In the formula (1-K1-16), compounds wherein $A^1$ is N, $A^2$ is O, and $A^3$ is $CR^{12}$;
In the formula (1-K1-16), compounds wherein $A^1$ is N, $A^2$ is S, and $A^3$ is N;
In the formula (1-K1-16), compounds wherein $A^1$ is N, $A^2$ is S, and $A^3$ is $CR^{12}$;
In the formula (1-K1-16), compounds wherein $A^1$ is $CR^5$, $A^2$ is $NR^6$, and $A^3$ is N;
In the formula (1-K1-16), compounds wherein $A^1$ is $CR^5$, $A^2$ is $NR^6$, and $A^3$ is $CR^{12}$;
In the formula (1-K1-16), compounds wherein $A^1$ is $CR^5$, $A^2$ is O, and $A^3$ is N;
In the formula (1-K1-16), compounds wherein $A^1$ is $CR^5$, $A^2$ is O, and $A^3$ is $CR^{12}$;
In the formula (1-K1-16), compounds wherein $A^1$ is $CR^5$, $A^2$ is S, and $A^3$ is N;
In the formula (1-K1-16), compounds wherein $A^1$ is $CR^5$, $A^2$ is S, and $A^3$ is $CR^{12}$;
Compounds represented by the formula (1-K1-5), the formula (1-K1-6), the formula (1-K1-7), the formula (1-K1-8), the formula (1-K1-9), the formula (1-K1-10), the formula (1-K1-11), the formula (1-K1-12) or the formula (1-K1-13);
Compounds represented by the formula (1-K1-8), the formula (1-K1-12) or the formula (1-K1-13);

Compounds represented by formula (1-K2),

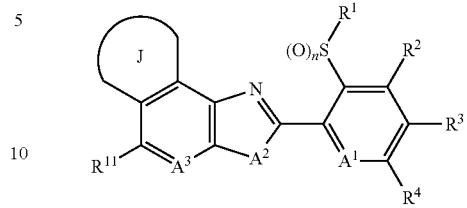

(1-K2)

wherein symbols represent the same meaning as described above, or N-oxides thereof;
In the formula (1-K2), compounds wherein $A^1$ is N;
In the formula (1-K2), compounds wherein $A^1$ is $CR^5$;
In the formula (1-K2), compounds wherein $A^2$ is $NR^6$;
In the formula (1-K2), compounds wherein $A^2$ is O;
In the formula (1-K2), compounds wherein $A^2$ is S;
In the formula (1-K2), compounds wherein $A^3$ is N;
In the formula (1-K2), compounds wherein $A^3$ is $CR^{12}$;
In the formula (1-K2), compounds wherein $A^1$ is N, and $A^2$ is $NR^6$;
In the formula (1-K2), compounds wherein $A^1$ is N, and $A^2$ is O;
In the formula (1-K2), compounds wherein $A^1$ is N, and $A^2$ is S;
In the formula (1-K2), compounds wherein $A^1$ is $CR^5$, and $A^2$ is $NR^6$;
In the formula (1-K2), compounds wherein $A^1$ is $CR^5$, and $A^2$ is O;
In the formula (1-K2), compounds wherein $A^1$ is $CR^5$, and $A^2$ is S;
In the formula (1-K2), compounds wherein $A^1$ is N, $A^2$ is $NR^6$, and $A^3$ is N;
In the formula (1-K2), compounds wherein $A^1$ is N, $A^2$ is $NR^6$, and $A^3$ is $CR^{12}$;
In the formula (1-K2), compounds wherein $A^1$ is N, $A^2$ is O, and $A^3$ is N;
In the formula (1-K2), compounds wherein $A^1$ is N, $A^2$ is O, and $A^3$ is $CR^{12}$;
In the formula (1-K2), compounds wherein $A^1$ is N, $A^2$ is S, and $A^3$ is N;
In the formula (1-K2), compounds wherein $A^1$ is N, $A^2$ is S, and $A^3$ is $CR^{12}$;
In the formula (1-K2), compounds wherein $A^1$ is $CR^5$, $A^2$ is $NR^6$, and $A^3$ is N;
In the formula (1-K2), compounds wherein $A^1$ is $CR^5$, $A^2$ is $NR^6$, and $A^3$ is $CR^{12}$;
In the formula (1-K2), compounds wherein $A^1$ is $CR^5$, $A^2$ is O, and $A^3$ is N;
In the formula (1-K2), compounds wherein $A^1$ is $CR^5$, $A^2$ is O, and $A^3$ is $CR^{12}$;
In the formula (1-K2), compounds wherein $A^1$ is $CR^5$, $A^2$ is S, and $A^3$ is N;
In the formula (1-K2), compounds wherein $A^1$ is $CR^5$, $A^2$ is S, and $A^3$ is $CR^{12}$;

Compounds represented by formula (1-K2-1),

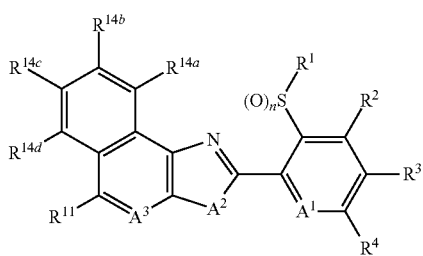

(1-K2-1)

wherein symbols represent the same meaning as described above, or N-oxides thereof;

In the formula (1-K2-1), compounds wherein $A^1$ is N;
In the formula (1-K2-1), compounds wherein $A^1$ is $CR^5$;
In the formula (1-K2-1), compounds wherein $A^2$ is $NR^6$;
In the formula (1-K2-1), compounds wherein $A^2$ is O;
In the formula (1-K2-1), compounds wherein $A^2$ is S;
In the formula (1-K2-1), compounds wherein $A^3$ is N;
In the formula (1-K2-1), compounds wherein $A^3$ is $CR^{12}$;
In the formula (1-K2-1), compounds wherein $A^1$ is N, and $A^2$ is $NR^6$;
In the formula (1-K2-1), compounds wherein $A^1$ is N, and $A^2$ is O;
In the formula (1-K2-1), compounds wherein $A^1$ is N, and $A^2$ is S;
In the formula (1-K2-1), compounds wherein $A^1$ is $CR^5$, and $A^2$ is $NR^6$;
In the formula (1-K2-1), compounds wherein $A^1$ is $CR^5$, and $A^2$ is O;
In the formula (1-K2-1), compounds wherein $A^1$ is $CR^5$, and $A^2$ is S;
In the formula (1-K2-1), compounds wherein $A^1$ is N, $A^2$ is $NR^6$, and $A^3$ is N;
In the formula (1-K2-1), compounds wherein $A^1$ is N, $A^2$ is $NR^6$, and $A^3$ is $CR^{12}$;
In the formula (1-K2-1), compounds wherein $A^1$ is N, $A^2$ is O, and $A^3$ is N;
In the formula (1-K2-1), compounds wherein $A^1$ is N, $A^2$ is O, and $A^3$ is $CR^{12}$;
In the formula (1-K2-1), compounds wherein $A^1$ is N, $A^2$ is S, and $A^3$ is N;
In the formula (1-K2-1), compounds wherein $A^1$ is N, $A^2$ is S, and $A^3$ is $CR^{12}$;
In the formula (1-K2-1), compounds wherein $A^1$ is $CR^5$, $A^2$ is $NR^6$, and $A^3$ is N;
In the formula (1-K2-1), compounds wherein $A^1$ is $CR^5$, $A^2$ is $NR^6$, and $A^3$ is $CR^{12}$;
In the formula (1-K2-1), compounds wherein $A^1$ is $CR^5$, $A^2$ is O, and $A^3$ is N;
In the formula (1-K2-1), compounds wherein $A^1$ is $CR^5$, $A^2$ is O, and $A^3$ is $CR^{12}$;
In the formula (1-K2-1), compounds wherein $A^1$ is $CR^5$, $A^2$ is S, and $A^3$ is N;
In the formula (1-K2-1), compounds wherein $A^1$ is $CR^5$, $A^2$ is S, and $A^3$ is $CR^{12}$;

Compounds represented by formula (1-K2-2),

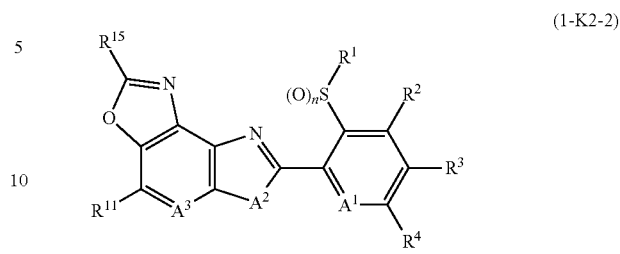

(1-K2-2)

wherein symbols represent the same meaning as described above, or N-oxides thereof;

In the formula (1-K2-2), compounds wherein $A^1$ is N;
In the formula (1-K2-2), compounds wherein $A^1$ is $CR^5$;
In the formula (1-K2-2), compounds wherein $A^2$ is $NR^6$;
In the formula (1-K2-2), compounds wherein $A^2$ is O;
In the formula (1-K2-2), compounds wherein $A^2$ is S;
In the formula (1-K2-2), compounds wherein $A^3$ is N;
In the formula (1-K2-2), compounds wherein $A^3$ is $CR^{12}$;
In the formula (1-K2-2), compounds wherein $A^1$ is N, and $A^2$ is $NR^6$;
In the formula (1-K2-2), compounds wherein $A^1$ is N, and $A^2$ is O;
In the formula (1-K2-2), compounds wherein $A^1$ is N, and $A^2$ is S;
In the formula (1-K2-2), compounds wherein $A^1$ is $CR^5$, and $A^2$ is $NR^6$;
In the formula (1-K2-2), compounds wherein $A^1$ is $CR^5$, and $A^2$ is O;
In the formula (1-K2-2), compounds wherein $A^1$ is $CR^5$, and $A^2$ is S;
In the formula (1-K2-2), compounds wherein $A^1$ is N, $A^2$ is $NR^6$, and $A^3$ is N;
In the formula (1-K2-2), compounds wherein $A^1$ is N, $A^2$ is $NR^6$, and $A^3$ is $CR^{12}$;
In the formula (1-K2-2), compounds wherein $A^1$ is N, $A^2$ is O, and $A^3$ is N;
In the formula (1-K2-2), compounds wherein $A^1$ is N, $A^2$ is O, and $A^3$ is $CR^{12}$;
In the formula (1-K2-2), compounds wherein $A^1$ is N, $A^2$ is S, and $A^3$ is N;
In the formula (1-K2-2), compounds wherein $A^1$ is N, $A^2$ is S, and $A^3$ is $CR^{12}$;
In the formula (1-K2-2), compounds wherein $A^1$ is $CR^5$, $A^2$ is $NR^6$, and $A^3$ is N;
In the formula (1-K2-2), compounds wherein $A^1$ is $CR^5$, $A^2$ is $NR^6$, and $A^3$ is $CR^{12}$;
In the formula (1-K2-2), compounds wherein $A^1$ is $CR^5$, $A^2$ is O, and $A^3$ is N;
In the formula (1-K2-2), compounds wherein $A^1$ is $CR^5$, $A^2$ is O, and $A^3$ is $CR^{12}$;
In the formula (1-K2-2), compounds wherein $A^1$ is $CR^5$, $A^2$ is S, and $A^3$ is N;
In the formula (1-K2-2), compounds wherein $A^1$ is $CR^5$, $A^2$ is S, and $A^3$ is $CR^{12}$;

Compounds represented by formula (1-K2-3),

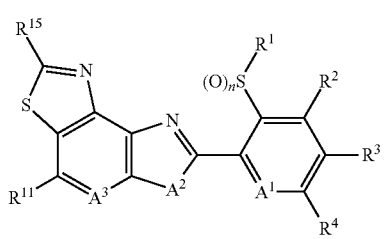

(1-K2-3)

wherein symbols represent the same meaning as described above, or N-oxides thereof;

In the formula (1-K2-3), compounds wherein $A^1$ is N;
In the formula (1-K2-3), compounds wherein $A^1$ is $CR^5$;
In the formula (1-K2-3), compounds wherein $A^2$ is $NR^6$;
In the formula (1-K2-3), compounds wherein $A^2$ is O;
In the formula (1-K2-3), compounds wherein $A^2$ is S;
In the formula (1-K2-3), compounds wherein $A^3$ is N;
In the formula (1-K2-3), compounds wherein $A^3$ is $CR^{12}$;
In the formula (1-K2-3), compounds wherein $A^1$ is N, and $A^2$ is $NR^6$;
In the formula (1-K2-3), compounds wherein $A^1$ is N, and $A^2$ is O;
In the formula (1-K2-3), compounds wherein $A^1$ is N, and $A^2$ is S;
In the formula (1-K2-3), compounds wherein $A^1$ is $CR^5$, and $A^2$ is $NR^6$;
In the formula (1-K2-3), compounds wherein $A^1$ is $CR^5$, and $A^2$ is O;
In the formula (1-K2-3), compounds wherein $A^1$ is $CR^5$, and $A^2$ is S;
In the formula (1-K2-3), compounds wherein $A^1$ is N, $A^2$ is $NR^6$, and $A^3$ is N;
In the formula (1-K2-3), compounds wherein $A^1$ is N, $A^2$ is $NR^6$, and $A^3$ is $CR^{12}$;
In the formula (1-K2-3), compounds wherein $A^1$ is N, $A^2$ is O, and $A^3$ is N;
In the formula (1-K2-3), compounds wherein $A^1$ is N, $A^2$ is O, and $A^3$ is $CR^{12}$;
In the formula (1-K2-3), compounds wherein $A^1$ is N, $A^2$ is S, and $A^3$ is N;
In the formula (1-K2-3), compounds wherein $A^1$ is N, $A^2$ is S, and $A^3$ is $CR^{12}$;
In the formula (1-K2-3), compounds wherein $A^1$ is $CR^5$, $A^2$ is $NR^6$, and $A^3$ is N;
In the formula (1-K2-3), compounds wherein $A^1$ is $CR^5$, $A^2$ is $NR^6$, and $A^3$ is $CR^{12}$;
In the formula (1-K2-3), compounds wherein $A^1$ is $CR^5$, $A^2$ is O, and $A^3$ is N;
In the formula (1-K2-3), compounds wherein $A^1$ is $CR^5$, $A^2$ is O, and $A^3$ is $CR^{12}$;
In the formula (1-K2-3), compounds wherein $A^1$ is $CR^5$, $A^2$ is S, and $A^3$ is N;
In the formula (1-K2-3), compounds wherein $A^1$ is $CR^5$, $A^2$ is S, and $A^3$ is $CR^{12}$;

Compounds represented by formula (1-K2-4),

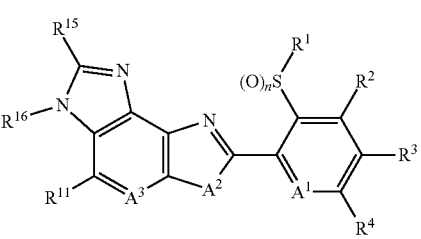

(1-K2-4)

wherein symbols represent the same meaning as described above, or N-oxides thereof;

In the formula (1-K2-4), compounds wherein $A^1$ is N;
In the formula (1-K2-4), compounds wherein $A^1$ is $CR^5$;
In the formula (1-K2-4), compounds wherein $A^2$ is $NR^6$;
In the formula (1-K2-4), compounds wherein $A^2$ is O;
In the formula (1-K2-4), compounds wherein $A^2$ is S;
In the formula (1-K2-4), compounds wherein $A^3$ is N;
In the formula (1-K2-4), compounds wherein $A^3$ is $CR^{12}$;
In the formula (1-K2-4), compounds wherein $A^1$ is N, and $A^2$ is $NR^6$;
In the formula (1-K2-4), compounds wherein $A^1$ is N, and $A^2$ is O;
In the formula (1-K2-4), compounds wherein $A^1$ is N, and $A^2$ is S;
In the formula (1-K2-4), compounds wherein $A^1$ is $CR^5$, and $A^2$ is $NR^6$;
In the formula (1-K2-4), compounds wherein $A^1$ is $CR^5$, and $A^2$ is O;
In the formula (1-K2-4), compounds wherein $A^1$ is $CR^5$, and $A^2$ is S;
In the formula (1-K2-4), compounds wherein $A^1$ is N, $A^2$ is $NR^6$, and $A^3$ is N;
In the formula (1-K2-4), compounds wherein $A^1$ is N, $A^2$ is $NR^6$, and $A^3$ is $CR^{12}$;
In the formula (1-K2-4), compounds wherein $A^1$ is N, $A^2$ is O, and $A^3$ is N;
In the formula (1-K2-4), compounds wherein $A^1$ is N, $A^2$ is O, and $A^3$ is $CR^{12}$;
In the formula (1-K2-4), compounds wherein $A^1$ is N, $A^2$ is S, and $A^3$ is N;
In the formula (1-K2-4), compounds wherein $A^1$ is N, $A^2$ is S, and $A^3$ is $CR^{12}$;
In the formula (1-K2-4), compounds wherein $A^1$ is $CR^5$, $A^2$ is $NR^6$, and $A^3$ is N;
In the formula (1-K2-4), compounds wherein $A^1$ is $CR^5$, $A^2$ is $NR^6$, and $A^3$ is $CR^{12}$;
In the formula (1-K2-4), compounds wherein $A^1$ is $CR^5$, $A^2$ is O, and $A^3$ is N;
In the formula (1-K2-4), compounds wherein $A^1$ is $CR^5$, $A^2$ is O, and $A^3$ is $CR^{12}$;
In the formula (1-K2-4), compounds wherein $A^1$ is $CR^5$, $A^2$ is S, and $A^3$ is N;
In the formula (1-K2-4), compounds wherein $A^1$ is $CR^5$, $A^2$ is S, and $A^3$ is $CR^{12}$;

Compounds represented by formula (1-K2-5),

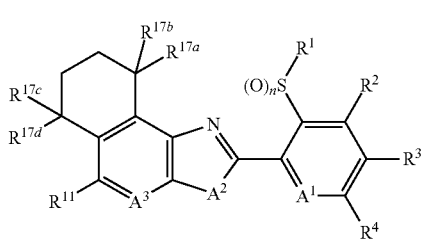

(1-K2-5)

wherein symbols represent the same meaning as described above, or N-oxides thereof;
In the formula (1-K2-5), compounds wherein $A^1$ is N;
In the formula (1-K2-5), compounds wherein $A^1$ is $CR^5$;
In the formula (1-K2-5), compounds wherein $A^2$ is $NR^6$;
In the formula (1-K2-5), compounds wherein $A^2$ is O;
In the formula (1-K2-5), compounds wherein $A^2$ is S;
In the formula (1-K2-5), compounds wherein $A^3$ is N;
In the formula (1-K2-5), compounds wherein $A^3$ is $CR^{12}$;
In the formula (1-K2-5), compounds wherein $A^1$ is N, and $A^2$ is $NR^6$;
In the formula (1-K2-5), compounds wherein $A^1$ is N, and $A^2$ is O;
In the formula (1-K2-5), compounds wherein $A^1$ is N, and $A^2$ is S;
In the formula (1-K2-5), compounds wherein $A^1$ is $CR^5$, and $A^2$ is $NR^6$;
In the formula (1-K2-5), compounds wherein $A^1$ is $CR^5$, and $A^2$ is O;
In the formula (1-K2-5), compounds wherein $A^1$ is $CR^5$, and $A^2$ is S;
In the formula (1-K2-5), compounds wherein $A^1$ is N, $A^2$ is $NR^6$, and $A^3$ is N;
In the formula (1-K2-5), compounds wherein $A^1$ is N, $A^2$ is $NR^6$, and $A^3$ is $CR^{12}$;
In the formula (1-K2-5), compounds wherein $A^1$ is N, $A^2$ is O, and $A^3$ is N;
In the formula (1-K2-5), compounds wherein $A^1$ is N, $A^2$ is O, and $A^3$ is $CR^{12}$;
In the formula (1-K2-5), compounds wherein $A^1$ is N, $A^2$ is S, and $A^3$ is N;
In the formula (1-K2-5), compounds wherein $A^1$ is N, $A^2$ is S, and $A^3$ is $CR^{12}$;
In the formula (1-K2-5), compounds wherein $A^1$ is $CR^5$, $A^2$ is $NR^6$, and $A^3$ is N;
In the formula (1-K2-5), compounds wherein $A^1$ is $CR^5$, $A^2$ is $NR^6$, and $A^3$ is $CR^{12}$;
In the formula (1-K2-5), compounds wherein $A^1$ is $CR^5$, $A^2$ is O, and $A^3$ is N;
In the formula (1-K2-5), compounds wherein $A^1$ is $CR^5$, $A^2$ is O, and $A^3$ is $CR^{12}$;
In the formula (1-K2-5), compounds wherein $A^1$ is $CR^5$, $A^2$ is S, and $A^3$ is N;
In the formula (1-K2-5), compounds wherein $A^1$ is $CR^5$, $A^2$ is S, and $A^3$ is $CR^{12}$;

Compounds represented by formula (1-K2-6),

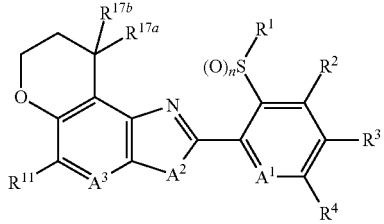

(1-K2-6)

wherein symbols represent the same meaning as described above, or N-oxides thereof;
In the formula (1-K2-6), compounds wherein $A^1$ is N;
In the formula (1-K2-6), compounds wherein $A^1$ is $CR^5$;
In the formula (1-K2-6), compounds wherein $A^2$ is $NR^6$;
In the formula (1-K2-6), compounds wherein $A^2$ is O;
In the formula (1-K2-6), compounds wherein $A^2$ is S;
In the formula (1-K2-6), compounds wherein $A^3$ is N;
In the formula (1-K2-6), compounds wherein $A^3$ is $CR^{12}$;
In the formula (1-K2-6), compounds wherein $A^1$ is N, and $A^2$ is $NR^6$;
In the formula (1-K2-6), compounds wherein $A^1$ is N, and $A^2$ is O;
In the formula (1-K2-6), compounds wherein $A^1$ is N, and $A^2$ is S;
In the formula (1-K2-6), compounds wherein $A^1$ is $CR^5$, and $A^2$ is $NR^6$;
In the formula (1-K2-6), compounds wherein $A^1$ is $CR^5$, and $A^2$ is O;
In the formula (1-K2-6), compounds wherein $A^1$ is $CR^5$, and $A^2$ is S;
In the formula (1-K2-6), compounds wherein $A^1$ is N, $A^2$ is $NR^6$, and $A^3$ is N;
In the formula (1-K2-6), compounds wherein $A^1$ is N, $A^2$ is $NR^6$, and $A^3$ is $CR^{12}$;
In the formula (1-K2-6), compounds wherein $A^1$ is N, $A^2$ is O, and $A^3$ is N;
In the formula (1-K2-6), compounds wherein $A^1$ is N, $A^2$ is O, and $A^3$ is $CR^{12}$;
In the formula (1-K2-6), compounds wherein $A^1$ is N, $A^2$ is S, and $A^3$ is N;
In the formula (1-K2-6), compounds wherein $A^1$ is N, $A^2$ is S, and $A^3$ is $CR^{12}$;
In the formula (1-K2-6), compounds wherein $A^1$ is $CR^5$, $A^2$ is $NR^6$, and $A^3$ is N;
In the formula (1-K2-6), compounds wherein $A^1$ is $CR^5$, $A^2$ is $NR^6$, and $A^3$ is $CR^{12}$;
In the formula (1-K2-6), compounds wherein $A^1$ is $CR^5$, $A^2$ is O, and $A^3$ is N;
In the formula (1-K2-6), compounds wherein $A^1$ is $CR^5$, $A^2$ is O, and $A^3$ is $CR^{12}$;
In the formula (1-K2-6), compounds wherein $A^1$ is $CR^5$, $A^2$ is S, and $A^3$ is N;
In the formula (1-K2-6), compounds wherein $A^1$ is $CR^5$, $A^2$ is S, and $A^3$ is $CR^{12}$;

Compounds represented by formula (1-K2-7),

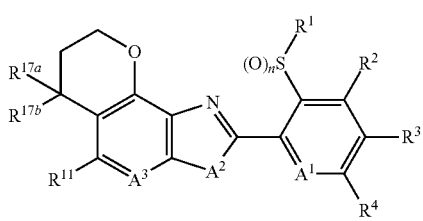

(1-K2-7)

wherein symbols represent the same meaning as described above, or N-oxides thereof;

In the formula (1-K2-7), compounds wherein $A^1$ is N;
In the formula (1-K2-7), compounds wherein $A^1$ is $CR^5$;
In the formula (1-K2-7), compounds wherein $A^2$ is $NR^6$;
In the formula (1-K2-7), compounds wherein $A^2$ is O;
In the formula (1-K2-7), compounds wherein $A^2$ is S;
In the formula (1-K2-7), compounds wherein $A^3$ is N;
In the formula (1-K2-7), compounds wherein $A^3$ is $CR^{12}$;
In the formula (1-K2-7), compounds wherein $A^1$ is N, and $A^2$ is $NR^6$;
In the formula (1-K2-7), compounds wherein $A^1$ is N, and $A^2$ is O;
In the formula (1-K2-7), compounds wherein $A^1$ is N, and $A^2$ is S;
In the formula (1-K2-7), compounds wherein $A^1$ is $CR^5$, and $A^2$ is $NR^6$;
In the formula (1-K2-7), compounds wherein $A^1$ is $CR^5$, and $A^2$ is O;
In the formula (1-K2-7), compounds wherein $A^1$ is $CR^5$, and $A^2$ is S;
In the formula (1-K2-7), compounds wherein $A^1$ is N, $A^2$ is $NR^6$, and $A^3$ is N;
In the formula (1-K2-7), compounds wherein $A^1$ is N, $A^2$ is $NR^6$, and $A^3$ is $CR^{12}$;
In the formula (1-K2-7), compounds wherein $A^1$ is N, $A^2$ is O, and $A^3$ is N;
In the formula (1-K2-7), compounds wherein $A^1$ is N, $A^2$ is O, and $A^3$ is $CR^{12}$;
In the formula (1-K2-7), compounds wherein $A^1$ is N, $A^2$ is S, and $A^3$ is N;
In the formula (1-K2-7), compounds wherein $A^1$ is N, $A^2$ is S, and $A^3$ is $CR^{12}$;
In the formula (1-K2-7), compounds wherein $A^1$ is $CR^5$, $A^2$ is $NR^6$, and $A^3$ is N;
In the formula (1-K2-7), compounds wherein $A^1$ is $CR^5$, $A^2$ is $NR^6$, and $A^3$ is $CR^{12}$;
In the formula (1-K2-7), compounds wherein $A^1$ is $CR^5$, $A^2$ is O, and $A^3$ is N;
In the formula (1-K2-7), compounds wherein $A^1$ is $CR^5$, $A^2$ is O, and $A^3$ is $CR^{12}$;
In the formula (1-K2-7), compounds wherein $A^1$ is $CR^5$, $A^2$ is S, and $A^3$ is N;
In the formula (1-K2-7), compounds wherein $A^1$ is $CR^5$, $A^2$ is S, and $A^3$ is $CR^{12}$;

Compounds represented by formula (1-K2-8),

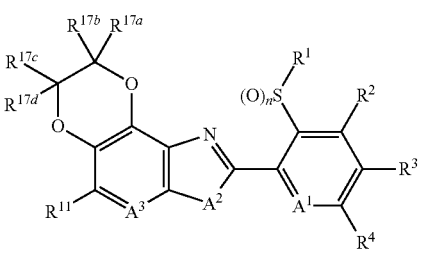

(1-K2-8)

wherein symbols represent the same meaning as described above, or N-oxides thereof;

In the formula (1-K2-8), compounds wherein $A^1$ is N;
In the formula (1-K2-8), compounds wherein $A^1$ is $CR^5$;
In the formula (1-K2-8), compounds wherein $A^2$ is $NR^6$;
In the formula (1-K2-8), compounds wherein $A^2$ is O;
In the formula (1-K2-8), compounds wherein $A^2$ is S;
In the formula (1-K2-8), compounds wherein $A^3$ is N;
In the formula (1-K2-8), compounds wherein $A^3$ is $CR^{12}$;
In the formula (1-K2-8), compounds wherein $A^1$ is N, and $A^2$ is $NR^6$;
In the formula (1-K2-8), compounds wherein $A^1$ is N, and $A^2$ is O;
In the formula (1-K2-8), compounds wherein $A^1$ is N, and $A^2$ is S;
In the formula (1-K2-8), compounds wherein $A^1$ is $CR^5$, and $A^2$ is $NR^6$;
In the formula (1-K2-8), compounds wherein $A^1$ is $CR^5$, and $A^2$ is O;
In the formula (1-K2-8), compounds wherein $A^1$ is $CR^5$, and $A^2$ is S;
In the formula (1-K2-8), compounds wherein $A^1$ is N, $A^2$ is $NR^6$, and $A^3$ is N;
In the formula (1-K2-8), compounds wherein $A^1$ is N, $A^2$ is $NR^6$, and $A^3$ is $CR^{12}$;
In the formula (1-K2-8), compounds wherein $A^1$ is N, $A^2$ is O, and $A^3$ is N;
In the formula (1-K2-8), compounds wherein $A^1$ is N, $A^2$ is O, and $A^3$ is $CR^{12}$;
In the formula (1-K2-8), compounds wherein $A^1$ is N, $A^2$ is S, and $A^3$ is N;
In the formula (1-K2-8), compounds wherein $A^1$ is N, $A^2$ is S, and $A^3$ is $CR^{12}$;
In the formula (1-K2-8), compounds wherein $A^1$ is $CR^5$, $A^2$ is $NR^6$, and $A^3$ is N;
In the formula (1-K2-8), compounds wherein $A^1$ is $CR^5$, $A^2$ is $NR^6$, and $A^3$ is $CR^{12}$;
In the formula (1-K2-8), compounds wherein $A^1$ is $CR^5$, $A^2$ is O, and $A^3$ is N;
In the formula (1-K2-8), compounds wherein $A^1$ is $CR^5$, $A^2$ is O, and $A^3$ is $CR^{12}$;
In the formula (1-K2-8), compounds wherein $A^1$ is $CR^5$, $A^2$ is S, and $A^3$ is N;
In the formula (1-K2-8), compounds wherein $A^1$ is $CR^5$, $A^2$ is S, and $A^3$ is $CR^{12}$;

Compounds represented by formula (1-K2-9),

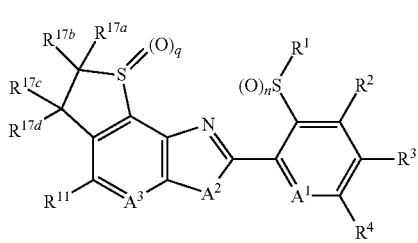

(1-K2-9)

wherein symbols represent the same meaning as described above, or N-oxides thereof;

In the formula (1-K2-9), compounds wherein $A^1$ is N;
In the formula (1-K2-9), compounds wherein $A^1$ is $CR^5$;
In the formula (1-K2-9), compounds wherein $A^2$ is $NR^6$;
In the formula (1-K2-9), compounds wherein $A^2$ is O;
In the formula (1-K2-9), compounds wherein $A^2$ is S;
In the formula (1-K2-9), compounds wherein $A^3$ is N;
In the formula (1-K2-9), compounds wherein $A^3$ is $CR^{12}$;
In the formula (1-K2-9), compounds wherein $A^1$ is N, and $A^2$ is $NR^6$;
In the formula (1-K2-9), compounds wherein $A^1$ is N, and $A^2$ is O;
In the formula (1-K2-9), compounds wherein $A^1$ is N, and $A^2$ is S;
In the formula (1-K2-9), compounds wherein $A^1$ is $CR^5$, and $A^2$ is $NR^6$;
In the formula (1-K2-9), compounds wherein $A^1$ is $CR^5$, and $A^2$ is O;
In the formula (1-K2-9), compounds wherein $A^1$ is $CR^5$, and $A^2$ is S;
In the formula (1-K2-9), compounds wherein $A^1$ is N, $A^2$ is $NR^6$, and $A^3$ is N;
In the formula (1-K2-9), compounds wherein $A^1$ is N, $A^2$ is $NR^6$, and $A^3$ is $CR^{12}$;
In the formula (1-K2-9), compounds wherein $A^1$ is N, $A^2$ is O, and $A^3$ is N;
In the formula (1-K2-9), compounds wherein $A^1$ is N, $A^2$ is O, and $A^3$ is $CR^{12}$;
In the formula (1-K2-9), compounds wherein $A^1$ is N, $A^2$ is S, and $A^3$ is N;
In the formula (1-K2-9), compounds wherein $A^1$ is N, $A^2$ is S, and $A^3$ is $CR^{12}$;
In the formula (1-K2-9), compounds wherein $A^1$ is $CR^5$, $A^2$ is $NR^6$, and $A^3$ is N;
In the formula (1-K2-9), compounds wherein $A^1$ is $CR^5$, $A^2$ is $NR^6$, and $A^3$ is $CR^{12}$;
In the formula (1-K2-9), compounds wherein $A^1$ is $CR^5$, $A^2$ is O, and $A^3$ is N;
In the formula (1-K2-9), compounds wherein $A^1$ is $CR^5$, $A^2$ is O, and $A^3$ is $CR^{12}$;
In the formula (1-K2-9), compounds wherein $A^1$ is $CR^5$, $A^2$ is S, and $A^3$ is N;
In the formula (1-K2-9), compounds wherein $A^1$ is $CR^5$, $A^2$ is S, and $A^3$ is $CR^{12}$;

Compounds represented by formula (1-K2-10),

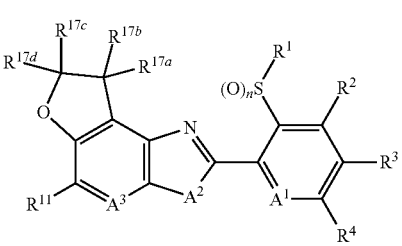

(1-K2-10)

wherein symbols represent the same meaning as described above, or N-oxides thereof;

In the formula (1-K2-10), compounds wherein $A^1$ is N;
In the formula (1-K2-10), compounds wherein $A^1$ is $CR^5$;
In the formula (1-K2-10), compounds wherein $A^2$ is $NR^6$;
In the formula (1-K2-10), compounds wherein $A^2$ is O;
In the formula (1-K2-10), compounds wherein $A^2$ is S;
In the formula (1-K2-10), compounds wherein $A^3$ is N;
In the formula (1-K2-10), compounds wherein $A^3$ is $CR^{12}$;
In the formula (1-K2-10), compounds wherein $A^1$ is N, and $A^2$ is $NR^6$;
In the formula (1-K2-10), compounds wherein $A^1$ is N, and $A^2$ is O;
In the formula (1-K2-10), compounds wherein $A^1$ is N, and $A^2$ is S;
In the formula (1-K2-10), compounds wherein $A^1$ is $CR^5$, and $A^2$ is $NR^6$;
In the formula (1-K2-10), compounds wherein $A^1$ is $CR^5$, and $A^2$ is O;
In the formula (1-K2-10), compounds wherein $A^1$ is $CR^5$, and $A^2$ is S;
In the formula (1-K2-10), compounds wherein $A^1$ is N, $A^2$ is $NR^6$, and $A^3$ is N;
In the formula (1-K2-10), compounds wherein $A^1$ is N, $A^2$ is $NR^6$, and $A^3$ is $CR^{12}$;
In the formula (1-K2-10), compounds wherein $A^1$ is N, $A^2$ is O, and $A^3$ is N;
In the formula (1-K2-10), compounds wherein $A^1$ is N, $A^2$ is O, and $A^3$ is $CR^{12}$;
In the formula (1-K2-10), compounds wherein $A^1$ is N, $A^2$ is S, and $A^3$ is N;
In the formula (1-K2-10), compounds wherein $A^1$ is N, $A^2$ is S, and $A^3$ is $CR^{12}$;
In the formula (1-K2-10), compounds wherein $A^1$ is $CR^5$, $A^2$ is $NR^6$, and $A^3$ is N;
In the formula (1-K2-10), compounds wherein $A^1$ is $CR^5$, $A^2$ is $NR^6$, and $A^3$ is $CR^{12}$;
In the formula (1-K2-10), compounds wherein $A^1$ is $CR^5$, $A^2$ is O, and $A^3$ is N;
In the formula (1-K2-10), compounds wherein $A^1$ is $CR^5$, $A^2$ is O, and $A^3$ is $CR^{12}$;
In the formula (1-K2-10), compounds wherein $A^1$ is $CR^5$, $A^2$ is S, and $A^3$ is N;
In the formula (1-K2-10), compounds wherein $A^1$ is $CR^5$, $A^2$ is S, and $A^3$ is $CR^{12}$;

Compounds represented by formula (1-K2-11),

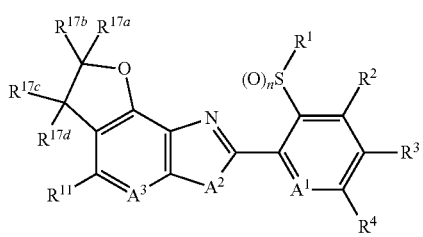
(1-K2-11)

Compounds represented by formula (1-K2-12),

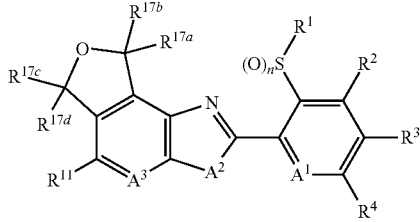
(1-K2-12)

wherein symbols represent the same meaning as described above, or N-oxides thereof;
In the formula (1-K2-11), compounds wherein $A^1$ is N;
In the formula (1-K2-11), compounds wherein $A^1$ is $CR^5$;
In the formula (1-K2-11), compounds wherein $A^2$ is $NR^6$;
In the formula (1-K2-11), compounds wherein $A^2$ is O;
In the formula (1-K2-11), compounds wherein $A^2$ is S;
In the formula (1-K2-11), compounds wherein $A^3$ is N;
In the formula (1-K2-11), compounds wherein $A^3$ is $CR^{12}$;
In the formula (1-K2-11), compounds wherein $A^1$ is N, and $A^2$ is $NR^6$;
In the formula (1-K2-11), compounds wherein $A^1$ is N, and $A^2$ is O;
In the formula (1-K2-11), compounds wherein $A^1$ is N, and $A^2$ is S;
In the formula (1-K2-11), compounds wherein $A^1$ is $CR^5$, and $A^2$ is $NR^6$;
In the formula (1-K2-11), compounds wherein $A^1$ is $CR^5$, and $A^2$ is O;
In the formula (1-K2-11), compounds wherein $A^1$ is $CR^5$, and $A^2$ is S;
In the formula (1-K2-11), compounds wherein $A^1$ is N, $A^2$ is $NR^6$, and $A^3$ is N;
In the formula (1-K2-11), compounds wherein $A^1$ is N, $A^2$ is $NR^6$, and $A^3$ is $CR^{12}$;
In the formula (1-K2-11), compounds wherein $A^1$ is N, $A^2$ is O, and $A^3$ is N;
In the formula (1-K2-11), compounds wherein $A^1$ is N, $A^2$ is O, and $A^3$ is $CR^{12}$;
In the formula (1-K2-11), compounds wherein $A^1$ is N, $A^2$ is S, and $A^3$ is N;
In the formula (1-K2-11), compounds wherein $A^1$ is N, $A^2$ is S, and $A^3$ is $CR^{12}$;
In the formula (1-K2-11), compounds wherein $A^1$ is $CR^5$, $A^2$ is $NR^6$, and $A^3$ is N;
In the formula (1-K2-11), compounds wherein $A^1$ is $CR^5$, $A^2$ is $NR^6$, and $A^3$ is $CR^{12}$;
In the formula (1-K2-11), compounds wherein $A^1$ is $CR^5$, $A^2$ is O, and $A^3$ is N;
In the formula (1-K2-11), compounds wherein $A^1$ is $CR^5$, $A^2$ is O, and $A^3$ is $CR^{12}$;
In the formula (1-K2-11), compounds wherein $A^1$ is $CR^5$, $A^2$ is S, and $A^3$ is N;
In the formula (1-K2-11), compounds wherein $A^1$ is $CR^5$, $A^2$ is S, and $A^3$ is $CR^{12}$;

wherein symbols represent the same meaning as described above, or N-oxides thereof;
In the formula (1-K2-12), compounds wherein $A^1$ is N;
In the formula (1-K2-12), compounds wherein $A^1$ is $CR^5$;
In the formula (1-K2-12), compounds wherein $A^2$ is $NR^6$;
In the formula (1-K2-12), compounds wherein $A^2$ is O;
In the formula (1-K2-12), compounds wherein $A^2$ is S;
In the formula (1-K2-12), compounds wherein $A^3$ is N;
In the formula (1-K2-12), compounds wherein $A^3$ is $CR^{12}$;
In the formula (1-K2-12), compounds wherein $A^1$ is N, and $A^2$ is $NR^6$;
In the formula (1-K2-12), compounds wherein $A^1$ is N, and $A^2$ is O;
In the formula (1-K2-12), compounds wherein $A^1$ is N, and $A^2$ is S;
In the formula (1-K2-12), compounds wherein $A^1$ is $CR^5$, and $A^2$ is $NR^6$;
In the formula (1-K2-12), compounds wherein $A^1$ is $CR^5$, and $A^2$ is O;
In the formula (1-K2-12), compounds wherein $A^1$ is $CR^5$, and $A^2$ is S;
In the formula (1-K2-12), compounds wherein $A^1$ is N, $A^2$ is $NR^6$, and $A^3$ is N;
In the formula (1-K2-12), compounds wherein $A^1$ is N, $A^2$ is $NR^6$, and $A^3$ is $CR^{12}$;
In the formula (1-K2-12), compounds wherein $A^1$ is N, $A^2$ is O, and $A^3$ is N;
In the formula (1-K2-12), compounds wherein $A^1$ is N, $A^2$ is O, and $A^3$ is $CR^{12}$;
In the formula (1-K2-12), compounds wherein $A^1$ is N, $A^2$ is S, and $A^3$ is N;
In the formula (1-K2-12), compounds wherein $A^1$ is N, $A^2$ is S, and $A^3$ is $CR^{12}$;
In the formula (1-K2-12), compounds wherein $A^1$ is $CR^5$, $A^2$ is $NR^6$, and $A^3$ is N;
In the formula (1-K2-12), compounds wherein $A^1$ is $CR^5$, $A^2$ is $NR^6$, and $A^3$ is $CR^{12}$;
In the formula (1-K2-12), compounds wherein $A^1$ is $CR^5$, $A^2$ is O, and $A^3$ is N;
In the formula (1-K2-12), compounds wherein $A^1$ is $CR^5$, $A^2$ is O, and $A^3$ is $CR^{12}$;
In the formula (1-K2-12), compounds wherein $A^1$ is $CR^5$, $A^2$ is S, and $A^3$ is N;
In the formula (1-K2-12), compounds wherein $A^1$ is $CR^5$, $A^2$ is S, and $A^3$ is $CR^{12}$;

Compounds represented by formula (1-K2-13),

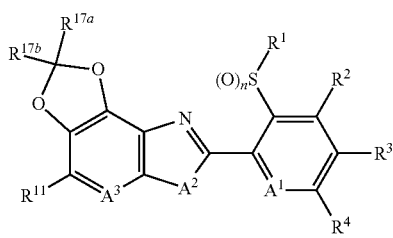

(1-K2-13)

wherein symbols represent the same meaning as described above, or N-oxides thereof;

In the formula (1-K2-13), compounds wherein $A^1$ is N;
In the formula (1-K2-13), compounds wherein $A^1$ is $CR^5$;
In the formula (1-K2-13), compounds wherein $A^2$ is $NR^6$;
In the formula (1-K2-13), compounds wherein $A^2$ is O;
In the formula (1-K2-13), compounds wherein $A^2$ is S;
In the formula (1-K2-13), compounds wherein $A^3$ is N;
In the formula (1-K2-13), compounds wherein $A^3$ is $CR^{12}$;
In the formula (1-K2-13), compounds wherein $A^1$ is N, and $A^2$ is $NR^6$;
In the formula (1-K2-13), compounds wherein $A^1$ is N, and $A^2$ is O;
In the formula (1-K2-13), compounds wherein $A^1$ is N, and $A^2$ is S;
In the formula (1-K2-13), compounds wherein $A^1$ is $CR^5$, and $A^2$ is $NR^6$;
In the formula (1-K2-13), compounds wherein $A^1$ is $CR^5$, and $A^2$ is O;
In the formula (1-K2-13), compounds wherein $A^1$ is $CR^5$, and $A^2$ is S;
In the formula (1-K2-13), compounds wherein $A^1$ is N, $A^2$ is $NR^6$, and $A^3$ is N;
In the formula (1-K2-13), compounds wherein $A^1$ is N, $A^2$ is $NR^6$, and $A^3$ is $CR^{12}$;
In the formula (1-K2-13), compounds wherein $A^1$ is N, $A^2$ is O, and $A^3$ is N;
In the formula (1-K2-13), compounds wherein $A^1$ is N, $A^2$ is O, and $A^3$ is $CR^{12}$;
In the formula (1-K2-13), compounds wherein $A^1$ is N, $A^2$ is S, and $A^3$ is N;
In the formula (1-K2-13), compounds wherein $A^1$ is N, $A^2$ is S, and $A^3$ is $CR^{12}$;
In the formula (1-K2-13), compounds wherein $A^1$ is $CR^5$, $A^2$ is $NR^6$, and $A^3$ is N;
In the formula (1-K2-13), compounds wherein $A^1$ is $CR^5$, $A^2$ is $NR^6$, and $A^3$ is $CR^{12}$;
In the formula (1-K2-13), compounds wherein $A^1$ is $CR^5$, $A^2$ is O, and $A^3$ is N;
In the formula (1-K2-13), compounds wherein $A^1$ is $CR^5$, $A^2$ is O, and $A^3$ is $CR^{12}$;
In the formula (1-K2-13), compounds wherein $A^1$ is $CR^5$, $A^2$ is S, and $A^3$ is N;
In the formula (1-K2-13), compounds wherein $A^1$ is $CR^5$, $A^2$ is S, and $A^3$ is $CR^{12}$;

Compounds represented by formula (1-K2-14),

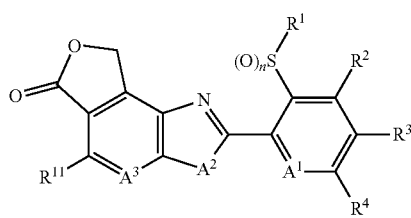

(1-K2-14)

wherein symbols represent the same meaning as described above, or N-oxides thereof;

In the formula (1-K2-14), compounds wherein $A^1$ is N;
In the formula (1-K2-14), compounds wherein $A^1$ is $CR^5$;
In the formula (1-K2-14), compounds wherein $A^2$ is $NR^6$;
In the formula (1-K2-14), compounds wherein $A^2$ is O;
In the formula (1-K2-14), compounds wherein $A^2$ is S;
In the formula (1-K2-14), compounds wherein $A^3$ is N;
In the formula (1-K2-14), compounds wherein $A^3$ is $CR^{12}$;
In the formula (1-K2-14), compounds wherein $A^1$ is N, and $A^2$ is $NR^6$;
In the formula (1-K2-14), compounds wherein $A^1$ is N, and $A^2$ is O;
In the formula (1-K2-14), compounds wherein $A^1$ is N, and $A^2$ is S;
In the formula (1-K2-14), compounds wherein $A^1$ is $CR^5$, and $A^2$ is $NR^6$;
In the formula (1-K2-14), compounds wherein $A^1$ is $CR^5$, and $A^2$ is O;
In the formula (1-K2-14), compounds wherein $A^1$ is $CR^5$, and $A^2$ is S;
In the formula (1-K2-14), compounds wherein $A^1$ is N, $A^2$ is $NR^6$, and $A^3$ is N;
In the formula (1-K2-14), compounds wherein $A^1$ is N, $A^2$ is $NR^6$, and $A^3$ is $CR^{12}$;
In the formula (1-K2-14), compounds wherein $A^1$ is N, $A^2$ is O, and $A^3$ is N;
In the formula (1-K2-14), compounds wherein $A^1$ is N, $A^2$ is O, and $A^3$ is $CR^{12}$;
In the formula (1-K2-14), compounds wherein $A^1$ is N, $A^2$ is S, and $A^3$ is N;
In the formula (1-K2-14), compounds wherein $A^1$ is N, $A^2$ is S, and $A^3$ is $CR^{12}$;
In the formula (1-K2-14), compounds wherein $A^1$ is $CR^5$, $A^2$ is $NR^6$, and $A^3$ is N;
In the formula (1-K2-14), compounds wherein $A^1$ is $CR^5$, $A^2$ is $NR^6$, and $A^3$ is $CR^{12}$;
In the formula (1-K2-14), compounds wherein $A^1$ is $CR^5$, $A^2$ is O, and $A^3$ is N;
In the formula (1-K2-14), compounds wherein $A^1$ is $CR^5$, $A^2$ is O, and $A^3$ is $CR^{12}$;
In the formula (1-K2-14), compounds wherein $A^1$ is $CR^5$, $A^2$ is S, and $A^3$ is N;
In the formula (1-K2-14), compounds wherein $A^1$ is $CR^5$, $A^2$ is S, and $A^3$ is $CR^{12}$;

Compounds represented by formula (1-K2-15),

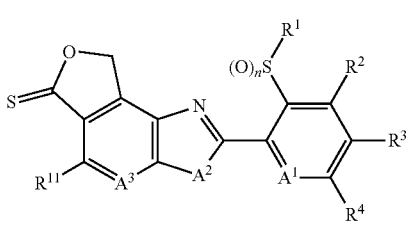
(1-K2-15)

wherein symbols represent the same meaning as described above, or N-oxides thereof;
In the formula (1-K2-15), compounds wherein $A^1$ is N;
In the formula (1-K2-15), compounds wherein $A^1$ is $CR^5$;
In the formula (1-K2-15), compounds wherein $A^2$ is $NR^6$;
In the formula (1-K2-15), compounds wherein $A^2$ is O;
In the formula (1-K2-15), compounds wherein $A^2$ is S;
In the formula (1-K2-15), compounds wherein $A^3$ is N;
In the formula (1-K2-15), compounds wherein $A^3$ is $CR^{12}$;
In the formula (1-K2-15), compounds wherein $A^1$ is N, and $A^2$ is $NR^6$;
In the formula (1-K2-15), compounds wherein $A^1$ is N, and $A^2$ is O;
In the formula (1-K2-15), compounds wherein $A^1$ is N, and $A^2$ is S;
In the formula (1-K2-15), compounds wherein $A^1$ is $CR^5$, and $A^2$ is $NR^6$;
In the formula (1-K2-15), compounds wherein $A^1$ is $CR^5$, and $A^2$ is O;
In the formula (1-K2-15), compounds wherein $A^1$ is $CR^5$, and $A^2$ is S;
In the formula (1-K2-15), compounds wherein $A^1$ is N, $A^2$ is $NR^6$, and $A^3$ is N;
In the formula (1-K2-15), compounds wherein $A^1$ is N, $A^2$ is $NR^6$, and $A^3$ is $CR^{12}$;
In the formula (1-K2-15), compounds wherein $A^1$ is N, $A^2$ is O, and $A^3$ is N;
In the formula (1-K2-15), compounds wherein $A^1$ is N, $A^2$ is O, and $A^3$ is $CR^{12}$;
In the formula (1-K2-15), compounds wherein $A^1$ is N, $A^2$ is S, and $A^3$ is N;
In the formula (1-K2-15), compounds wherein $A^1$ is N, $A^2$ is S, and $A^3$ is $CR^{12}$;
In the formula (1-K2-15), compounds wherein $A^1$ is $CR^5$, $A^2$ is $NR^6$, and $A^3$ is N;
In the formula (1-K2-15), compounds wherein $A^1$ is $CR^5$, $A^2$ is $NR^6$, and $A^3$ is $CR^{12}$;
In the formula (1-K2-15), compounds wherein $A^1$ is $CR^5$, $A^2$ is O, and $A^3$ is N;
In the formula (1-K2-15), compounds wherein $A^1$ is $CR^5$, $A^2$ is O, and $A^3$ is $CR^{12}$;
In the formula (1-K2-15), compounds wherein $A^1$ is $CR^5$, $A^2$ is S, and $A^3$ is N;
In the formula (1-K2-15), compounds wherein $A^1$ is $CR^5$, $A^2$ is S, and $A^3$ is $CR^{12}$;

Compounds represented by formula (1-K2-16),

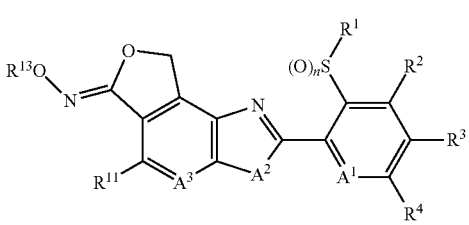
(1-K2-16)

wherein symbols represent the same meaning as described above, or N-oxides thereof;
In the formula (1-K2-16), compounds wherein $A^1$ is N;
In the formula (1-K2-16), compounds wherein $A^1$ is $CR^5$;
In the formula (1-K2-16), compounds wherein $A^2$ is $NR^6$;
In the formula (1-K2-16), compounds wherein $A^2$ is O;
In the formula (1-K2-16), compounds wherein $A^2$ is S;
In the formula (1-K2-16), compounds wherein $A^3$ is N;
In the formula (1-K2-16), compounds wherein $A^3$ is $CR^{12}$;
In the formula (1-K2-16), compounds wherein $A^1$ is N, and $A^2$ is $NR^6$;
In the formula (1-K2-16), compounds wherein $A^1$ is N, and $A^2$ is O;
In the formula (1-K2-16), compounds wherein $A^1$ is N, and $A^2$ is S;
In the formula (1-K2-16), compounds wherein $A^1$ is $CR^5$, and $A^2$ is $NR^6$;
In the formula (1-K2-16), compounds wherein $A^1$ is $CR^5$, and $A^2$ is O;
In the formula (1-K2-16), compounds wherein $A^1$ is $CR^5$, and $A^2$ is S;
In the formula (1-K2-16), compounds wherein $A^1$ is N, $A^2$ is $NR^6$, and $A^3$ is N;
In the formula (1-K2-16), compounds wherein $A^1$ is N, $A^2$ is $NR^6$, and $A^3$ is $CR^{12}$;
In the formula (1-K2-16), compounds wherein $A^1$ is N, $A^2$ is O, and $A^3$ is N;
In the formula (1-K2-16), compounds wherein $A^1$ is N, $A^2$ is O, and $A^3$ is $CR^{12}$;
In the formula (1-K2-16), compounds wherein $A^1$ is N, $A^2$ is S, and $A^3$ is N;
In the formula (1-K2-16), compounds wherein $A^1$ is N, $A^2$ is S, and $A^3$ is $CR^{12}$;
In the formula (1-K2-16), compounds wherein $A^1$ is $CR^5$, $A^2$ is $NR^6$, and $A^3$ is N;
In the formula (1-K2-16), compounds wherein $A^1$ is $CR^5$, $A^2$ is $NR^6$, and $A^3$ is $CR^{12}$;
In the formula (1-K2-16), compounds wherein $A^1$ is $CR^5$, $A^2$ is O, and $A^3$ is N;
In the formula (1-K2-16), compounds wherein $A^1$ is $CR^5$, $A^2$ is O, and $A^3$ is $CR^{12}$;
In the formula (1-K2-16), compounds wherein $A^1$ is $CR^5$, $A^2$ is S, and $A^3$ is N;
In the formula (1-K2-16), compounds wherein $A^1$ is $CR^5$, $A^2$ is S, and $A^3$ is $CR^{12}$;

Compounds represented by formula (1-K3),

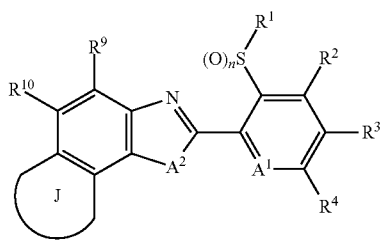

(1-K3)

wherein symbols represent the same meaning as described above, or N-oxides thereof;
In the formula (1-K3), compounds wherein $A^1$ is N;
In the formula (1-K3), compounds wherein $A^1$ is $CR^5$;
In the formula (1-K3), compounds wherein $A^2$ is $NR^6$;
In the formula (1-K3), compounds wherein $A^2$ is O;
In the formula (1-K3), compounds wherein $A^2$ is S;
In the formula (1-K3), compounds wherein $A^1$ is N, and $A^2$ is $NR^6$;
In the formula (1-K3), compounds wherein $A^1$ is N, and $A^2$ is O;
In the formula (1-K3), compounds wherein $A^1$ is N, and $A^2$ is S;
In the formula (1-K3), compounds wherein $A^1$ is $CR^5$, and $A^2$ is $NR^6$;
In the formula (1-K3), compounds wherein $A^1$ is $CR^5$, and $A^2$ is O;
In the formula (1-K3), compounds wherein $A^1$ is $CR^5$, and $A^2$ is S;
Compounds represented by formula (1-K3-1),

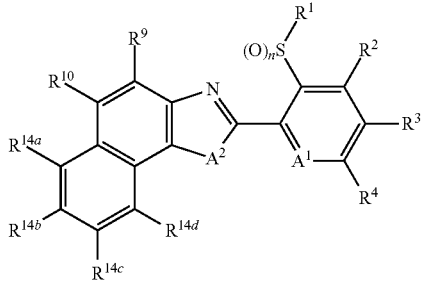

(1-K3-1)

wherein symbols represent the same meaning as described above, or N-oxides thereof;
In the formula (1-K3-1), compounds wherein $A^1$ is N;
In the formula (1-K3-1), compounds wherein $A^1$ is $CR^5$;
In the formula (1-K3-1), compounds wherein $A^2$ is $NR^6$;
In the formula (1-K3-1), compounds wherein $A^2$ is O;
In the formula (1-K3-1), compounds wherein $A^2$ is S;
In the formula (1-K3-1), compounds wherein $A^1$ is N, and $A^2$ is $NR^6$;
In the formula (1-K3-1), compounds wherein $A^1$ is N, and $A^2$ is O;
In the formula (1-K3-1), compounds wherein $A^1$ is N, and $A^2$ is S;
In the formula (1-K3-1), compounds wherein $A^1$ is $CR^5$, and $A^2$ is $NR^6$;
In the formula (1-K3-1), compounds wherein $A^1$ is $CR^5$, and $A^2$ is O;
In the formula (1-K3-1), compounds wherein $A^1$ is $CR^5$, and $A^2$ is S;
Compounds represented by formula (1-K3-2),

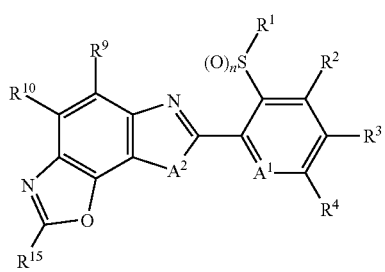

(1-K3-2)

wherein symbols represent the same meaning as described above, or N-oxides thereof;
In the formula (1-K3-2), compounds wherein $A^1$ is N;
In the formula (1-K3-2), compounds wherein $A^1$ is $CR^5$;
In the formula (1-K3-2), compounds wherein $A^2$ is $NR^6$;
In the formula (1-K3-2), compounds wherein $A^2$ is O;
In the formula (1-K3-2), compounds wherein $A^2$ is S;
In the formula (1-K3-2), compounds wherein $A^1$ is N, and $A^2$ is $NR^6$;
In the formula (1-K3-2), compounds wherein $A^1$ is N, and $A^2$ is O;
In the formula (1-K3-2), compounds wherein $A^1$ is N, and $A^2$ is S;
In the formula (1-K3-2), compounds wherein $A^1$ is $CR^5$, and $A^2$ is $NR^6$;
In the formula (1-K3-2), compounds wherein $A^1$ is $CR^5$, and $A^2$ is O;
In the formula (1-K3-2), compounds wherein $A^1$ is $CR^5$, and $A^2$ is S;
Compounds represented by formula (1-K3-3),

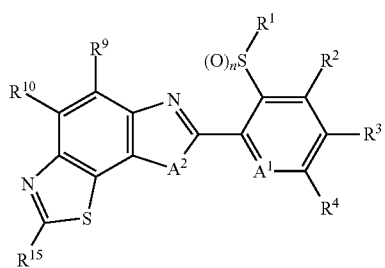

(1-K3-3)

wherein symbols represent the same meaning as described above, or N-oxides thereof;
In the formula (1-K3-3), compounds wherein $A^1$ is N;
In the formula (1-K3-3), compounds wherein $A^1$ is $CR^5$;
In the formula (1-K3-3), compounds wherein $A^2$ is $NR^6$;
In the formula (1-K3-3), compounds wherein $A^2$ is O;
In the formula (1-K3-3), compounds wherein $A^2$ is S;
In the formula (1-K3-3), compounds wherein $A^1$ is N, and $A^2$ is $NR^6$;
In the formula (1-K3-3), compounds wherein $A^1$ is N, and $A^2$ is O;
In the formula (1-K3-3), compounds wherein $A^1$ is N, and $A^2$ is S;

In the formula (1-K3-3), compounds wherein $A^1$ is $CR^5$, and $A^2$ is $NR^6$;
In the formula (1-K3-3), compounds wherein $A^1$ is $CR^5$, and $A^2$ is O;
In the formula (1-K3-3), compounds wherein $A^1$ is $CR^5$, and $A^2$ is S;
Compounds represented by formula (1-K3-4),

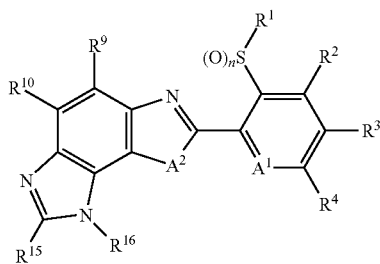

(1-K3-4)

wherein symbols represent the same meaning as described above, or N-oxides thereof;
In the formula (1-K3-4), compounds wherein $A^1$ is N;
In the formula (1-K3-4), compounds wherein $A^1$ is $CR^5$;
In the formula (1-K3-4), compounds wherein $A^2$ is $NR^6$;
In the formula (1-K3-4), compounds wherein $A^2$ is O;
In the formula (1-K3-4), compounds wherein $A^2$ is S;
In the formula (1-K3-4), compounds wherein $A^1$ is N, and $A^2$ is $NR^6$;
In the formula (1-K3-4), compounds wherein $A^1$ is N, and $A^2$ is O;
In the formula (1-K3-4), compounds wherein $A^1$ is N, and $A^2$ is S;
In the formula (1-K3-4), compounds wherein $A^1$ is $CR^5$, and $A^2$ is $NR^6$;
In the formula (1-K3-4), compounds wherein $A^1$ is $CR^5$, and $A^2$ is O;
In the formula (1-K3-4), compounds wherein $A^1$ is $CR^5$, and $A^2$ is S;
Compounds represented by formula (1-K3-5),

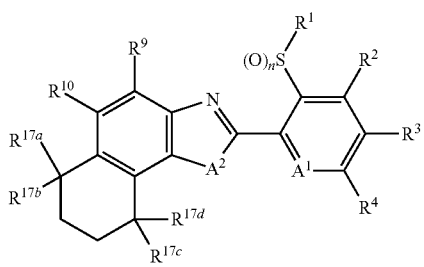

(1-K3-5)

wherein symbols represent the same meaning as described above, or N-oxides thereof;
In the formula (1-K3-5), compounds wherein $A^1$ is N;
In the formula (1-K3-5), compounds wherein $A^1$ is $CR^5$;
In the formula (1-K3-5), compounds wherein $A^2$ is $NR^6$;
In the formula (1-K3-5), compounds wherein $A^2$ is O;
In the formula (1-K3-5), compounds wherein $A^2$ is S;
In the formula (1-K3-5), compounds wherein $A^1$ is N, and $A^2$ is $NR^6$;
In the formula (1-K3-5), compounds wherein $A^1$ is N, and $A^2$ is O;

In the formula (1-K3-5), compounds wherein $A^1$ is N, and $A^2$ is S;
In the formula (1-K3-5), compounds wherein $A^1$ is $CR^5$, and $A^2$ is $NR^6$;
In the formula (1-K3-5), compounds wherein $A^1$ is $CR^5$, and $A^2$ is O;
In the formula (1-K3-5), compounds wherein $A^1$ is $CR^5$, and $A^2$ is S;
Compounds represented by formula (1-K3-6),

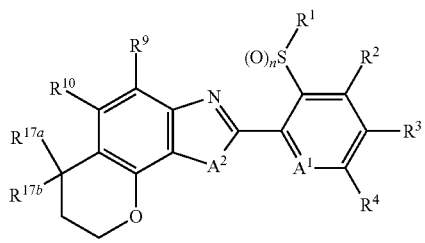

(1-K3-6)

wherein symbols represent the same meaning as described above, or N-oxides thereof;
In the formula (1-K3-6), compounds wherein $A^1$ is N;
In the formula (1-K3-6), compounds wherein $A^1$ is $CR^5$;
In the formula (1-K3-6), compounds wherein $A^2$ is $NR^6$;
In the formula (1-K3-6), compounds wherein $A^2$ is O;
In the formula (1-K3-6), compounds wherein $A^2$ is S;
In the formula (1-K3-6), compounds wherein $A^1$ is N, and $A^2$ is $NR^6$;
In the formula (1-K3-6), compounds wherein $A^1$ is N, and $A^2$ is O;
In the formula (1-K3-6), compounds wherein $A^1$ is N, and $A^2$ is S;
In the formula (1-K3-6), compounds wherein $A^1$ is $CR^5$, and $A^2$ is $NR^6$;
In the formula (1-K3-6), compounds wherein $A^1$ is $CR^5$, and $A^2$ is O;
In the formula (1-K3), compounds wherein $A^1$ is $CR^5$, and $A^2$ is S;
Compounds represented by formula (1-K3-7),

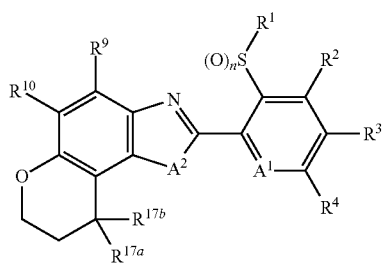

(1-K3-7)

wherein symbols represent the same meaning as described above, or N-oxides thereof;
In the formula (1-K3-7), compounds wherein $A^1$ is N;
In the formula (1-K3-7), compounds wherein $A^1$ is $CR^5$;
In the formula (1-K3-7), compounds wherein $A^2$ is $NR^6$;
In the formula (1-K3-7), compounds wherein $A^2$ is O;
In the formula (1-K3-7), compounds wherein $A^2$ is S;
In the formula (1-K3-7), compounds wherein $A^1$ is N, and $A^2$ is $NR^6$;
In the formula (1-K3-7), compounds wherein $A^1$ is N, and $A^2$ is O;

In the formula (1-K3-7), compounds wherein $A^1$ is N, and $A^2$ is S;
In the formula (1-K3-7), compounds wherein $A^1$ is $CR^5$, and $A^2$ is $NR^6$;
In the formula (1-K3-7), compounds wherein $A^1$ is $CR^5$, and $A^2$ is O;
In the formula (1-K3-7), compounds wherein $A^1$ is $CR^5$, and $A^2$ is S;
Compounds represented by formula (1-K3-8),

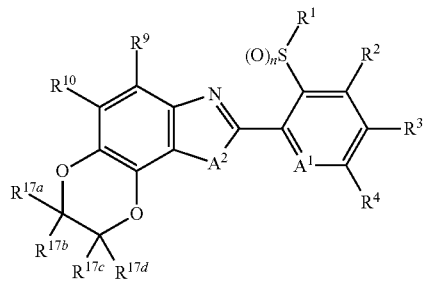

(1-K3-8)

wherein symbols represent the same meaning as described above, or N-oxides thereof;
In the formula (1-K3-8), compounds wherein $A^1$ is N;
In the formula (1-K3-8), compounds wherein $A^1$ is $CR^5$;
In the formula (1-K3-8), compounds wherein $A^2$ is $NR^6$;
In the formula (1-K3-8), compounds wherein $A^2$ is O;
In the formula (1-K3-8), compounds wherein $A^2$ is S;
In the formula (1-K3-8), compounds wherein $A^1$ is N, and $A^2$ is $NR^6$;
In the formula (1-K3-8), compounds wherein $A^1$ is N, and $A^2$ is O;
In the formula (1-K3-8), compounds wherein $A^1$ is N, and $A^2$ is S;
In the formula (1-K3-8), compounds wherein $A^1$ is $CR^5$, and $A^2$ is $NR^6$;
In the formula (1-K3-8), compounds wherein $A^1$ is $CR^5$, and $A^2$ is O;
In the formula (1-K3-8), compounds wherein $A^1$ is $CR^5$, and $A^2$ is S;
Compounds represented by formula (1-K3-9),

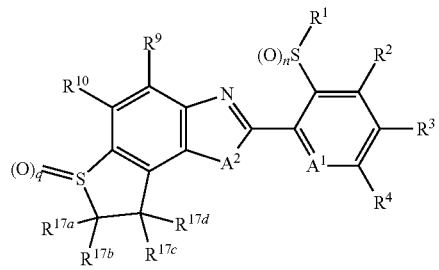

(1-K3-9)

wherein symbols represent the same meaning as described above, or N-oxides thereof;
In the formula (1-K3-9), compounds wherein $A^1$ is N;
In the formula (1-K3-9), compounds wherein $A^1$ is $CR^5$;
In the formula (1-K3-9), compounds wherein $A^2$ is $NR^6$;
In the formula (1-K3-9), compounds wherein $A^2$ is O;
In the formula (1-K3-9), compounds wherein $A^2$ is S;
In the formula (1-K3-9), compounds wherein $A^1$ is N, and $A^2$ is $NR^6$;
In the formula (1-K3-9), compounds wherein $A^1$ is N, and $A^2$ is O;
In the formula (1-K3-9), compounds wherein $A^1$ is N, and $A^2$ is S;
In the formula (1-K3-9), compounds wherein $A^1$ is $CR^5$, and $A^2$ is $NR^6$;
In the formula (1-K3-9), compounds wherein $A^1$ is $CR^5$, and $A^2$ is O;
In the formula (1-K3-9), compounds wherein $A^1$ is $CR^5$, and $A^2$ is S;
Compounds represented by formula (1-K3-10),

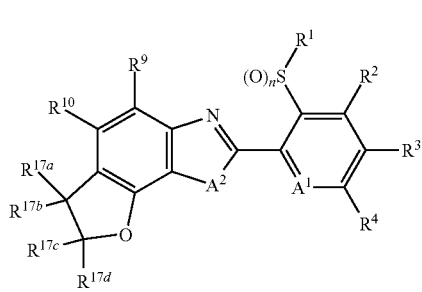

(1-K3-10)

wherein symbols represent the same meaning as described above, or N-oxides thereof;
In the formula (1-K3-10), compounds wherein $A^1$ is N;
In the formula (1-K3-10), compounds wherein $A^1$ is $CR^5$;
In the formula (1-K3-10), compounds wherein $A^2$ is $NR^6$;
In the formula (1-K3-10), compounds wherein $A^2$ is O;
In the formula (1-K3-10), compounds wherein $A^2$ is S;
In the formula (1-K3-10), compounds wherein $A^1$ is N, and $A^2$ is $NR^6$;
In the formula (1-K3-10), compounds wherein $A^1$ is N, and $A^2$ is O;
In the formula (1-K3-10), compounds wherein $A^1$ is N, and $A^2$ is S;
In the formula (1-K3-10), compounds wherein $A^1$ is $CR^5$, and $A^2$ is $NR^6$;
In the formula (1-K3-10), compounds wherein $A^1$ is $CR^5$, and $A^2$ is O;
In the formula (1-K3-10), compounds wherein $A^1$ is $CR^5$, and $A^2$ is S;
Compounds represented by formula (1-K3-11),

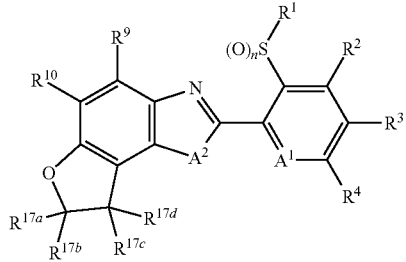

(1-K3-11)

wherein symbols represent the same meaning as described above, or N-oxides thereof;
In the formula (1-K3-11), compounds wherein $A^1$ is N;
In the formula (1-K3-11), compounds wherein $A^1$ is $CR^5$;
In the formula (1-K3-11), compounds wherein $A^2$ is $NR^6$;
In the formula (1-K3-11), compounds wherein $A^2$ is O;
In the formula (1-K3-11), compounds wherein $A^2$ is S;

In the formula (1-K3-11), compounds wherein $A^1$ is N, and $A^2$ is $NR^6$;
In the formula (1-K3-11), compounds wherein $A^1$ is N, and $A^2$ is O;
In the formula (1-K3-11), compounds wherein $A^1$ is N, and $A^2$ is S;
In the formula (1-K3-11), compounds wherein $A^1$ is $CR^5$, and $A^2$ is $NR^6$;
In the formula (1-K3-11), compounds wherein $A^1$ is $CR^5$, and $A^2$ is O;
In the formula (1-K3-11), compounds wherein $A^1$ is $CR^5$, and $A^2$ is S;
Compounds represented by formula (1-K3-12),

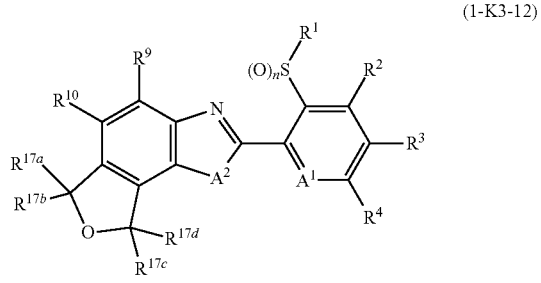

(1-K3-12)

wherein symbols represent the same meaning as described above, or N-oxides thereof;
In the formula (1-K3-12), compounds wherein $A^1$ is N;
In the formula (1-K3-12), compounds wherein $A^1$ is $CR^5$;
In the formula (1-K3-12), compounds wherein $A^2$ is $NR^6$;
In the formula (1-K3-12), compounds wherein $A^2$ is O;
In the formula (1-K3-12), compounds wherein $A^2$ is S;
In the formula (1-K3-12), compounds wherein $A^1$ is N, and $A^2$ is $NR^6$;
In the formula (1-K3-12), compounds wherein $A^1$ is N, and $A^2$ is O;
In the formula (1-K3-12), compounds wherein $A^1$ is N, and $A^2$ is S;
In the formula (1-K3-12), compounds wherein $A^1$ is $CR^5$, and $A^2$ is $NR^6$;
In the formula (1-K3-12), compounds wherein $A^1$ is $CR^5$, and $A^2$ is O;
In the formula (1-K3-12), compounds wherein $A^1$ is $CR^5$, and $A^2$ is S;
Compounds represented by formula (1-K3-13),

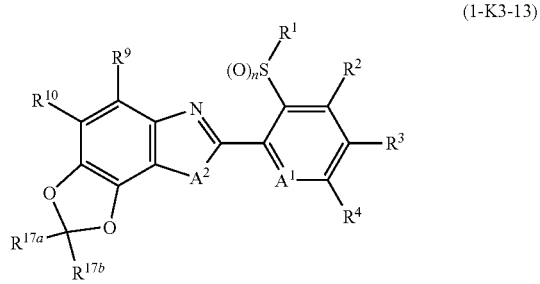

(1-K3-13)

wherein symbols represent the same meaning as described above, or N-oxides thereof;
In the formula (1-K3-13), compounds wherein $A^1$ is N;
In the formula (1-K3-13), compounds wherein $A^1$ is $CR^5$;
In the formula (1-K3-13), compounds wherein $A^2$ is $NR^6$;
In the formula (1-K3-13), compounds wherein $A^2$ is O;
In the formula (1-K3-13), compounds wherein $A^2$ is S;
In the formula (1-K3-13), compounds wherein $A^1$ is N, and $A^2$ is $NR^6$;
In the formula (1-K3-13), compounds wherein $A^1$ is N, and $A^2$ is O;
In the formula (1-K3-13), compounds wherein $A^1$ is N, and $A^2$ is S;
In the formula (1-K3-13), compounds wherein $A^1$ is $CR^5$, and $A^2$ is $NR^6$;
In the formula (1-K3-13), compounds wherein $A^1$ is $CR^5$, and $A^2$ is O;
In the formula (1-K3-13), compounds wherein $A^1$ is $CR^5$, and $A^2$ is S;
Compounds represented by formula (1-K3-14),

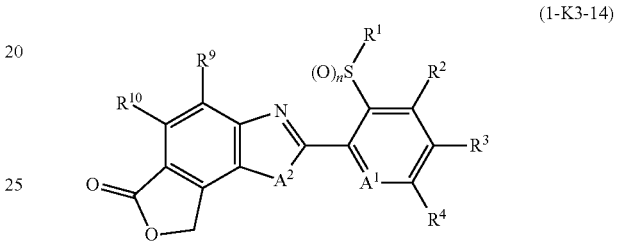

(1-K3-14)

wherein symbols represent the same meaning as described above, or N-oxides thereof;
In the formula (1-K3-14), compounds wherein $A^1$ is N;
In the formula (1-K3-14), compounds wherein $A^1$ is $CR^5$;
In the formula (1-K3-14), compounds wherein $A^2$ is $NR^6$;
In the formula (1-K3-14), compounds wherein $A^2$ is O;
In the formula (1-K3-14), compounds wherein $A^2$ is S;
In the formula (1-K3-14), compounds wherein $A^1$ is N, and $A^2$ is $NR^6$;
In the formula (1-K3-14), compounds wherein $A^1$ is N, and $A^2$ is O;
In the formula (1-K3-14), compounds wherein $A^1$ is N, and $A^2$ is S;
In the formula (1-K3-14), compounds wherein $A^1$ is $CR^5$, and $A^2$ is $NR^6$;
In the formula (1-K3-14), compounds wherein $A^1$ is $CR^5$, and $A^2$ is O;
In the formula (1-K3-14), compounds wherein $A^1$ is $CR^5$, and $A^2$ is S;
Compounds represented by formula (1-K3-15),

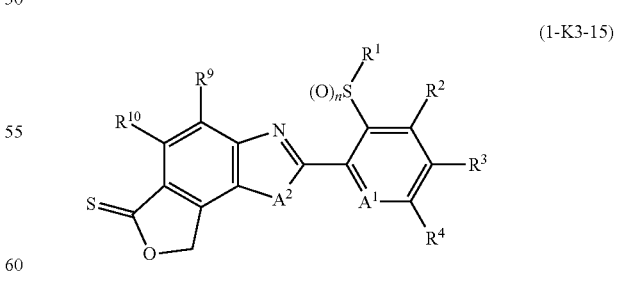

(1-K3-15)

wherein symbols represent the same meaning as described above, or N-oxides thereof;
In the formula (1-K3-15), compounds wherein $A^1$ is N;
In the formula (1-K3-15), compounds wherein $A^1$ is $CR^5$;
In the formula (1-K3-15), compounds wherein $A^2$ is $NR^6$;
In the formula (1-K3-15), compounds wherein $A^2$ is O;

In the formula (1-K3-15), compounds wherein $A^2$ is S;
In the formula (1-K3-15), compounds wherein $A^1$ is N, and $A^2$ is $NR^6$;
In the formula (1-K3-15), compounds wherein $A^1$ is N, and $A^2$ is O;
In the formula (1-K3-15), compounds wherein $A^1$ is N, and $A^2$ is S;
In the formula (1-K3-15), compounds wherein $A^1$ is $CR^5$, and $A^2$ is $NR^6$;
In the formula (1-K3-15), compounds wherein $A^1$ is $CR^5$, and $A^2$ is O;
In the formula (1-K3-15), compounds wherein $A^1$ is $CR^5$, and $A^2$ is S;
Compounds represented by formula (1-K3-16),

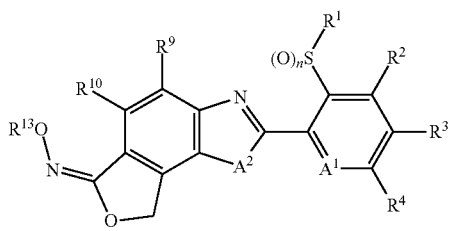

(1-K3-16)

wherein symbols represent the same meaning as described above, or N-oxides thereof;
In the formula (1-K3-16), compounds wherein $A^1$ is N;
In the formula (1-K3-16), compounds wherein $A^1$ is $CR^5$;
In the formula (1-K3-16), compounds wherein $A^2$ is $NR^6$;
In the formula (1-K3-16), compounds wherein $A^2$ is O;
In the formula (1-K3-16), compounds wherein $A^2$ is S;
In the formula (1-K3-16), compounds wherein $A^1$ is N, and $A^2$ is $NR^6$;
In the formula (1-K3-16), compounds wherein $A^1$ is N, and $A^2$ is O;
In the formula (1-K3-16), compounds wherein $A^1$ is N, and $A^2$ is S;
In the formula (1-K3-16), compounds wherein $A^1$ is $CR^5$, and $A^2$ is $NR^6$;
In the formula (1-K3-16), compounds wherein $A^1$ is $CR^5$, and $A^2$ is O;
In the formula (1-K3-16), compounds wherein $A^1$ is $CR^5$, and $A^2$ is S;
In the formula (1), compounds wherein $R^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms, or a C3 to C6 cycloalkyl group optionally having one or more halogen atoms or one or more C1 to C3 alkyl groups, $R^2$, $R^4$ and $R^5$ are the same or different and are a C1 to C3 alkyl group optionally having one or more halogen atoms, a halogen atom or a hydrogen atom, $R^3$ is a C1 to C6 alkyl group optionally having one or more halogen atoms, a 5- or 6-membered heterocyclic group optionally having one or more atoms or groups selected from group δ, $OR^7$, $S(O)_mR^7$, $C(O)R^7$, $CO_2R^7$, $C(O)NR^7R^8$, a cyano group, a halogen atom or a hydrogen atom, $R^6$ is a C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom, and $R^7$ and $R^8$ are the same or different and are a C1 to C6 alkyl group optionally having one or more halogen atoms or a hydrogen atom;

In the formula (1),
$A^1$ is N, $A^2$ is $NR^6$, $A^3$ is $CR^{12}$,
$R^1$ is a C1 to C6 chain hydrocarbon group optionally having one or more atoms or groups selected from group α,
$R^2$, $R^3$, $R^4$, $R^5$, $R^9$ and $R^{12}$ are a hydrogen atom,
$R^6$ is a C1 to C6 chain hydrocarbon group optionally having one or more atoms or groups selected from group γ,
$R^{10}$ and $R^{11}$, together with the carbon atoms to which they are bound, form ring J, and
the ring J represents a 5-, 6-, 7- or 8-membered non-aromatic ring (wherein the 5-, 6-, 7- or 8-membered non-aromatic ring optionally has one or more halogen atoms).

N-Oxides Represented by Formula (1A)

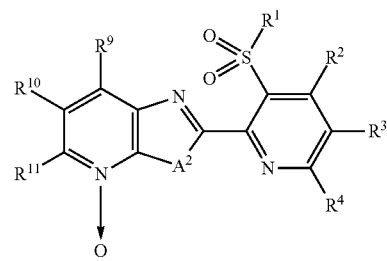

(1A)

wherein symbols represent the same meaning as described above;

N-Oxides Represented by Formula (1B)

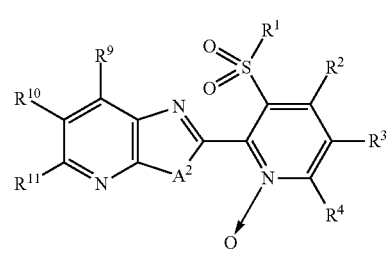

(1B)

wherein symbols represent the same meaning as described above;

N-Oxides Represented by Formula (1C)

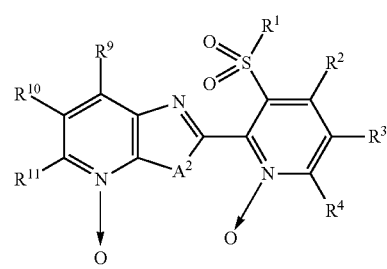

(1C)

wherein symbols represent the same meaning as described above;
N-Oxides Represented by Formula (1D)

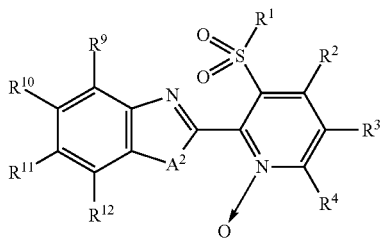

(1D)

wherein symbols represent the same meaning as described above;
N-Oxides Represented by Formula (1E)

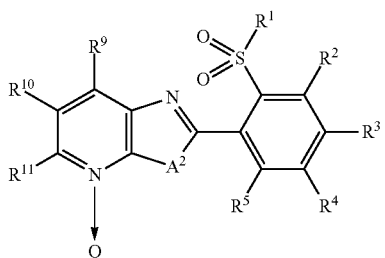

(1E)

wherein symbols represent the same meaning as described above.

Next, the method for producing the compound of the present invention will be described.

The compound of the present invention and the intermediate compound can be produced, for example, according to the following (Production Method 1) to (Production Method 14).

(Production Method 1)

The compound of the present invention wherein n is 1 or 2 in the formula (1) can be produced by oxidizing the compound of the present invention wherein n is 0.

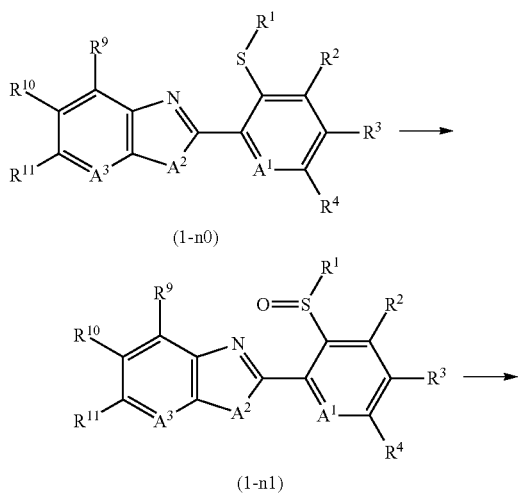

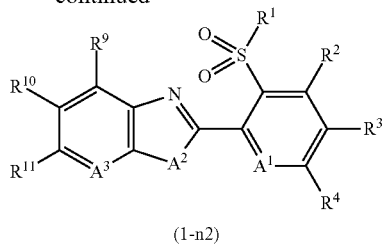

(1-n2)

In the formula, symbols represent the same meaning as in the formula (1).

The compound of the present invention (1-n1) in which n is 1 in the formula (1) can be produced by reacting the compound of the present invention (1-n0) in which n is 0 with an oxidizing agent.

The reaction is usually carried out in a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperbenzoic acid.

In the reaction, the oxidizing agent is usually used in a ratio of 1 to 3 mol, based on 1 mol of the compound of the present invention (1-n0). Preferably, the oxidizing agent is used in a ratio of 1 to 1.2 mol, based on 1 mol of the compound of the present invention (1-n0).

The reaction temperature is usually within the range of −50 to 50° C. The reaction time is usually within the range of 0.1 to 12 hours.

After completion of the reaction, the reaction mixture is subjected to post-treatment operations, for example, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to drying and concentration, whereby the compound of the present invention (1-n1) can be isolated. The isolated compound of the present invention (1-n1) also can be further purified by chromatography, recrystallization, or the like.

The compound of the present invention (1-n2) in which n is 2 in the formula (1) can be produced by reacting the compound of the present invention (1-n1) in which n is 1 with an oxidizing agent.

The reaction is usually carried out in a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid, aqueous hydrogen peroxide and oxone (registered trademark).

The reaction can be also carried out, in the presence of a catalyst, as necessary. Examples of the catalyst include tungstic acid, sodium tungstate or potassium tungstate.

In the reaction, the oxidizing agent is usually used in a ratio of 1 to 4 mol, and the catalyst is usually used in a ratio of 0.01 to 0.5 mol, based on 1 mol of the compound of the present invention (1-n1). Preferably, the oxidizing agent is used in a ratio of 1 to 2 mol, and the catalyst is used in a ratio of 0.05 to 0.2 mol, based on 1 mol of the compound of the present invention (1-n1).

The reaction temperature is usually within the range of −50 to 100° C. The reaction time is usually within the range of 0.1 to 12 hours.

After completion of the reaction, the reaction mixture is subjected to post-treatment operations, for example, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to drying and concentration, whereby the compound of the present invention (1-n2) can be isolated. The compound of the present invention (1-n2) also can be further purified by chromatography, recrystallization, or the like.

Here, during the synthesis of the compound of the present invention (1-n2) in which n is 2, an N-oxide of the compound of the present invention is produced in some cases.

In addition, the compound of the present invention (1-n2) in which n is 2 in the formula (1) can be produced by a one-step reaction (one pot), by reacting the compound of the present invention (1-n0) in which n is 0 with an oxidizing agent.

The reaction is usually carried out in a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid, aqueous hydrogen peroxide and oxone (registered trademark).

The reaction can be also carried out, in the presence of a catalyst, as necessary. Examples of the catalyst include tungstic acid, sodium tungstate and potassium tungstate.

In the reaction, the oxidizing agent is usually used in a ratio of 2 to 5 mol, and the catalyst is usually used in a ratio of 0.01 to 0.5 mol, based on 1 mol of the compound of the present invention (1-n0). Preferably, the oxidizing agent is used in a ratio of 2 to 3 mol, and the catalyst is used in a ratio of 0.05 to 0.2 mol, based on 1 mol of the compound of the present invention (1-n0).

The reaction temperature is usually within the range of 0 to 120° C. The reaction time is usually within the range of 0.1 to 12 hours.

After completion of the reaction, the reaction mixture is subjected to post-treatment operations, for example, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to drying and concentration, whereby the compound of the present invention (1-n2) can be isolated. The isolated compound of the present invention (1-n2) also can be further purified by chromatography, recrystallization, or the like.

Here, during the synthesis of the compound of the present invention (1-n2) in which n is 2, an N-oxide of the compound of the present invention is produced in some cases.
(Production Method 2-1)

Examples of the N-oxide of the compound of the present invention include the compounds of the present invention (1A) to (1E) and the like, and the compound of the present invention (1A), the compound of the present invention (1B) and/or the compound of the present invention (1C) can be produced by reacting the compound of the present invention (1-n2-A$^1$=N-A$^3$=N) wherein n is 2, A$^1$ is N, and A$^3$ is N with an oxidizing agent.

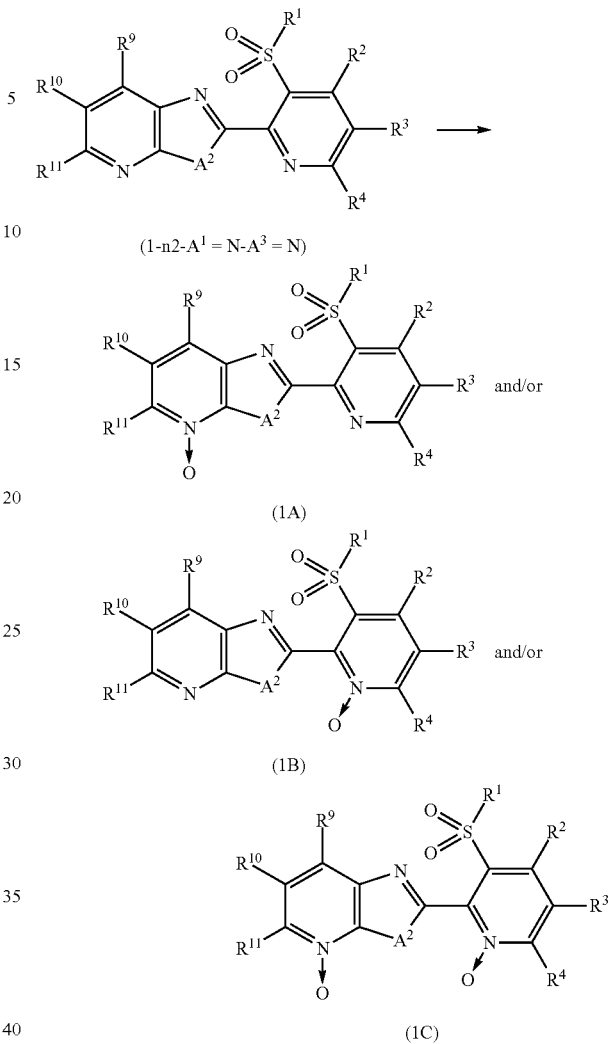

In the formula, symbols represent the same meaning as in the formula (1).

The reaction is usually carried out in a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid, aqueous hydrogen peroxide and oxone (registered trademark).

The reaction can be carried out, in the presence of a catalyst, as necessary. Examples of the catalyst include tungstic acid, sodium tungstate and potassium tungstate.

In the reaction, the oxidizing agent is usually used in a ratio of 1 to 10 mol, and the catalyst is usually used in a ratio of 0.01 to 0.5 mol, based on 1 mol of the compound of the present invention (1-n2-A$^1$=N-A$^3$=N). Preferably, the oxidizing agent is used in a ratio of 2 to 5 mol, and the catalyst is used in a ratio of 0.05 to 0.2 mol, based on 1 mol of the compound of the present invention (1-n2-A$^1$=N-A$^3$=N).

The reaction temperature is usually within the range of 20 to 120° C. The reaction time is usually within the range of 0.1 to 48 hours.

After completion of the reaction, the reaction mixture is subjected to post-treatment operations, for example, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and subjected to drying and concentration, whereby the compound of the present invention (1A), the compound of the present invention (1B) and/or the compound of the present invention (1C) can be isolated. The isolated compound of the present invention (1A), compound of the present invention (1B) and/or the compound of the present invention (1C) also can be further purified by chromatography, recrystallization, or the like.

(Production Method 2-2)

Examples of the N-oxide of the compound of the present invention wherein $A^1$ is N, and $A^3$ is $CR^{12}$, include the compound of the present invention (1D) and the like, and the compound of the present invention (1D) can be produced by oxidizing the compound of the present invention ($1\text{-}n2\text{-}A^1=N\text{-}A^3=CR^{12}$) wherein n is 2, $A^1$ is N, and $A^3$ is $CR^{12}$.

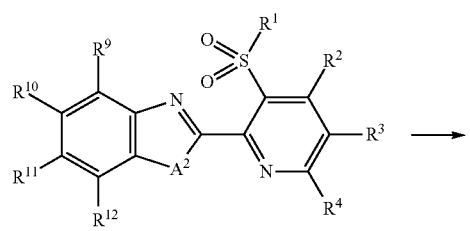

($1\text{-}n2\text{-}A^1 = N\text{-}A^3 = CR^{12}$)

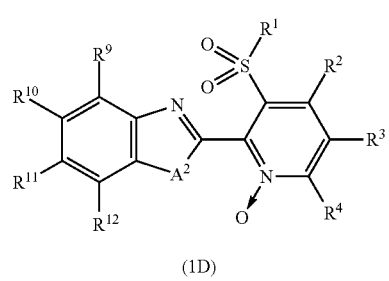

(1D)

In the formula, symbols represent the same meaning as in the formula (1).

The compound of the present invention (1D) can be produced, using the compound of the present invention ($1\text{-}n2\text{-}A^1=N\text{-}A^3=CR^{12}$) in place of the compound of the present invention ($1\text{-}n2\text{-}A^1=N\text{-}A^3=N$), in accordance with the method of Production Method 2-1.

(Production Method 2-3)

Examples of the N-oxide of the compound of the present invention wherein $A^1$ is $CR^5$, and $A^3$ is N, include the compound of the present invention (1E) and the like, and the compound of the present invention (1E) can be produced by oxidizing the compound of the present invention ($1\text{-}n2\text{-}A^1=CR^5\text{-}A^3=N$) wherein n is 2, $A^1$ is $CR^5$, and $A^3$ is N.

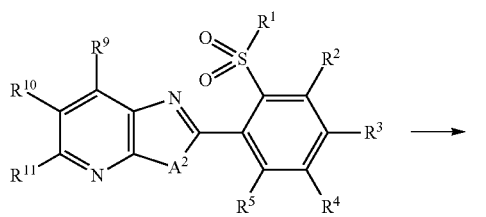

($1\text{-}n2\text{-}A^1 = CR^5\text{-}A^3 = N$)

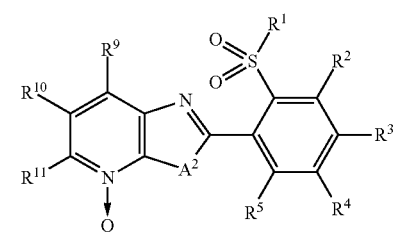

(1E)

In the formula, symbols represent the same meaning as in the formula (1).

The compound of the present invention (1E) can be produced, using the compound of the present invention ($1\text{-}n2\text{-}A^1=CR^5\text{-}A^3=N$) in place of the compound of the present invention ($1\text{-}n2\text{-}A^1=N\text{-}A^3=N$), in accordance with the method of Production Method 2-1.

(Production Method 3-1)

The compound of the present invention can be produced by reacting intermediate compound (M1) with intermediate compound (M2) to produce intermediate compound (M3), and then intramolecularly condensing the obtained intermediate compound (M3), or produced by a one-step reaction (one pot), by reacting the intermediate compound (M1) with the intermediate compound (M2).

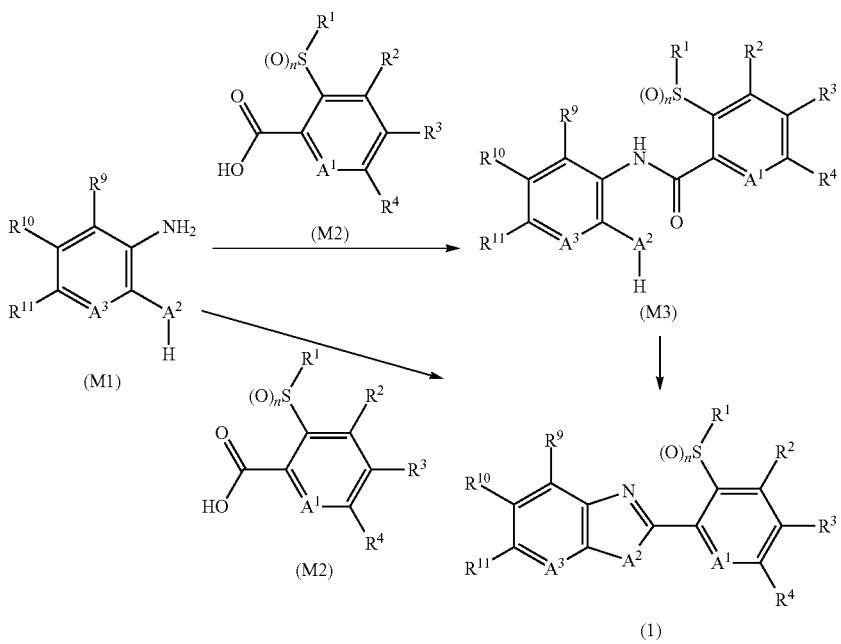

In the formula, symbols represent the same meaning as in the formula (1).

The intermediate compound (M3) can be produced by reacting the intermediate compound (M1) with the intermediate compound (M2), in the presence of a condensing agent.

The reaction is usually carried out in a solvent. Examples of the solvent include ethers such as 1,4-dioxane, diethyl ether, tetrahydrofuran (hereinafter, referred to as THF) and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as N,N-dimethylformamide (hereinafter, referred to as DMF), N-methyl pyrrolidone (hereinafter, referred to as NMP), 1,3-dimethyl-2-imidazolidinone and dimethyl sulfoxide (hereinafter, referred to as DMSO), nitrogen-containing aromatic compounds such as pyridine and quinolone, and mixtures thereof.

Examples of the condensing agent include carbodiimides such as 1-ethyl-3-(3-dimethylaminopropyl)carbodiimide hydrochloride (hereinafter, referred to as EDAC) and 1,3-dicyclohexylcarbodiimide.

The reaction can be also carried out, in the presence of a catalyst, as necessary. Examples of the catalyst include 1-hydroxybenzotriazole (hereinafter, referred to as HOBt).

In the reaction, the intermediate compound (M2) is usually used in a ratio of 0.5 to 2 mol, the condensing agent is usually used in a ratio of 1 to 5 mol, and the catalyst is usually used in a ratio of 0.01 to 1 mol, based on 1 mol of the intermediate compound (M1).

The reaction temperature is usually within the range of 0 to 120° C. The reaction time is usually within the range of 0.1 to 24 hours.

After completion of the reaction, the intermediate compound (M3) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated intermediate compound (M3) also can be further purified by recrystallization, chromatography, or the like.

The compound of the present invention (1) can be produced by intramolecular condensation of the intermediate compound (M3).

The reaction is usually carried out in a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, 1,3-dimethyl-2-imidazolidinone and DMSO, nitrogen-containing aromatic compounds such as pyridine and quinoline, and mixtures thereof.

In the reaction, a condensing agent, an acid, a base or a chlorinating agent can be used, as necessary.

Examples of the condensing agent include acetic anhydride, trifluoroacetic anhydride, EDAC, a mixture of triphenylphosphine, a base and carbon tetrachloride or carbon tetrabromide, and a mixture of triphenylphosphine and an azodiester such as diethyl azodicarboxylate.

Examples of the acid include sulfonic acids such as p-toluenesulfonic acid, carboxylic acids such as acetic acid, and polyphosphoric acid.

Examples of the base include nitrogen-containing heterocyclic compounds such as pyridine, picoline, 2,6-lutidine, 1,8-diazabicyclo[5.4.0]undec-7-ene (hereinafter, referred to as DBU) and 1,5-diazabicyclo[4.3.0]non-5-ene, tertiary amines such as triethylamine and N,N-diisopropylethylamine, and inorganic bases such as tripotassium phosphate, potassium carbonate and sodium hydride.

Examples of the chlorinating agent include phosphorus oxychloride.

In the reaction, when a condensing agent is used, the condensing agent is usually used in a ratio of 1 to 5 mol, when an acid is used, the acid is usually used in a ratio of 0.1 to 5 mol, when a base is used, the base is usually used in a ratio of 1 to 5 mol, and when a chlorinating agent is used, the chlorinating agent is usually used in a ratio of 1 to 5 mol, based on 1 mol of the intermediate compound (M3).

The reaction temperature is usually within the range of 0 to 200° C. The reaction time is usually within the range of 0.1 to 24 hours.

After completion of the reaction, the compound of the present invention (1) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated compound of the present invention (1) also can be further purified by recrystallization, chromatography, or the like.

The compound of the present invention (1) can be produced by a one-step reaction (one pot) by reacting the intermediate compound (M1) with the intermediate compound (M2), in the presence of a condensing agent.

The reaction is usually carried out in a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, 1,3-dimethyl-2-imidazolidinone and DMSO, nitrogen-containing aromatic compounds such as pyridine and quinoline, and mixtures thereof.

Examples of the condensing agent used in the reaction include carbodiimides such as EDAC and 1,3-dicyclohexylcarbodiimide, and boric acid.

The reaction can be also carried out by adding a catalyst, as necessary.

Examples of the catalyst used in the reaction include 1-hydroxybenzotriazole.

In the reaction, the intermediate compound (M2) is usually used in a ratio of 0.5 to 2 mol, the condensing agent is usually used in a ratio of 1 to 5 mol, and the catalyst is usually used in a ratio of 0.01 to 1 mol, based on 1 mol of the intermediate compound (M1).

The reaction temperature is usually within the range of 0 to 200° C. The reaction time is usually within the range of 0.1 to 24 hours.

After completion of the reaction, the compound of the present invention (1) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated compound of the present invention (1) also can be further purified by recrystallization, chromatography, or the like.

(Production Method 3-2)

The compound of the present invention (1) can be produced by reacting the intermediate compound (M1) with intermediate compound (M4) to produce the intermediate compound (M3), and then intramolecularly condensing the obtained intermediate compound (M3).

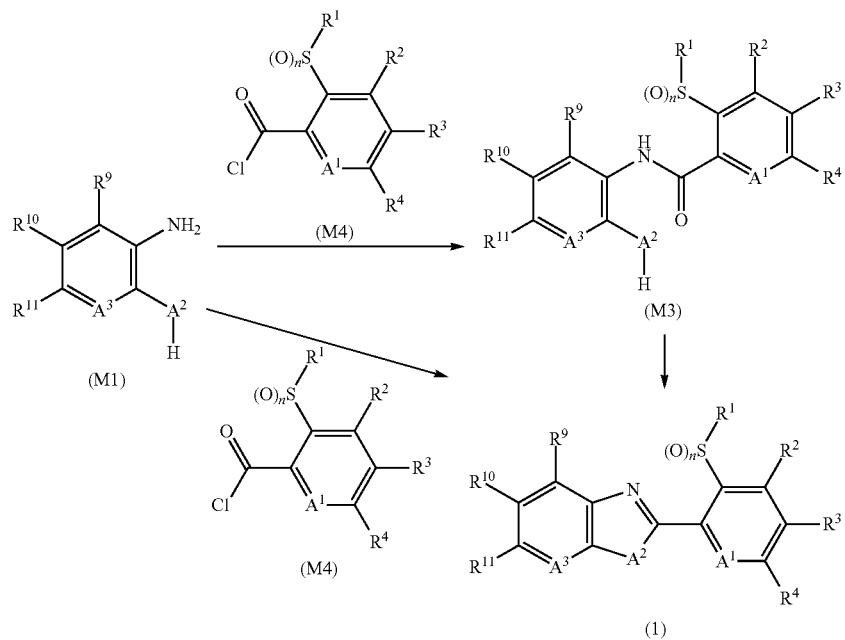

In the formula, symbols represent the same meaning as in the formula (1).

The intermediate compound (M3) can be produced by reacting the intermediate compound (M1) with the intermediate compound (M4).

When the reaction is carried out in a solvent, examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out, in the presence of a base, as necessary. Examples of the base include alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M4) is usually used in a ratio of 1 to 3 mol, and the base is usually used in a ratio of 1 to 10 mol, based on 1 mol of the intermediate compound (M1).

The reaction temperature is usually within the range of −20 to 100° C. The reaction time is usually within the range of 0.1 to 24 hours.

After completion of the reaction, the reaction mixture is subjected to post-treatment operations, for example, water is added to the reaction mixture, then the mixture is extracted with an organic solvent, and the organic layer is subjected to drying and concentration, whereby the intermediate compound (M3) can be isolated. The isolated intermediate compound (M3) also can be further purified by chromatography, recrystallization, or the like.

The compound of the present invention (1) can be produced by intramolecular condensation of the intermediate compound (M3), according to the method described in Production Method 3-1.

The compound of the present invention (1) can be produced by a one-step reaction (one pot) by reacting the intermediate compound (M1) with the intermediate compound (M4).

When the reaction is carried out in a solvent, examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, and mixtures thereof.

The reaction can be also carried out, in the presence of a base, as necessary. Examples of the base include alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M4) is usually used in a ratio of 1 to 3 mol, and the base is usually used in a ratio of 1 to 10 mol, based on 1 mol of the intermediate compound (M1).

The reaction temperature is usually within the range of 20 to 200° C. The reaction time is usually within the range of 0.1 to 24 hours.

After completion of the reaction, the reaction mixture is subjected to post-treatment operations, for example, water is added to the reaction mixture, then the mixture is extracted with an organic solvent, and the organic layer is subjected to drying and concentration, whereby the compound of the present invention (1) can be isolated. The isolated compound of the present invention (1) also can be further purified by chromatography, recrystallization, or the like.

(Production Method 4-1)

The compound of the present invention (1-$A^2$=S-$A^3$=N) wherein $A^2$ is S, and $A^3$ is N in the formula (1), can be produced by reacting intermediate compound (M5) with the intermediate compound (M2) to produce intermediate compound (M6), and then reacting the obtained intermediate compound (M6) with a sulfurizing agent.

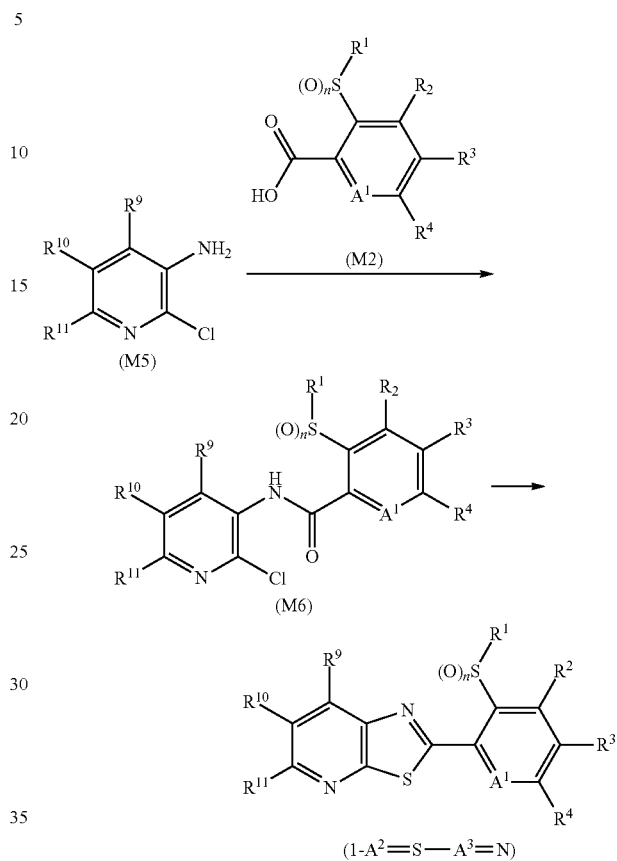

In the formula, symbols represent the same meaning as in the formula (1).

The intermediate compound (M6) can be produced by reacting the intermediate compound (M5) with the intermediate compound (M2), in the presence of a dehydration condensing agent.

The reaction is usually carried out in a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, nitrogen-containing aromatic compounds such as pyridine and quinoline, and mixtures thereof.

Examples of the dehydration condensing agent include carbodiimides such as EDAC and 1,3-dicyclohexylcarbodiimide, and BOP reagent.

In the reaction, the intermediate compound (M2) is usually used in a ratio of 1 to 3 mol, and the dehydration condensing agent is usually used in a ratio of 1 to 5 mol, based on 1 mol of the intermediate compound (M5).

The reaction temperature is usually within the range of 0 to 200° C. The reaction time is usually within the range of 0.1 to 24 hours.

After completion of the reaction, the reaction mixture is subjected to post-treatment operations, for example, water is added to the reaction mixture, then the mixture is extracted with an organic solvent, and the organic layer is subjected to drying and concentration, whereby the intermediate compound (M6) can be isolated. The isolated intermediate compound (M6) also can be further purified by chromatography, recrystallization, or the like.

The compound of the present invention (1-$A^2$=S-$A^3$=N) can be produced by reacting the intermediate compound (M6) with a sulfurizing agent.

The reaction is usually carried out in a solvent. Examples of the solvent include ethers such as 1,4-dioxane, diethyl ether, THF, tert-butyl methyl ether and diglyme, halogenated hydrocarbons such as dichloromethane, chloroform, carbon tetrachloride, 1,2-dichloroethane and chlorobenzene, aromatic hydrocarbons such as toluene, benzene and xylene, nitriles such as acetonitrile, nitrogen-containing aromatic compounds such as pyridine, picoline, lutidine and quinoline, and mixtures thereof.

Examples of the sulfurizing agent include diphosphorus pentasulfide and Lawesson's reagent (2,4-bis-(4-methoxyphenyl)-1,3-dithia-2,4-diphosphetane-2,4-disulfide).

In the reaction, the sulfurizing agent is usually used in a ratio of 1 to 3 mol, based on 1 mol of the intermediate compound (M6).

The reaction temperature is usually within the range of 0° C. to 200° C. The reaction time is usually within the range of 1 to 24 hours.

After completion of the reaction, the compound of the present invention (1-$A^2$=S-$A^3$=N) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated compound of the present invention (1-$A^2$=S-$A^3$=N) also can be further purified by recrystallization, chromatography, or the like.

(Production Method 4-2)

The compound of the present invention (1-$A^2$=S-$A^3$=N) wherein $A^2$ is S, and $A^3$ is N in the formula (1), can be produced by reacting intermediate compound (M5) with the intermediate compound (M4) to produce intermediate compound (M6), and then reacting the obtained intermediate compound (M6) with a sulfurizing agent.

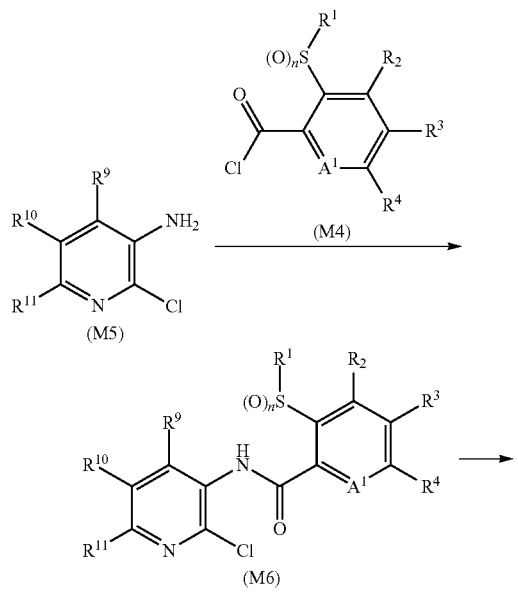

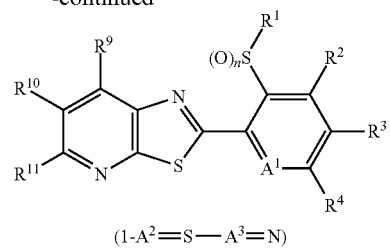

When the reaction is carried out in a solvent, examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, aprotic polar solvents such as DMF, NMP and DMSO, nitrogen-containing aromatic compounds such as pyridine and quinoline, and mixtures thereof.

The reaction can be also carried out, in the presence of a base, as necessary. Examples of the base include alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the intermediate compound (M4) is usually used in a ratio of 1 to 3 mol, and the base is usually used in a ratio of 1 to 5 mol, based on 1 mol of the intermediate compound (M5).

The reaction temperature is usually within the range of 0 to 200° C. The reaction time is usually within the range of 0.1 to 24 hours.

After completion of the reaction, the reaction mixture is subjected to post-treatment operations, for example, water is added to the reaction mixture, then the mixture is extracted with an organic solvent, and the organic layer is subjected to drying and concentration, whereby the intermediate compound (M6) can be isolated. The isolated intermediate compound (M6) also can be further purified by chromatography, recrystallization, or the like.

The compound of the present invention (1-$A^2$=S-$A^3$=N) can be produced by reacting the intermediate compound (M6) with a sulfurizing agent, according to the method described in Production Method 4-1.

(Production Method 5)

The compound of the present invention can be produced by reacting the intermediate compound (M1) with intermediate compound (M7), in the presence of an oxidizing agent.

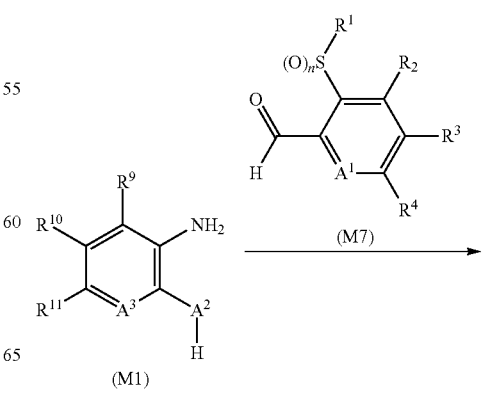

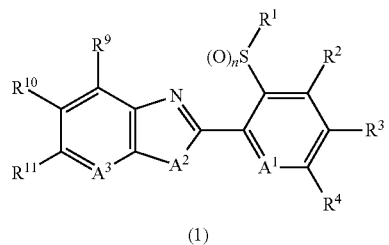

(1)

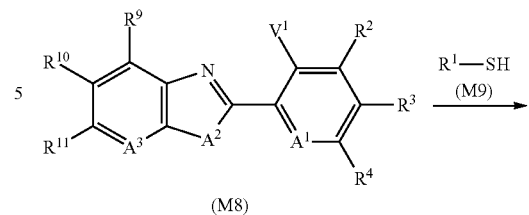

(M8)

In the formula, symbols represent the same meaning as in the formula (1).

The reaction is usually carried out in a solvent. Examples of the solvent include alcohols such as methanol and ethanol, ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, aromatic hydrocarbons such as toluene, benzene and xylene, esters such as ethyl acetate and butyl acetate, nitriles such as acetonitrile, aprotic polar solvents such as DMF, NMP, 1,3-dimethyl-2-imidazolidinone and DMSO, nitrogen-containing aromatic compounds such as pyridine and quinoline, and mixtures thereof.

Examples of the oxidizing agent include oxygen, copper (II) chloride and DDQ.

The reaction can be also carried out, in the presence of an acid, as necessary. Examples of the acid include sulfonic acids such as p-toluenesulfonic acid, carboxylic acids such as acetic acid, and polyphosphoric acid.

Also, the reaction can be carried out, in the presence of a sulfite, as necessary. Examples of the sulfite include sodium bisulfite and sodium disulfite.

In the reaction, the intermediate compound (M7) is usually used in a ratio of 1 to 2 mol, the oxidizing agent is usually used in a ratio of 1 to 5 mol, the acid is usually used in a ratio of 0.1 to 2 mol, and the sulfite is usually used in a ratio of 1 to 5 mol, based on 1 mol of the intermediate compound (M1).

The reaction temperature is usually within the range of 0 to 200° C. The reaction time is usually within the range of 0.1 to 24 hours.

After completion of the reaction, the compound of the present invention (1) can be isolated by adding the reaction mixture to water, then extracting the mixture with an organic solvent, and concentrating the organic layer; collecting by filtration a solid generated by adding the reaction mixture to water; or collecting by filtration a solid generated in the reaction mixture. The isolated compound of the present invention (1) also can be further purified by recrystallization, chromatography, or the like.

(Production Method 6)

The compound of the present invention (1-n0) wherein n is 0 in the formula (1) can be produced by reacting intermediate compound (M8) with compound (M9), in the presence of a base.

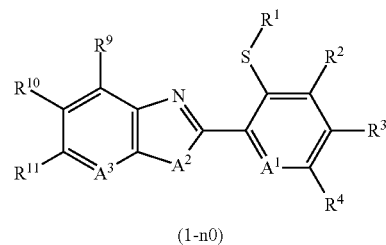

(1-n0)

In the formula, symbols represent the same meaning as described above.

The reaction is usually carried out in a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, water, and mixtures thereof.

Examples of the base include alkali metal carbonates such as sodium carbonate and potassium carbonate, and alkali metal hydrides such as sodium hydride.

In the reaction, the compound (M9) is usually used in a ratio of 1 to 10 mol, and the base is usually used in a ratio of 1 to 10 mol, based on 1 mol of the intermediate compound (M8).

The reaction temperature is usually within the range of 0 to 150° C. The reaction time is usually within the range of 0.5 to 24 hours.

After completion of the reaction, the reaction mixture is subjected to post-treatment operations, for example, the reaction mixture is extracted with an organic solvent, and the organic layer is subjected drying and concentration, whereby the compound of the present invention (1-n0) wherein n is 0 can be isolated. The isolated compound of the present invention (1-n0) wherein n is 0 also can be further purified by chromatography, recrystallization, or the like.

In the reaction, $V^1$ is preferably a fluorine atom or a chlorine atom.

(Production Method 7)

The intermediate compound (M8) can be produced by reacting the intermediate compound (M1) with intermediate compound (M10) or intermediate compound (M11) to produce intermediate compound (M12), and then intramolecularly condensing the obtained intermediate compound (M12).

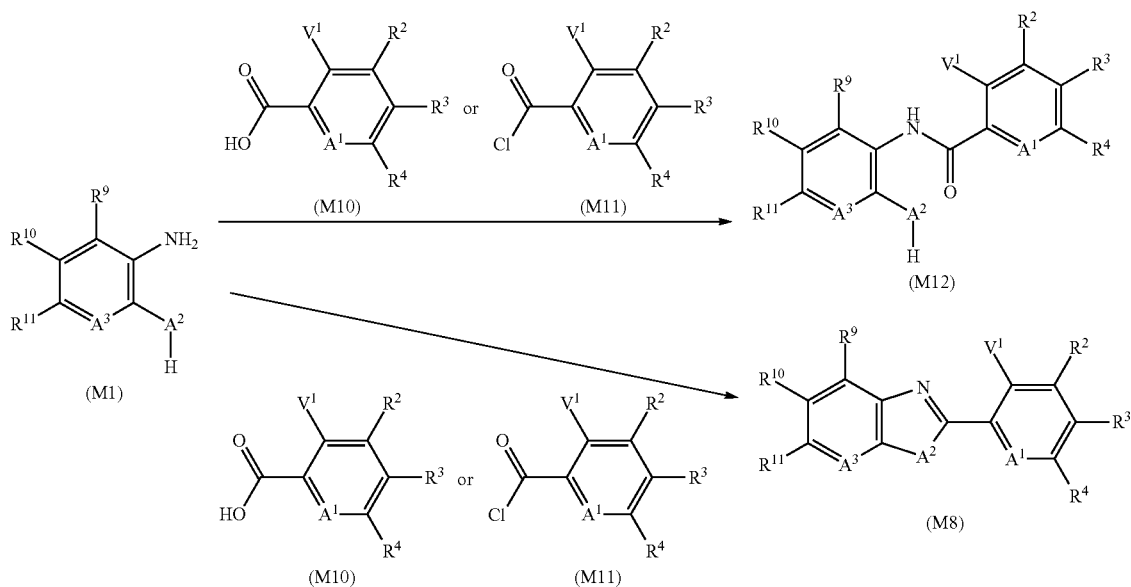

In the formula, symbols represent the same meaning as described above.

The intermediate compound (M12) can be produced, using the intermediate compound (M10) in place of the intermediate compound (M2), in accordance with the method of Production Method 3-1.

The intermediate compound (M12) can be produced, using the intermediate compound (M11) in place of the intermediate compound (M4), in accordance with the method of Production Method 3-2.

The intermediate compound (M8) can be produced, using the intermediate compound (M12) in place of the intermediate compound (M3), in accordance with the method of Production Method 3-1.

Also, the intermediate compound (M8) can be produced by a one-step reaction (one pot), using the intermediate compound (M10) in place of the intermediate compound (M2), in accordance with the method of Production Method 3-1.

Also, the intermediate compound (M8) can be produced by a one-step reaction (one pot), using the intermediate compound (M11) in place of the intermediate compound (M4), in accordance with the method of Production Method 3-2.

In these reactions, $V^1$ is preferably a fluorine atom or a chlorine atom.

(Production Method 8)

The compound of the present invention (1-n0) in which n is 0 in the formula (1) can be produced by reacting the intermediate compound (M8) with a sulfurizing agent to produce intermediate compound (M13) and reacting the intermediate compound (M13) with compound (M14), in the presence of a base.

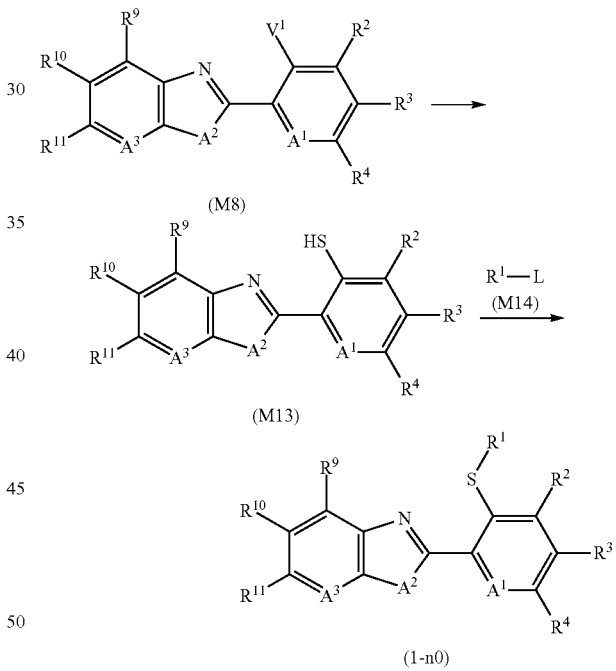

In the formula, L represents a leaving group such as a chlorine atom, a bromine atom, an iodine atom, a trifluoromethanesulfonyloxy group or a methanesulfonyloxy group, and other symbols represent the same meaning as described above.

The intermediate compound (M13) can be produced by reacting the intermediate compound (M8) with a sulfurizing agent.

The reaction is usually carried out in a solvent. Examples of the solvent include ethers such as THF, ethylene glycol dimethyl ether, MTBE and 1,4-dioxane, aromatic hydrocarbons such as toluene and xylene, nitriles such as acetonitrile, aprotic polar solvents such as DMF, NMP and DMSO, water, and mixtures thereof.

Examples of the sulfurizing agent include sodium sulfide and sodium sulfide nonahydrate.

In the reaction, the sulfurizing agent is usually used in a ratio of 1 to 2 mol, based on 1 mol of the intermediate compound (M8).

The reaction temperature is usually within the range of 0 to 150° C. The reaction time is usually within the range of 0.5 to 24 hours.

After completion of the reaction, the reaction mixture is subjected to post-treatment operations, for example, the reaction mixture is extracted with an organic solvent, and the organic layer is subjected to drying and concentration, whereby the intermediate compound (M13) can be isolated. The isolated intermediate compound (M13) also can be further purified by chromatography, recrystallization, or the like.

In the reaction, $V^1$ is preferably a fluorine atom or a chlorine atom.

The compound of the present invention (1-n0) can be produced by reacting the intermediate compound (M13) with the compound (M14), in the presence of a base.

The reaction is usually carried out in a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

In the reaction, the compound (M14) is usually used in a ratio of 1 to 10 mol, and the base is usually used in a ratio of 1 to 10 mol, based on 1 mol of the intermediate compound (M13).

The reaction temperature is usually within the range of 0 to 100° C. The reaction time is usually within the range of 0.1 to 24 hours.

After completion of the reaction, the reaction mixture is subjected to post-treatment operations, for example, the reaction mixture is extracted with an organic solvent, and the organic layer is subjected to drying and concentration, whereby the compound of the present invention (1-n0) wherein n is 0 can be isolated. The isolated compound of the present invention (1-n0) also can be further purified by chromatography, recrystallization, or the like.

(Production Method 9)

The compound of the present invention (1-$A^2$=$NR^{6a}$) wherein $A^2$ is $NR^{6a}$ in the formula (1) can be produced by reacting the compound of the present invention (1-$A^2$=NH) wherein $A^2$ is NH in the formula (1) with compound (M15), in the presence of a base.

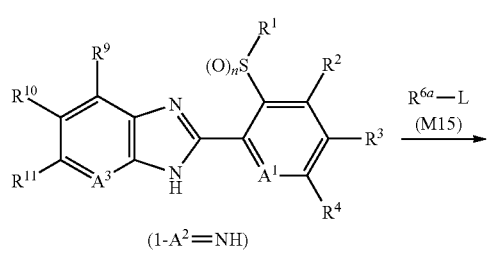

(1-$A^2$=NH)

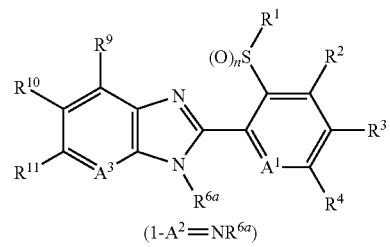

(1-$A^2$=$NR^{6a}$)

In the formula, $R^{6a}$ represents a C1 to C6 chain hydrocarbon group optionally having one or more atoms or groups selected from group γ, C(O)$R^7$ or $CO_2R^7$, and other symbols represent the same meaning as described above.

The reaction is usually carried out in a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, and mixtures thereof.

Examples of the base include hydrides of alkali metals and alkaline earth metals such as sodium hydride, potassium hydride and calcium hydride, inorganic bases such as sodium carbonate and potassium carbonate, and organic bases such as triethylamine.

In the reaction, the compound (M15) is usually used in a ratio of 1 to 5 mol, and the base is usually used in a ratio of 1 to 3 mol, based on 1 mol of the compound of the present invention (1-$A^2$=NH).

The reaction temperature is usually within the range of 0 to 100° C. The reaction time is usually within the range of 0.1 to 24 hours.

After completion of the reaction, the reaction mixture is subjected to post-treatment operations, for example, the reaction mixture is extracted with an organic solvent, and the organic layer is subjected to drying and concentration, whereby the compound of the present invention (1-$A^2$=$NR^{6a}$) can be isolated. The isolated compound of the present invention (1-$A^2$=$NR^{6a}$) also can be further purified by chromatography, recrystallization, or the like.

(Production Method 10)

The intermediate compound (M2) can be produced by hydrolyzing intermediate compound (M16). The intermediate compound (M4) can be produced by reacting the intermediate compound (M2) in the presence of a chlorinating agent.

(M16)

-continued

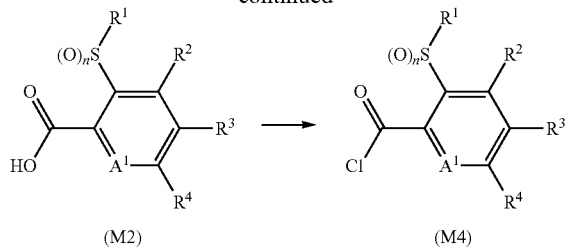

In the formula, symbols represent the same meaning as in the formula (1).

Production Method (10-1)

The intermediate compound (M2) can be produced by hydrolyzing the intermediate compound (M16).

When the hydrolysis reaction is carried out with an acid, an aqueous solution of the acid is usually used as a solvent. Examples of the acid include mineral acids such as hydrochloric acid, nitric acid, phosphoric acid and sulfuric acid, and carboxylic acids such as acetic acid and trifluoroacetic acid.

In the hydrolysis reaction, the acid is usually used in a ratio of 1 mol or more, based on 1 mol of the intermediate compound (M16).

The reaction temperature is usually within the range of 0 to 100° C. The reaction time is usually within the range of 0.1 to 24 hours.

After completion of the reaction, the reaction mixture is subjected to post-treatment operations, for example, the reaction mixture is extracted with an organic solvent, and the organic layer is subjected to drying and concentration, whereby the intermediate compound (M2) can be isolated. The isolated intermediate compound (M2) also can be further purified by chromatography, recrystallization, or the like.

When the hydrolysis reaction is carried out with a base, the reaction is usually carried out in a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide.

In the reaction, the base is usually used in a ratio of 1 to 10 mol, based on 1 mol of the intermediate compound (M16).

The reaction temperature is usually within the range of 0 to 120° C. The reaction time is usually within the range of 0.1 to 24 hours.

After completion of the reaction, the reaction mixture is subjected to post-treatment operations, for example, the reaction solution is acidified, then the reaction mixture is extracted with an organic solvent, and the organic layer is subjected to drying and concentration, whereby the intermediate compound (M2) can be isolated. The isolated intermediate compound (M2) also can be further purified by chromatography, recrystallization, or the like.

(Production Method 10-2)

The intermediate compound (M4) can be produced by reacting the intermediate compound (M2) with a chlorinating agent.

The reaction is usually carried out in a solvent. Examples of the solvent include ethers such as THF, ethylene glycol dimethyl ether, tert-butyl methyl ether and 1,4-dioxane, aromatic hydrocarbons such as toluene and xylene, aliphatic halogenated hydrocarbons such as dichloromethane and chloroform, and mixtures thereof.

Examples of the chlorinating agent include thionyl chloride, oxalyl dichloride and phosphorus oxychloride.

In the reaction, the chlorinating agent is usually used in a ratio of 1 to 5 mol, based on 1 mol of the intermediate compound (M2).

The reaction temperature is usually within the range of 0 to 100° C. The reaction time is usually within the range of 0.1 to 24 hours.

After completion of the reaction, the intermediate compound (M4) can be isolated by distilling the solvent.

(Production Method 11)

The intermediate compound (M2), the intermediate compound (M7) or the intermediate compound (M16) can be produced by reacting the intermediate compound (M10), intermediate compound (M17) or intermediate compound (M18), with the compound (M9), respectively, and oxidizing the obtained compound as necessary.

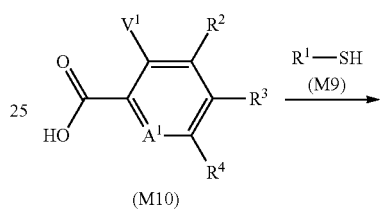

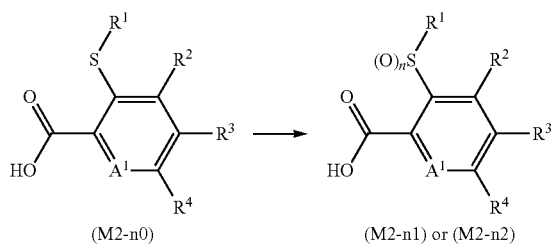

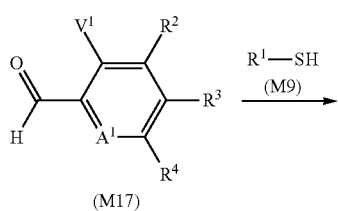

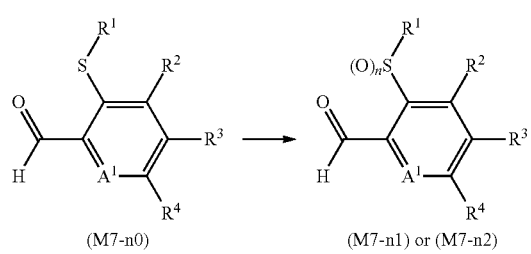

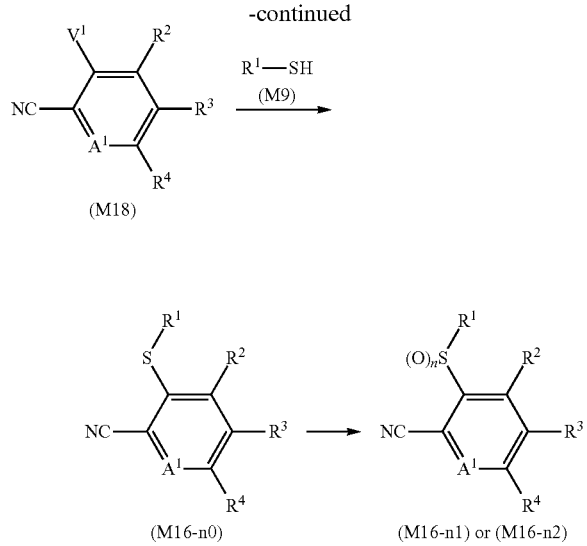

(M18)

(M16-n0) → (M16-n1) or (M16-n2)

In the formula, symbols represent the same meaning as described above.

The intermediate compound (M2-n0) in which n is 0 can be produced, using the intermediate compound (M10) in place of the intermediate compound (M8), in accordance with the method of Production Method 6.

The intermediate compound (M7-n0) in which n is 0 can be produced, using the intermediate compound (M17) in place of the intermediate compound (M8), in accordance with the method of Production Method 6.

The intermediate compound (M16-n0) in which n is 0 can be produced, using the intermediate compound (M18) in place of the intermediate compound (M8), in accordance with the method of Production Method 6.

The intermediate compound (M2-n1) or (M2-n2) in which n is 1 or 2 can be produced, using the intermediate compound (M2-n0) in which n is 0 in the intermediate compound (M2) in place of the compound of the present invention (1-n0) in which n is 0 in the formula (1), in accordance with the method of Production Method 1.

The intermediate compound (M7-n1) or (M7-n2) in which n is 1 or 2 can be produced, using the intermediate compound (M7-n0) in which n is 0 in the intermediate compound (M7) in place of the compound of the present invention (1-n0) in which n is 0 in the formula (1), in accordance with the method of Production Method 1.

The intermediate compound (M16-n1) or (M16-n2) in which n is 1 or 2 can be produced, using the intermediate compound (M16-n0) in which n is 0 in the intermediate compound (M16) in place of the compound of the present invention (1-n0) in which n is 0 in the formula (1), in accordance with the method of Production Method 1.

In the reaction, $V^1$ is preferably a fluorine atom or a chlorine atom.

(Production Method 12)

Intermediate compound (M19) is reacted with compound (M20) or intermediate compound (M21) is nitrated to produce intermediate compound (M22), and then the intermediate compound (M22) is reduced, whereby intermediate compound (M1-$A^2$=$NR^6$) in which $A^2$ is $NR^6$ in the intermediate compound (M1) can be produced.

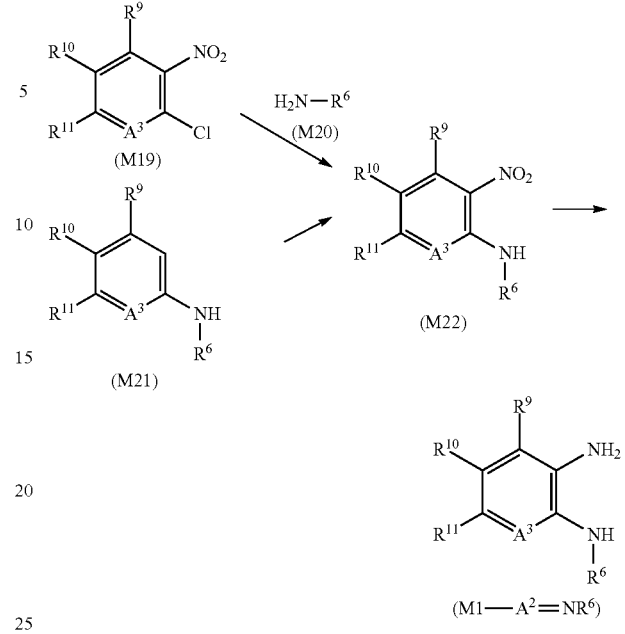

In the formula, symbols represent the same meaning as in the formula (1).

(Production Method 12-1)

Also, the intermediate compound (M22) can be produced by reacting the intermediate compound (M19) with the compound (M20).

The reaction is usually carried out in a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, aprotic polar solvents such as DMF, NMP and DMSO, water, and mixtures thereof.

The reaction can be also carried out, in the presence of a base, as necessary. Examples of the base include of alkali metal hydrides such as sodium hydride, alkali metal carbonates such as sodium carbonate and potassium carbonate, tertiary amines such as triethylamine and N,N-diisopropylethylamine, and nitrogen-containing aromatic compounds such as pyridine and 4-dimethylaminopyridine.

In the reaction, the compound (M20) is usually used in a ratio of 1 to 10 mol, and the base is usually used in a ratio of 0 to 10 mol, based on 1 mol of the intermediate compound (M19).

The reaction temperature is usually within the range of 0 to 150° C. The reaction time is usually within the range of 0.5 to 24 hours.

After completion of the reaction, the reaction mixture is subjected to post-treatment operations, for example, the reaction mixture is extracted with an organic solvent, and the organic layer is subjected to drying and concentration, whereby the intermediate compound (M22) can be isolated. The isolated intermediate compound (M22) also can be further purified by chromatography, recrystallization, or the like.

(Production Method 12-2)

The intermediate compound (M22) can be produced by reacting the intermediate compound (M21) with a nitrating agent.

The reaction is usually carried out in a solvent. Examples of the solvent include aliphatic halogenated hydrocarbons such as dichloromethane and chloroform, acetic acid, concentrated sulfuric acid, concentrated nitric acid, water, and mixtures thereof.

Examples of the nitrating agent include concentrated nitric acid.

In the reaction, the nitrating agent is usually used in a ratio of 1 to 3 mol, based on 1 mol of the intermediate compound (M21).

The reaction temperature is usually within the range of −10 to 100° C. The reaction time is usually within the range of 0.1 to 24 hours.

After completion of the reaction, the reaction mixture is subjected to post-treatment operations, for example, the reaction mixture is added to water and extracted with an organic solvent, and the organic layer is subjected to drying and concentration, whereby the intermediate compound (M22) can be isolated. The isolated intermediate compound (M22) also can be further purified by chromatography, recrystallization, or the like.

(Production Method 12-3)

Intermediate compound (M1-$A^2$=$NR^6$) in which $A^2$ is $NR^6$ in the formula (1) can be produced by reacting the intermediate compound (M22) with hydrogen, in the presence of a hydrogenation catalyst.

The reaction is carried out in a solvent, usually in a hydrogen atmosphere of 1 to 100 atmospheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include transition metal compounds such as palladium carbon, palladium hydroxide, Raney nickel, and platinum oxide.

In the reaction, the hydrogen is usually used in a ratio of 3 mol, and the hydrogenation catalyst is usually used in a ratio of 0.001 to 0.5 mol, based on 1 mol of the intermediate compound (M22).

The reaction can be also carried out, in the presence of an acid, abase or the like, as necessary. Examples of the acid include acetic acid and hydrochloric acid, and examples of the base include tertiary amines such as triethylamine and magnesium oxide.

The reaction temperature is usually within the range of −20 to 100° C. The reaction time is usually within the range of 0.1 to 24 hours.

After completion of the reaction, the reaction mixture is subjected to post-treatment operations, for example, the reaction mixture is filtered, and the filtrate is extracted with an organic solvent as necessary, and the organic layer is subjected to drying and concentration, whereby the intermediate compound (M1-$A^2$=$NR^6$) can be isolated. The isolated intermediate compound (M1-$A^2$=$NR^6$) also can be further purified by chromatography, recrystallization, or the like.

Also, the intermediate compound (M1-$A^2$=$NR^6$) can be produced by reacting the intermediate compound (M22) with a reducing agent.

The reaction is usually carried out in a solvent. Examples of the solvent include ethers such as THF, ethylene glycol dimethyl ether, tert-butyl methyl ether and 1,4-dioxane, esters such as ethyl acetate and butyl acetate, alcohols such as methanol and ethanol, aprotic polar solvents such as DMF, NMP and DMSO, and mixtures thereof.

The reaction can be carried out, for example, in the presence of a reducing agent; an acid such as hydrochloric acid and acetic acid; and water.

Examples of the reducing agent include metal powder such as iron powder and zinc powder and tin dichloride.

In the reaction, the reducing agent is usually used in a ratio of 3 to 10 mol, the acid is usually used in a ratio of 0.01 mol or more, and water is usually used in a ratio of 1 mol or more, based on 1 mol of the intermediate compound (M22).

The reaction temperature is usually within the range of 0 to 100° C. The reaction time is usually within the range of 0.1 to 24 hours.

After completion of the reaction, the reaction mixture is subjected to post-treatment operations, for example, water is added to the reaction mixture, then the mixture is extracted with an organic solvent, and the organic layer is subjected to drying and concentration, whereby the intermediate compound (M1-$A^2$=$NR^6$) can be isolated. The isolated intermediate compound (M1-$A^2$=$NR^6$) also can be purified by chromatography, recrystallization, or the like.

(Production Method 13)

Intermediate compound (M19) is hydrolyzed in the presence of abase, or intermediate compound (M23) is nitrated to produce intermediate compound (M24), and then the obtained intermediate compound (M24) is reduced, whereby intermediate compound (M1-$A^2$=O) in which $A^2$ is an oxygen atom in the intermediate compound (M1) can be produced.

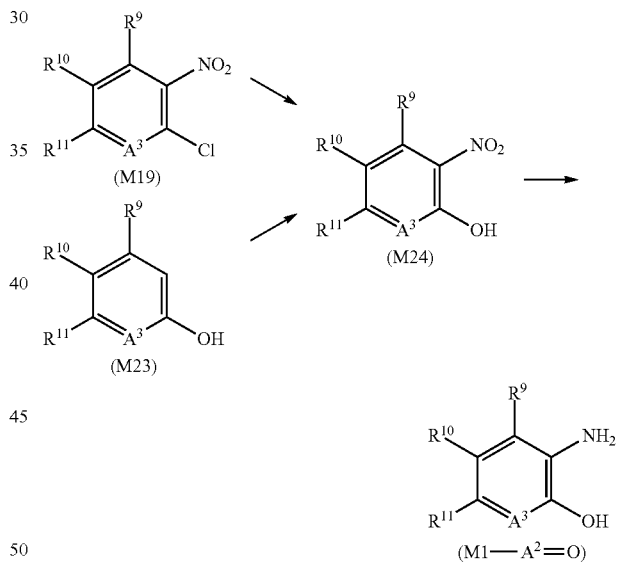

In the formula, symbols represent the same meaning as in the formula (1).

(Production Method 13-1)

The intermediate compound (M24) can be produced by hydrolyzing the intermediate compound (M19), in the presence of a base.

The reaction is usually carried out in a solvent. Examples of the solvent include ethers such as THF, ethylene glycol dimethyl ether, tert-butyl methyl ether and 1,4-dioxane, alcohols such as tert-butanol, water, and mixtures thereof.

Examples of the base include alkali metal hydroxides such as sodium hydroxide and potassium hydroxide.

In the reaction, the base is usually used in a ratio of 1 to 10 mol, based on 1 mol of the intermediate compound (M19).

The reaction temperature is usually within the range of 0 to 120° C. The reaction time is usually within the range of 0.1 to 24 hours.

After completion of the reaction, the reaction mixture is subjected to post-treatment operations, for example, the reaction solution is acidified, then the reaction mixture is extracted with an organic solvent, and the organic layer is subjected to drying and concentration, whereby the intermediate compound (M24) can be isolated. The isolated intermediate compound (M24) also can be further purified by chromatography, recrystallization, or the like.

(Production Method 13-2)

The intermediate compound (M24) can be produced, using the intermediate compound (M23) in place of the intermediate compound (M21), in accordance with the method of Production Method 12-2.

(Production Method 13-3)

The intermediate compound (M1-$A^2$=O) can be produced, using the intermediate compound (M24) in place of the intermediate compound (M22), in accordance with the method of Production Method 12-3.

(Production Method 14)

The intermediate compound (M1-$A^2$=S) in which $A^2$ is a sulfur atom in the formula (M1) can be produced by reacting the intermediate compound (M19) with thiourea in the presence of a base to produce intermediate compound (M25) and then reacting the obtained intermediate compound (M25) with a reducing agent.

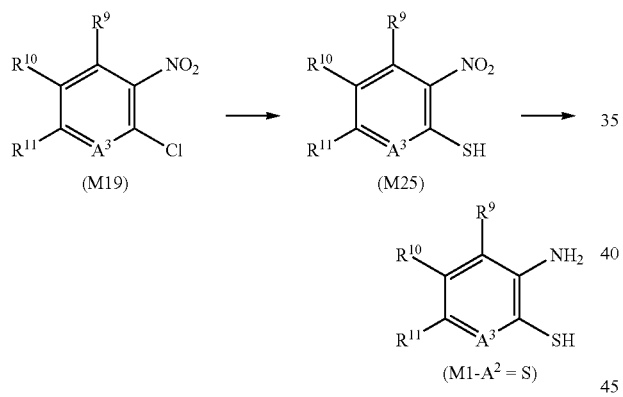

In the formula, symbols represent the same meaning as in the formula (1).

The intermediate compound (M25) can be produced by reacting the intermediate compound (M19) with thiourea, in the presence of a base.

The reaction is usually carried out in a solvent. Examples of the solvent include alcohols such as methanol and ethanol, water, and mixtures thereof.

Examples of the base include alkali metal hydroxides such as sodium hydroxide and potassium hydroxide.

In the reaction, thiourea is usually used in a ratio of 0.5 to 3 mol, and the base is usually used in a ratio of 1 to 10 mol, based on 1 mol of the intermediate compound (M19).

The reaction temperature is usually within the range of 0 to 100° C. The reaction time is usually within the range of 0.1 to 24 hours.

After completion of the reaction, the reaction mixture is subjected to post-treatment operations, for example, an acid is added to the reaction mixture, then the mixture is extracted with an organic solvent, and the organic layer is subjected to drying and concentration, whereby the intermediate compound (M25) can be isolated. The isolated intermediate compound (M25) also can be further purified by chromatography, recrystallization, or the like.

The intermediate compound (M1-$A^2$=S) can be produced, using the intermediate compound (M25) in place of the intermediate compound (M22), in accordance with the method of Production Method 12-3.

Next, specific examples of the compound of the present invention are shown below.

In the formula (1-K1-1),

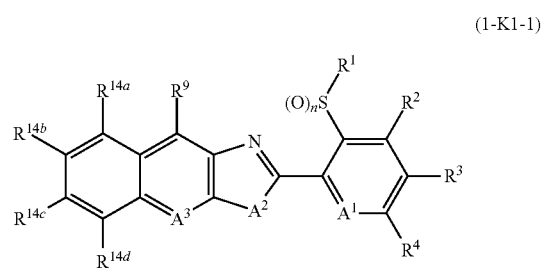

(1-K1-1)

compounds of the present invention wherein $R^{14a}$, $R^{14b}$, $R^{14c}$, $R^{14d}$, $R^2$, $R^4$ and $R^9$ are a hydrogen atom, $A^1$ is N, $A^2$ is NCH$_3$, $A^3$ is CH, and $R^1$, $R^3$ and n are as in the combinations shown in [Table 1] to [Table 3];

TABLE 1

| $R^1$ | $R^3$ | n |
|---|---|---|
| Me | H | 0 |
| Et | H | 0 |
| Pr | H | 0 |
| iPr | H | 0 |
| CF$_2$CF$_3$ | H | 0 |
| CH$_2$CH=CH$_2$ | H | 0 |
| CH$_2$C≡CH | H | 0 |
| CycPr | H | 0 |
| CH$_2$CycPr | H | 0 |
| Me | CF$_3$ | 0 |
| Et | CF$_3$ | 0 |
| Pr | CF$_3$ | 0 |
| iPr | CF$_3$ | 0 |
| CH$_2$CF$_3$ | CF$_3$ | 0 |
| CH$_2$CH=CH$_2$ | CF$_3$ | 0 |
| CH$_2$C≡CH | CF$_3$ | 0 |
| CycPr | CF$_3$ | 0 |
| CH$_2$CycPr | CF$_3$ | 0 |

TABLE 2

| $R^1$ | $R^3$ | n |
|---|---|---|
| Me | H | 1 |
| Et | H | 1 |
| Pr | H | 1 |
| iPr | H | 1 |
| CF$_2$CF$_3$ | H | 1 |
| CH$_2$CH=CH$_2$ | H | 1 |
| CH$_2$C≡CH | H | 1 |
| CycPr | H | 1 |
| CH$_2$CycPr | H | 1 |
| Me | CF$_3$ | 1 |
| Et | CF$_3$ | 1 |
| Pr | CF$_3$ | 1 |
| iPr | CF$_3$ | 1 |
| CH$_2$CF$_3$ | CF$_3$ | 1 |
| CH$_2$CH=CH$_2$ | CF$_3$ | 1 |
| CH$_2$C≡CH | CF$_3$ | 1 |

TABLE 2-continued

| $R^1$ | $R^3$ | n |
|---|---|---|
| CycPr | $CF_3$ | 1 |
| $CH_2$CycPr | $CF_3$ | 1 |

TABLE 3

| $R^1$ | $R^3$ | n |
|---|---|---|
| Me | H | 2 |
| Et | H | 2 |
| Pr | H | 2 |
| iPr | H | 2 |
| $CF_2CF_3$ | H | 2 |
| $CH_2CH{=}CH_2$ | H | 2 |
| $CH_2C{\equiv}CH$ | H | 2 |
| CycPr | H | 2 |
| $CH_2$CycPr | H | 2 |
| Me | $CF_3$ | 2 |
| Et | $CF_3$ | 2 |
| Pr | $CF_3$ | 2 |
| iPr | $CF_3$ | 2 |
| $CH_2CF_3$ | $CF_3$ | 2 |
| $CH_2CH{=}CH_2$ | $CF_3$ | 2 |
| $CH_2C{\equiv}CH$ | $CF_3$ | 2 |
| CycPr | $CF_3$ | 2 |
| $CH_2$CycPr | $CF_3$ | 2 |

(In [Table 1] to [Table 3] above, Me represents a methyl group, Et represents an ethyl group, Pr represents a propyl group, iPr represents an iso-propyl group, t-Bu represents a tert-butyl group, and CycPr represents a cyclopropyl group.)

In the formula (1-K1-1), compounds of the present invention wherein $R^{14a}$, $R^{14b}$, $R^{14c}$, $R^{14d}$, $R^2$, $R^4$ and $R^9$ are a hydrogen atom, $A^1$ is CH, $A^2$ is $NCH_3$, $A^3$ is CH, and $R^1$, $R^3$ and n are as in the combinations shown in [Table 1] to [Table 3];

In the formula (1-K1-1), compounds of the present invention wherein $R^{14a}$, $R^{14b}$, $R^{14c}$, $R^{14d}$, $R^2$, $R^4$ and $R^9$ are a hydrogen atom, $A^1$ is N, $A^2$ is S, $A^3$ is CH, and $R^1$, $R^3$ and n are as in the combinations shown in [Table 1] to [Table 3];

In the formula (1-K1-1), compounds of the present invention wherein $R^{14a}$, $R^{14b}$, $R^{14c}$, $R^{14d}$, $R^2$, $R^4$ and $R^9$ are a hydrogen atom, $A^1$ is CH, $A^2$ is S, $A^3$ is CH, and $R^1$, $R^3$ and n are as in the combinations shown in [Table 1] to [Table 3];

In the formula (1-K1-1), compounds of the present invention wherein $R^{14a}$, $R^{14b}$, $R^{14c}$, $R^{14d}$, $R^2$, $R^4$ and $R^9$ are a hydrogen atom, $A^1$ is N, $A^2$ is O, $A^3$ is CH, and $R^1$, $R^3$ and n are as in the combinations shown in [Table 1] to [Table 3];

In the formula (1-K1-1), compounds of the present invention wherein $R^{14a}$, $R^{14b}$, $R^{14c}$, $R^{14d}$, $R^2$, $R^4$ and $R^9$ are a hydrogen atom, $A^1$ is CH, $A^2$ is O, $A^3$ is CH, and $R^1$, $R^3$ and n are as in the combinations shown in [Table 1] to [Table 3];

In the formula (1-K1-2),

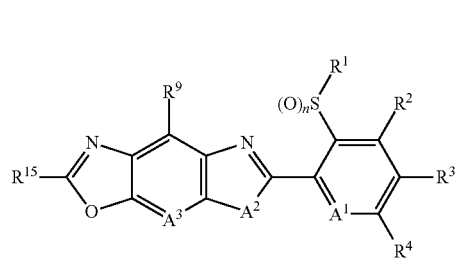

(1-K1-2)

compounds of the present invention wherein $R^2$, $R^4$ and $R^9$ are a hydrogen atom, $R^{15}$ is a trifluoromethyl group, $A^1$ is N, $A^2$ is $NCH_3$, $A^3$ is CH, and $R^1$, $R^3$ and n are as in the combinations shown in [Table 1] to [Table 3];

In the formula (1-K1-2), compounds of the present invention wherein $R^2$, $R^4$ and $R^9$ are a hydrogen atom, $R^{15}$ is a trifluoromethyl group, $A^1$ is CH, $A^2$ is $NCH_3$, $A^3$ is CH, and $R^1$, $R^3$ and n are as in the combinations shown in [Table 1] to [Table 3];

In the formula (1-K1-2), compounds of the present invention wherein $R^2$, $R^4$ and $R^9$ are a hydrogen atom, $R^{15}$ is a trifluoromethyl group, $A^1$ is N, $A^2$ is S, $A^3$ is CH, and $R^1$, $R^3$ and n are as in the combinations shown in [Table 1] to [Table 3];

In the formula (1-K1-2), compounds of the present invention wherein $R^2$, $R^4$ and $R^9$ are a hydrogen atom, $R^{15}$ is a trifluoromethyl group, $A^1$ is CH, $A^2$ is S, $A^3$ is CH, and $R^1$, $R^3$ and n are as in the combinations shown in [Table 1] to [Table 3];

In the formula (1-K1-2), compounds of the present invention wherein $R^2$, $R^4$ and $R^9$ are a hydrogen atom, $R^{15}$ is a trifluoromethyl group, $A^1$ is N, $A^2$ is O, $A^3$ is CH, and $R^1$, $R^3$ and n are as in the combinations shown in [Table 1] to [Table 3];

In the formula (1-K1-2), compounds of the present invention wherein $R^2$, $R^4$ and $R^9$ are a hydrogen atom, $R^{15}$ is a trifluoromethyl group, $A^1$ is CH, $A^2$ is O, $A^3$ is CH, and $R^1$, $R^3$ and n are as in the combinations shown in [Table 1] to [Table 3];

In the formula (1-K1-3),

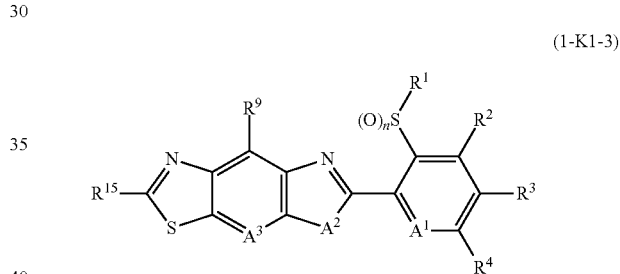

(1-K1-3)

compounds of the present invention wherein $R^2$, $R^4$ and $R^9$ are a hydrogen atom, $R^{15}$ is a trifluoromethyl group, $A^1$ is N, $A^2$ is $NCH_3$, $A^3$ is CH, and $R^1$, $R^3$ and n are as in the combinations shown in [Table 1] to [Table 3];

In the formula (1-K1-3), compounds of the present invention wherein $R^2$, $R^4$ and $R^9$ are a hydrogen atom, $R^{15}$ is a trifluoromethyl group, $A^1$ is CH, $A^2$ is $NCH_3$, $A^3$ is CH, and $R^1$, $R^3$ and n are as in the combinations shown in [Table 1] to [Table 3];

In the formula (1-K1-3), compounds of the present invention wherein $R^2$, $R^4$ and $R^9$ are a hydrogen atom, $R^{15}$ is a trifluoromethyl group, $A^1$ is N, $A^2$ is S, $A^3$ is CH, and $R^1$, $R^3$ and n are as in the combinations shown in [Table 1] to [Table 3];

In the formula (1-K1-3), compounds of the present invention wherein $R^2$, $R^4$ and $R^9$ are a hydrogen atom, $R^{15}$ is a trifluoromethyl group, $A^1$ is CH, $A^2$ is S, $A^3$ is CH, and $R^1$, $R^3$ and n are as in the combinations shown in [Table 1] to [Table 3];

In the formula (1-K1-3), compounds of the present invention wherein $R^2$, $R^4$ and $R^9$ are a hydrogen atom, $R^{15}$ is a trifluoromethyl group, $A^1$ is N, $A^2$ is O, $A^3$ is CH, and $R^1$, $R^3$ and n are as in the combinations shown in [Table 1] to [Table 3];

In the formula (1-K1-3), compounds of the present invention wherein $R^2$, $R^4$ and $R^9$ are a hydrogen atom, $R^{15}$ is a trifluoromethyl group, $A^1$ is CH, $A^2$ is O, $A^3$ is CH, and $R^1$, $R^3$ and n are as in the combinations shown in [Table 1] to [Table 3];
In the formula (1-K1-4), (1-K1-4)

$$\text{[Structure 1-K1-4]}$$

compounds of the present invention wherein $R^2$, $R^4$ and $R^9$ are a hydrogen atom, $R^{15}$ is a trifluoromethyl group, $R^{16}$ is a methyl group, $A^1$ is N, $A^2$ is $NCH_3$, $A^3$ is CH, and $R^1$, $R^3$ and n are as in the combinations shown in [Table 1] to [Table 3];
In the formula (1-K1-4), compounds of the present invention wherein $R^2$, $R^4$ and $R^9$ are a hydrogen atom, $R^{15}$ is a trifluoromethyl group, $R^{16}$ is a methyl group, $A^1$ is CH, $A^2$ is $NCH_3$, $A^3$ is CH, and $R^1$, $R^3$ and n are as in the combinations shown in [Table 1] to [Table 3];
In the formula (1-K1-4), compounds of the present invention wherein $R^2$, $R^4$ and $R^9$ are a hydrogen atom, $R^{15}$ is a trifluoromethyl group, $R^{16}$ is a methyl group, $A^1$ is N, $A^2$ is S, $A^3$ is CH, and $R^1$, $R^3$ and n are as in the combinations shown in [Table 1] to [Table 3];
In the formula (1-K1-4), compounds of the present invention wherein $R^2$, $R^4$ and $R^9$ are a hydrogen atom, $R^{15}$ is a trifluoromethyl group, $R^{16}$ is a methyl group, $A^1$ is CH, $A^2$ is S, $A^3$ is CH, and $R^1$, $R^3$ and n are as in the combinations shown in [Table 1] to [Table 3];
In the formula (1-K1-4), compounds of the present invention wherein $R^2$, $R^4$ and $R^9$ are a hydrogen atom, $R^{15}$ is a trifluoromethyl group, $R^{16}$ is a methyl group, $A^1$ is N, $A^2$ is O, $A^3$ is CH, and $R^1$, $R^3$ and n are as in the combinations shown in [Table 1] to [Table 3];
In the formula (1-K1-4), compounds of the present invention wherein $R^2$, $R^4$ and $R^9$ are a hydrogen atom, $R^{15}$ is a trifluoromethyl group, $R^{16}$ is a methyl group, $A^1$ is CH, $A^2$ is O, $A^3$ is CH, and $R^1$, $R^3$ and n are as in the combinations shown in [Table 1] to [Table 3];
In the formula (1-K1-5), (1-K1-5)

$$\text{[Structure 1-K1-5]}$$

compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];
In the formula (1-K1-5), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];
In the formula (1-K1-5), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];
In the formula (1-K1-5), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];
In the formula (1-K1-5), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];
In the formula (1-K1-5), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];
In the formula (1-K1-6), (1-K1-6)

$$\text{[Structure 1-K1-6]}$$

compounds of the present invention wherein $R^2$, $R^4$ and $R^9$ are a hydrogen atom, $R^{17a}$ and $R^{17b}$ are a fluorine atom, $A^1$ is N, $A^2$ is $NCH_3$, $A^3$ is CH, and $R^1$, $R^3$ and n are as in the combinations shown in [Table 1] to [Table 3];
In the formula (1-K1-6), compounds of the present invention wherein $R^2$, $R^4$ and $R^9$ are a hydrogen atom, $R^{17a}$ and $R^{17b}$ are a fluorine atom, $A^1$ is CH, $A^2$ is $NCH_3$, $A^3$ is CH, and $R^1$, $R^3$ and n are as in the combinations shown in [Table 1] to [Table 3];
In the formula (1-K1-6), compounds of the present invention wherein $R^2$, $R^4$ and $R^9$ are a hydrogen atom, $R^{17a}$ and $R^{17b}$ are a fluorine atom, $A^1$ is N, $A^2$ is S, $A^3$ is CH, and $R^1$, $R^3$ and n are as in the combinations shown in [Table 1] to [Table 3];
In the formula (1-K1-6), compounds of the present invention wherein $R^2$, $R^4$ and $R^9$ are a hydrogen atom, $R^{17a}$ and $R^{17b}$ are a fluorine atom, $A^1$ is CH, $A^2$ is S, $A^3$ is CH, and $R^1$, $R^3$ and n are as in the combinations shown in [Table 1] to [Table 3];
In the formula (1-K1-6), compounds of the present invention wherein $R^2$, $R^4$ and $R^9$ are a hydrogen atom, $R^{17a}$ and $R^{17b}$ are a fluorine atom, $A^1$ is N, $A^2$ is O, $A^3$ is CH, and $R^1$, $R^3$ and n are as in the combinations shown in [Table 1] to [Table 3];
In the formula (1-K1-6), compounds of the present invention wherein $R^2$, $R^4$ and $R^9$ are a hydrogen atom, $R^{17a}$ and $R^{17b}$ are a fluorine atom, $A^1$ is CH, $A^2$ is O, $A^3$ is CH, and $R^1$, $R^3$ and n are as in the combinations shown in [Table 1] to [Table 3];

In the formula (1-K1-7), (1-K1-7)

compounds of the present invention wherein $R^2$, $R^4$ and $R^9$ are a hydrogen atom, $R^{17a}$ and $R^{17b}$ are a fluorine atom, $A^1$ is N, $A^2$ is $NCH_3$, $A^3$ is CH, and $R^1$, $R^3$ and n are as in the combinations shown in [Table 1] to [Table 3];
In the formula (1-K1-7), compounds of the present invention wherein $R^2$, $R^4$ and $R^9$ are a hydrogen atom, $R^{17a}$ and $R^{17b}$ are a fluorine atom, $A^1$ is CH, $A^2$ is $NCH_3$, $A^3$ is CH, and $R^1$, $R^3$ and n are as in the combinations shown in [Table 1] to [Table 3];
In the formula (1-K1-7), compounds of the present invention wherein $R^2$, $R^4$ and $R^9$ are a hydrogen atom, $R^{17a}$ and $R^{17b}$ are a fluorine atom, $A^1$ is N, $A^2$ is S, $A^3$ is CH, and $R^1$, $R^3$ and n are as in the combinations shown in [Table 1] to [Table 3];
In the formula (1-K1-7), compounds of the present invention wherein $R^2$, $R^4$ and $R^9$ are a hydrogen atom, $R^{17a}$ and $R^{17b}$ are a fluorine atom, $A^1$ is CH, $A^2$ is S, $A^3$ is CH, and $R^1$, $R^3$ and n are as in the combinations shown in [Table 1] to [Table 3];
In the formula (1-K1-7), compounds of the present invention wherein $R^2$, $R^4$ and $R^9$ are a hydrogen atom, $R^{17a}$ and $R^{17b}$ are a fluorine atom, $A^1$ is N, $A^2$ is O, $A^3$ is CH, and $R^1$, $R^3$ and n are as in the combinations shown in [Table 1] to [Table 3];
In the formula (1-K1-7), compounds of the present invention wherein $R^2$, $R^4$ and $R^9$ are a hydrogen atom, $R^{17a}$ and $R^{17b}$ are a fluorine atom, $A^1$ is CH, $A^2$ is O, $A^3$ is CH, and $R^1$, $R^3$ and n are as in the combinations shown in [Table 1] to [Table 3];
In the formula (1-K1-8), (1-K1-8)

compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];
In the formula (1-K1-8), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];
In the formula (1-K1-8), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];
In the formula (1-K1-8), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];
In the formula (1-K1-8), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];
In the formula (1-K1-8), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];
In the formula (1-K1-9), (1-K1-9)

compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, q is 0, and $R^1$, $R^3$ and n are as in the combinations shown in [Table 1] to [Table 3];
In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, q is 0, and $R^1$, $R^3$ and n are as in the combinations shown in [Table 1] to [Table 3];
In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, q is 0, and $R^1$, $R^3$ and n are as in the combinations shown in [Table 1] to [Table 3];
In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, q is 0, and $R^1$, $R^3$ and n are as in the combinations shown in [Table 1] to [Table 3];
In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, q is 0, and $R^1$, $R^3$ and n are as in the combinations shown in [Table 1] to [Table 3];
In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, q is 0, and $R^1$, $R^3$ and n are as in the combinations shown in [Table 1] to [Table 3];
In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, q is 2, and $R^1$, $R^3$ and n are as in the combinations shown in [Table 1] to [Table 3];

In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, q is 2, and $R^1$, $R^3$ and n are as in the combinations shown in [Table 1] to [Table 3];

In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, q is 2, and $R^1$, $R^3$ and n are as in the combinations shown in [Table 1] to [Table 3];

In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, q is 2, and $R^1$, $R^3$ and n are as in the combinations shown in [Table 1] to [Table 3];

In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, q is 2, and $R^1$, $R^3$ and n are as in the combinations shown in [Table 1] to [Table 3];

In the formula (1-K1-9), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, q is 2, and $R^1$, $R^3$ and n are as in the combinations shown in [Table 1] to [Table 3];

In the formula (1-K1-10), (1-K1-10)

compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K1-10), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K1-10), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K1-10), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K1-10), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K1-10), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K1-11), (1-K1-11)

compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K1-11), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K1-11), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K1-11), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K1-11), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K1-11), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K1-12), (1-K1-12)

compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K1-12), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K1-12), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K1-12), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K1-12), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K1-12), compounds of the present invention wherein $R^2$, $R^4$ and $R^9$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K1-13), (1-K1-13)

compounds of the present invention wherein $R^2$, $R^4$ and $R^9$ are a hydrogen atom, $R^{17a}$ and $R^{17b}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K1-13), compounds of the present invention wherein $R^2$, $R^4$ and $R^9$ are a hydrogen atom, $R^{17a}$ and $R^{17b}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K1-13), compounds of the present invention wherein $R^2$, $R^4$ and $R^9$ are a hydrogen atom, $R^{17a}$ and $R^{17b}$ are a fluorine atom, $A^1$ is N, $A^2$ is S, $A^3$ is CH, and $R^1$, $R^3$ and n are as in the combinations shown in [Table 1] to [Table 3];

In the formula (1-K1-13), compounds of the present invention wherein $R^2$, $R^4$ and $R^9$ are a hydrogen atom, $R^{17a}$ and $R^{17b}$ are a fluorine atom, $A^1$ is CH, $A^2$ is S, $A^3$ is CH, and $R^1$, $R^3$ and n are as in the combinations shown in [Table 1] to [Table 3];

In the formula (1-K1-13), compounds of the present invention wherein $R^2$, $R^4$ and $R^9$ are a hydrogen atom, $R^{17a}$ and $R^{17b}$ are a fluorine atom, $A^1$ is N, $A^2$ is O, $A^3$ is CH, and $R^1$, $R^3$ and n are as in the combinations shown in [Table 1] to [Table 3];

In the formula (1-K1-13), compounds of the present invention wherein $R^2$, $R^4$ and $R^9$ are a hydrogen atom, $R^{17a}$ and $R^{17b}$ are a fluorine atom, $A^1$ is CH, $A^2$ is O, $A^3$ is CH, and $R^1$, $R^3$ and n are as in the combinations shown in [Table 1] to [Table 3];

In the formula (1-K1-14), (1-K1-14)

compounds of the present invention wherein $R^2$, $R^4$ and $R^9$ are a hydrogen atom, $A^1$ is N, $A^2$ is $NCH_3$, $A^3$ is CH, and $R^1$, $R^3$ and n are as in the combinations shown in [Table 1] to [Table 3];

In the formula (1-K1-14), compounds of the present invention wherein $R^2$, $R^4$ and $R^9$ are a hydrogen atom, $A^1$ is CH, $A^2$ is $NCH_3$, $A^3$ is CH, and $R^1$, $R^3$ and n are as in the combinations shown in [Table 1] to [Table 3];

In the formula (1-K1-14), compounds of the present invention wherein $R^2$, $R^4$ and $R^9$ are a hydrogen atom, $A^1$ is N, $A^2$ is S, $A^3$ is CH, and $R^1$, $R^3$ and n are as in the combinations shown in [Table 1] to [Table 3];

In the formula (1-K1-14), compounds of the present invention wherein $R^2$, $R^4$ and $R^9$ are a hydrogen atom, $A^1$ is CH, $A^2$ is S, $A^3$ is CH, and $R^1$, $R^3$ and n are as in the combinations shown in [Table 1] to [Table 3];

In the formula (1-K1-14), compounds of the present invention wherein $R^2$, $R^4$ and $R^9$ are a hydrogen atom, $A^1$ is N, $A^2$ is O, $A^3$ is CH, and $R^1$, $R^3$ and n are as in the combinations shown in [Table 1] to [Table 3];

In the formula (1-K1-14), compounds of the present invention wherein $R^2$, $R^4$ and $R^9$ are a hydrogen atom, $A^1$ is CH, $A^2$ is O, $A^3$ is CH, and $R^1$, $R^3$ and n are as in the combinations shown in [Table 1] to [Table 3];

In the formula (1-K1-15), (1-K1-15)

compounds of the present invention wherein $R^2$, $R^4$ and $R^9$ are a hydrogen atom, $A^1$ is N, $A^2$ is $NCH_3$, $A^3$ is CH, and $R^1$, $R^3$ and n are as in the combinations shown in [Table 1] to [Table 3];

In the formula (1-K1-15), compounds of the present invention wherein $R^2$, $R^4$ and $R^9$ are a hydrogen atom, $A^1$ is CH, $A^2$ is $NCH_3$, $A^3$ is CH, and $R^1$, $R^3$ and n are as in the combinations shown in [Table 1] to [Table 3];

In the formula (1-K1-15), compounds of the present invention wherein $R^2$, $R^4$ and $R^9$ are a hydrogen atom, $A^1$ is N, $A^2$ is S, $A^3$ is CH, and $R^1$, $R^3$ and n are as in the combinations shown in [Table 1] to [Table 3];

In the formula (1-K1-15), compounds of the present invention wherein $R^2$, $R^4$ and $R^9$ are a hydrogen atom, $A^1$ is CH, $A^2$ is S, $A^3$ is CH, and $R^1$, $R^3$ and n are as in the combinations shown in [Table 1] to [Table 3];

In the formula (1-K1-15), compounds of the present invention wherein $R^2$, $R^4$ and $R^9$ are a hydrogen atom, $A^1$ is N, $A^2$ is O, $A^3$ is CH, and $R^1$, $R^3$ and n are as in the combinations shown in [Table 1] to [Table 3];

In the formula (1-K1-15), compounds of the present invention wherein $R^2$, $R^4$ and $R^9$ are a hydrogen atom, $A^1$ is CH, $A^2$ is O, $A^3$ is CH, and $R^1$, $R^3$ and n are as in the combinations shown in [Table 1] to [Table 3];

In the formula (1-K1-16), $$\text{(1-K1-16)}$$

compounds of the present invention wherein $R^2$, $R^4$ and $R^9$ are a hydrogen atom, $R^{13}$ is a methyl group, $A^1$ is N, $A^2$ is $NCH_3$, $A^3$ is CH, and $R^1$, $R^3$ and n are as in the combinations shown in [Table 1] to [Table 3];

In the formula (1-K1-16), compounds of the present invention wherein $R^2$, $R^4$ and $R^9$ are a hydrogen atom, $R^{13}$ is a methyl group, $A^1$ is CH, $A^2$ is $NCH_3$, $A^3$ is CH, and $R^1$, $R^3$ and n are as in the combinations shown in [Table 1] to [Table 3];

In the formula (1-K1-16), compounds of the present invention wherein $R^2$, $R^4$ and $R^9$ are a hydrogen atom, $R^{13}$ is a methyl group, $A^1$ is N, $A^2$ is S, $A^3$ is CH, and $R^1$, $R^3$ and n are as in the combinations shown in [Table 1] to [Table 3];

In the formula (1-K1-16), compounds of the present invention wherein $R^2$, $R^4$ and $R^9$ are a hydrogen atom, $R^{13}$ is a methyl group, $A^1$ is CH, $A^2$ is S, $A^3$ is CH, and $R^1$, $R^3$ and n are as in the combinations shown in [Table 1] to [Table 3];

In the formula (1-K1-16), compounds of the present invention wherein $R^2$, $R^4$ and $R^9$ are a hydrogen atom, $R^{13}$ is a methyl group, $A^1$ is N, $A^2$ is O, $A^3$ is CH, and $R^1$, $R^3$ and n are as in the combinations shown in [Table 1] to [Table 3];

In the formula (1-K1-16), compounds of the present invention wherein $R^2$, $R^4$ and $R^9$ are a hydrogen atom, $R^{13}$ is a methyl group, $A^1$ is CH, $A^2$ is O, $A^3$ is CH, and $R^1$, $R^3$ and n are as in the combinations shown in [Table 1] to [Table 3];

In the formula (1-K2-1), $$\text{(1-K2-1)}$$

compounds of the present invention wherein $R^{14a}$, $R^{14b}$, $R^{14c}$ and $R^{14d}$, $R^2$, $R^4$ and $R^{11}$ are a hydrogen atom, $A^1$ is N, $A^2$ is $NCH_3$, $A^3$ is CH, and $R^1$, $R^3$ and n are as in the combinations shown in [Table 1] to [Table 3];

In the formula (1-K2-1), compounds of the present invention wherein $R^{14a}$, $R^{14b}$, $R^{14c}$, $R^{14d}$, $R^2$, $R^4$ and $R^{11}$ are a hydrogen atom, $A^1$ is CH, $A^2$ is $NCH_3$, $A^3$ is CH, and $R^1$, $R^3$ and n are as in the combinations shown in [Table 1] to [Table 3];

In the formula (1-K2-1), compounds of the present invention wherein $R^{14a}$, $R^{14b}$, $R^{14c}$, $R^{14d}$, $R^2$, $R^4$ and $R^{11}$ are a hydrogen atom, $A^1$ is N, $A^2$ is S, $A^3$ is CH, and $R^1$, $R^3$ and n are as in the combinations shown in [Table 1] to [Table 3];

In the formula (1-K2-1), compounds of the present invention wherein $R^{14a}$, $R^{14b}$, $R^{14c}$, $R^{14d}$, $R^2$, $R^4$ and $R^{11}$ are a hydrogen atom, $A^1$ is CH, $A^2$ is S, $A^3$ is CH, and $R^1$, $R^3$ and n are as in the combinations shown in [Table 1] to [Table 3];

In the formula (1-K2-1), compounds of the present invention wherein $R^{14a}$, $R^{14b}$, $R^{14c}$, $R^{14d}$, $R^2$, $R^4$ and $R^{11}$ are a hydrogen atom, $A^1$ is N, $A^2$ is O, $A^3$ is CH, and $R^1$, $R^3$ and n are as in the combinations shown in [Table 1] to [Table 3];

In the formula (1-K2-1), compounds of the present invention wherein $R^{14a}$, $R^{14b}$, $R^{14c}$, $R^{14d}$, $R^2$, $R^4$ and $R^{11}$ are a hydrogen atom, $A^1$ is CH, $A^2$ is O, $A^3$ is CH, and $R^1$, $R^3$ and n are as in the combinations shown in [Table 1] to [Table 3];

In the formula (1-K2-2), $$\text{(1-K2-2)}$$

compounds of the present invention wherein $R^2$, $R^4$ and $R^{11}$ are a hydrogen atom, $R^{15}$ is a trifluoromethyl group, $A^1$ is N, $A^2$ is $NCH_3$, $A^3$ is CH, and $R^1$, $R^3$ and n are as in the combinations shown in [Table 1] to [Table 3];

In the formula (1-K2-2), compounds of the present invention wherein $R^2$, $R^4$ and $R^{11}$ are a hydrogen atom, $R^{15}$ is a trifluoromethyl group, $A^1$ is CH, $A^2$ is $NCH_3$, $A^3$ is CH, and $R^1$, $R^3$ and n are as in the combinations shown in [Table 1] to [Table 3];

In the formula (1-K2-2), compounds of the present invention wherein $R^2$, $R^4$ and $R^{11}$ are a hydrogen atom, $R^{15}$ is a trifluoromethyl group, $A^1$ is N, $A^2$ is S, $A^3$ is CH, and $R^1$, $R^3$ and n are as in the combinations shown in [Table 1] to [Table 3];

In the formula (1-K2-2), compounds of the present invention wherein $R^2$, $R^4$ and $R^{11}$ are a hydrogen atom, $R^{15}$ is a trifluoromethyl group, $A^1$ is CH, $A^2$ is S, $A^3$ is CH, and $R^1$, $R^3$ and n are as in the combinations shown in [Table 1] to [Table 3];

In the formula (1-K2-2), compounds of the present invention wherein $R^2$, $R^4$ and $R^{11}$ are a hydrogen atom, $R^{15}$ is a trifluoromethyl group, $A^1$ is N, $A^2$ is O, $A^3$ is CH, and $R^1$, $R^3$ and n are as in the combinations shown in [Table 1] to [Table 3];

In the formula (1-K2-2), compounds of the present invention wherein $R^2$, $R^4$ and $R^{11}$ are a hydrogen atom, $R^{15}$ is a trifluoromethyl group, $A^1$ is CH, $A^2$ is O, $A^3$ is CH, and $R^1$, $R^3$ and n are as in the combinations shown in [Table 1] to [Table 3];

In the formula (1-K2-3), $$\text{(1-K2-3)}$$

compounds of the present invention wherein $R^2$, $R^4$ and $R^{11}$ are a hydrogen atom, $R^{15}$ is a trifluoromethyl group, $A^1$ is N, $A^2$ is $NCH_3$, $A^3$ is CH, and $R^1$, $R^3$ and n are as in the combinations shown in [Table 1] to [Table 3];

In the formula (1-K2-3), compounds of the present invention wherein $R^2$, $R^4$ and $R^{11}$ are a hydrogen atom, $R^{15}$ is a trifluoromethyl group, $A^1$ is CH, $A^2$ is $NCH_3$, $A^3$ is CH, and $R^1$, $R^3$ and n are as in the combinations shown in [Table 1] to [Table 3];

In the formula (1-K2-3), compounds of the present invention wherein $R^2$, $R^4$ and $R^{11}$ are a hydrogen atom, $R^{15}$ is a trifluoromethyl group, $A^1$ is N, $A^2$ is S, $A^3$ is CH, and $R^1$, $R^3$ and n are as in the combinations shown in [Table 1] to [Table 3];

In the formula (1-K2-3), compounds of the present invention wherein $R^2$, $R^4$ and $R^{11}$ are a hydrogen atom, $R^{15}$ is a trifluoromethyl group, $A^1$ is CH, $A^2$ is S, $A^3$ is CH, and $R^1$, $R^3$ and n are as in the combinations shown in [Table 1] to [Table 3];

In the formula (1-K2-3), compounds of the present invention wherein $R^2$, $R^4$ and $R^{11}$ are a hydrogen atom, $R^{15}$ is a trifluoromethyl group, $A^1$ is N, $A^2$ is O, $A^3$ is CH, and $R^1$, $R^3$ and n are as in the combinations shown in [Table 1] to [Table 3];

In the formula (1-K2-3), compounds of the present invention wherein $R^2$, $R^4$ and $R^{11}$ are a hydrogen atom, $R^{15}$ is a trifluoromethyl group, $A^1$ is CH, $A^2$ is O, $A^3$ is CH, and $R^1$, $R^3$ and n are as in the combinations shown in [Table 1] to [Table 3];

In the formula (1-K2-4), $$\text{(1-K2-4)}$$

compounds of the present invention wherein $R^2$, $R^4$ and $R^{11}$ are a hydrogen atom, $R^{15}$ is a trifluoromethyl group, $R^{16}$ is a methyl group, $A^1$ is N, $A^2$ is $NCH_3$, $A^3$ is CH, and $R^1$, $R^3$ and n are as in the combinations shown in [Table 1] to [Table 3];

In the formula (1-K2-4), compounds of the present invention wherein $R^2$, $R^4$ and $R^{11}$ are a hydrogen atom, $R^{15}$ is a trifluoromethyl group, $R^{16}$ is a methyl group, $A^1$ is CH, $A^2$ is $NCH_3$, $A^3$ is CH, and $R^1$, $R^3$ and n are as in the combinations shown in [Table 1] to [Table 3];

In the formula (1-K2-4), compounds of the present invention wherein $R^2$, $R^4$ and $R^{11}$ are a hydrogen atom, $R^{15}$ is a trifluoromethyl group, $R^{16}$ is a methyl group, $A^1$ is N, $A^2$ is S, $A^3$ is CH, and $R^1$, $R^3$ and n are as in the combinations shown in [Table 1] to [Table 3];

In the formula (1-K2-4), compounds of the present invention wherein $R^2$, $R^4$ and $R^{11}$ are a hydrogen atom, $R^{15}$ is a trifluoromethyl group, $R^{16}$ is a methyl group, $A^1$ is CH, $A^2$ is S, $A^3$ is CH, and $R^1$, $R^3$ and n are as in the combinations shown in [Table 1] to [Table 3];

In the formula (1-K2-4), compounds of the present invention wherein $R^2$, $R^4$ and $R^{11}$ are a hydrogen atom, $R^{15}$ is a trifluoromethyl group, $R^{16}$ is a methyl group, $A^1$ is N, $A^2$ is O, $A^3$ is CH, and $R^1$, $R^3$ and n are as in the combinations shown in [Table 1] to [Table 3];

In the formula (1-K2-4), compounds of the present invention wherein $R^2$, $R^4$ and $R^{11}$ are a hydrogen atom, $R^{15}$ is a trifluoromethyl group, $R^{16}$ is a methyl group, $A^1$ is CH, $A^2$ is O, $A^3$ is CH, and $R^1$, $R^3$ and n are as in the combinations shown in [Table 1] to [Table 3];

In the formula (1-K2-5), $$\text{(1-K2-5)}$$

compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-5), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-5), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K2-5), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-5), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K2-5), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-6), (1-K2-6)

[Chemical structure]

compounds of the present invention wherein $R^2$, $R^4$ and $R^{11}$ are a hydrogen atom, $R^{17a}$ and $R^{17b}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-6), compounds of the present invention wherein $R^2$, $R^4$ and $R^{11}$ are a hydrogen atom, $R^{17a}$ and $R^{17b}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-6), compounds of the present invention wherein $R^2$, $R^4$ and $R^{11}$ are a hydrogen atom, $R^{17a}$ and $R^{17b}$ are a fluorine atom, $A^1$ is N, $A^2$ is S, $A^3$ is CH, and $R^1$, $R^3$ and n are as in the combinations shown in [Table 1] to [Table 3];

In the formula (1-K2-6), compounds of the present invention wherein $R^2$, $R^4$ and $R^{11}$ are a hydrogen atom, $R^{17a}$ and $R^{17b}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-6), compounds of the present invention wherein $R^2$, $R^4$ and $R^{11}$ are a hydrogen atom, $R^{17a}$ and $R^{17b}$ are a fluorine atom, $A^1$ is N, $A^2$ is O, $A^3$ is CH, and $R^1$, $R^3$ and n are as in the combinations shown in [Table 1] to [Table 3];

In the formula (1-K2-6), compounds of the present invention wherein $R^2$, $R^4$ and $R^{11}$ are a hydrogen atom, $R^{17a}$ and $R^{17b}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-7), (1-K2-7)

[Chemical structure]

compounds of the present invention wherein $R^2$, $R^4$ and $R^{11}$ are a hydrogen atom, $R^{17a}$ and $R^{17b}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-7), compounds of the present invention wherein $R^2$, $R^4$ and $R^{11}$ are a hydrogen atom, $R^{17a}$ and $R^{17b}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-7), compounds of the present invention wherein $R^2$, $R^4$ and $R^{11}$ are a hydrogen atom, $R^{17a}$ and $R^{17b}$ are a fluorine atom, $A^1$ is N, $A^2$ is S, $A^3$ is CH, and $R^1$, $R^3$ and n are as in the combinations shown in [Table 1] to [Table 3];

In the formula (1-K2-7), compounds of the present invention wherein $R^2$, $R^4$ and $R^{11}$ are a hydrogen atom, $R^{17a}$ and $R^{17b}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-7), compounds of the present invention wherein $R^2$, $R^4$ and $R^{11}$ are a hydrogen atom, $R^{17a}$ and $R^{17b}$ are a fluorine atom, $A^1$ is N, $A^2$ is O, $A^3$ is CH, and $R^1$, $R^3$ and n are as in the combinations shown in [Table 1] to [Table 3];

In the formula (1-K2-7), compounds of the present invention wherein $R^2$, $R^4$ and $R^{11}$ are a hydrogen atom, $R^{17a}$ and $R^{17b}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-8), (1-K2-8)

[Chemical structure]

compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-8), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-8), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K2-8), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-8), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K2-8), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-9), (1-K2-9)

compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, q is 0, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, q is 0, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, q is 0, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, q is 0, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, q is 0, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, q is 0, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, q is 2, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, q is 2, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, q is 2, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, q is 2, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, q is 2, and $R^1$, $R^3$ and n are as in the combinations shown in [Table 1] to [Table 3];

In the formula (1-K2-9), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, q is 2, and $R^1$, $R^3$ and n are as in the combinations shown in [Table 1] to [Table 3];

In the formula (1-K2-10), (1-K2-10)

compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-10), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-10), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K2-10), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-10), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K2-10), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-11), (1-K2-11)

compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-11), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-11), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K2-11), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-11), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K2-11), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-12), (1-K2-12)

compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-12), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-12), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is S, $A^3$ is CH, and $R^1$, $R^3$ and n are as in the combinations shown in [Table 1] to [Table 3];

In the formula (1-K2-12), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-12), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is N, $A^2$ is O, $A^3$ is CH, and $R^1$, $R^3$ and n are as in the combinations shown in [Table 1] to [Table 3];

In the formula (1-K2-12), compounds of the present invention wherein $R^2$, $R^4$ and $R^{11}$ are a hydrogen atom, $R^{17a}$, $R^{17b}$, $R^{17c}$ and $R^{17d}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-13), (1-K2-13)

compounds of the present invention wherein $R^2$, $R^4$ and $R^{11}$ are a hydrogen atom, $R^{17a}$ and $R^{17b}$ are a fluorine atom, $A^1$ is N, $A^2$ is $NCH_3$, $A^3$ is CH, and $R^1$, $R^3$ and n are as in the combinations shown in [Table 1] to [Table 3];

In the formula (1-K2-13), compounds of the present invention wherein $R^2$, $R^4$ and $R^{11}$ are a hydrogen atom, $R^{17a}$ and $R^{17b}$ are a fluorine atom, $A^1$ is CH, $A^2$ is $NCH_3$, $A^3$ is CH, and $R^1$, $R^3$ and n are as in the combinations shown in [Table 1] to [Table 3];

In the formula (1-K2-13), compounds of the present invention wherein $R^2$, $R^4$ and $R^{11}$ are a hydrogen atom, $R^{17a}$ and $R^{17b}$ are a fluorine atom, $A^1$ is N, $A^2$ is S, $A^3$ is CH, and $R^1$, $R^3$ and n are as in the combinations shown in [Table 1] to [Table 3];

In the formula (1-K2-13), compounds of the present invention wherein $R^2$, $R^4$ and $R^{11}$ are a hydrogen atom, $R^{17a}$ and $R^{17b}$ are a fluorine atom, $A^1$ is CH, $A^2$ is S, $A^3$ is CH, and $R^1$, $R^3$ and n are as in the combinations shown in [Table 1] to [Table 3];

In the formula (1-K2-13), compounds of the present invention wherein $R^2$, $R^4$ and $R^{11}$ are a hydrogen atom, $R^{17a}$ and $R^{17b}$ are a fluorine atom, $A^1$ is N, $A^2$ is O, $A^3$ is CH, and $R^1$, $R^3$ and n are as in the combinations shown in [Table 1] to [Table 3];

In the formula (1-K2-13), compounds of the present invention wherein $R^2$, $R^4$ and $R^{11}$ are a hydrogen atom, $R^{17a}$ and $R^{17b}$ are a fluorine atom, $A^1$ is CH, $A^2$ is O, $A^3$ is CH, and $R^1$, $R^3$ and n are as in the combinations shown in [Table 1] to [Table 3];

In the formula (1-K2-14), (1-K2-14)

compounds of the present invention wherein $R^2$, $R^4$ and $R^{11}$ are a hydrogen atom, $A^1$ is N, $A^2$ is $NCH_3$, $A^3$ is CH, and $R^1$, $R^3$ and n are as in the combinations shown in [Table 1] to [Table 3];

In the formula (1-K2-14), compounds of the present invention wherein $R^2$, $R^4$ and $R^{11}$ are a hydrogen atom, $A^1$ is CH, $A^2$ is $NCH_3$, $A^3$ is CH, and $R^1$, $R^3$ and n are as in the combinations shown in [Table 1] to [Table 3];

In the formula (1-K2-14), compounds of the present invention wherein $R^2$, $R^4$ and $R^{11}$ are a hydrogen atom, $A^1$ is N, $A^2$ is S, is CH, and $R^1$, $R^3$ and n areas in the combinations shown in [Table 1] to [Table 3];
In the formula (1-K2-14), compounds of the present invention wherein $R^2$, $R^4$ and $R^{11}$ are a hydrogen atom, $A^1$ is CH, $A^2$ is S, $A^3$ is CH, and $R^1$, $R^3$ and n are as in the combinations shown in [Table 1] to [Table 3];
In the formula (1-K2-14), compounds of the present invention wherein $R^2$, $R^4$ and $R^{11}$ are a hydrogen atom, $A^1$ is N, $A^2$ is O, $A^3$ is CH, and $R^1$, $R^3$ and n areas in the combinations shown in [Table 1] to [Table 3];
In the formula (1-K2-14), compounds of the present invention wherein $R^2$, $R^4$ and $R^{11}$ are a hydrogen atom, $A^1$ is CH, $A^2$ is O, $A^3$ is CH, and $R^1$, $R^3$ and n are as in the combinations shown in [Table 1] to [Table 3];
In the formula (1-K2-15), (1-K2-15)

compounds of the present invention wherein $R^2$, $R^4$ and $R^{11}$ are a hydrogen atom, $A^1$ is N, $A^2$ is $NCH_3$, $A^3$ is CH, and $R^1$, $R^3$ and n are as in the combinations shown in [Table 1] to [Table 3];
In the formula (1-K2-15), compounds of the present invention wherein $R^2$, $R^4$ and $R^{11}$ are a hydrogen atom, $A^1$ is CH, $A^2$ is $NCH_3$, $A^3$ is CH, and $R^1$, $R^3$ and n are as in the combinations shown in [Table 1] to [Table 3];
In the formula (1-K2-15), compounds of the present invention wherein $R^2$, $R^4$ and $R^{11}$ are a hydrogen atom, $A^1$ is N, $A^2$ is S, $A^3$ is CH, and $R^1$, $R^3$ and n are as in the combinations shown in [Table 1] to [Table 3];
In the formula (1-K2-15), compounds of the present invention wherein $R^2$, $R^4$ and $R^{11}$ are a hydrogen atom, $A^1$ is CH, $A^2$ is S, $A^3$ is CH, and $R^1$, $R^3$ and n are as in the combinations shown in [Table 1] to [Table 3];
In the formula (1-K2-15), compounds of the present invention wherein $R^2$, $R^4$ and $R^{11}$ are a hydrogen atom, $A^1$ is N, $A^2$ is O, $A^3$ is CH, and $R^1$, $R^3$ and n are as in the combinations shown in [Table 1] to [Table 3];
In the formula (1-K2-15), compounds of the present invention wherein $R^2$, $R^4$ and $R^{11}$ are a hydrogen atom, $A^1$ is CH, $A^2$ is O, $A^3$ is CH, and $R^1$, $R^3$ and n are as in the combinations shown in [Table 1] to [Table 3];
In the formula (1-K2-16), (1-K2-16)

compounds of the present invention wherein $R^2$, $R^4$ and $R^{11}$ are a hydrogen atom, $R^{13}$ is a methyl group, $A^1$ is N, $A^2$ is $NCH_3$, $A^3$ is CH, and $R^1$, $R^3$ and n are as in the combinations shown in [Table 1] to [Table 3];
In the formula (1-K2-16), compounds of the present invention wherein $R^2$, $R^4$ and $R^{11}$ are a hydrogen atom, $R^{13}$ is a methyl group, $A^1$ is CH, $A^2$ is $NCH_3$, $A^3$ is CH, and $R^1$, $R^3$ and n are as in the combinations shown in [Table 1] to [Table 3];
In the formula (1-K2-16), compounds of the present invention wherein $R^2$, $R^4$ and $R^{11}$ are a hydrogen atom, $R^{13}$ is a methyl group, $A^1$ is N, $A^2$ is S, $A^3$ is CH, and $R^1$, $R^3$ and n are as in the combinations shown in [Table 1] to [Table 3];
In the formula (1-K2-16), compounds of the present invention wherein $R^2$, $R^4$ and $R^{11}$ are a hydrogen atom, $R^{13}$ is a methyl group, $A^1$ is CH, $A^2$ is S, $A^3$ is CH, and $R^1$, $R^3$ and n are as in the combinations shown in [Table 1] to [Table 3];
In the formula (1-K2-16), compounds of the present invention wherein $R^2$, $R^4$ and $R^{11}$ are a hydrogen atom, $R^{13}$ is a methyl group, $A^1$ is N, $A^2$ is O, $A^3$ is CH, and $R^1$, $R^3$ and n are as in the combinations shown in [Table 1] to [Table 3];
In the formula (1-K2-16), compounds of the present invention wherein $R^2$, $R^4$ and $R^{11}$ are a hydrogen atom, $R^{13}$ is a methyl group, $A^1$ is CH, $A^2$ is O, $A^3$ is CH, and $R^1$, $R^3$ and n are as in the combinations shown in [Table 1] to [Table 3];
In the formula (1-K3-1), (1-K3-1)

compounds of the present invention wherein $R^{14a}$, $R^{14b}$, $R^{14c}$, $R^{14d}$, $R^2$, $R^4$, $R^9$ and $R^{10}$ are a hydrogen atom, $A^1$ is N, $A^2$ is $NCH_3$, and $R^1$, $R^3$ and n are as in the combinations shown in [Table 1] to [Table 3];
In the formula (1-K3-1), compounds of the present invention wherein $R^{14a}$, $R^{14b}$, $R^{14c}$, $R^{14d}$, $R^2$, $R^4$, $R^9$ and $R^{10}$ are a hydrogen atom, $A^1$ is CH, $A^2$ is $NCH_3$, and $R^1$, $R^3$ and n are as in the combinations shown in [Table 1] to [Table 3];
In the formula (1-K3-1), compounds of the present invention wherein $R^{14a}$, $R^{14b}$, $R^{14c}$, $R^{14d}$, $R^2$, $R^4$, $R^9$ and $R^{10}$ are a hydrogen atom, $A^1$ is N, $A^2$ is S, and $R^1$, $R^3$ and n are as in the combinations shown in [Table 1] to [Table 3];
In the formula (1-K3-1), compounds of the present invention wherein $R^{14a}$, $R^{14b}$, $R^{14c}$, $R^{14d}$, $R^2$, $R^4$, $R^9$ and $R^{10}$ are a hydrogen atom, $A^1$ is CH, $A^2$ is S, and $R^1$, $R^3$ and n are as in the combinations shown in [Table 1] to [Table 3];
In the formula (1-K3-1), compounds of the present invention wherein $R^{14a}$, $R^{14b}$, $R^{14c}$, $R^{14d}$, $R^2$, $R^4$, $R^9$ and $R^{10}$ are a hydrogen atom, $A^1$ is N, $A^2$ is O, and $R^1$, $R^3$ and n are as in the combinations shown in [Table 1] to [Table 3];
In the formula (1-K3-1), compounds of the present invention wherein $R^{14a}$, $R^{14b}$, $R^{14c}$, $R^{14d}$, $R^2$, $R^4$, $R^9$ and $R^{10}$ are a hydrogen atom, $A^1$ is CH, $A^2$ is O, and $R^1$, $R^3$ and n are as in the combinations shown in [Table 1] to [Table 3];

In the formula (1-K3-2), (1-K3-2)

compounds of the present invention wherein $R^2$, $R^4$, $R^9$ and $R^{10}$ are a hydrogen atom, $R^{15}$ is a trifluoromethyl group, $A^1$ is N, $A^2$ is NCH$_3$, and $R^1$, $R^3$ and n are as in the combinations shown in [Table 1] to [Table 3];

In the formula (1-K3-2), compounds of the present invention wherein $R^2$, $R^4$, $R^9$ and $R^{10}$ are a hydrogen atom, $R^{15}$ is a trifluoromethyl group, $A^1$ is CH, $A^2$ is NCH$_3$, and $R^1$, $R^3$ and n are as in the combinations shown in [Table 1] to [Table 3];

In the formula (1-K3-2), compounds of the present invention wherein $R^2$, $R^4$, $R^9$ and $R^{10}$ are a hydrogen atom, $R^{15}$ is a trifluoromethyl group, $A^1$ is N, $A^2$ is S, and $R^1$, $R^3$ and n are as in the combinations shown in [Table 1] to [Table 3];

In the formula (1-K3-2), compounds of the present invention wherein $R^2$, $R^4$, $R^9$ and $R^{10}$ are a hydrogen atom, $R^{15}$ is a trifluoromethyl group, $A^1$ is CH, $A^2$ is S, and $R^1$, $R^3$ and n are as in the combinations shown in [Table 1] to [Table 3];

In the formula (1-K3-2), compounds of the present invention wherein $R^2$, $R^4$, $R^9$ and $R^{10}$ are a hydrogen atom, $R^{15}$ is a trifluoromethyl group, $A^1$ is N, $A^2$ is O, and $R^1$, $R^3$ and n are as in the combinations shown in [Table 1] to [Table 3];

In the formula (1-K3-2), compounds of the present invention wherein $R^2$, $R^4$, $R^9$ and $R^{19}$ are a hydrogen atom, $R^{15}$ is a trifluoromethyl group, $A^1$ is CH, $A^2$ is O, and $R^1$, $R^3$ and n are as in the combinations shown in [Table 1] to [Table 3];

In the formula (1-K3-3), (1-K3-3)

compounds of the present invention wherein $R^2$, $R^4$, $R^9$ and $R^{10}$ are a hydrogen atom, $R^{15}$ is a trifluoromethyl group, $A^1$ is N, $A^2$ is NCH$_3$, and $R^1$, $R^3$ and n are as in the combinations shown in [Table 1] to [Table 3];

In the formula (1-K3-3), compounds of the present invention wherein $R^2$, $R^4$, $R^9$ and $R^{10}$ are a hydrogen atom, $R^{15}$ is a trifluoromethyl group, $A^1$ is CH, $A^2$ is NCH$_3$, and $R^1$, $R^3$ and n are as in the combinations shown in [Table 1] to [Table 3];

In the formula (1-K3-3), compounds of the present invention wherein $R^2$, $R^4$, $R^9$ and $R^{10}$ are a hydrogen atom, $R^{15}$ is a trifluoromethyl group, $A^1$ is N, $A^2$ is S, and $R^1$, $R^3$ and n are as in the combinations shown in [Table 1] to [Table 3];

In the formula (1-K3-3), compounds of the present invention wherein $R^2$, $R^4$, $R^9$ and $R^{10}$ are a hydrogen atom, $R^{15}$ is a trifluoromethyl group, $A^1$ is CH, $A^2$ is S, and $R^1$, $R^3$ and n are as in the combinations shown in [Table 1] to [Table 3];

In the formula (1-K3-3), compounds of the present invention wherein $R^2$, $R^4$, $R^9$ and $R^{10}$ are a hydrogen atom, $R^{15}$ is a trifluoromethyl group, $A^1$ is N, $A^2$ is O, and $R^1$, $R^3$ and n are as in the combinations shown in [Table 1] to [Table 3];

In the formula (1-K3-3), compounds of the present invention wherein $R^2$, $R^4$, $R^9$ and $R^{10}$ are a hydrogen atom, $R^{15}$ is a trifluoromethyl group, $A^1$ is CH, $A^2$ is O, and $R^1$, $R^3$ and n are as in the combinations shown in [Table 1] to [Table 3];

In the formula (1-K3-4), (1-K3-4)

compounds of the present invention wherein $R^2$, $R^4$, $R^9$ and $R^{10}$ are a hydrogen atom, $R^{15}$ is a trifluoromethyl group, $R^{16}$ is a methyl group, $A^1$ is N, $A^2$ is NCH$_3$, and $R^1$, $R^3$ and n are as in the combinations shown in [Table 1] to [Table 3];

In the formula (1-K3-4), compounds of the present invention wherein $R^2$, $R^4$, $R^9$ and $R^{10}$ are a hydrogen atom, $R^{15}$ is a trifluoromethyl group, $R^{16}$ is a methyl group, $A^1$ is CH, $A^2$ is NCH$_3$, and $R^1$, $R^3$ and n are as in the combinations shown in [Table 1] to [Table 3];

In the formula (1-K3-4), compounds of the present invention wherein $R^2$, $R^4$, $R^9$ and $R^{10}$ are a hydrogen atom, $R^{15}$ is a trifluoromethyl group, $R^{16}$ is a methyl group, $A^1$ is N, $A^2$ is S, and $R^1$, $R^3$ and n are as in the combinations shown in [Table 1] to [Table 3];

In the formula (1-K3-4), compounds of the present invention wherein $R^2$, $R^4$, $R^9$ and $R^{19}$ are a hydrogen atom, $R^{15}$ is a trifluoromethyl group, $R^{16}$ is a methyl group, $A^1$ is CH, $A^2$ is S, and $R^1$, $R^3$ and n are as in the combinations shown in [Table 1] to [Table 3];

In the formula (1-K3-4), compounds of the present invention wherein $R^2$, $R^4$, $R^9$ and $R^{10}$ are a hydrogen atom, $R^{15}$ is a trifluoromethyl group, $R^{16}$ is a methyl group, $A^1$ is N, $A^2$ is O, and $R^1$, $R^3$ and n are as in the combinations shown in [Table 1] to [Table 3];

In the formula (1-K3-4), compounds of the present invention wherein $R^2$, $R^4$, $R^9$ and $R^{10}$ are a hydrogen atom, $R^{15}$ is a trifluoromethyl group, $R^{16}$ is a methyl group, $A^1$ is CH, $A^2$ is O, and $R^1$, $R^3$ and n are as in the combinations shown in [Table 1] to [Table 3];

In the formula (1-K3-5), $$\text{(1-K3-5)}$$

compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is $NCH_3$, and $R^1$, $R^3$ and n are as in the combinations shown in [Table 1] to [Table 3];

In the formula (1-K3-5), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is $NCH_3$, and $R^1$, $R^3$ and n are as in the combinations shown in [Table 1] to [Table 3];

In the formula (1-K3-5), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, and $R^1$, $R^3$ and n are as in the combinations shown in [Table 1] to [Table 3];

In the formula (1-K3-5), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, and $R^1$, $R^3$ and n are as in the combinations shown in [Table 1] to [Table 3];

In the formula (1-K3-5), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, and $R^1$, $R^3$ and n are as in the combinations shown in [Table 1] to [Table 3];

In the formula (1-K3-5), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, and $R^1$, $R^3$ and n are as in the combinations shown in [Table 1] to [Table 3];

In the formula (1-K3-6), $$\text{(1-K3-6)}$$

compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is $NCH_3$, and $R^1$, $R^3$ and n are as in the combinations shown in [Table 1] to [Table 3];

In the formula (1-K3-6), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is $NCH_3$, and $R^1$, $R^3$ and n are as in the combinations shown in [Table 1] to [Table 3];

In the formula (1-K3-6), compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is S, and $R^1$, $R^3$ and n are as in the combinations shown in [Table 1] to [Table 3];

In the formula (1-K3-6), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is S, and $R^1$, $R^3$ and n are as in the combinations shown in [Table 1] to [Table 3];

In the formula (1-K3-6), compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is O, and $R^1$, $R^3$ and n are as in the combinations shown in [Table 1] to [Table 3];

In the formula (1-K3-6), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is O, and $R^1$, $R^3$ and n are as in the combinations shown in [Table 1] to [Table 3];

In the formula (1-K3-7), $$\text{(1-K3-7)}$$

compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is $NCH_3$, and $R^1$, $R^3$ and n are as in the combinations shown in [Table 1] to [Table 3];

In the formula (1-K3-7), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is $NCH_3$, and $R^1$, $R^3$ and n are as in the combinations shown in [Table 1] to [Table 3];

In the formula (1-K3-7), compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is S, and $R^1$, $R^3$ and n are as in the combinations shown in [Table 1] to [Table 3];

In the formula (1-K3-7), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is S, and $R^1$, $R^3$ and n are as in the combinations shown in [Table 1] to [Table 3];

In the formula (1-K3-7), compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is O, and $R^1$, $R^3$ and n are as in the combinations shown in [Table 1] to [Table 3];

In the formula (1-K3-7), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is O, and $R^1$, $R^3$ and n are as in the combinations shown in [Table 1] to [Table 3];

In the formula (1-K3-8), (1-K3-8)

[Structure with R¹, R², R³, R⁴, R⁹, R¹⁰, R¹⁷ᵃ, R¹⁷ᵇ, R¹⁷ᶜ, R¹⁷ᵈ, A¹, A², (O)ₙS]

compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is NCH₃, and $R^1$, $R^3$ and n are as in the combinations shown in [Table 1] to [Table 3];
In the formula (1-K3-8), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is NCH₃, and $R^1$, $R^3$ and n are as in the combinations shown in [Table 1] to [Table 3];
In the formula (1-K3-8), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, and $R^1$, $R^3$ and n are as in the combinations shown in [Table 1] to [Table 3];
In the formula (1-K3-8), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, and $R^1$, $R^3$ and n are as in the combinations shown in [Table 1] to [Table 3];
In the formula (1-K3-8), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, and $R^1$, $R^3$ and n are as in the combinations shown in [Table 1] to [Table 3];
In the formula (1-K3-8), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, and $R^1$, $R^3$ and n are as in the combinations shown in [Table 1] to [Table 3];
In the formula (1-K3-9), (1-K3-9)

[Structure with R¹, R², R³, R⁴, R⁹, R¹⁰, R¹⁷ᵃ, R¹⁷ᵇ, R¹⁷ᶜ, R¹⁷ᵈ, A¹, A², (O)ₙS, (O)_qS]

compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is NCH₃, q is 0, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is NCH₃, q is 0, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, q is 0, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, q is 0, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, q is 0, and $R^4$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, q is 0, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is NCH₃, q is 2, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is NCH₃, q is 2, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, q is 2, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, q is 2, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, q is 2, and $R^1$, $R^3$ and n are as in the combinations shown in [Table 1] to [Table 3];
In the formula (1-K3-9), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, q is 2, and $R^1$, $R^3$ and n are as in the combinations shown in [Table 1] to [Table 3];
In the formula (1-K3-10), (1-K3-10)

[Structure with R¹, R², R³, R⁴, R⁹, R¹⁰, R¹⁷ᵃ, R¹⁷ᵇ, R¹⁷ᶜ, R¹⁷ᵈ, A¹, A², (O)ₙS, O]

compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is $NCH_3$, and $R^1$, $R^3$ and n are as in the combinations shown in [Table 1] to [Table 3];

In the formula (1-K3-10), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is $NCH_3$, and $R^1$, $R^3$ and n are as in the combinations shown in [Table 1] to [Table 3];

In the formula (1-K3-10), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, and $R^1$, $R^3$ and n are as in the combinations shown in [Table 1] to [Table 3];

In the formula (1-K3-10), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, and $R^1$, $R^3$ and n are as in the combinations shown in [Table 1] to [Table 3];

In the formula (1-K3-10), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, and $R^1$, $R^3$ and n are as in the combinations shown in [Table 1] to [Table 3];

In the formula (1-K3-10), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, and $R^1$, $R^3$ and n are as in the combinations shown in [Table 1] to [Table 3];

In the formula (1-K3-11), (1-K3-11)

compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is $NCH_3$, and $R^1$, $R^3$ and n are as in the combinations shown in [Table 1] to [Table 3];

In the formula (1-K3-11), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is $NCH_3$, and $R^1$, $R^3$ and n are as in the combinations shown in [Table 1] to [Table 3];

In the formula (1-K3-11), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, and $R^1$, $R^3$ and n are as in the combinations shown in [Table 1] to [Table 3];

In the formula (1-K3-11), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, and $R^1$, $R^3$ and n are as in the combinations shown in [Table 1] to [Table 3];

In the formula (1-K3-11), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, and $R^1$, $R^3$ and n are as in the combinations shown in [Table 1] to [Table 3];

In the formula (1-K3-11), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, and $R^1$, $R^3$ and n are as in the combinations shown in [Table 1] to [Table 3];

In the formula (1-K3-12), (1-K3-12)

compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is $NCH_3$, and $R^1$, $R^3$ and n are as in the combinations shown in [Table 1] to [Table 3];

In the formula (1-K3-12), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is $NCH_3$, and $R^1$, $R^3$ and n are as in the combinations shown in [Table 1] to [Table 3];

In the formula (1-K3-12), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is S, and $R^1$, $R^3$ and n are as in the combinations shown in [Table 1] to [Table 3];

In the formula (1-K3-12), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is S, and $R^1$, $R^3$ and n are as in the combinations shown in [Table 1] to [Table 3];

In the formula (1-K3-12), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is N, $A^2$ is O, and $R^1$, $R^3$ and n are as in the combinations shown in [Table 1] to [Table 3];

In the formula (1-K3-12), compounds of the present invention wherein $R^2$, $R^4$, $R^9$ and $R^{10}$ are a hydrogen atom, $R^{17a}$, $R^{17b}$, $R^{17c}$ and $R^{17d}$ are a fluorine atom, $A^1$ is CH, $A^2$ is O, and $R^2$, $R^3$ and n are as in the combinations shown in [Table 1] to [Table 3];

In the formula (1-K3-13), (1-K3-13)

compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is $NCH_3$, and $R^1$, $R^3$ and n are as in the combinations shown in [Table 1] to [Table 3];

In the formula (1-K3-13), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is $NCH_3$, and $R^1$, $R^3$ and n are as in the combinations shown in [Table 1] to [Table 3];

In the formula (1-K3-13), compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is S, and $R^1$, $R^3$ and n are as in the combinations shown in [Table 1] to [Table 3];

In the formula (1-K3-13), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is S, and $R^1$, $R^3$ and n are as in the combinations shown in [Table 1] to [Table 3];

In the formula (1-K3-13), compounds of the present invention wherein $R^2$, $R^4$, $R^9$ and $R^{10}$ are a hydrogen atom, $R^{17a}$ and $R^{17b}$ are a fluorine atom, $A^1$ is N, $A^2$ is O, and $R^1$, $R^3$ and n are as in the combinations shown in [Table 1] to [Table 3];

In the formula (1-K3-13), compounds of the present invention wherein $R^2$, $R^4$, $R^9$ and $R^{10}$ are a hydrogen atom, $R^{17a}$ and $R^{17b}$ are a fluorine atom, $A^1$ is CH, $A^2$ is O, and $R^1$, $R^3$ and n are as in the combinations shown in [Table 1] to [Table 3];

In the formula (1-K3-14), (1-K3-14)

compounds of the present invention wherein $R^2$, $R^4$, $R^9$ and $R^{10}$ are a hydrogen atom, $A^1$ is N, $A^2$ is $NCH_3$, and $R^1$, $R^3$ and n are as in the combinations shown in [Table 1] to [Table 3];

In the formula (1-K3-14), compounds of the present invention wherein $R^2$, $R^4$, $R^9$ and $R^{10}$ are a hydrogen atom, $A^1$ is CH, $A^2$ is $NCH_3$, and $R^1$, $R^3$ and n are as in the combinations shown in [Table 1] to [Table 3];

In the formula (1-K3-14), compounds of the present invention wherein $R^2$, $R^4$, $R^9$ and $R^{10}$ are a hydrogen atom, $A^1$ is N, $A^2$ is S, and $R^1$, $R^3$ and n are as in the combinations shown in [Table 1] to [Table 3];

In the formula (1-K3-14), compounds of the present invention wherein $R^2$, $R^4$, $R^9$ and $R^{10}$ are a hydrogen atom, $A^1$ is CH, $A^2$ is S, and $R^1$, $R^3$ and n are as in the combinations shown in [Table 1] to [Table 3];

In the formula (1-K3-14), compounds of the present invention wherein $R^2$, $R^4$, $R^9$ and $R^{10}$ are a hydrogen atom, $A^1$ is N, $A^2$ is O, and $R^1$, $R^3$ and n are as in the combinations shown in [Table 1] to [Table 3];

In the formula (1-K3-14), compounds of the present invention wherein $R^2$, $R^4$, $R^9$ and $R^{10}$ are a hydrogen atom, $A^1$ is CH, $A^2$ is O, and $R^1$, $R^3$ and n are as in the combinations shown in [Table 1] to [Table 3];

In the formula (1-K3-15), (1-K3-15)

compounds of the present invention wherein $R^2$, $R^4$, $R^9$ and $R^{10}$ are a hydrogen atom, $A^1$ is N, $A^2$ is $NCH_3$, and $R^1$, $R^3$ and n are as in the combinations shown in [Table 1] to [Table 3];

In the formula (1-K3-15), compounds of the present invention wherein $R^2$, $R^4$, $R^9$ and $R^{10}$ are a hydrogen atom, $A^1$ is CH, $A^2$ is $NCH_3$, and $R^1$, $R^3$ and n are as in the combinations shown in [Table 1] to [Table 3];

In the formula (1-K3-15), compounds of the present invention wherein $R^2$, $R^4$, $R^9$ and $R^{10}$ are a hydrogen atom, $A^1$ is N, $A^2$ is S, and $R^1$, $R^3$ and n are as in the combinations shown in [Table 1] to [Table 3];

In the formula (1-K3-15), compounds of the present invention wherein $R^2$, $R^4$, $R^9$ and $R^{10}$ are a hydrogen atom, $A^1$ is CH, $A^2$ is S, and $R^1$, $R^3$ and n are as in the combinations shown in [Table 1] to [Table 3];

In the formula (1-K3-15), compounds of the present invention wherein $R^2$, $R^4$, $R^9$ and $R^{10}$ are a hydrogen atom, $A^1$ is N, $A^2$ is O, and $R^1$, $R^3$ and n are as in the combinations shown in [Table 1] to [Table 3];

In the formula (1-K3-15), compounds of the present invention wherein $R^2$, $R^4$, $R^9$ and $R^{10}$ are a hydrogen atom, $A^1$ is CH, $A^2$ is O, and $R^1$, $R^3$ and n are as in the combinations shown in [Table 1] to [Table 3];

In the formula (1-K3-16), (1-K3-16)

compounds of the present invention wherein $R^2$, $R^4$, $R^9$ and $R^{19}$ are a hydrogen atom, $R^{13}$ is a methyl group, $A^1$ is N, $A^2$ is $NCH_3$, and $R^1$, $R^3$ and n are as in the combinations shown in [Table 1] to [Table 3];

In the formula (1-K3-16), compounds of the present invention wherein $R^2$, $R^4$, $R^9$ and $R^{10}$ are a hydrogen atom, $R^{13}$ is a methyl group, $A^1$ is CH, $A^2$ is $NCH_3$, and $R^1$, $R^3$ and n are as in the combinations shown in [Table 1] to [Table 3];

In the formula (1-K3-16), compounds of the present invention wherein $R^2$, $R^4$, $R^9$ and $R^{10}$ are a hydrogen atom, $R^{13}$ is a methyl group, $A^1$ is N, $A^2$ is S, and $R^1$, $R^3$ and n are as in the combinations shown in [Table 1] to [Table 3];

In the formula (1-K3-16), compounds of the present invention wherein $R^2$, $R^4$, $R^9$ and $R^{10}$ are a hydrogen atom, $R^{13}$ is a methyl group, $A^1$ is CH, $A^2$ is S, and $R^1$, $R^3$ and n are as in the combinations shown in [Table 1] to [Table 3];

In the formula (1-K3-16), compounds of the present invention wherein $R^2$, $R^4$, $R^9$ and $R^{10}$ are a hydrogen atom, $R^{13}$ is a methyl group, $A^1$ is N, $A^2$ is O, and $R^1$, $R^3$ and n are as in the combinations shown in [Table 1] to [Table 3];

In the formula (1-K3-16), compounds of the present invention wherein $R^2$, $R^4$, $R^9$ and $R^{10}$ are a hydrogen atom, $R^{13}$ is a methyl group, $A^1$ is CH, $A^2$ is O, and $R^1$, $R^3$ and n are as in the combinations shown in [Table 1] to [Table 3];

In the formula (1D-K1-8),

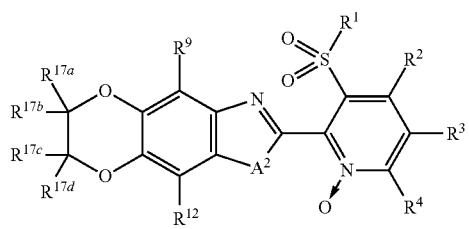

(1D-K1-8)

compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is $NCH_3$, and $R^1$ and $R^3$ are as in the combinations shown in [Table 4];

TABLE 4

| $R^1$ | $R^3$ |
| --- | --- |
| Me | H |
| Et | H |
| Pr | H |
| iPr | H |
| $CF_2CF_3$ | H |
| $CH_2CH=CH_2$ | H |
| $CH_2C\equiv CH$ | H |
| CycPr | H |
| $CH_2CycPr$ | H |
| Me | $CF_3$ |
| Et | $CF_3$ |
| Pr | $CF_3$ |
| iPr | $CF_3$ |
| $CH_2CF_3$ | $CF_3$ |
| $CH_2CH=CH_2$ | $CF_3$ |
| $CH_2C\equiv CH$ | $CF_3$ |
| CycPr | $CF_3$ |
| $CH_2CycPr$ | $CF_3$ |

In the formula (1D-K1-8), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is S, and $R^1$ and $R^3$ are as in the combinations shown in [Table 4];

In the formula (1D-K1-8), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is O, and $R^1$ and $R^3$ are as in the combinations shown in [Table 4];

In the formula (1D-K1-9),

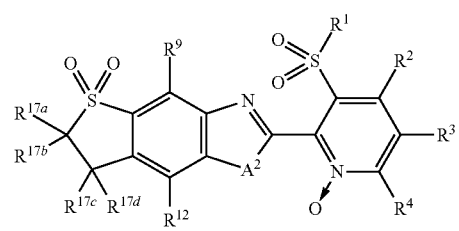

(1D-K1-9)

compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is $NCH_3$, and $R^1$ and $R^3$ are as in the combinations shown in [Table 4];

In the formula (1D-K1-9), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is S, and $R^1$ and $R^3$ are as in the combinations shown in [Table 4];

In the formula (1D-K1-9), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is O, and $R^1$ and $R^3$ are as in the combinations shown in [Table 4];

In the formula (1D-K1-10),

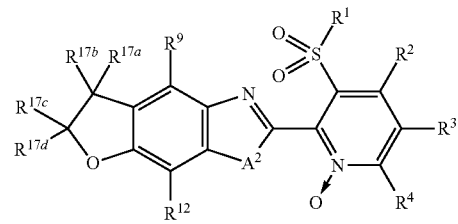

(1D-K1-10)

compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is $NCH_3$, and $R^4$ and $R^3$ are as in the combinations shown in [Table 4];

In the formula (1D-K1-10), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is S, and $R^1$ and $R^3$ are as in the combinations shown in [Table 4];

In the formula (1D-K1-10), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is O, and $R^1$ and $R^3$ are as in the combinations shown in [Table 4];

In the formula (1D-K1-11),

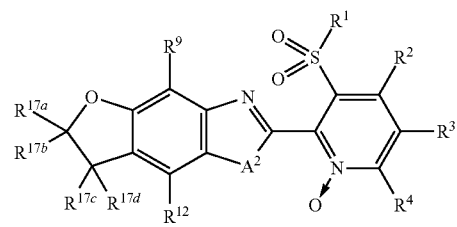

(1D-K1-11)

compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is $NCH_3$, and $R^1$ and $R^3$ are as in the combinations shown in [Table 4];
In the formula (1D-K1-11), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is S, and $R^1$ and $R^3$ are as in the combinations shown in [Table 4];
In the formula (1D-K1-11), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is O, and $R^1$ and $R^3$ are as in the combinations shown in [Table 4];
In the formula (1D-K1-12),

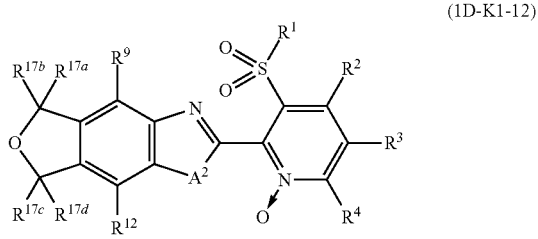

(1D-K1-12)

compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is $NCH_3$, and $R^1$ and $R^3$ are as in the combinations shown in [Table 4];
In the formula (1D-K1-12), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is S, and $R^1$ and $R^3$ are as in the combinations shown in [Table 4];
In the formula (1D-K1-12), compounds of the present invention wherein $R^2$, $R^4$, $R^9$ and $R^{12}$ are a hydrogen atom, $R^{17a}$, $R^{17b}$, $R^{17c}$ and $R^{17d}$ are a fluorine atom, $A^2$ is O, and $R^1$ and $R^3$ are as in the combinations shown in [Table 4];
In the formula (1D-K1-13),

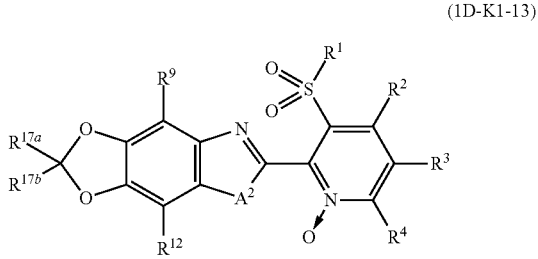

(1D-K1-13)

compounds of the present invention wherein $R^2$, $R^4$, $R^9$ and $R^{12}$ are a hydrogen atom, $R^{17a}$ and $R^{17b}$ are a fluorine atom, $A^2$ is $NCH_3$, and $R^1$ and $R^3$ are as in the combinations shown in [Table 4];
In the formula (1D-K1-13), compounds of the present invention wherein $R^2$, $R^4$, $R^9$ and $R^{12}$ are a hydrogen atom, $R^{17a}$ and $R^{17b}$ are a fluorine atom, $A^2$ is 5, and $R^1$ and $R^3$ are as in the combinations shown in [Table 4]; and
In the formula (1D-K1-13), compounds of the present invention wherein $R^2$, $R^4$, $R^9$ and $R^{12}$ are a hydrogen atom, $R^{17a}$ and $R^{17b}$ are a fluorine atom, $A^2$ is O, and $R^1$ and $R^3$ are as in the combinations shown in [Table 4].

Examples of the pest on which the compound of the present invention has an effect include arthropod pests such as pest insects and pest mites and pest nematoda. Specifically, examples of the pests include those shown below.

Hemiptera: Delphacidae such as *Laodelphax striatellus*, *Nilaparvata lugens*, and *Sogatella furcifera*, Deltocephalidae such as *Nephotettix cincticeps*, *Nephotettix virescens*, and *Empoasca onukii*, Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*, Pentatomidae such as *Nezara antennata*, *Riptortus clavetus*, *Leptocorisa chinensis*, *Eysarcoris parvus*, and *Halyomorpha mista*, Aleyrodidae such as *Trialeurodes vaporariorum*, *Bemisia tabaci*, *Dialeurodes citri*, and *Aleurocanthus spiniferus*, Coccidae such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*, Noctuidae such as *Spodoptera litura*, *Spodoptera exigua*, *Pseudaletia separata*, *Mamestra brassicae*, *Agrotis ipsilon*, *Plusia nigrisigna*, *Thoricoplusia* spp., *Heliothis* spp., and *Helicoverpa* spp., Pieridae such as *Pieris rapae*, *Adoxophyes* spp., Tortricidae such as *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: Culex such as *Culex pipiens pallens*, *Culex tritaeniorhynchus*, and *Culex quinquefasciatus*, *Aedes* spp. such as *Aedes aegypti* and *Aedes albopictus*, *Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae*, *Hydrellia griseola*, *Liriomyza sativae*, *Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus*, Hippoboscidae, and Stomoxys.

Coleoptera: Diabrotica such as *Diabrotica virgifera virgifera* and *Diabrotica undecimpunctata howardi*, Scarabaeidae such as *Anomala cuprea*, *Anomala rufocuprea*, and *Popillia japonica*, Curculionidae such as *Sitophilus zeamais*, *Lissorhoptrus oryzophilus*, *Callosobruchuys chienensis*, *Echinocnemus squameus*, *Anthonomus grandis*, and *Sphenophorus venatus*, Tenebrionidae such as *Tenebrio molitor* and *Tribolium castaneum*, Chrysomelidae such as *Oulema oryzae*, *Aulacophora femoralis*, *Phyllotreta striolata*, and *Leptinotarsa decemlineata*, Dermestidae such as *Anthrenus verbasci* and *Dermestes maculates*, Anobiidae such as *Lasioderma serricorne*, Epilachna such as *Epilachna vigintioctopunctata*, *Lyctus brunneus*, Scolytidae such as *Tomicus*

*piniperda*, Bostrychidae, Ptinidae, Cerambycidae such as *Anoplophora malasiaca*, *Agriotes* spp., and *Paederus fuscipes*.

Orthoptera: *Locusta migratoria*, *Gryllotalpa africana*, *Oxya yezoensis*, *Oxya japonica*, and *Grylloidea*.

Aphaniptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, and *Linognathus setosus*.

Mallophaga: *Dalmalinia ovis*, *Dalmalinia bovis*, *Menopon gallinae*, *Trichodectes canis*, and *Felicola subrostrata*.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, and *Pratylenchus neglectus*.

Blattodea: *Blattella germanica*, *Periplaneta fuliginosa*, *Periplaneta americana*, *Periplaneta brunnea*, and *Blatta orientalis*.

Isoptera: *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, and *Sinocapritermes mushae*.

Acarina: Tetranychidae such as *Tetranychus urticae*, *Tetranychus kanzawai*, *Panonychus citri*, *Panonychus ulmi*, and *Oligonychus* spp., Eriophyidae such as *Aculops pelekassi*, *Phyllocoptruta citri*, *Aculops lycopersici*, *Calacarus carinatus*, *Acaphylla theavagrans*, *Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus*, *Cheyletus malaccensis*, *Cheyletus moorei*, and *Cheyletiella yasguri*, Sarcoptidae such as *Octodectes cynotis* and *Sacroptes scabiei*, Demodicidae such as *Demodex canis*, Listrophoridae, Cryptostigmata, Dermanyssidae such as *Ornithonyssus bacoti*, *Ornithonyssus sylvairum*, and *Dermanyssus gallinae*, Trombiculidae such as *Leptotrombidium akamushi*, Arachnida such as *Chiracanthium japonicum* and *Latrodectus hasseltii*, and the like.

Chilopoda: *Thereuonema hilgendorfi* and *Scolopendra subspinipes*.

Diplopoda: *Oxidus gracilis* and *Nedyopus tambanus*.

Isopoda: *Armadillidium vulgare*.

Gastropoda: *Limax marginatus* and *Limax flavus*.

The pest control agent of the present invention contains the compound of the present invention and an inert carrier.

The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, smoking agents, poisonous bait formulations, resin formulations, shampoo agents, paste formulations, foam agents, carbon dioxide preparations, tablets, and the like. These formulations may be processed into mosquito repellent coil, electric mosquito repellent mat, mosquito repellent liquid formulation, smoking agent, fumigant, sheet formulation, spot-on agent, or oral treatment agent, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like, synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as phthalate esters (dimethyl phthalate, dioctyl phthalate, etc.), adipate esters or stearic acid may be added to these base materials as necessary. The resin formulation is obtained by kneading a compound into the base material using an ordinary kneading apparatus, and then molding it by injection molding, extrusion molding, press molding or the like, and the resin formulation obtained can be further subjected to molding or cutting step as necessary to be processed into a plate, film, taped, reticular or string resin formulation. These resin formulations are processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing accidental ingestion by children and pets such as red pepper powder, a pest attractant flavor such as cheese flavor, onion flavor and peanut oil or the like are added as necessary.

The method for controlling pests of the present invention is carried out by applying an effective amount of the compound of the present invention to a pest directly and/or a pest-infested area (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g in the amount of the compound of the present invention per 10000 m². When the pest control agent of the present invention is formulated into an emulsifiable concentrate, a wettable powder, a flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly applied by being sprayed on a pest or a plant such as crops which should be protected from pests, and also may be applied to a soil in order to control a pest that infests in the soil of cultivated land.

Also, the resin formulation processed into a sheet or string can be also applied by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 m² of an area to be treated, in the case of using it on a planar area, and is usually 0.01 to 500 mg in an amount of the compound of the present invention per 1 m³ of a space to be treated, in the case of using it in a space. When the pest control agent of the present invention is formulated into an emulsifiable concentrate, a wettable powder, a flowable or the like, the pest control agent is usually diluted with water for an application so as to have a concentration of the active ingredient of 0.1 to 10000 ppm, and oil formulations, aerosols, smoking agents, poisonous bait formulations and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation on to an animal, when non-systemic control is intended. The amount of the compound of the present invention when administered to an animal body is usually within the range from 0.1 to 1000 mg per 1 kg of the weight of an animal.

The pest control agent of the present invention can be used in the farmlands where the following crops are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, camellia, hydrangea, sasanqua, *Illicium religiosum*, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse-chestnut, etc.), sweet viburnum, *Podocarpus macrophyllus*, Japanese cedar, Japanese cypress, croton, spindle tree, Japanese photinia, etc.

Grass: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc.), biofuel plants (Jatropha, curcas, safflower, *Camelina alyssum*, switchgrass, miscanthus, reed canary grass, *Arundo donax*, kenaf, cassava, willow, algae, etc.), foliage plants, etc.

The crops also contain genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, herbicide and synergist are shown below.

Active Ingredients of Insecticide (1) Organic Phosphorus Compounds acephate, aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS, 3RS; 1RS, 3SR)-2,2-dimethyl-3-prop-1-enylcyclopropanecarboxylate, 2,3,5,6-tetrafluoro-4-methylbenzyl (EZ)-(1RS, 3RS; 1RS, 3SR)-2,2-dimethyl-3-prop-1-enylcyclopropanecarboxylate, 2,3,5,6-tetrafluoro-4-(methoxymethyl)benzyl (1RS, 3RS; 1RS, 3SR)-2,2-dimethyl-3-(2-methyl-1-propenyl)cyclopropanecarboxylate, and 2,3,5,6-tetrafluoro-4-(methoxymethyl)benzyl (EZ)-(1RS, 3RS; 1RS, 3SR)-2,2-dimethyl-3-(2-cyano-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof;

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil, nicotine-sulfate; avermectin-B, bromopropylate, buprofezin, chlorphenapyr, cyantraniliprole, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, cyantraniliprole, compounds represented by
the following formula (K):

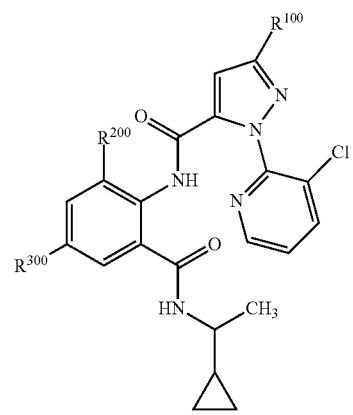

wherein $R^{100}$ represents chlorine, bromine or a trifluoromethyl group, $R^{200}$ represents chlorine, bromine or a methyl group, and $R^{300}$ represents chlorine, bromine or a cyano group, and compounds represented by
the following formula (L):

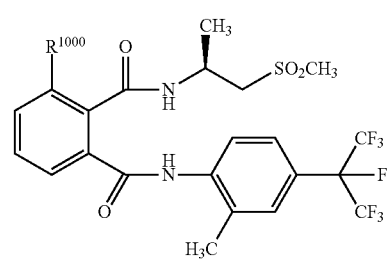

wherein $R^{1000}$ represents chlorine, bromine or iodine.

Active Ingredients of Miticide acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite: BPPS, polynactins, pyridaben, pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol, methyisothiocyanate, morantel tartarate, and imicyafos.

Active Ingredients of Fungicide (1) Azole Fungicidal Compounds propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

(2) Cyclic Amine Fungicidal Compounds compounds such as fenpropimorph, tridemorph, and fenpropidin;

carbendezim, benomyl, thiabendazole, and thiophanate-methyl;

(3) Other Fungicidal Compounds procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Herbicide (1) Phenoxy Fatty Acid Herbicidal Compounds 2,4-PA, MCP, MCPB, phenothiol, mecoprop, fluroxypyr, triclopyr, clomeprop, and naproanilide.

(2) Benzoate Herbicidal Compounds 2,3,6-TBA, dicamba, clopyralid, picloram, aminopyralid, quinclorac, and quinmerac.

(3) Urea Herbicidal Compounds diuron, linuron, chlortoluron, isoproturon, fluometuron, isouron, tebuthiuron, methabenzthiazuron, cumyluron, daimuron, and methyl-daimuron.

(4) Triazine Herbicidal Compounds atrazine, ametoryn, cyanazine, simazine, propazine, simetryn, dimethametryn, prometryn, metribuzin, triaziflam, and indaziflam.

(5) Bipyridinium Herbicidal Compounds paraquat and diquat.

(6) Hydroxybenzonitrile Herbicidal Compounds bromoxynil and ioxynil.

(7) Dinitroaniline Herbicidal Compounds pendimethalin, prodiamine, and trifluralin.

(8) Organophosphorus Herbicidal Compounds amiprofos-methyl, butamifos, bensulide, piperophos, anilofos, glyphosate, glufosinate, glufosinate-P, and bialaphos.

(9) Carbamate Herbicidal Compounds di-allate, tri-allate, EPIC, butylate, benthiocarb, esprocarb, molinate, dimepiperate, swep, chlorpropham, phenmedipham, phenisopham, pyributicarb, and asulam.

(10) Acid Amide Herbicidal Compounds propanil, propyzamide, bromobutide, and etobenzanid.

(11) Chloroacetanilide Herbicidal Compounds acetochlor, alachlor, butachlor, dimethenamid, propachlor, metazachlor, metolachlor, pretilachlor, thenylchlor, and pethoxamid.

(12) Diphenyl Ether Herbicidal Compounds acifluorfen-sodium, bifenox, oxyfluorfen, lactofen, fomesafen, chlomethoxynil, and aclonifen.

(13) Cyclic Imide Herbicidal Compounds oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds benzofenap, pyrazolate, pyrazoxyfen, topramezone, and pyrasulfotole.

(15) Triketone Herbicidal Compounds isoxaflutole, benzobicyclon, sulcotrione, mesotrione, tembotrione, and tefuryltrione.

(16) Aryloxyphenoxypropionate Herbicidal Compounds clodinafop-propargyl, cyhalofop-butyl, diclofop-methyl, fenoxaprop-ethyl, fluazifop-butyl, haloxyfop-methyl, quizalofop-ethyl, and metamifop.

(17) Trione Oxime Herbicidal Compounds alloxydim-sodium, sethoxydim, butroxydim, clethodim, cloproxydim, cycloxydim, tepraloxydim, tralkoxydim, and profoxydim.

(18) Sulfonyl Urea Herbicidal Compounds chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.

(19) Imidazolinone Herbicidal Compounds imazamethabenz-methyl, imazamethapyr, imazamox, imazapyr, imazaquin, and imazethapyr.

(20) Sulfonamide Herbicidal Compounds flumetsulam, metosulam, diclosulam, florasulam, cloransulam-methyl, penoxsulam, and pyroxsulam.

(21) Pyrimidinyloxybenzoate Herbicidal Compounds pyrithiobac-sodium, bispyribac-sodium, pyriminobac-methyl, pyribenzoxim, pyriftalid, and pyrimisulfan.

(22) Other Herbicidal Compounds bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist piperonyl butoxide, sesamex, sulfoxide, N-(2-ethylhexyl)-8,9,10-trinorborn-5-ene-2,3-dicarboximide (MGK 264), N-decylimidazole), WARF-antiresistant, TBPT, TPP, IBP, PSCP, methyl iodide (CH₃I), t-phenylbutenone, diethylmaleate, DMC, FDMC, ETP, and ETN.

EXAMPLES

Hereinbelow, the present invention will be further described in detail by production examples, formulation examples, test examples, and the like. However, the present invention is not limited to these examples.

First, the production examples for the production of the compounds of the present invention are shown below.

Production Example 1-1

5,6-Dichloro-1,1,3,3-tetrafluoro-1,3-dihydroisobenzofuran was obtained from 4,5-dichlorophthalic acid, according to the method described in Reference Production Example 1 of JP-A-8-81457.

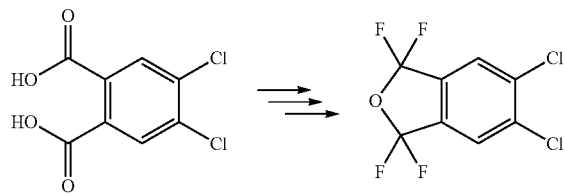 [SMILES: O=C(O)c1cc(Cl)c(Cl)cc1C(=O)O ; FC1(F)OC(F)(F)c2cc(Cl)c(Cl)cc21]

Production Example 1-2

5-Hydroxy-6-nitro-1,1,3,3-tetrafluoro-1,3-dihydroisobenzofuran was obtained from 5,6-dichloro-1,1,3,3-tetrafluoro-1,3-dihydroisobenzofuran, according to the method described in Example 1 of JP-A-8-81457.

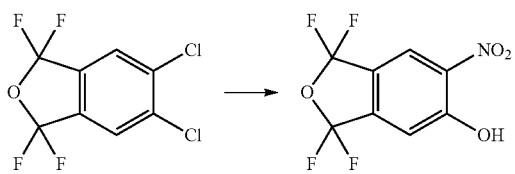 [SMILES: FC1(F)OC(F)(F)c2cc(Cl)c(Cl)cc21 ; O=[N+]([O-])c1cc2c(cc1O)C(F)(F)OC2(F)F]

Production Example 1-3

5-Chloro-6-nitro-1,1,3,3-tetrafluoro-1,3-dihydroisobenzofuran was obtained from 5-hydroxy-6-nitro-1,1,3,3-tetrafluoro-1,3-dihydroisobenzofuran, according to the method described in Reference Production Example 2 of JP-A-8-81457.

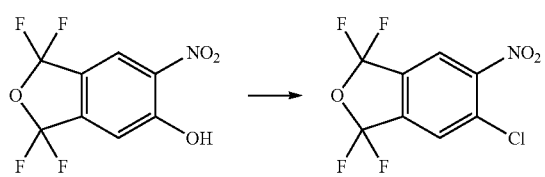 [SMILES: O=[N+]([O-])c1cc2c(cc1O)C(F)(F)OC2(F)F ; O=[N+]([O-])c1cc2c(cc1Cl)C(F)(F)OC2(F)F]

Production Example 1-4

5 ml of a 40% aqueous methylamine solution was added to a mixture of 4.0 g of 5-chloro-6-nitro-1,1,3,3-tetrafluoro-1,3-dihydroisobenzofuran and 5 ml of DMF under ice cooling, and the mixture was stirred at room temperature for 3 hours. Water was added to the reaction mixture, and the precipitated deposit was filtered and washed with water, and then dried under reduced pressure to obtain 3.47 g of 5-methylamino-6-nitro-1,1,3,3-tetrafluoro-1,3-dihydroisobenzofuran.

5-Methylamino-6-nitro-1,1,3,3-tetrafluoro-1,3-dihydroisobenzofuran

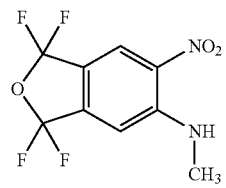 [SMILES: CNc1cc2c(cc1[N+](=O)[O-])C(F)(F)OC2(F)F]

$^1$H-NMR (CDCl₃) δ: 8.50 (s, 1H), 8.41 (brs, 1H), 7.07 (s, 1H), 3.13 (d, J=4.9 Hz, 3H)

Production Example 1-5

A mixture of 2.6 g of iron powder, 4.0 mL of acetic acid, 30 mL of THF and 6 mL of water was stirred at 70° C., and 3.4 g of 5-methylamino-6-nitro-1,1,3,3-tetrafluoro-1,3-dihydroisobenzofuran was added thereto, and then the mixture was stirred at 70° C. for 3 hours. The reaction mixture was cooled to room temperature, and filtered through celite (registered trademark). The filtrate was concentrated under reduced pressure, a saturated aqueous sodium bicarbonate solution was added thereto, and the mixture was extracted with ethyl acetate. The organic layer was dried over anhydrous sodium sulfate, and concentrated under reduced pressure to obtain 2.58 g of N-methyl-1,1,3,3-tetrafluoro-1,3-dihydroisobenzofuran-5,6-diamine.

N-Methyl-1,1,3,3-tetrafluoro-1,3-dihydroisobenzofuran-5,6-diamine

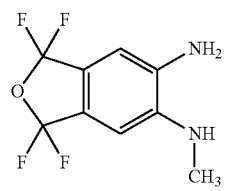

$^1$H-NMR (CDCl₃) δ: 6.84 (s, 1H), 6.72 (s, 1H), 3.83 (brs, 1H), 3.65 (brs, 2H), 2.94 (d, J=5.1 Hz, 3H)

Production Example 1-6

A mixture of 0.25 g of N-methyl-1,1,3,3-tetrafluoro-1,3-dihydroisobenzofuran-5,6-diamine, 0.19 g of 3-ethylsulfanylpicolinic acid, 0.20 g of EDAC, 14 mg of HOBt and 5 ml of pyridine was stirred at room temperature for 5 hours. Water was added to the reaction mixture, and the mixture was extracted with ethyl acetate. The organic layer was washed with a saturated aqueous sodium bicarbonate solution and saturated saline water and dried over anhydrous sodium sulfate, and then concentrated under reduced pressure to obtain 3-ethylsulfanyl-N-(6-methylamino-1,1,3,3-tetrafluoro-1,3-dihydroisobenzofuran-5-yl) picolinamide.

3-Ethylsulfanyl-N-(6-methylamino-1,1,3,3-tetrafluoro-1,3-dihydroisobenzofuran-5-yl) picolinamide

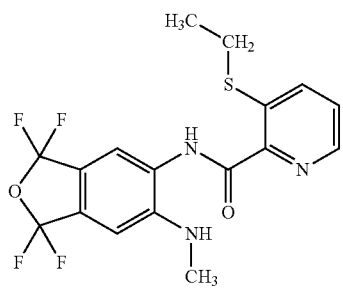 [SMILES: CCSc1cccnc1C(=O)Nc1cc2c(cc1NC)C(F)(F)OC2(F)F]

Production Example 1-7

A mixture of the whole amount of 3-ethylsulfanyl-N-(6-methylamino-1,1,3,3-tetrafluoro-1,3-dihydroisobenzofuran-5-yl)picolinamide obtained in Production Example 1-6 above and 10 ml of acetic acid was stirred under heat-refluxing for 5 hours. The reaction mixture was cooled to room temperature, and then concentrated under reduced pressure. The crude product was subjected to a silica gel column chromatography to obtain 0.41 g of 2-(3-ethylsulfanylpyridin-2-yl)-1-methyl-5,5,7,7-tetrafluoro-5,7-dihydro-1H-fluo[3',4':4,5]benzo[1,2-d]imidazole (hereinafter, referred to as Compound of Present Invention 1-1).

Compound of Present Invention 1-1

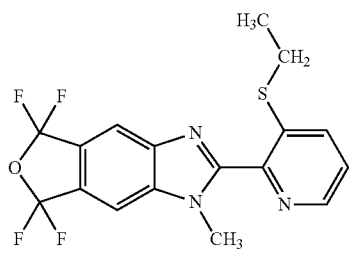 [SMILES: CCSc1cccnc1-c1nc2cc3c(cc2n1C)C(F)(F)OC3(F)F]

$^1$H-NMR (CDCl$_3$) δ: 8.53 (1H, dd), 8.11 (1H, s), 7.80 (1H, dd), 7.70 (1H, s), 7.41 (1H, dd), 3.99 (3H, s), 2.96 (2H, q), 1.34 (3H, t)

Production Example 2

0.42 g of m-chloroperbenzoic acid (purity of 65% or more) was added to a mixture of Compound of Present Invention 1-1 (0.29 g) and 9 ml of chloroform under ice cooling, and then the mixture was stirred at room temperature for 2 hours. A 10% aqueous sodium sulfite solution was added to the reaction mixture, and the mixture was extracted with chloroform. The organic layer was washed with a saturated aqueous sodium bicarbonate solution, then dried over anhydrous sodium sulfate, and concentrated under reduced pressure. The resulting residue was subjected to a silica gel column chromatography to obtain 0.23 g of 2-(3-ethylsulfonylpyridin-2-yl)-1-methyl-5,5,7,7-tetrafluoro-5,7-dihydro-1H-fluo[3',4':4,5]benzo[1,2-d]imidazole (hereinafter, referred to as Compound of Present Invention 1-2).

Compound of Present Invention 1-2

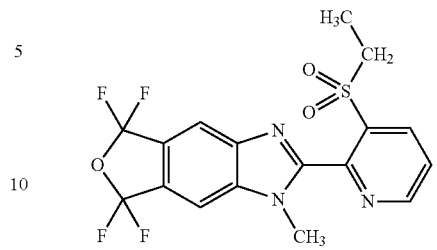

$^1$H-NMR (CDCl$_3$) δ: 9.01 (1H, dd), 8.54 (1H, dd), 8.03 (1H, s), 7.77-7.72 (2H, m), 3.83 (3H, s), 3.78 (2H, q), 1.36 (3H, t)

Production Example 3-1

A mixture of 6.8 g of 5-hydroxy-6-nitro-1,1,3,3-tetrafluoro-1,3-dihydroisobenzofuran and 20 ml of acetic acid was added dropwise to a mixture of 7.8 g of electrolytic iron, 20 ml of acetic acid and 20 ml of water heated to 80° C., and then the mixture was stirred for 1 hour. The reaction mixture was cooled to room temperature, then water was added thereto, and the mixture was extracted twice with ethyl acetate. The combined organic layer was washed with water, a saturated aqueous sodium bicarbonate solution and saturated saline water, and dried over anhydrous magnesium sulfate, then activated carbon was added thereto, and the mixture was filtered through celite (registered trademark). The filtrate was concentrated under reduced pressure to obtain 4.43 g of 6-amino-5-hydroxy-1,1,3,3-tetrafluoro-1,3-dihydroisobenzofuran.

6-Amino-5-hydroxy-1,1,3,3-tetrafluoro-1,3-dihydroisobenzofuran

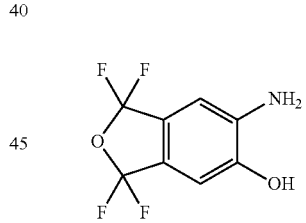

$^1$H-NMR (DMSO-d$_6$) δ: 10.65 (brs, 1H), 6.90 (s, 1H), 6.84 (s, 1H), 5.70 (brs, 2H)

Production Example 3-2

A mixture of 0.5 g of 6-amino-5-hydroxy-1,1,3,3-tetrafluoro-1,3-dihydroisobenzofuran, 0.49 g of 3-ethylsulfanylpicolinic acid, 0.51 g of EDAC, and 6 ml of THF was stirred at room temperature for 2 hours. 0.32 g of 3-ethylsulfanylpicolinic acid and 0.42 g of EDAC were added to the reaction mixture, and the mixture was stirred at room temperature for 2.5 hours. An aqueous 3M sodium hydroxide solution was added to the reaction mixture, and the mixture was stirred at room temperature for 2 hours, and then extracted with ethyl acetate. The organic layer was washed with a saturated aqueous ammonium chloride solution and saturated saline water, then dried over anhydrous sodium sulfate and concentrated under reduced pressure to obtain 1.03 g of 3-ethylsulfanyl-N-(1,1,3,3-tetrafluoro-6-hydroxy-1,3-dihydroisobenzofuran-5-yl)picolinamide.

3-Ethylsulfanyl-N-(1,1,3,3-tetrafluoro-6-hydroxy-1,3-dihydroisobenzofuran-5-yl)picolinamide

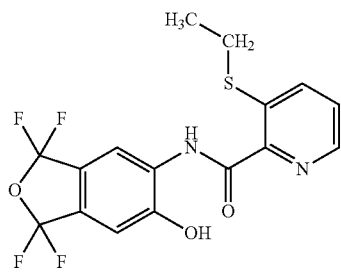 [SMILES: CCSc1cccnc1C(=O)Nc1cc2c(cc1O)C(F)(F)OC2(F)F]

Production Example 3-3

A mixture of 1.03 g of 3-ethylsulfanyl-N-(1,1,3,3-tetrafluoro-6-hydroxy-1,3-dihydroisobenzofuran-5-yl)picolinamide, 0.99 g of DMEAD (registered trademark), 1.04 g of triphenylphosphine and 15 ml of THF was stirred at room temperature for 30 minutes and at 50° C. for 1 hour. The reaction mixture cooled to room temperature was concentrated under reduced pressure, then water was added, and the mixture was extracted with ethyl acetate. The organic layer was washed with a saturated aqueous sodium bicarbonate solution and saturated saline water, then dried over anhydrous sodium sulfate, and concentrated under reduced pressure. The resulting residue was subjected to a silica gel column chromatography to obtain 0.50 g of 2-(3-ethylsulfanylpyridin-2-yl)-5,5,7,7-tetrafluoro-5,7-dihydro-fluo[3',4':4,5]benzo[1,2-d]oxazole (hereinafter, referred to as Compound of Present Invention 1-3).
Compound of Present Invention 1-3

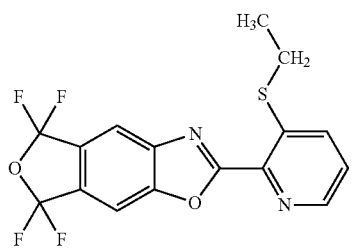 [SMILES: CCSc1cccnc1-c1nc2cc3c(cc2o1)C(F)(F)OC3(F)F]

$^1$H-NMR (CDCl$_3$) δ: 8.62 (1H, dd), 8.17 (1H, d), 7.92 (1H, d), 7.81 (1H, dd), 7.46 (1H, dd), 3.08 (2H, q), 1.48 (3H, t)

Production Example 4

0.48 g of m-chloroperbenzoic acid (purity of 65% or more) was added to a mixture of Compound of Present Invention 1-3 (0.35 g) and 10 ml of chloroform under ice cooling, and then the mixture was stirred at room temperature for 2 hours. A 10% aqueous sodium sulfite solution was added to the reaction mixture, and the mixture was extracted with chloroform. The organic layer was washed with a saturated aqueous sodium bicarbonate solution, then dried over anhydrous sodium sulfate, and concentrated under reduced pressure. The resulting residue was subjected to a silica gel column chromatography to obtain 0.38 g of 2-(3-ethylsulfonylpyridin-2-yl)-5,5,7,7-tetrafluoro-5,7-dihydro-fluo[3',4':4,5]benzo[1,2-d]oxazole (hereinafter, referred to as Compound of Present Invention 1-4).
Compound of Present Invention 1-4

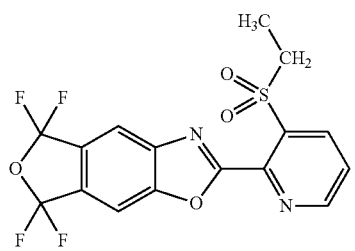 [SMILES: CCS(=O)(=O)c1cccnc1-c1nc2cc3c(cc2o1)C(F)(F)OC3(F)F]

$^1$H-NMR (CDCl$_3$) δ: 9.06 (1H, dd), 8.60 (1H, dd), 8.13 (1H, s), 7.95 (1H, s), 7.79 (1H, dd), 3.94 (2H, q), 1.44 (3H, t)

The compounds described in the production examples described above and the compounds produced by production methods according to the methods described in the production examples described above are shown in the tables.

The compounds of the present invention represented by the formula (1).

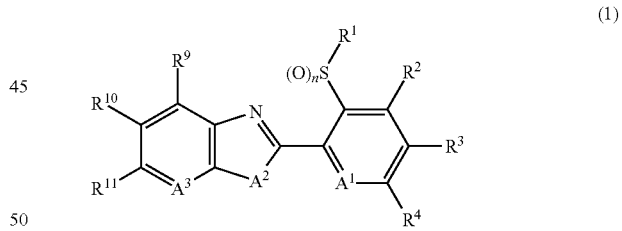

(1)

In the formula, $A^1$, $A^2$, $A^3$, $R^1$, $R^2$, $R^3$, $R^4$, $R^9$, $R^{10}$, $R^{11}$ and n represent the combinations shown in [Table 5] to [Table 6] shown below.

TABLE 5

| Compound of Present Invention | $A^1$ | $A^2$ | $A^3$ | $R^1$ | $R^2$ | $R^3$ | $R^4$ | $R^9$ | $R^{10}$ | $R^{11}$ | n |
|---|---|---|---|---|---|---|---|---|---|---|---|
| 1-1 | N | NMe | CH | Et | H | H | H | H | —CF$_2$OCF$_2$— | | 0 |
| 1-2 | N | NMe | CH | Et | H | H | H | H | —CF$_2$OCF$_2$— | | 2 |
| 1-3 | N | O | CH | Et | H | H | H | H | —CF$_2$OCF$_2$— | | 0 |
| 1-4 | N | O | CH | Et | H | H | H | H | —CF$_2$OCF$_2$— | | 2 |
| 1-5 | CH | NMe | CH | Et | H | H | H | H | —CF$_2$OCF$_2$— | | 0 |
| 1-6 | CH | NMe | CH | Et | H | H | H | H | —CF$_2$OCF$_2$— | | 2 |
| 1-7 | CH | NMe | CH | Et | H | CF$_3$ | H | H | —CF$_2$OCF$_2$— | | 0 |

TABLE 5-continued

| Compound of Present Invention | A¹ | A² | A³ | R¹ | R² | R³ | R⁴ | R⁹ | R¹⁰ | R¹¹ | n |
|---|---|---|---|---|---|---|---|---|---|---|---|
| 1-8 | CH | NMe | CH | Et | H | CF$_3$ | H | H | | —CF$_2$OCF$_2$— | 2 |
| 1-9 | CH | O | CH | Et | H | H | H | H | | —CF$_2$OCF$_2$— | 0 |
| 1-10 | CH | O | CH | Et | H | H | H | H | | —CF$_2$OCF$_2$— | 2 |
| 1-11 | CH | O | CH | Et | H | CF$_3$ | H | H | | —CF$_2$OCF$_2$— | 0 |
| 1-12 | CH | O | CH | Et | H | CF$_3$ | H | H | | —CF$_2$OCF$_2$— | 2 |
| 1-13 | N | NMe | CH | Et | H | CF$_3$ | H | H | | —CF$_2$OCF$_2$— | 0 |
| 1-14 | N | NMe | CH | Et | H | CF$_3$ | H | H | | —CF$_2$OCF$_2$— | 2 |
| 1-15 | N | S | CH | Et | H | H | H | H | | —CF$_2$OCF$_2$— | 0 |
| 1-16 | N | S | CH | Et | H | H | H | H | | —CF$_2$OCF$_2$— | 2 |
| 1-17 | N | S | CH | Et | H | CF$_3$ | H | H | | —CF$_2$OCF$_2$— | 0 |
| 1-18 | N | S | CH | Et | H | CF$_3$ | H | H | | —CF$_2$OCF$_2$— | 2 |
| 1-19 | N | O | CH | Et | H | CF$_3$ | H | H | | —CF$_2$OCF$_2$— | 0 |
| 1-20 | N | O | CH | Et | H | CF$_3$ | H | H | | —CF$_2$OCF$_2$— | 2 |

TABLE 6

| Compound of Present Invention | A¹ | A² | A³ | R¹ | R² | R³ | R⁴ | R⁹ | R¹⁰ | R¹¹ | n |
|---|---|---|---|---|---|---|---|---|---|---|---|
| 1-21 | N | NMe | CH | Et | H | H | H | H | | —CH=CH—CH=CH— | 0 |
| 1-22 | N | NMe | CH | Et | H | H | H | H | | —CH=CH—CH=CH— | 2 |
| 1-23 | CH | O | CH | Et | H | H | H | H | | —CH=CH—CH=CH— | 2 |
| 1-24 | N | O | CH | Et | H | H | H | H | | —CH=CH—CH=CH— | 2 |
| 1-25 | CH | NH | CH | Et | H | H | H | H | | —CH=CH—CH=CH— | 0 |
| 1-26 | N | NH | CH | Et | H | H | H | H | | —CH=CH—CH=CH— | 0 |
| 1-27 | CH | O | CH | Et | H | H | H | H | | —CH=CH—CH=CH— | 0 |
| 1-28 | N | O | CH | Et | H | H | H | H | | —CH=CH—CH=CH— | 0 |
| 1-29 | CH | NMe | CH | Et | H | H | H | H | | —OCF$_2$O— | 0 |
| 1-30 | CH | NMe | CH | Et | H | H | H | H | | —OCF$_2$O— | 2 |

In [Table 5] to [Table 6] above, Me represents a methyl group, and Et represents an ethyl group.

$^1$H-NMR data of the compounds of the present invention shown in [Table 5] to [Table 6] are shown below.

Compound of Present Invention 1-21
$^1$H-NMR (CDCl$_3$) δ: 8.53 (1H, dd), 8.39 (1H, s), 8.03 (1H, d), 7.98 (1H, d), 7.82 (1H, s), 7.77 (1H, dd), 7.49-7.34 (3H, m), 3.95 (3H, s), 2.92 (2H, q), 1.32 (3H, t)

Compound of Present Invention 1-22
$^1$H-NMR (CDCl$_3$) δ: 9.00 (1H, dd), 8.54 (1H, dd), 8.28 (1H, s), 8.04-7.99 (2H, m), 7.86 (1H, s), 7.71 (1H, dd), 7.48-7.41 (2H, m), 3.87 (2H, q), 3.82 (3H, s), 1.35 (3H, t)

Compound of Present Invention 1-23
$^1$H-NMR (CDCl$_3$) δ: 8.29-8.26 (2H, m), 8.07 (1H, dd), 8.05-7.96 (3H, m), 7.86-7.76 (2H, m), 7.56-7.48 (2H, m), 3.90 (2H, q), 1.43 (3H, t)

Compound of Present Invention 1-24
$^1$H-NMR (CDCl$_3$) δ: 9.08-9.04 (1H, m), 8.62 (1H, dt), 8.33 (1H, s), 8.08-8.00 (3H, m), 7.75 (1H, ddd), 7.57-7.50 (2H, m), 4.11 (2H, q), 1.46 (3H, t)

Compound of Present Invention 1-25
$^1$H-NMR (CDCl$_3$) δ: 11.31 (1H, s), 8.59-8.57 (1H, m), 8.31 (1H, s), 8.05-7.91 (3H, m), 7.65-7.62 (1H, m), 7.51-7.40 (4H, m), 2.90 (2H, q), 1.25 (3H, t)

Compound of Present Invention 1-26
$^1$H-NMR (CDCl$_3$) δ: 10.51 (1H, d), 8.57-8.25 (2H, m), 8.05-7.31 (7H, m), 3.12-2.93 (2H, m), 1.54-1.43 (3H, m)

Compound of Present Invention 1-27
$^1$H-NMR (CDCl$_3$) δ: 8.33 (1H, s), 8.27 (1H, dd), 8.05-7.95 (3H, m), 7.54-7.43 (4H, m), 7.33-7.29 (1H, m), 3.09 (2H, q), 1.47 (3H, t)

Compound of Present Invention 1-28
$^1$H-NMR (CDCl$_3$) δ: 8.63 (1H, dd), 8.40 (1H, s), 8.06-7.98 (3H, m), 7.80 (1H, dd), 7.54-7.49 (2H, m), 7.43 (1H, dd), 3.08 (2H, q), 1.50 (3H, t)

Compound of Present Invention 1-29
$^1$H-NMR (CDCl$_3$) δ: 7.50-7.42 (4H, m), 7.35-7.29 (1H, m), 7.09 (1H, s), 3.63 (3H, s), 2.83 (2H, q), 1.22 (3H, t)

Compound of Present Invention 1-30
$^1$H-NMR (CDCl$_3$) δ: 8.23-8.17 (1H, m), 7.84-7.74 (2H, m), 7.57-7.52 (1H, m), 7.41 (1H, s), 7.10 (1H, s), 3.57 (3H, s), 3.49-3.25 (2H, m), 1.21 (3H, q)

Next, formulation examples of the compound of the present invention are shown. The part in the formulation example represents part by weight.

Formulation Example 1

10 parts of any one of Compounds of Present Invention 1-1 to 1-30 is dissolved in a mixture of 35 parts of xylene and 35 parts of DMF, and 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1-1 to 1-30 is further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to and mixed with 2 parts of any one of Compounds of Present Invention 1-1 to 1-30. Subsequently, an appropriate amount of water is added to this mixture, and the mixture is further stirred, granulated with a granulator, and forced-air dried to obtain each granule.

Formulation Example 4

1 part of any one of Compounds of Present Invention 1-1 to 1-30 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate and eliminate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1-1 to 1-30 and 55 parts of water are mixed, and finely pulverized by wet grinding method to obtain each flowable.

Formulation Example 6

0.1 parts of any one of Compounds of Present Invention 1-1 to 1-30 is dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1-1 to 1-30 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait formulation.

Formulation Example 8

0.1 parts of any one of Compounds of Present Invention 1-1 to 1-30 and 49.9 parts of Neothiozol (Chuo Kasei Co., Ltd.) are filled into an aerosol can, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1-1 to 1-30, 0.01 parts of BHT (2,6-di-tert-butyl-4-methylphenol), 5 parts of xylene, 3.39 parts of deodorized kerosene and 1 part of emulsifier {RHEODOL MO-60 (manufactured by Kao Corporation)} are mixed and dissolved, and the resulting solution and 50 parts of distilled water are filled into an aerosol container. A valve is attached to the container, and then 40 parts of a propellant (LPG) is filled under pressure through the valve to obtain an aqueous aerosol.

Formulation Example 10

0.1 g of any one of Compounds of Present Invention 1-1 to 1-30 is dissolved in 2 ml of propylene glycol, and a porous ceramic plate with a size of 4.0 cm×4.0 cm and 1.2 cm in thickness is impregnated with the solution to obtain a heating type smoking agent.

Formulation Example 11

5 parts of any one of Compounds of Present Invention 1-1 to 1-30 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from a molding machine through a molding die to obtain a rod-shaped molded body with a size of 15 cm in length and 3 mm in diameter.

Formulation Example 12

5 parts of any one of Compounds of Present Invention 1-1 to 1-30 and 95 parts of a soft vinyl chloride resin are melt-kneaded with a closed pressurizing kneader (manufactured by Moriyama Works), and the resulting kneaded matter is extruded from a molding machine through a molding die to obtain a rod-shaped molded body with a size of 15 cm in length and 3 mm in diameter.

Formulation Example 13

100 mg of any one of Compounds of Present Invention 1-1 to 1-30, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture was compressed to an appropriate size to obtain a tablet.

Formulation Example 14

25 mg of any one of Compounds of Present Invention 1-1 to 1-30, 60 mg of lactose, 25 mg of corn starch, 6 mg of carmellose calcium and an appropriate amount of 5% hydroxypropyl methylcellulose, and the resulting mixture is filled into a hard shell gelatin capsule or a hydroxypropyl methylcellulose capsule to obtain an encapsulated formulation.

Formulation Example 15

Distilled water is added to 1000 mg of any one of Compounds of Present Invention 1-1 to 1-30, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that a final total volume is 100 ml, and the mixture is mixed to obtain a suspension for oral administration.

Formulation Example 16

5 parts of any one of Compounds of Present Invention 1-1 to 1-30 is dissolved in 5 parts of polysorbate 85, 3 parts of benzyl alcohol and 30 parts of propylene glycol, and a phosphate buffer is added to this solution so as to have a pH of 6.0 to 6.5, and then water is added to have a total amount of 100 parts to obtain a liquid formulation for oral administration.

Formulation Example 17

5 parts of aluminum distearate is dispersed in 57 parts of fractionated palm oil and 3 parts of polysorbate 85 under heating and cooled to room temperature to obtain an oily vehicle, and then 25 parts of saccharin is dispersed in the oily vehicle. Further, 10 parts of any one of Compounds of Present Invention 1-1 to 1-30 is added thereto to obtain a paste formulation for oral administration.

Formulation Example 18

5 parts of any one of Compounds of Present Invention 1-1 to 1-30 and 95 parts of limestone filler are mixed, and a granule for oral administration is obtained using wet granulation method.

Formulation Example 19

5 parts of any one of Compounds of Present Invention 1-1 to 1-30 is dissolved in 80 parts of diethylene glycol monoethyl ether, and 15 parts of propylene carbonate is mixed therewith to obtain a spot-on solution.

Formulation Example 20

10 parts of any one of Compounds of Present Invention 1-1 to 1-30 is dissolved in 70 parts of diethylene glycol monoethyl ether, and 20 parts of 2-octyl dodecanol is mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1-1 to 1-30, and the mixture is sufficiently stirred and mixed until it becomes a uniform solution, and then 19.5 parts of water is added and further sufficiently stirred and mixed to obtain a shampoo agent as a uniform solution.

Formulation Example 22

0.15 parts of any one of Compounds of Present Invention 1-1 to 1-30, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1-1 to 1-30 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention is shown as test examples.

Test Example 1

The formulations of Compounds of Present Invention 1-1, 1-2, 1-3 and 1-4 obtained in Formulation Example 5 were diluted with water so as to have a concentration of the active ingredient of 500 ppm to prepare a test drug solution.

On the other hand, on a cucumber seedling (the first true leaf stage) planted in a plastic cup was inoculated with about 30 *Aphis gossypii* (whole stage), and left for a day. 20 ml of the test drug solution was sprayed on the seedling.

Six days after spraying, the number of surviving *Aphis gossypii* parasitic on the leaves of the cucumber was examined, and the control value was calculated according to the following equation:

$$\text{Control value (\%)} = \{1-(Cb \times Tai)/(Cai \times Tb)\} \times 100$$

wherein the symbols represent as follows:
Cb: the number of insects in a non-treated section before treatment
Cai: the number of surviving parasitic insects in a non-treated section on observation
Tb: the number of insects in a treated section before treatment
Tai: the number of surviving parasitic insects in a treated section on observation wherein the non-treated section refers to a section where the test drug solution prepared by diluting the formulation obtained as in Formulation Example 5 but not containing the compound of the present invention with the same amount of water as in the treated section was sprayed.

As a result, in the treated-section where the test drug solution containing each of Compounds of Present Invention 1-1, 1-2, 1-3 and 1-4 was used, the control value was 90% or more.

Test Example 2

The formulation of Compound of Present Invention 1-2 as obtained in Formulation Example 5 was diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated about 30 *Aphis gossypii* (whole stage), and further kept in the greenhouse for 6 days, then the number of surviving *Aphis gossypii* parasitic on the leaves of the cucumber was examined, and the control value was calculated according to the following equation:

$$\text{Control value (\%)} = \{1-(Cb \times Tai)/(Cai \times Tb)\} \times 100$$

wherein the symbols represent as follows:
Cb: the number of insects in a non-treated section before treatment
Cai: the number of surviving parasitic insects in a non-treated section on observation
Tb: the number of insects in a treated section before treatment
Tai: the number of surviving parasitic insects in a treated section on observation wherein the non-treated section refers to a section where the test drug solution prepared by diluting the formulation obtained as in Formulation Example 5 but not containing the compound of the present invention with the same amount of water as in the treated section was sprayed.

As a result, in the treated section where the test drug solution containing Compound of Present Invention 1-2 was used, the control value was 90% or more.

Test Example 3

The formulations of Compounds of Present Invention 1-1, 1-2 and 1-4 as obtained in Formulation Example 5 were diluted with water, so as to have a concentration of the active ingredient of 500 ppm, to prepare a test drug solution.

On a rice seedling in the second leaf stage planted in a polyethylene cup was sprayed 10 ml of each test drug solution. After air-drying, 20 third-fourth instar larvae of *Nilaparvata lugens* were released, and kept in the greenhouse at 25° C. After 6 days, the number of surviving *Nilaparvata lugens* parasitic on the rice was examined, and the control value was calculated according to the following equation:

Control value (%)={1−($Cb \times Tai$)/($Cai \times Tb$)}×100 wherein the symbols represent as follows:

Cb: the number of insects in a non-treated section before treatment

Cai: the number of surviving parasitic insects in a non-treated section on observation Tb: the number of insects in a treated section before treatment Tai: the number of surviving parasitic insects in a treated section on observation wherein the non-treated section refers to a section where the test drug solution prepared by diluting the formulation obtained as in Formulation Example 5 but not containing the compound of the present invention with the same amount of water as in the treated section was sprayed.

As a result, in the treated-section where the test drug solution containing each of Compounds of Present Invention 1-1, 1-2 and 1-4 was used, the control value was 90% or more.

Test Example 4

The formulations of Compounds of Present Invention 1-1, 1-2 and 1-4 as obtained in Formulation Example 5 were diluted with water, so as to have a concentration of the active ingredient of 500 ppm, to prepare a test drug solution.

On the other hand, a rice seedling (2 weeks after sowing, the second leaf stage) planted in a plastic cup was drenched at its foot with 5 ml of each test drug solution, and kept in a greenhouse at 25° C. for 7 days. 20 third-fourth instar larvae of *Nilaparvata lugens* were released, and further kept in the greenhouse for 6 days, then the number of surviving *Nilaparvata lugens* parasitic on the rice leaves was examined, and the control value was calculated according to the following equation:

Control value (%)={1−($Cb \times Tai$)/($Cai \times Tb$)}×100 wherein the symbols represent as follows:

Cb: the number of insects in a non-treated section before treatment

Cai: the number of surviving parasitic insects in a non-treated section on observation Tb: the number of insects in a treated section before treatment Tai: the number of surviving parasitic insects in a treated section on observation wherein the non-treated section refers to a section where the test drug solution prepared by diluting the formulation obtained as in Formulation Example 5 but not containing the compound of the present invention with the same amount of water as in the treated section was sprayed.

As a result, in the treated-section where the test drug solution containing each of Compounds of Present Invention 1-1, 1-2 and 1-4 was used, the control value was 90% or more.

Test Example 5

The formulation of the compound of the present invention as obtained in Formulation Example 5 is diluted with water, so as to have a concentration of the active ingredient of 500 ppm, to prepare a test drug solution.

On the other hand, *Bemisia tabaci* adult is released on a tomato seedling (the third true leaf stage) planted in a polyethylene cup, and made to lay eggs for about 72 hours. The tomato seedling is kept in a greenhouse for 8 days, and when instar larvae hatch from the eggs, the above test drug solution is sprayed at a rate of 20 ml/cup, and the cup is kept in a greenhouse at 25° C. After 7 days, the number of surviving instar larvae on the tomato leaves is examined. The control value is calculated according to the following equation, and then the sufficient effects are recognized.

Control value (%)={1−($Cb \times Tai$)/($Cai \times Tb$)}×100

In the equation, the symbols represent as follows.

Cb: the number of instar larvae in a non-treated section before treatment

Cai: the number of surviving instar larvae in a non-treated section on observation Tb: the number of instar larvae in a treated section before treatment Tai: the number of surviving instar larvae in a treated section on observation Here, the non-treated section refers to a section where the test drug solution prepared by diluting the formulation obtained as in Formulation Example 5 but not containing the compound of the present invention with the same amount of water as in the treated section was sprayed.

Test Example 6

The formulations of Compounds of Present Invention 1-1, 1-2, 1-3 and 1-4 obtained in Formulation Example 5 were diluted with water so as to have a concentration of the active ingredient of 500 ppm to prepare a test drug solution.

On the other hand, on cabbage at the third leaf stage planted in a polyethylene cup was sprayed, at a rate 20 mL/cup, the test drug solution. After the drug solution was dried, the foliage part was cut off, and then placed in a 50 mL volume cup. Five second instar larvae of *Plutella xylostella* were released into the cup, and the cup was sealed with a lid. After the cup was kept at 25° C. for 5 days, the number of dead insects was counted. The death rate was calculated according to the following equation.

Death rate(%)=(Number of dead insects/Number of tested insects)×100

As a result, in the treated-section where each test drug solution of Compounds of Present Invention 1-1, 1-2, 1-3 and 1-4 was used, the death rate was 80% or more.

Test Example 7

The formulations of Compounds of Present Invention 1-1, 1-2, 1-3 and 1-4, as obtained in Formulation Example 5 were diluted with water, so as to have a concentration of the active ingredient of 500 ppm, to prepare a test spray solution.

On the other hand, an apple tree was planted in a plastic cup, and grown until the seventh-eighth true leaf was spread. To the apple tree was sprayed, at a rate of 20 mL/cup, the test drug solution. After the drug solution was dried, 60 first-instar larvae of *Adoxophyes orana fasciata* were released, and covered with a plastic cup the bottom of which was cut off and on which a filter paper was put, with the plastic cup cover placed upside-down. After 7 days, the number of dead insects was counted, and the death rate was calculated according to the following equation.

Death rate(%)=(Number of dead insects/Number of tested insects)×100

As a result, in the treated-section where each test drug solution of Compounds of Present Invention 1-1, 1-2, 1-3 and 1-4 was used, the death rate was 90% or more.

Test Example 8

The formulation of Compound of Present Invention 1-2 as obtained in Formulation Example 5 was diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 10 female imagoes of *Musca domestica* were released, and the cup was sealed with a lid. After 24 hours, the life and death of *Musca domestica* was examined, the number of dead insects was counted, and the death rate was calculated according to the following equation.

Death rate(%)=(Number of dead insects/Number of tested insects)×100

As a result, in the treated section where the test drug solution containing Compound of Present Invention 1-2 was used, the death rate was 100%.

Test Example 9

The formulation of Compound of Present Invention 1-4 as obtained in Formulation Example 5 was diluted with water, so as to have a concentration of the active ingredient of 500 ppm, to prepare a test drug solution.

A filter paper having a diameter of 5.5 cm was spread on the bottom of a polyethylene cup having the same diameter and 0.7 ml of the test drug solution was added dropwise onto the filter paper, and 30 mg of sucrose was uniformly placed as bait. Into the polyethylene cup, 2 male imagoes of *Blattella germanica* were released, and the cup was sealed with a lid. After 6 days, the life and death of *Blattella germanica* was examined, the number of dead insects was counted, and the death rate was calculated according to the following equation.

Death rate(%)=(Number of dead insects/Number of tested insects)×100

As a result, in the treated section where the test drug solution containing Compound of Present Invention 1-4 was used, the death rate was 100%.

Test Example 10

The formulations of Compounds of Present Invention 1-1, 1-2, 1-3 and 1-4 obtained in Formulation Example 5 were diluted with water so as to have a concentration of the active ingredient of 500 ppm to prepare a test drug solution.

0.7 ml of the test drug solution was added to 100 ml of ion-exchanged water (active ingredient concentration: 3.5 ppm). 20 last-instar larvae of *Culex pipiens pallens* were released into the solution. One day later, the life and death of the *Culex pipiens pallens* was examined, and the number of dead insects was counted to calculate the death rate.

Death rate(%)=(Number of dead insects/Number of tested insects)×100

As a result, in the treated-section where each test drug solution of Compounds of Present Invention 1-1, 1-2, 1-3 and 1-4 was used, the death rate was 95% or more.

Test Example 11

2 mg of each of the compounds of the present invention is weighed in a screw tube (Maruemu No. 5; 27×55 mm), 0.2 mL of acetone is added thereto, and the screw tube is sealed with a cap to dissolve the compound. The screw tube is rotated and inverted to uniformity coat the drug solution onto the whole inner wall of the tube. After removing the cap, the solution is air-dried for about 2 hours, then unfed nymphal ticks, *Haemaphysalis longicornis* (5 ticks/group) are released, and the tube is sealed with the cap. After 2 days, the number of dead insects is counted, and the death rate is calculated according to the following equation, and then the sufficient effects are recognized.

Death rate(%)=100×(Number of dead insects/Number of tested insects)

INDUSTRIAL APPLICABILITY

The compound of the present invention has a control effect on pests and is useful as an active ingredient of a pest control agent.

The invention claimed is:
1. A method for controlling pests comprising applying an effective amount of a fused heterocyclic compound of formula (1) or an N-oxide thereof to a pest or a pest-infected area:

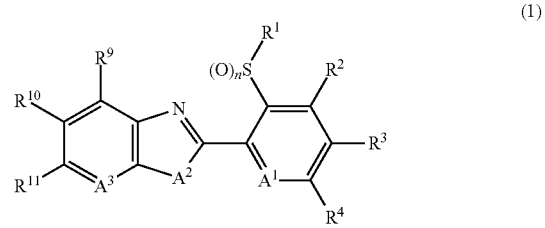

(1)

wherein
$A^1$ represents N or $CR^5$;
$A^2$ represents $NR^6$, S or O;
$A^3$ represents $CR^{12}$;
$R^1$ represents a C1 to C6 chain hydrocarbon group optionally having one or more atoms or groups selected from group α or a C3 to C6 alicyclic hydrocarbon group optionally having one or more atoms or groups selected from group β;
$R^2$, $R^4$ and $R^5$ are the same or different and represent a C1 to C3 alkyl group optionally having one or more halogen atoms, $OR^7$, $S(O)_mR^7$, $SO_2NR^7R^8$, $C(O)R^7$, $CO_2R^7$, $C(O)NR^7R^8$, $NR^7R^8$, $NR^7C(O)R^8$, $NR^7CO_2R^8$, a cyano group, a nitro group, a halogen atom or a hydrogen atom;
$R^3$ represents a C1 to C6 chain hydrocarbon group optionally having one or more atoms or groups selected from group α, a phenyl group optionally having one or more atoms or groups selected from group δ, a 5- or 6-membered heterocyclic group optionally having one or more atoms or groups selected from group δ, OR$^7$, S(O)$_m$R$^7$, SO$_2$NR$^7$R$^8$, C(O)R$^7$, CO$_2$R$^7$, C(O)NR$^7$R$^8$, NR$^7$R$^8$, NR$^7$C(O)R$^8$, NR$^7$CO$_2$R$^8$, a cyano group, a nitro group, a halogen atom or a hydrogen atom;

R$^6$ represents a C1 to C6 chain hydrocarbon group optionally having one or more atoms or groups selected from group γ, C(O)R$^7$, CO$_2$R$^7$ or a hydrogen atom;

R$^7$ and R$^8$ are the same or different and represent a C1 to C6 chain hydrocarbon group optionally having one or more halogen atoms or a hydrogen atom;

R$^{10}$ and R$^{11}$ together with the carbon atoms to which they are bound form ring J;

R$^9$ and R$^{12}$ are the same or different and represent a C1 to C6 chain hydrocarbon group optionally having one or more atoms or groups selected from group α, OR$^7$, S(O)$_m$R$^7$, SO$_2$NR$^7$R$^8$, C(O)R$^7$, CO$_2$R$^7$, C(O)NR$^7$R$^8$, NR$^7$R$^8$, NR$^7$C(O)R$^8$, NR$^7$CO$_2$R$^8$, a cyano group, a nitro group, a halogen atom or a hydrogen atom;

the ring J is a benzene ring, a 5- or 6-membered aromatic heterocyclic ring or a 5-, 6-, 7- or 8-membered non-aromatic ring, wherein the benzene ring and the 5- or 6-membered aromatic heterocyclic ring optionally have one or more atoms or groups selected from group δ, and the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring;

n represents 0, 1 or 2; and m represents 0, 1 or 2, wherein, in S(O)$_m$R$^7$, when m is 1 or 2, R$^7$ represents a C1 to C6 chain hydrocarbon group optionally having one or more halogen atoms;

Group α is selected from the group consisting of C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms, Group β is selected from the group consisting of C1 to C6 alkyl groups optionally having one or more halogen atoms, C1 to C6 alkoxy groups optionally having one or more halogen atoms, and halogen atoms, Group γ is selected from the group consisting of C1 to C6 alkoxy groups optionally having one or more halogen atoms, C1 to C6 alkylsulfanyl groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, phenyl groups optionally having one or more atoms or groups selected from group δ, 5- or 6-membered heterocyclic groups optionally having one or more atoms or groups selected from group δ, cyano groups, hydroxy groups, and halogen atoms, Group δ is selected from the group consisting of C1 to C3 alkyl groups optionally having one or more halogen atoms, C1 to C3 alkoxy groups optionally having one or more halogen atoms, C1 to C3 alkylamino groups optionally having one or more halogen atoms, C2 to C6 dialkylamino groups optionally having one or more halogen atoms, C1 to C3 alkylsulfanyl groups optionally having one or more halogen atoms, C1 to C3 alkylsulfinyl groups optionally having one or more halogen atoms, C1 to C3 alkylsulfonyl groups optionally having one or more halogen atoms, C2 to C4 alkylcarbonyl groups optionally having one or more halogen atoms, C2 to C4 alkoxycarbonyl groups optionally having one or more halogen atoms, nitro groups, amino groups, cyano groups, and halogen atoms, Group ε is selected from the group consisting of C1 to C3 alkyl groups optionally having one or more halogen atoms, C1 to C3 alkoxy groups optionally having one or more halogen atoms, C1 to C3 alkylamino groups optionally having one or more halogen atoms, C2 to C6 dialkylamino groups optionally having one or more halogen atoms, C1 to C3 alkylsulfanyl groups optionally having one or more halogen atoms, C1 to C3 alkylsulfinyl groups optionally having one or more halogen atoms, C1 to C3 alkylsulfonyl groups optionally having one or more halogen atoms, C2 to C4 alkylcarbonyl groups optionally having one or more halogen atoms, C2 to C4 alkoxycarbonyl groups optionally having one or more halogen atoms, nitro groups, amino groups, cyano groups, halogen atoms, divalent groups represented by =S, divalent groups represented by =O, and divalent groups represented by =NOR$^{13}$, wherein R$^{13}$ represents a C1 to C6 alkyl group optionally having one or more halogen atoms or a hydrogen atom, and when the fused heterocyclic compound is an N-oxide thereof, n represents 2, and m represents 2.

2. The method according to claim 1, wherein

R$^1$ is a C1 to C6 alkyl group optionally having one or more halogen atoms or one or more cyclopropyl groups (wherein the cyclopropyl group optionally has one or more halogen atoms or one or more C1 to C3 alkyl groups), a C2 to C6 alkenyl group optionally having one or more halogen atoms, a C2 to C6 alkynyl group optionally having one or more halogen atoms or a C3 to C6 cycloalkyl group optionally having one or more halogen atoms or one or more C1 to C3 alkyl groups;

R$^2$, R$^4$ and R$^5$ are the same or different and are a C1 to C3 alkyl group optionally having one or more halogen atoms, a halogen atom or a hydrogen atom;

R$^3$ is a C1 to C6 alkyl group optionally having one or more halogen atoms, a 5- or 6-membered heterocyclic group optionally having one or more atoms or groups selected from group δ, OR$^7$, S(O)$_m$R$^7$, C(O)R$^7$, CO$_2$R$^7$, C(O)NR$^7$R$^8$, a cyano group, a halogen atom or a hydrogen atom;

R$^6$ is C1 to C6 alkyl group optionally having one or more halogen atoms, a C2 to C6 alkenyl group optionally having one or more halogen atoms, a C2 to C6 alkynyl group optionally having one or more halogen atoms, a C1 to C3 alkyl group having a thiazolyl group optionally having one or more atoms or groups selected from group δ, a C1 to C3 alkyl group having a pyridyl group optionally having one or more atoms or groups selected from group δ or a hydrogen atom; and $R^7$ and $R^8$ are the same or different and are a C1 to C6 alkyl group optionally having one or more halogen atoms or a hydrogen atom.

3. The method according to claim 1, wherein the ring J is a benzene ring, wherein the benzene ring optionally has one or more atoms or groups selected from group δ.

4. The method according to claim 1, wherein the ring J is a 5- or 6-membered aromatic heterocyclic ring, wherein the 5- or 6-membered aromatic heterocyclic ring optionally has one or more atoms or groups selected from group δ.

5. The method according to claim 1, wherein the ring J is a 5-, 6-, 7- or 8-membered non-aromatic ring, wherein the 5-, 6-, 7- or 8-membered non-aromatic ring optionally has one or more atoms or groups selected from group ε, and when the one or more groups selected from group ε are a divalent group represented by =S, a divalent group represented by =O or a divalent group represented by =NOR$^{13}$, each divalent group binds to the same carbon among carbons constituting the ring of the 5-, 6-, 7- or 8-membered non-aromatic ring.

6. The method according to claim 1, wherein $A^1$ is N.
7. The method according to claim 1, wherein $A^1$ is $CR^5$.
8. The method according to claim 1, wherein $A^2$ is $NR^6$.
9. The method according to claim 1, wherein $A^2$ is S.
10. The method according to claim 1, wherein $A^2$ is O.

* * * * *